US010414753B2

(12) United States Patent
Tso et al.

(10) Patent No.: US 10,414,753 B2
(45) Date of Patent: Sep. 17, 2019

(54) AMIDE COMPOUNDS AND METHOD FOR MAKING AND USING

(71) Applicant: Rigel Pharmaceuticals, Inc., South San Francisco, CA (US)

(72) Inventors: Kin Tso, San Francisco, CA (US); Hui Li, Santa Clara, CA (US); Yan Chen, Foster City, CA (US); Rose Yen, San Francisco, CA (US); Vanessa Taylor, San Francisco, CA (US); Thilo Heckrodt, San Francisco, CA (US); Rajinder Singh, Belmont, CA (US); Simon Shaw, Oakland, CA (US)

(73) Assignee: Rigel Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 15/793,743

(22) Filed: Oct. 25, 2017

(65) Prior Publication Data

US 2018/0111917 A1 Apr. 26, 2018

Related U.S. Application Data

(60) Provisional application No. 62/413,299, filed on Oct. 26, 2016.

(51) Int. Cl.

| | |
|---|---|
| ***C07D 401/14*** | (2006.01) |
| ***C07D 401/12*** | (2006.01) |
| ***C07D 413/14*** | (2006.01) |
| ***C07D 403/14*** | (2006.01) |
| ***C07D 403/12*** | (2006.01) |
| ***C07D 405/14*** | (2006.01) |
| ***C07D 471/04*** | (2006.01) |

(52) U.S. Cl.

CPC ......... *C07D 401/14* (2013.01); *C07D 401/12* (2013.01); *C07D 403/12* (2013.01); *C07D 403/14* (2013.01); *C07D 405/14* (2013.01); *C07D 413/14* (2013.01); *C07D 471/04* (2013.01)

(58) Field of Classification Search

None

See application file for complete search history.

(56) References Cited

FOREIGN PATENT DOCUMENTS

| | | |
|---|---|---|
| WO | WO 2015/069594 | 5/2015 |
| WO | WO 2016/172560 | 10/2016 |

*Primary Examiner* — Kamal A Saeed

(74) *Attorney, Agent, or Firm* — Travis Young; Klarquist Sparkman, LLP

(57) ABSTRACT

Disclosed embodiments concern novel interleukin receptor associated kinases (IRAK) inhibitors and compositions comprising such inhibitors. Also disclosed are methods of making and using the compounds and compositions. The disclosed compounds and/or compositions may be used to treat or prevent an IRAK-associated disease or condition.

29 Claims, No Drawings

AMIDE COMPOUNDS AND METHOD FOR MAKING AND USING

CROSS REFERENCE TO RELATED APPLICATION

This application claims the benefit of the earlier filing date of U.S. provisional patent application No. 62/413,299, filed Oct. 26, 2016, which is incorporated herein by reference in its entirety.

FIELD

This disclosure concerns amide compounds, and embodiments of a method for making and using the compounds, such as for inhibiting interleukin receptor-associated kinase (IRAK), and for treating diseases and conditions related to IRAK.

BACKGROUND

Interleukin-1 receptor-associated kinases (IRAKs) are important mediators of signaling processes, such as toll-like receptors (TLR) and interleukin-1 receptor (IL-1R) signaling processes. IRAKs have been implicated in modulating signaling networks that control inflammation, apoptosis, and cellular differentiation. Four IRAK genes have been identified in the human genome (IRAK1, IRAK2, IRAK3 and IRAK4), and studies have revealed distinct, non-redundant biological roles. IRAK1 and IRAK4 have been shown to exhibit kinase activity.

SUMMARY

Certain disclosed embodiments concern compounds having a formula 1

1

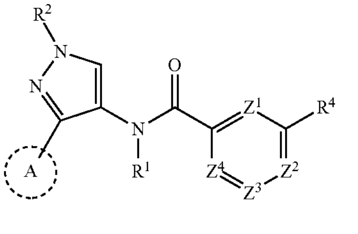

and/or a salt thereof. A person of ordinary skill in the art will appreciate that compounds within formula 1 also can be solvates, including hydrates, N-oxides and/or prodrugs thereof. With reference to formula 1, ring A is aromatic or heterocycloaliphatic. Ring A may be aryl, heteroaryl, 5-membered heterocycloaliphatic, or 6-membered heterocycloaliphatic, such as phenyl, pyridinyl, pyrazinyl, pyrrolidinyl, piperidinyl, or morpholino, and in certain embodiments, ring A is heteroaryl, 5-membered heterocycloaliphatic, or 6-membered heterocycloaliphatic, such as pyridinyl, pyrazinyl, pyrrolidinyl, piperidinyl, or morpholino. In particular embodiments, ring A is pyridin-2-yl. In other examples, ring A is

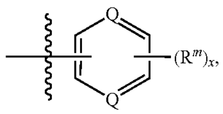 or 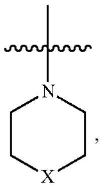, where X is a bond, O, or $CH_2$, such as

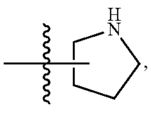, 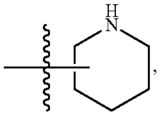, or 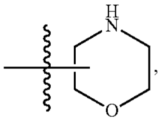, and where each Q independently is CH, $CR^m$ or N, $R^m$ is $R^b$, and x is 0, 1, or 2. In some embodiments, at least one Q is N. $R^b$ is independently for each occurrence —OH, —$CF_3$, —CN, —$OR^c$, —$SO_2R^c$, —$NR^dR^d$, —$N(H)SO_2R^c$, —C(O)OH, —$N(H)C(O)R^c$, —$C(O)OR^c$, —$C(O)NR^dR^d$, =O, or halogen. $R^c$ is independently for each occurrence $C_{1-6}$alkyl, $C_{3-6}$cycloalkyl, $C_{3-6}$heteroalicyclyl, aralkyl, $C_{1-6}$alkyl substituted with 1, 2 or 3 $R^e$, $C_{5-10}$aromatic, $C_{5-10}$aromatic substituted with 1, 2 or 3 $R^e$. $R^d$ is independently for each occurrence H, $C_{1-6}$alkyl optionally substituted with 1, 2 or 3 $R^e$, $C_{3-6}$cycloalkyl optionally substituted with 1, 2 or 3 $R^e$, $C_{3-6}$heteroalicyclyl optionally substituted with 1, 2 or 3 $R^e$, $C_{5-10}$aromatic optionally substituted with 1, 2 or 3 $R^a$ or $R^b$, or two $R^d$ groups together with the nitrogen bound thereto form a $C_{3-6}$heteroalicyclyl moiety optionally substituted with $C_{1-6}$alkyl and optionally interrupted with one or two —O— or —$N(R^g)$ wherein $R^g$ is $R^{70}$. $R^a$ is independently for each occurrence H, D, $C_{1-6}$alkyl, $C_{3-6}$cycloalkyl, $C_{5-10}$aromatic, or $C_{3-6}$heterocycloaliphatic. And $R^e$ is independently for each occurrence halogen, $C_{1-6}$alkyl, $C_{3-6}$cycloalkyl, or —$OR^a$.

$R^1$ may be H, aliphatic, or heteroaliphatic, and in some embodiments, $R^1$ is H or $C_{1-6}$ alkyl. $R^2$ is H, aliphatic, heteroaliphatic, or heterocyclyl, and may be H, 3- to 10-membered heteroaliphatic, tetrahydropyranyl, oxetanyl, cyclobutyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic. In some embodiments, $R^2$ is $R^a$, $R^a$ substituted with $R^b$, $R^a$ substituted with 1 or 2 $R^c$, or $R^a$ substituted with $R^d$. And in particular embodiments, $R^2$ is H, $CH_3$,

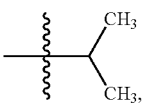, 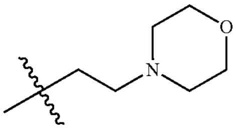,

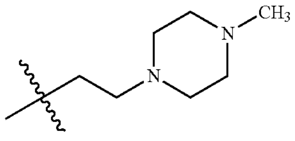, 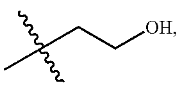,

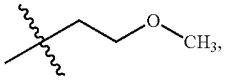, 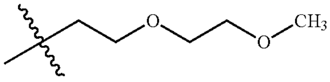,

-continued

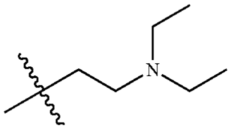,
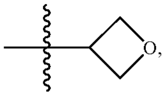

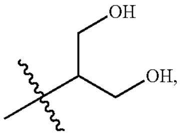
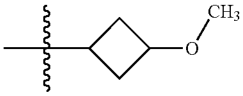,

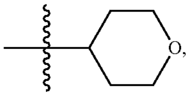 or 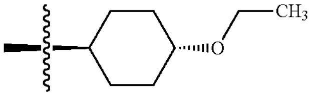.

In certain embodiments of formula 1, ring A is pyridinyl, pyrazinyl, pyrrolidinyl, piperidinyl, or morpholino; $R^1$ is H; and/or $R^2$ is H, 3- to 10-membered heteroaliphatic, tetrahydropyranyl, oxetanyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic.

Also with respect to formula 1, each $Z^1$, $Z^2$, $Z^3$, and $Z^4$ independently is N or $CR^3$, wherein at least one of $Z^1$, $Z^2$, $Z^3$, and $Z^4$ is N and each $R^3$ independently is H, aliphatic, or heteroaliphatic. $R^4$ may be halogen, heteroaryl, heterocycloaliphatic, aryl, —NH-heteroaryl, or —O-heteroaryl.

In some embodiments, the

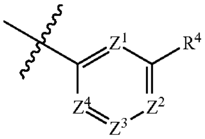

moiety is pyridinyl, pyrimidinyl, or pyrazinyl. In some examples, $Z^1$ is N. In other examples, $Z^1$ is N, and $Z^2$, $Z^3$, and $Z^4$ are $CR^3$; $Z^1$ and $Z^2$ are N, and $Z^3$ and $Z^4$ are $CR^3$; $Z^1$ and $Z^3$ are N, and $Z^2$ and $Z^4$ are $CR^3$; $Z^1$ and $Z^4$ are N, and $Z^2$ and $Z^3$ are $CR^3$; or $Z^3$ is N, and $Z^1$, $Z^2$, and $Z^4$ are $CR^3$. In any embodiments, $R^1$ may be H.

$R^4$ may be halogen, heterocycloaliphatic, aryl, heteroaryl, —NH-heteroaryl, or —O-heteroaryl, such as Br, 5- to 10-membered heteroaryl, 3- to 6-membered heterocycloaliphatic, 6- to 10-membered aryl, —NH-(5- to 10-membered heteroaryl), or —O-(5- to 10-membered heteroaryl). In some embodiments, $R^4$ is pyridinyl, pyrimidinyl, pyrazolyl, —NH-pyrazolyl, pyrrolyl, —O-pyridinyl, —NH-pyridinyl, indolyl, furanyl, —NH-benzopyrazolyl, pyrrolopyridinyl, phenyl, tetrahydropyridinyl, piperidinyl, or 2-oxo-1,2-dihydropyridinyl. In other examples, $R^4$ is Br,

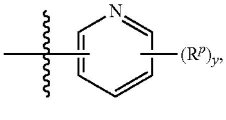
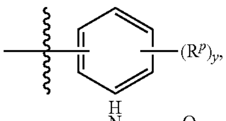
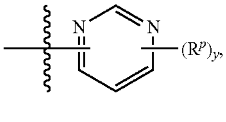
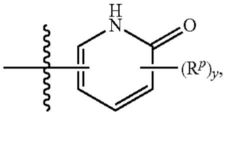

-continued

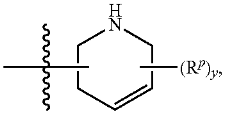
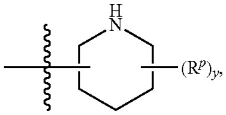

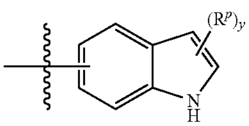,
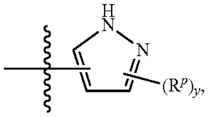

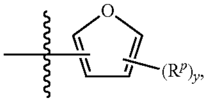
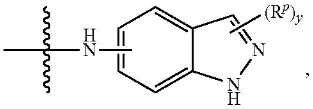,

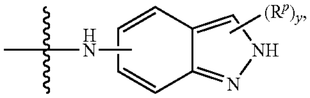

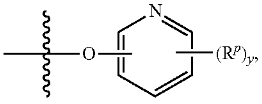
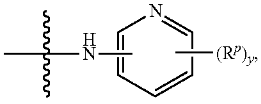

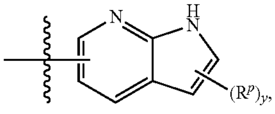
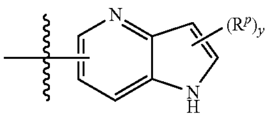,

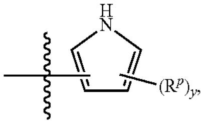 or 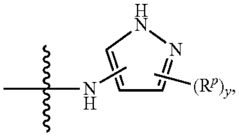

where y is 0, 1 or 2, and each $R^p$ independently is $R^a$, $R^b$, $R^a$ substituted with $R^b$, or $R^a$ substituted with $R^c$. Each $R^p$ independently may be —$CH_3$, —$OCH_3$, —$NH_2$, —$CF_3$, F, —CN,

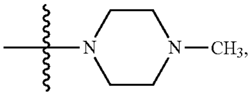
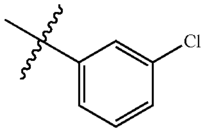,

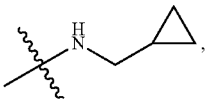,
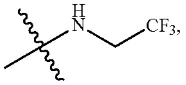

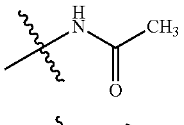,
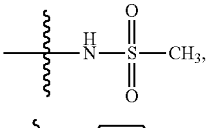
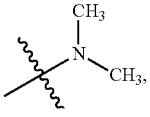

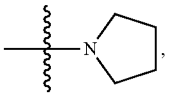,
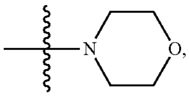
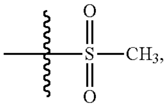

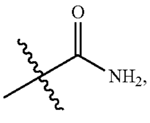
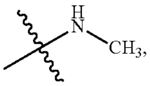
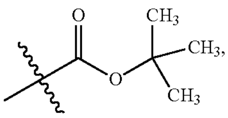

-continued

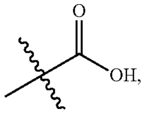, 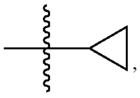, 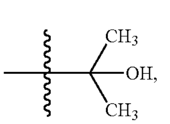,

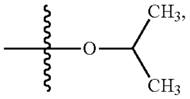, 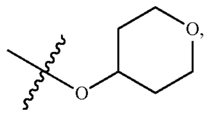,

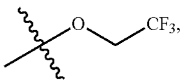, 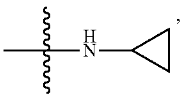, 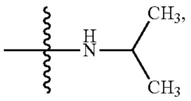,

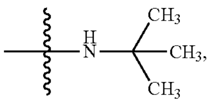, 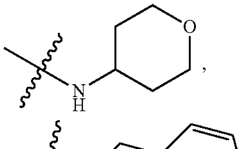,

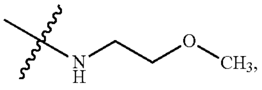, 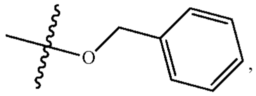,

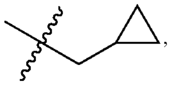, or 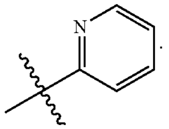.

$R^4$ may be $R^a$, $R^b$, $R^a$ substituted with $R^b$, or $R^a$ substituted with $R^c$, and in particular embodiments, $R^4$ is Br; unsubstituted pyridinyl; pyridinyl substituted with $C_{1-6}$alkyl, haloalkyl, amino, heterocycloaliphatic, cycloalkyl, —CN, alkoxy, —O-heterocycloaliphatic, —NH-heterocycloaliphatic, halogen, sulfonamide, —O-benzyl, carboxyl, sulfonyl, —NH-cycloalkyl, or amide; unsubstituted pyrimidinyl; unsubstituted pyrazolyl; pyrazolyl substituted with $C_{1-6}$alkyl; unsubstituted —NH-pyrazolyl; —NH-pyrazolyl substituted with $C_{1-6}$alkyl, or heteroaryl; pyrrolyl; unsubstituted —O-pyridinyl; —O-pyridinyl substituted with amino; —NH-pyridinyl substituted with $C_{1-6}$alkyl, haloalkyl, or heterocycloaliphatic; unsubstituted indolyl; indolyl substituted with alkoxy; furanyl; —NH—benzopyrazolyl; pyrrolopyridinyl; unsubstituted phenyl; phenyl substituted with halogen, $C_{1-6}$alkyl, alkoxy, —CN, amino, or sulfonamide; unsubstituted tetrahydropyridinyl; tetrahydropyridinyl substituted with tert-butoxycarbonyl; piperidinyl; or 2-oxo-1,2-dihydropyridinyl.

Disclosed compounds also may have a formula 2

2

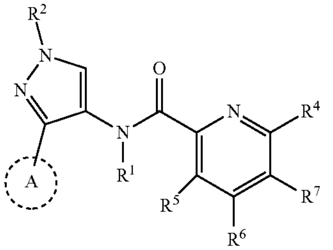

and/or a salt, solvate, N-oxide, and/or prodrug thereof, where the common substituents are as stated for formula 1, and each of $R^5$, $R^6$, and $R^7$ independently is H or alkyl, such as $C_{1-6}$ alkyl. In some examples, each of $R^5$, $R^6$, and $R^7$ is H. In some embodiments of formula 2, ring A is pyridin-2-yl, pyrazine-2-yl, pyrrolidin-1-yl, piperidin-1-yl, or morpholino.

Also disclosed are compounds having formula 3

3

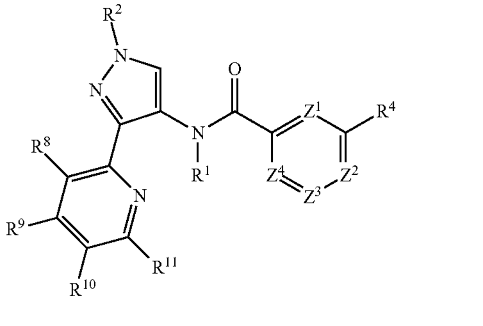

and/or a salt, solvate, N-oxide, and/or prodrug thereof, where the common substituents are as stated for formulas 1 and 2, and each of $R^8$, $R^9$, $R^{10}$ and $R^{11}$ independently is H, aliphatic, halogen, heterocycloaliphatic, alkoxy, or —O-heterocycloaliphatic, such as H, halogen, 3- to 6-membered heterocycloaliphatic, alkoxy, or —O-(3- to 6-membered heterocycloaliphatic). In certain embodiments, $R^8$ is H or halogen; $R^9$ and $R^{11}$ are H; and/or $R^{10}$ is H, F, morpholino, N-methylpiperidin-1-yl, methoxy, 2-hydroxy-2-methylpropoxy, or —O-oxetanyl. And in particular embodiments, each of $R^8$, $R^9$, and $R^{11}$ is H; $R^9$ and $R^{11}$ are H, and $R^8$ and $R^{10}$ are F; or each of $R^8$, $R^9$, $R^{10}$ and $R^{11}$ is H.

Disclosed compounds also may have a formula 8

8

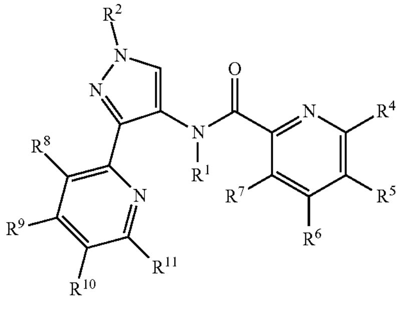

and/or a salt, solvate, N-oxide, and/or prodrug thereof, where the substituents are as stated for formulas 1-3. In certain embodiments, $R^1$ is H; $R^2$ is H, 3- to 10-membered heteroaliphatic, tetrahydropyranyl, oxetanyl, cyclobutyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic; $R^4$ is Br; unsubstituted pyridinyl; pyridinyl substituted with $C_{1-6}$alkyl, haloalkyl, amino, heterocycloaliphatic, cycloalkyl, —CN, alkoxy, —O-heterocycloaliphatic, —NH-heterocycloaliphatic, halogen, sulfonamide, —O-benzyl, carboxyl, sulfonyl, —NH-cycloalkyl, or amide; unsubstituted pyrimidinyl; unsubstituted pyrazolyl; pyrazolyl substituted with $C_{1-6}$alkyl; unsubstituted —NH-pyrazolyl; —NH-pyrazolyl substituted with $C_{1-6}$alkyl, or heteroaryl; pyrrolyl; unsubstituted —O-pyridinyl; —O-pyridinyl substituted with amino; —NH-pyridinyl substituted with $C_{1-6}$alkyl, haloalkyl, or heterocycloaliphatic; unsubstituted indolyl; indolyl substituted with alkoxy; furanyl; —NH-benzopyrazolyl; pyrrolopyridinyl; unsubstituted phenyl; phenyl substituted with halogen, $C_{1-6}$alkyl, alkoxy, —CN, amino, or sulfonamide; unsubstituted tetrahydropyridinyl; tetrahydropyridinyl substituted with tert-butoxycarbonyl; piperidinyl; or 2-oxo-1,2-dihydropyridinyl; $R^8$ is H or F; $R^9$ and $R^{11}$ are H; and $R^{10}$ is H, F, morpholino, N-methylpiperidinyl, methoxy, 2-hydroxy-2-methylpropoxy, or —O-oxetanyl. And in particular embodiments, each of $R^8$, $R^9$, $R^{10}$ and $R^{11}$ is H; $R^8$, $R^9$, and $R^{11}$ is H and $R^{10}$ is 3- to 6-membered morpholino or N-methylpiperidinyl, methoxy, 2-hydroxy-2-methylpropoxy, or —O-oxetanyl; or $R^8$ and $R^{10}$ are F, and $R^9$ and $R^{11}$ are H.

Compounds according to the present disclosure also may be formulated as compositions comprising one or more compounds according to any of formulas 1-9, and a pharmaceutically acceptable excipient. Such compositions also may include an additional therapeutic agent.

Methods for making and using such compounds and compositions also are disclosed. For example, one disclosed embodiment of a method for using compounds within formulas 1-9 comprises administering to a subject in need thereof an effective amount of a compound, two or more compounds, or a composition comprising at least one compound, according to any or all of formulas 1-9. The method may be particularly suitable for treating a disease or condition for which an IRAK inhibitor is indicated, including an IRAK1, IRAK2, IRAK3 and/or IRAK4 inhibitor. The disease may be an auto-immune disease, an inflammatory disorder, a cardiovascular disease, a neurodegenerative disorder, an allergic disorder, a multi-organ failure, a kidney disease, a platelet aggregation malady, cancer, transplantation, sperm motility, erythrocyte deficiency, graft rejection, lung injury, respiratory disease, ischemic condition, bacterial infection, viral infection, immune regulatory disorder, or a combination thereof.

Disclosed embodiments of a method for using compounds according to formulas 1-9 also include inhibiting an IRAK protein by contacting the IRAK protein with an effective amount of a compound or compounds, or composition comprising a compound or compounds, according to any or all of formulas 1-9 wherein the compound has an $EC_{50}$ of from greater than 0 to 5 μM, typically from 0 to 1 μM, and with many disclosed compounds having an $EC_{50}$ substantially lower than 1 μM. The IRAK protein may be in a subject, or the method may comprise contacting the IRAK protein in vitro.

The foregoing and other objects, features, and advantages of the invention will become more apparent from the following detailed description.

DETAILED DESCRIPTION

I. Definitions

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference.

Unless otherwise indicated, all numbers expressing quantities of components, molecular weights, percentages, temperatures, times, and so forth, as used in the specification or claims are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood to one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

When chemical structures are depicted or described, unless explicitly stated otherwise, all carbons are assumed to include hydrogen so that each carbon conforms to a valence of four. For example, in the structure on the left-hand side of the schematic below there are nine hydrogen atoms implied. The nine hydrogen atoms are depicted in the right-hand structure.

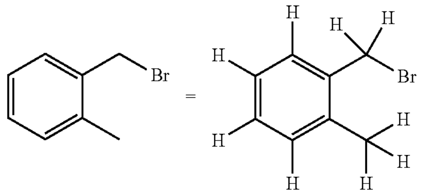

Sometimes a particular atom in a structure is described in textual formula as having a hydrogen or hydrogen atoms, for example $—CH_2CH_2—$. It will be understood by a person of ordinary skill in the art that the aforementioned descriptive techniques are common in the chemical arts to provide brevity and simplicity to description of organic structures.

If a group R is depicted as "floating" on a ring system, as for example in the group:

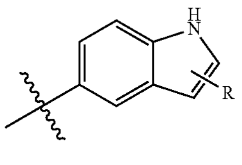

then, unless otherwise defined, a substituent R can reside on any atom of the fused bicyclic ring system, excluding the atom carrying the bond with the " " symbol so long as a stable structure is formed. In the example depicted, the R group can reside on an atom in either the 5-membered or the 6-membered ring of the indolyl ring system.

When there are more than one such depicted "floating" groups, as for example in the formulae:

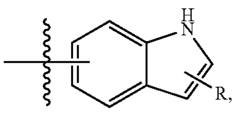 or 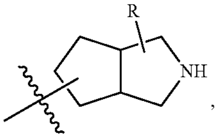, or

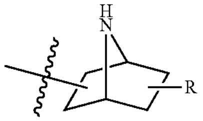

where there are two groups, namely, the R and the bond indicating attachment to a parent structure; then, unless otherwise defined, the "floating" groups can reside on any atoms of the ring system, again assuming each replaces a depicted, implied, or expressly defined hydrogen on the ring system and a chemically stable compound would be formed by such an arrangement.

When a group R is depicted as existing on a ring system containing saturated carbons, as for example in the formula:

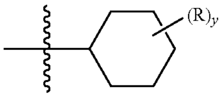

where, in this example, y can be more than one, assuming each replaces a currently depicted, implied, or expressly defined hydrogen on the ring; then, unless otherwise defined, two R's can reside on the same carbon. A simple example is when R is a methyl group. The depicted structure can exist as a geminal dimethyl on a carbon of the depicted ring (an "annular" carbon). In another example, two R's on the same carbon, including that same carbon, can form a ring, thus creating a spirocyclic ring (a "spirocyclyl" group) structure. For example, shown below two Rs can form a piperidine ring in a spirocyclic arrangement with the cyclohexane, as

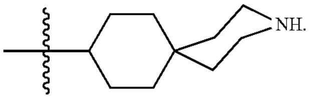 [SMILES: *C1CCC2(CCNCC2)CC1]

As used herein, the term "substituted" refers to all subsequent modifiers in a term, for example in the term "substituted aryl$C_{1-8}$alkyl," substitution may occur on the "$C_{1-8}$alkyl" portion, the "aryl" portion or both portions of the aryl$C_{1-8}$alkyl group.

"Substituted," when used to modify a specified group or moiety, means that at least one, and perhaps two or more, hydrogen atoms of the specified group or moiety is independently replaced with the same or different substituent groups as defined below. In a particular embodiment, a group, moiety or substituent may be substituted or unsubstituted, unless expressly defined as either "unsubstituted" or "substituted." Accordingly, any of the groups specified herein may be unsubstituted or substituted. In particular embodiments, the substituent may or may not be expressly defined as substituted, but is still contemplated to be optionally substituted. For example, an "alkyl" or a "pyrazolyl" moiety may be unsubstituted or substituted, but an "unsubstituted alkyl" or an "unsubstituted pyrazolyl" is not substituted.

"Substituents" or "substituent groups" for substituting for one or more hydrogen atoms on saturated carbon atoms in the specified group or moiety are, unless otherwise specified, $—R^{60}$, halo, $=O$, $—OR^{70}$, $—SR^{70}$, $—N(R^{80})_2$, haloalkyl, perhaloalkyl, —CN, $—NO_2$, $=N_2$, $—N_3$, $—SO_2R^{70}$, $—SO_3^-M^+$, $—SO_3R^{70}$, $—OSO_2R^{70}$, $—OSO_3^-M^+$, $—OSO_3R^{70}$, $—P(O)(O^-)_2(M^+)_2$, $—P(O)(O^-)_2M^{2+}$, $—P(O)(OR^{70})O^-M^+$, $—P(O)(OR^{70})_2$, $—C(O)R^{70}$, $—C(S)R^{70}$, $—C(NR^{70})R^{70}$, $—CO_2^-M^+$, $—CO_2R^{70}$, $—C(S)OR^{70}$, $—C(O)N(R^{80})_2$, $—C(NR^{70})(R^{80})_2$, $—OC(O)R^{70}$, $—OC(S)R^{70}$, $—OCO_2^-M^+$, $—OCO_2R^{70}$, $—OC(S)OR^{70}$, $—NR^{70}C(O)R^{70}$, $—NR^{70}C(S)R^{70}$, $—NR^{70}CO_2^-M^+$, $—NR^{70}CO_2R^{70}$, $—NR^{70}C(S)OR^{70}$, $—NR^{70}C(O)N(R^{80})_2$, $—NR^{70}C(NR^{70})R^{70}$ and $—NR^{70}C(NR^{70})N(R^{80})_2$, where $R^{60}$ is $C_{1-10}$aliphatic, heteroaliphatic, or cycloaliphatic, typically, $C_{1-6}$aliphatic, more typically $C_{1-6}$alkyl, where $R^{60}$ optionally may be substituted; each $R^{70}$ is independently for each occurrence hydrogen or $R^{60}$; each $R^{80}$ is independently for each occurrence $R^{70}$ or alternatively, two $R^{80}$ groups, taken together with the nitrogen atom to which they are bonded, form a 3- to 7-membered heterocycloaliphatic, which optionally includes from 1 to 4 of the same or different additional heteroatoms selected from O, N and S, of which N optionally has $R^{70}$ substitution, such as H or $C_1$-$C_3$alkyl substitution; and each $M^+$ is a counter ion with a net single positive charge. Each $M^+$ is independently for each occurrence, for example, an alkali metal ion, such as $K^+$, $Na^+$, $Li^+$; an ammonium ion, such as $^+N(R^{60})_4$; a protonated amino acid ion, such as a lysine ion, or an arginine ion; or an alkaline metal earth ion, such as $[Ca^{2+}]_{0.5}$, $[Mg^{2+}]_{0.5}$, or $[Ba^{2+}]_{0.5}$ (a subscript "0.5" means, for example, that one of the counter ions for such divalent alkali earth ions can be an ionized form of a compound of the invention and the other a typical counter ion such as chloride, or two ionized compounds can serve as counter ions for such divalent alkali earth ions, or a doubly ionized compound can serve as the counter ion for such divalent alkali earth ions). As specific examples, $—N(R^{80})_2$ includes $—NH_2$, —NH-alkyl, —NH-pyrrolidin-3-yl, N-pyrrolidinyl, N-piperazinyl, 4N-methyl-piperazin-1-yl, N-morpholinyl and the like. Any two hydrogen atoms on a single carbon also can be replaced with, for example, $=O$, $=NR^{70}$, $=N—OR^{70}$, $=N_2$ or $=S$.

Substituent groups for replacing hydrogen atoms on unsaturated carbon atoms in groups containing unsaturated carbons are, unless otherwise specified, $—R^{60}$, halo, $—O^-M^+$, $—OR^{70}$, $—SR^{70}$, $—S^-M^+$, $—N(R^{80})_2$, haloalkyl, perhaloalkyl, —CN, —OCN, —SCN, —NO, $—NO_2$, $—N_3$, $—SO_2R^{70}$, $—SO_3^-M^+$, $—SO_3R^{70}$, $—OSO_2R^{70}$, $—OSO_3^-M^+$, $—OSO_3R^{70}$, $—PO_3^{-2}(M^+)_2$, $—PO_3^{-2}M^{2+}$, $—P(O)(OR^{70})O^-M^+$, $—P(O)(OR^{70})_2$, $—C(O)R^{70}$, $—C(S)R^{70}$, $—C(NR^{70})R^{70}$, $—CO_2^-M^+$, $—CO_2R^{70}$, $—C(S)OR^{70}$, $—C(O)NR^{80}R^{80}$, $—C(NR^{70})N(R^{80})_2$, $—OC(O)R^{70}$, $—OC(S)R^{70}$, $—OCO_2^-M^+$, $—OCO_2R^{70}$, $—OC(S)OR^{70}$, $—NR^{70}C(O)R^{70}$, $—NR^{70}C(S)R^{70}$, $—NR^{70}CO_2^-M^+$, $—NR^{70}CO_2R^{70}$, $—NR^{70}C(S)OR^{70}$, $—NR^{70}C(O)N(R^{80})_2$, $—NR^{70}C(NR^{70})R^{70}$ and $—NR^{70}C(NR^{70})N(R^{80})_2$, where $R^{60}$, $R^{70}$, $R^{80}$ and $M^+$ are as previously defined, provided that in case of substituted alkene or alkyne, the substituents are not $—O^-M^+$, $—OR^{70}$, $—SR^{70}$, or $—S^-M^+$.

Substituent groups for replacing hydrogen atoms on nitrogen atoms in groups containing such nitrogen atoms are, unless otherwise specified, $—R^{60}$, $—O^-M^+$, $—OR^{70}$, $—SR^{70}$, $—S^-M^+$, $—N(R^{80})_2$, haloalkyl, perhaloalkyl, —CN, —NO, $—NO_2$, $—S(O)_2R^{70}$, $—SO_3^-M^+$, $—SO_3R^{70}$, $—OS(O)_2R^{70}$, $—OSO_3^-M^+$, $—OSO_3R^{70}$, $—PO_3^{-2}(M^+)_2$, $—PO_3^{-2}M^{2+}$, $—P(O)(OR^{70})O^-M^+$, $—P(O)(OR^{70})(OR^{70})$, —C(O)$R^{70}$, —C(S)$R^{70}$, —C($NR^{70}$)$R^{70}$, —$CO_2R^{70}$, —C(S)$OR^{70}$, —C(O)$NR^{80}R^{80}$, —C($NR^{70}$)$NR^{80}R^{80}$, —OC(O)$R^{70}$, —OC(S)$R^{70}$, —$OCO_2R^{70}$, —OC(S)$OR^{70}$, —$NR^{70}$C(O)$R^{70}$, —$NR^{70}$C(S)$R^{70}$, —$NR^{70}CO_2R^{70}$, —$NR^{70}$C(S)$OR^{70}$, —$NR^{70}$C(O)N($R^{80}$)$_2$, —$NR^{70}$C($NR^{70}$)$R^{70}$ and —$NR^{70}$C($NR^{70}$)N($R^{80}$)$_2$, where $R^{60}$, $R^{70}$, $R^{80}$ and $M^+$ are as previously defined.

In one embodiment, a group that is substituted has at least one substituent up to the number of substituents possible for a particular moiety, such as 1 substituent, 2 substituents, 3 substituents, or 4 substituents.

Additionally, in embodiments where a group or moiety is substituted with a substituted substituent, the nesting of such substituted substituents is limited to three, thereby preventing the formation of polymers. Thus, in a group or moiety comprising a first group that is a substituent on a second group that is itself a substituent on a third group, which is attached to the parent structure, the first (outermost) group can only be substituted with unsubstituted substituents. For example, in a group comprising -(aryl-1)-(aryl-2)-(aryl-3), aryl-3 can only be substituted with substituents that are not themselves substituted.

Any group or moiety defined herein can be connected to any other portion of a disclosed structure, such as a parent or core structure, as would be understood by a person of ordinary skill in the art, such as by considering valence rules, comparison to exemplary species, and/or considering functionality, unless the connectivity of the group or moiety to the other portion of the structure is expressly stated, or is implied by context.

"Acyl" refers to the group —C(O)R, where R is H, aliphatic, heteroaliphatic, heterocyclic or aromatic. Exemplary acyl moieties include, but are not limited to, —C(O)H, —C(O)alkyl, —C(O)$C_1$-$C_6$alkyl, —C(O)$C_1$-$C_6$haloalkyl, —C(O)cycloalkyl, —C(O)alkenyl, —C(O)cycloalkenyl, —C(O)aryl, —C(O)heteroaryl, or —C(O)heterocyclyl. Specific examples include, —C(O)H, —C(O)Me, —C(O)Et, or —C(O)cyclopropyl.

"Aliphatic" refers to a substantially hydrocarbon-based group or moiety. An aliphatic group or moiety can be acyclic, including alkyl, alkenyl, or alkynyl groups, cyclic versions thereof, such as cycloaliphatic groups or moieties including cycloalkyl, cycloalkenyl or cycloalkynyl, and further including straight- and branched-chain arrangements, and all stereo and position isomers as well. Unless expressly stated otherwise, an aliphatic group contains from one to twenty-five carbon atoms ($C_{1-25}$); for example, from one to fifteen ($C_{1-15}$), from one to ten ($C_{1-10}$), from one to six ($C_{1-6}$), or from one to four carbon atoms ($C_{1-4}$) for an acyclic aliphatic group or moiety, or from three to fifteen ($C_{3-15}$) from three to ten ($C_{3-10}$), from three to six ($C_{3-6}$), or from three to four ($C_{3-4}$) carbon atoms for a cycloaliphatic group or moiety. An aliphatic group may be substituted or unsubstituted, unless expressly referred to as an "unsubstituted aliphatic" or a "substituted aliphatic." An aliphatic group can be substituted with one or more substituents (up to two substituents for each methylene carbon in an aliphatic chain, or up to one substituent for each carbon of a —C═C— double bond in an aliphatic chain, or up to one substituent for a carbon of a terminal methine group).

"Lower aliphatic" refers to an aliphatic group containing from one to ten carbon atoms ($C_{1-10}$), such as from one to six ($C_{1-6}$), or from one to four ($C_{1-4}$) carbon atoms; or from three to ten ($C_{3-10}$), such as from three to six ($C_{3-6}$) carbon atoms for a lower cycloaliphatic group.

"Alkoxy" refers to the group —OR, where R is a substituted or unsubstituted alkyl or a substituted or unsubstituted cycloalkyl group. In certain examples R is a $C_{1-6}$ alkyl group or a $C_{3-6}$cycloalkyl group. Methoxy (—$OCH_3$) and ethoxy (—$OCH_2CH_3$) are exemplary alkoxy groups. In a substituted alkoxy, R is substituted alkyl or substituted cycloalkyl, examples of which in the presently disclosed compounds include haloalkoxy groups, such as —$OCF_2H$.

"Alkoxyalkyl" refers to the group -alkyl-OR, where R is a substituted or unsubstituted alkyl or a substituted or unsubstituted cycloalkyl group.

"Alkyl" refers to a saturated aliphatic hydrocarbyl group having from 1 to 25 ($C_{1-25}$) carbon atoms, typically 1 to 10 ($C_{1-10}$) carbon atoms such as 1 to 6 ($C_{1-6}$) carbon atoms. An alkyl moiety may be substituted or unsubstituted. This term includes, by way of example, linear and branched hydrocarbyl groups such as methyl ($CH_3$), ethyl (—$CH_2CH_3$), n-propyl (—$CH_2CH_2CH_3$), isopropyl (—$CH(CH_3)_2$), n-butyl (—$CH_2CH_2CH_2CH_3$), isobutyl (—$CH_2CH_2(CH_3)_2$), sec-butyl (—$CH(CH_3)(CH_2CH_3)$), t-butyl (—$C(CH_3)_3$), n-pentyl (—$CH_2CH_2CH_2CH_2CH_3$), and neopentyl (—$CH_2C(CH_3)_3$).

"Amino" refers to the group —$NH_2$, —NHR, or —NRR, where each R independently is selected from H, aliphatic, heteroaliphatic, aromatic, including both aryl and heteroaryl, or heterocycloaliphatic, or two R groups together with the nitrogen attached thereto form a heterocyclic ring. Examples of such heterocyclic rings include those wherein two R groups together with the nitrogen to which they are attached form a —$(CH_2)_{2-5}$— ring optionally interrupted by one or two heteroatom groups, such as —O— or —N($R^g$) such as in the groups

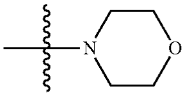

and

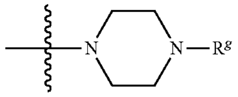

wherein $R^g$ is $R^{70}$, —C(O)$R^{70}$, —C(O)$OR^{60}$ or —C(O)N($R^{80}$)$_2$.

"Amide" or "carboxamide" refers to the group —N(R)acyl, or —C(O)amino, where R is hydrogen, heteroaliphatic or aliphatic, such as alkyl, particularly $C_{1-6}$alkyl.

"Aromatic" refers to a cyclic, conjugated group or moiety of, unless specified otherwise, from 5 to 15 ring atoms having a single ring (e.g., phenyl, pyridinyl, or pyrazolyl) or multiple condensed rings in which at least one ring is aromatic (e.g., naphthyl, indolyl, or pyrazolopyridinyl), that is at least one ring, and optionally multiple condensed rings, have a continuous, delocalized π-electron system. Typically, the number of out of plane π-electrons corresponds to the Hückel rule (4n+2). The point of attachment to the parent structure typically is through an aromatic portion of the condensed ring system. For example,

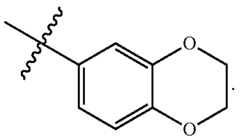 [SMILES: *c1ccc2c(c1)OCCO2]

However, in certain examples, context or express disclosure may indicate that the point of attachment is through a non-aromatic portion of the condensed ring system. For example,

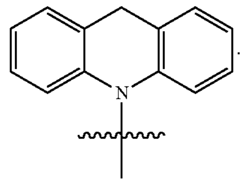 [SMILES: *N1c2ccccc2Cc2ccccc21]

An aromatic group or moiety may comprise only carbon atoms in the ring, such as in an aryl group or moiety, or it may comprise one or more ring carbon atoms and one or more ring heteroatoms comprising a lone pair of electrons (e.g. S, O, N, P, or Si), such as in a heteroaryl group or moiety. Unless otherwise stated, an aromatic group may be substituted or unsubstituted.

"Aryl" refers to an aromatic carbocyclic group of, unless specified otherwise, from 6 to 15 carbon atoms having a single ring (e.g., phenyl) or multiple condensed rings in which at least one ring is aromatic (e.g., 1,2,3,4-tetrahydroquinoline, benzodioxole, and the like). If any aromatic ring portion contains a heteroatom, the group is heteroaryl and not aryl. Aryl groups may be, for example, monocyclic, bicyclic, tricyclic or tetracyclic. Unless otherwise stated, an aryl group may be substituted or unsubstituted.

"Araliphatic" refers to an aryl group attached to the parent via an aliphatic moiety. Araliphatic includes aralkyl or arylalkyl groups such as benzyl and phenylethyl.

"Carboxyl" or "carboxylate" refers to —$CO_2H$, —C(O)O or salts thereof.

"Carboxyl ester" or "carboxy ester" refers to the group —C(O)OR, where R is aliphatic, heteroaliphatic, cyclic, heterocyclic, and aromatic, including both aryl and heteroaryl.

"Cyano" refers to the group —CN.

"Cycloaliphatic" refers to a cyclic aliphatic group having a single ring (e.g., cyclohexyl), or multiple rings, such as in a fused, bridged or spirocyclic system, at least one of which is aliphatic. Typically, the point of attachment to the parent structure is through an aliphatic portion of the multiple ring system. Cycloaliphatic includes saturated and unsaturated systems, including cycloalkyl, cycloalkenyl and cycloalkynyl. A cycloaliphatic group may contain from three to twenty-five carbon atoms; for example, from three to fifteen, from three to ten, or from three to six carbon atoms. Unless otherwise stated, a cycloaliphatic group may be substituted or unsubstituted. Exemplary cycloaliphatic groups include, but are not limited to, cyclopropyl, cyclobutyl, cyclopentyl, cyclohexyl, cycloheptyl, cyclopentenyl, or cyclohexenyl.

"Halo," "halide" or "halogen" refers to fluoro, chloro, bromo or iodo.

"Haloalkyl" refers to an alkyl moiety substituted with one or more halogens. Exemplary haloalkyl moieties include —$CH_2F$, —$CHF_2$ and —$CF_3$.

"Heteroaliphatic" refers to an aliphatic compound or group having at least one heteroatom and at least one carbon atom, i.e., one or more carbon atoms from an aliphatic compound or group comprising at least two carbon atoms, has been replaced with an atom having at least one lone pair of electrons, typically nitrogen, oxygen, phosphorus, silicon, or sulfur. Heteroaliphatic compounds or groups may be substituted or unsubstituted, branched or unbranched, chiral or achiral, and/or acyclic or cyclic, such as a heterocycloaliphatic group.

"Heteroaryl" refers to an aromatic group or moiety of, unless specified otherwise, from 5 to 15 ring atoms comprising at least one carbon atom and at least one heteroatom, such as N, S, O, P, or Si. A heteroaryl group or moiety may comprise a single ring (e.g., pyridinyl, pyrimidinyl or pyrazolyl) or multiple condensed rings (e.g., indolyl, benzopyrazolyl, or pyrazolopyridinyl). Heteroaryl groups or moiety may be, for example, monocyclic, bicyclic, tricyclic or tetracyclic. Unless otherwise stated, a heteroaryl group or moiety may be substituted or unsubstituted.

"Heterocyclyl," "heterocyclo" and "heterocycle" refer to both aromatic and non-aromatic ring systems, and more specifically refer to a stable three- to fifteen-membered ring moiety comprising at least one carbon atom, and typically plural carbon atoms, and at least one, such as from one to five, heteroatoms. The heteroatom(s) may be nitrogen, phosphorus, oxygen, silicon or sulfur atom(s). The heterocyclyl moiety may be a monocyclic moiety, or may comprise multiple rings, such as in a bicyclic or tricyclic ring system, provided that at least one of the rings contains a heteroatom. Such a multiple ring moiety can include fused or bridged ring systems as well as spirocyclic systems; and any nitrogen, phosphorus, carbon, silicon or sulfur atoms in the heterocyclyl moiety can be optionally oxidized to various oxidation states. For convenience, nitrogens, particularly, but not exclusively, those defined as annular aromatic nitrogens, are meant to include their corresponding N-oxide form, although not explicitly defined as such in a particular example. Thus, for a compound having, for example, a pyridinyl ring, the corresponding pyridinyl-N-oxide is included as another compound of the invention, unless expressly excluded or excluded by context. In addition, annular nitrogen atoms can be optionally quaternized. Heterocycle includes heteroaryl moieties, and heteroalicyclyl or heterocycloaliphatic moieties, which are heterocyclyl rings that are partially or fully saturated. Examples of heterocyclyl groups include, but are not limited to, azetidinyl, oxetanyl, acridinyl, benzodioxolyl, benzodioxanyl, benzofuranyl, carbazoyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, quinolinyl, isoquinolinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, dihydropyridinyl, tetrahydropyridinyl, pyridinyl, pyrazinyl, pyrimidinyl, pyridazinyl, oxazolyl, oxazolinyl, oxazolidinyl, triazolyl, isoxazolyl, isoxazolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzoxazolyl, furyl, diazabicycloheptane, diazapane, diazepine, tetrahydrofuryl, tetrahydropyranyl, thienyl, benzothienyl, thiamorpholinyl, thiamorpholinyl sulfoxide, thiamorpholinyl sulfone, dioxaphospholanyl, and oxadiazolyl.

"Hydroxyl" refers to the group —OH.

"Nitro" refers to the group —$NO_2$.

"Phosphate" refers to the group —O—P(O)(OR')$_2$, where each —OR' independently is —OH; —O-aliphatic, such as —O-alkyl or —O-cycloalkyl; —O-aromatic, including both —O-aryl and —O-heteroaryl; —O-aralkyl; or —OR' is —$O^-M^+$, where each $M^+$ is a positively charged counterion. By way of example, $M^+$ may be an alkali metal ion, such as $K^+$, $Na^+$, $Li^+$; an ammonium ion, such as $^+N(R'')_4$ where R'' is H, aliphatic, heterocyclyl or aryl; or an alkaline earth ion, such as $[Ca^{2+}]_{0.5}$, $[Mg^{2+}]_{0.5}$, or $[Ba^{2+}]_{0.5}$. Phosphonooxyalkyl refers to the group -alkyl-phosphate, such as, for example, $—CH_2OP(O)(OH)_2$, or a salt thereof, such as $—CH_2OP(O)(O^- Na^+)_2$, and (((dialkoxyphosphoryl)oxy) alkyl) refers to the dialkyl ester of a phosphonooxyalkyl group, such as, for example, $—CH_2OP(O)(O\text{-tert-butyl})_2$.

"Phosphonate" refers to the group $—P(O)(OR')_2$, where each —OR' independently is —OH; —O-aliphatic such as —O-alkyl or —O-cycloalkyl; —O-aromatic, including both —O-aryl and —O-heteroaryl; or —O-aralkyl; or —OR' is $—O^-M^+$, where each $M^+$ is a positively charged counterion. By way of example, $M^+$ may be an alkali metal ion, such as $K^+$, $Na^+$, $Li^+$; an ammonium ion, such as $+N(R'')_4$ where R" is H, aliphatic, heterocyclyl or aryl; or an alkaline earth metal ion, such as $[Ca^{2+}]_{0.5}$, $[Mg^{2+}]_{0.5}$, or $[Ba^{2+}]_{0.5}$. Phosphonoalkyl refers to the group -alkyl-phosphonate, such as, for example, $—CH_2P(O)(OH)_2$, or $—CH_2P(O)(O^- Na^+)_2$, and ((dialkoxyphosphoryl)alkyl) refers to the dialkyl ester of a phosphonoalkyl group, such as, for example, $—CH_2P(O)(O\text{-tert-butyl})_2$.

"Patient" or "Subject" refers to mammals and other animals, particularly humans. Thus disclosed methods are applicable to both human therapy and veterinary applications.

"Pharmaceutically acceptable excipient" refers to a substance, other than the active ingredient, that is included in a formulation of the active ingredient. As used herein, an excipient may be incorporated within particles of a pharmaceutical composition, or it may be physically mixed with particles of a pharmaceutical composition. An excipient can be used, for example, to dilute an active agent and/or to modify properties of a pharmaceutical composition. Excipients can include, but are not limited to, antiadherents, binders, coatings, enteric coatings, disintegrants, flavorings, sweeteners, colorants, lubricants, glidants, sorbents, preservatives, adjuvants, carriers or vehicles. Excipients may be starches and modified starches, cellulose and cellulose derivatives, saccharides and their derivatives such as disaccharides, polysaccharides and sugar alcohols, protein, synthetic polymers, crosslinked polymers, antioxidants, amino acids or preservatives. Exemplary excipients include, but are not limited to, magnesium stearate, stearic acid, vegetable stearin, sucrose, lactose, starches, hydroxypropyl cellulose, hydroxypropyl methylcellulose, xylitol, sorbitol, maltitol, gelatin, polyvinylpyrrolidone (PVP), polyethyleneglycol (PEG), tocopheryl polyethylene glycol 1000 succinate (also known as vitamin E TPGS, or TPGS), carboxy methyl cellulose, dipalmitoyl phosphatidyl choline (DPPC), vitamin A, vitamin E, vitamin C, retinyl palmitate, selenium, cysteine, methionine, citric acid, sodium citrate, methyl paraben, propyl paraben, sugar, silica, talc, magnesium carbonate, sodium starch glycolate, tartrazine, aspartame, benzalkonium chloride, sesame oil, propyl gallate, sodium metabisulphite or lanolin.

An "adjuvant" is an excipient that modifies the effect of other agents, typically the active ingredient. Adjuvants are often pharmacological and/or immunological agents. An adjuvant may modify the effect of an active ingredient by increasing an immune response. An adjuvant may also act as a stabilizing agent for a formulation. Exemplary adjuvants include, but are not limited to, aluminum hydroxide, alum, aluminum phosphate, killed bacteria, squalene, detergents, cytokines, paraffin oil, and combination adjuvants, such as Freund's complete adjuvant or Freund's incomplete adjuvant.

"Pharmaceutically acceptable carrier" refers to an excipient that is a carrier or vehicle, such as a suspension aid, solubilizing aid, or aerosolization aid. *Remington: The Science and Practice of Pharmacy*, The University of the Sciences in Philadelphia, Editor, Lippincott, Williams, & Wilkins, Philadelphia, Pa., 21st Edition (2005), incorporated herein by reference, describes exemplary compositions and formulations suitable for pharmaceutical delivery of one or more therapeutic compositions and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. In some examples, the pharmaceutically acceptable carrier may be sterile to be suitable for administration to a subject (for example, by parenteral, intramuscular, or subcutaneous injection). In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

"Pharmaceutically acceptable salt" refers to pharmaceutically acceptable salts of a compound that are derived from a variety of organic and inorganic counter ions as will be known to a person of ordinary skill in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate, and the like. "Pharmaceutically acceptable acid addition salts" are a subset of "pharmaceutically acceptable salts" that retain the biological effectiveness of the free bases while formed by acid partners. In particular, the disclosed compounds form salts with a variety of pharmaceutically acceptable acids, including, without limitation, inorganic acids such as hydrochloric acid, hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid and the like. "Pharmaceutically acceptable base addition salts" are a subset of "pharmaceutically acceptable salts" that are derived from inorganic bases such as sodium, potassium, lithium, ammonium, calcium, magnesium, iron, zinc, copper, manganese, aluminum salts and the like. Exemplary salts are the ammonium, potassium, sodium, calcium, and magnesium salts. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Exemplary organic bases are isopropylamine, diethylamine, tris(hydroxymethyl)aminomethane (Tris), ethanolamine, trimethylamine, dicyclohexylamine, choline, and caffeine. (See, for example, S. M. Berge, et al., "Pharmaceutical Salts," J. Pharm. Sci., 1977; 66:1-19 which is incorporated herein by reference.) In particular disclosed embodiments, amide compounds may be a formate, trifluoroactate, hydrochloride or sodium salt.

"Effective amount" with respect to a compound or composition refer to an amount of the compound or composition sufficient to achieve a particular desired result, such as to inhibit a protein or enzyme, particularly an IRAK kinase; to elicit a desired biological or medical response in a tissue, system, subject or patient; to treat a specified disorder or disease; to ameliorate or eradicate one or more of its symptoms; and/or to prevent the occurrence of the disease or disorder. The amount of a compound which constitutes an "effective amount" may vary depending on the compound, the desired result, the disease state and its severity, the age of the patient to be treated, and the like.

"Prodrug" refers to compounds that are transformed in vivo to yield a biologically active compound, particularly the parent compound, for example, by hydrolysis in the gut or enzymatic conversion. Common examples of prodrug moieties include, but are not limited to, ester and amide forms of a compound having an active form bearing a carboxylic acid moiety. Examples of pharmaceutically acceptable esters of the compounds of this invention include, but are not limited to, esters of phosphate groups and carboxylic acids, such as aliphatic esters, particularly alkyl esters (for example $C_{1-6}$alkyl esters). Other prodrug moieties include phosphate esters, such as —$CH_2$—O—P(O)(OR')$_2$ or a salt thereof, wherein R' is H or $C_{1-6}$alkyl. Acceptable esters also include cycloalkyl esters and arylalkyl esters such as, but not limited to benzyl. Examples of pharmaceutically acceptable amides of the compounds of this invention include, but are not limited to, primary amides, and secondary and tertiary alkyl amides (for example with between about one and about six carbons). Amides and esters of disclosed exemplary embodiments of compounds according to the present invention can be prepared according to conventional methods. A thorough discussion of prodrugs is provided in T. Higuchi and V. Stella, "Pro-drugs as Novel Delivery Systems," Vol 14 of the A.C.S. Symposium Series, and in Bioreversible Carriers in Drug Design, ed. Edward B. Roche, American Pharmaceutical Association and Pergamon Press, 1987, both of which are incorporated herein by reference for all purposes.

"Solvate" refers to a complex formed by combination of solvent molecules with molecules or ions of a solute. The solvent can be an organic solvent, an inorganic solvent, or a mixture of both. Exemplary solvents include, but are not limited to, alcohols, such as methanol, ethanol, propanol; amides such as N,N-dialiphatic amides, such as N,N-dimethylformamide; tetrahydrofuran; alkylsulfoxides, such as dimethylsulfoxide; water; and combinations thereof. The compounds described herein can exist in un-solvated as well as solvated forms when combined with solvents, pharmaceutically acceptable or not, such as water, ethanol, and the like. Solvated forms of the presently disclosed compounds are within the scope of the embodiments disclosed herein.

"Sulfonamide" refers to the group or moiety —$SO_2$amino, or —N(R)sulfonyl, where R is H, aliphatic, heteroaliphatic, cyclic, heterocyclic, including aromatic, both aryl and heteroaryl.

"Sulfanyl" refers to the group or —SH, —S-aliphatic, —S-heteroaliphatic, —S-cyclic, —S-heterocyclyl, including —S-aromatic, both-S-aryl and —S-heteroaryl.

"Sulfinyl" refers to the group or moiety —S(O)H, —S(O)aliphatic, —S(O)heteroaliphatic, —S(O)cyclic, —S(O)heterocyclyl, including aromatic, both-S(O)aryl and —S(O)heteroaryl.

"Sulfonyl" refers to the group: —$SO_2$H, —$SO_2$aliphatic, —$SO_2$heteroaliphatic, —$SO_2$cyclic, —$SO_2$heterocyclyl, including aromatic sulfonyls, including both —$SO_2$aryl and —$SO_2$heteroaryl.

"Treating" or "treatment" as used herein concerns treatment of a disease or condition of interest in a patient or subject, particularly a human having the disease or condition of interest, and includes by way of example, and without limitation:

(i) preventing the disease or condition from occurring in a patient or subject, in particular, when such patient or subject is predisposed to the condition but has not yet been diagnosed as having it;

(ii) inhibiting the disease or condition, for example, arresting or slowing its development;

(iii) relieving the disease or condition, for example, causing regression of the disease or condition or a symptom thereof; or (iv) stabilizing the disease or condition.

As used herein, the terms "disease" and "condition" can be used interchangeably or can be different in that the particular malady or condition may not have a known causative agent (so that etiology has not yet been determined) and it is therefore not yet recognized as a disease but only as an undesirable condition or syndrome, where a more or less specific set of symptoms have been identified by clinicians.

The above definitions and the following general formulas are not intended to include impermissible substitution patterns (e.g., methyl substituted with 5 fluoro groups). Such impermissible substitution patterns are easily recognized by a person having ordinary skill in the art.

Any of the groups referred to herein may be optionally substituted by at least one, possibly two or more, substituents as defined herein. That is, a substituted group has at least one, possible two or more, substitutable hydrogens replaced by a substituent or substituents as defined herein, unless the context indicates otherwise or a particular structural formula precludes substitution.

A person of ordinary skill in the art will appreciate that compounds may exhibit the phenomena of tautomerism, conformational isomerism, geometric isomerism, and/or optical isomerism. For example, certain disclosed compounds can include one or more chiral centers and/or double bonds and as a consequence can exist as stereoisomers, such as double-bond isomers (i.e., geometric isomers), enantiomers, diasteromers, and mixtures thereof, such as racemic mixtures. As another example, certain disclosed compounds can exist in several tautomeric forms, including the enol form, the keto form, and mixtures thereof. As the various compound names, formulae and compound drawings within the specification and claims can represent only one of the possible tautomeric, conformational isomeric, optical isomeric, or geometric isomeric forms, a person of ordinary skill in the art will appreciate that the disclosed compounds encompass any tautomeric, conformational isomeric, optical isomeric, and/or geometric isomeric forms of the compounds described herein, as well as mixtures of these various different isomeric forms. In cases of limited rotation, e.g. around the amide bond or between two directly attached rings such as the pyrazolyl and pyridinyl rings, atropisomers are also possible and are also specifically included in the compounds of the invention.

In any embodiments, any or all hydrogens present in the compound, or in a particular group or moiety within the compound, may be replaced by a deuterium or a tritium. Thus, a recitation of alkyl includes deuterated alkyl, where from one to the maximum number of hydrogens present may be replaced by deuterium. For example, ethyl may be $C_2H_5$ or $C_2H_5$ where from 1 to 5 hydrogens are replaced by deuterium, such as in $C_2D_xH_{5-x}$.

II. IRAK-Active Compounds and Compositions Comprising IRAK-Active Compounds

A. Amide Compounds

Disclosed herein are amide compounds, methods of making the compounds, and methods of using the compounds. In one embodiment the disclosed compounds are tyrosine kinase inhibitors. In a particular embodiment the compounds are useful in blocking one or more cytokine signaling pathways, such as the IL-17 signaling pathway. For certain embodiments, the amide compounds are useful for treating conditions in which inhibition of an interleukin-1 receptor-associated kinase (IRAK) pathway is therapeutically useful. In some embodiments, the compounds directly inhibit an IRAK protein, such as IRAK1, IRAK2, IRAK3, IRAK4, or a combination thereof.

Exemplary amide compounds within the scope of the present invention have a general formula 1

1

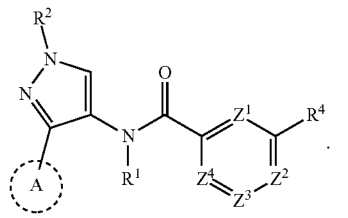

A person of ordinary skill in the art will appreciate that salts, prodrugs, N-oxides and/or solvates including hydrates, of such compounds also can be formed, and accordingly salts, prodrugs, N-oxides and/or solvates are understood to be included within the scope of disclosed general formulas 1-9.

With reference to formula 1, Ring A is aromatic, including both aryl and heteroaryl, or heterocyclyl, such as heterocycloaliphatic. In some embodiments, ring A is a 6-membered aryl, a 6-membered heteroaryl, or a 5- or 6-membered heterocycloaliphatic. In some embodiments, ring A is phenyl, pyridinyl, pyrazinyl, or heterocycloaliphatic, such as pyrrolidinyl, piperidinyl, or morpholino.

In some embodiments, ring A is

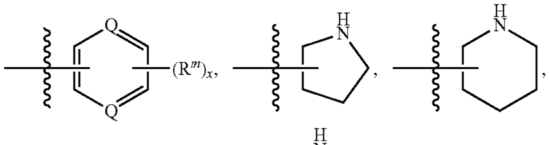

or

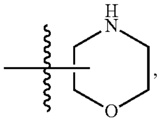

where each Q independently is CH, $CR^m$ or N, $R^m$ is $R^b$ and x is 0, 1, or 2.

$R^a$ is independently for each occurrence H, D, $C_{1-6}$alkyl, $C_{3-6}$cycloalkyl, $C_{5-10}$aromatic, or $C_{3-6}$heterocycloaliphatic;

$R^b$ is independently for each occurrence —OH, —$CF_3$, —CN, —$OR^c$, —$SO_2R^c$, —$NR^dR^d$, —$N(H)SO_2R^c$, —C(O)OH, —$N(H)C(O)R^c$, —$C(O)OR^c$, —C(O)$NR^dR^d$, =O, or halogen;

$R^c$ is independently for each occurrence $C_{1-6}$alkyl, $C_{3-6}$cycloalkyl, $C_{3-6}$heteroalicyclyl, aralkyl, $C_{1-6}$alkyl substituted with 1, 2 or 3 $R^e$, $C_{5-10}$aromatic, $C_{5-10}$aromatic substituted with 1, 2 or 3 $R^e$;

$R^d$ is independently for each occurrence H, $C_{1-6}$alkyl optionally substituted with 1, 2 or 3 $R^e$, $C_{3-6}$cycloalkyl optionally substituted with 1, 2 or 3 $R^e$, $C_{3-6}$heteroalicyclyl optionally substituted with 1, 2 or 3 $R^e$, $C_{5-10}$aromatic optionally substituted with 1, 2 or 3 $R^a$ or $R^b$, or two $R^d$ groups together with the nitrogen bound thereto form a $C_{3-6}$heteroalicyclyl moiety optionally substituted with $C_{1-6}$alkyl and optionally interrupted with one or two —O— or —$N(R^g)$ wherein $R^g$ is $R^{70}$; and $R^e$ is independently for each occurrence halogen, $C_{1-6}$alkyl, $C_{3-6}$cycloalkyl, or —$OR^a$.

In certain embodiments, ring A is

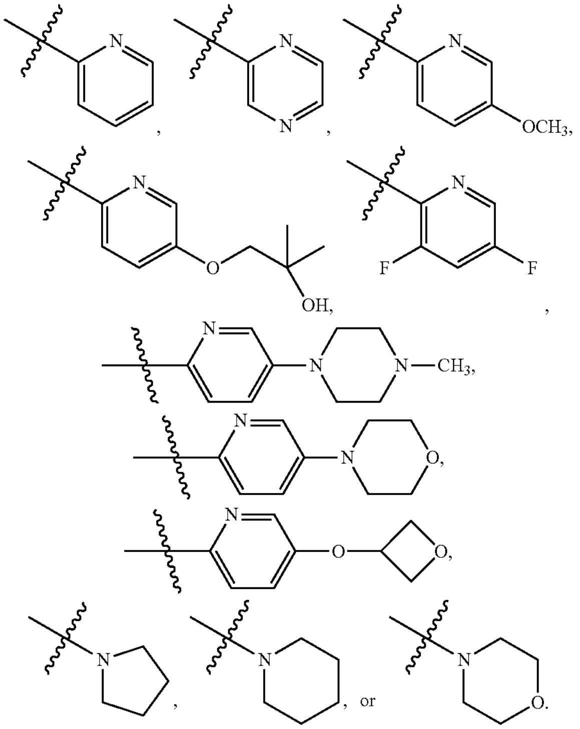

$R^1$ is H, aliphatic, such as alkyl, including $C_{1-6}$ alkyl, or heteroaliphatic. In particular embodiments, $R^1$ is H.

$R^2$ is H; aliphatic, including alkyl, alkenyl, alkynyl, and cycloaliphatic, such as cycloalkyl; heteroaliphatic; or heterocyclyl. In some embodiments, $R^2$ is H, $C_{3-6}$cycloalkyl, heterocycloaliphatic, such as 3- to 6-membered heterocycloaliphatic, or heteroaliphatic, such as 3- to 10-membered heteroaliphatic.

In some embodiments, $R^2$ is H, $C_{1-6}$alkyl, heteroaliphatic, such as 3- to 10-membered heteroaliphatic, tetrahydropyranyl, oxetanyl, cyclobutyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic.

In some embodiments, $R^2$ is $R^a$, $R^a$ substituted with $R^b$, $R^a$ substituted with 1 or 2 $R^c$, or $R^a$ substituted with $R^d$. $R^2$ may be H, $CH_3$,

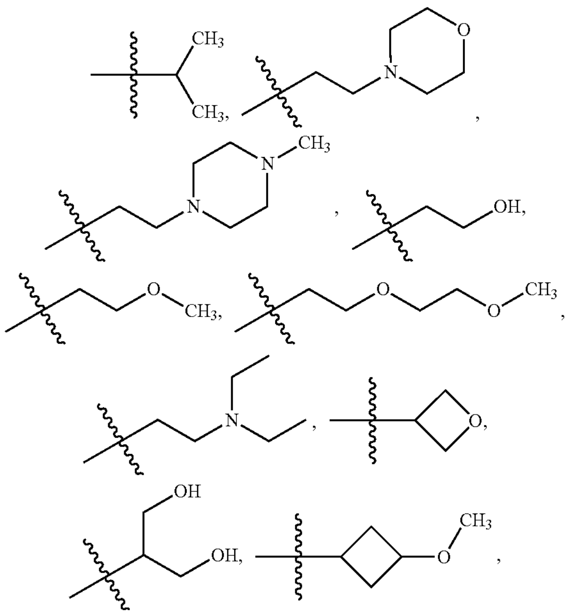

or

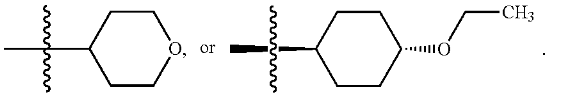

.

In particular embodiments, ring A is phenyl, pyridinyl, pyrazinyl, or heterocycloaliphatic, such as pyrrolidinyl, piperidinyl, or morpholino; $R^1$ is H; and $R^2$ is H, heteroaliphatic, such as 3- to 10-membered heteroaliphatic, tetrahydropyranyl, oxetanyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic.

With respect to formula 1, ring A may be: 1A) aryl; 1B) heteroaryl; 1C) heterocycloaliphatic; 1D) phenyl; 1E) pyridinyl; 1F) pyrazinyl; 1G) piperazin-1-yl, 1H) morpholino; 11) pyrrolidin-1-yl; 1J) pyridin-2-yl; 1K) pyrazine-2-yl; 1L) 5-(2-hydroxy-2-methylpropoxy)pyridin-2-yl; 1M) 5-oxetan-3-yloxypyridin-2-yl; 1N) 5-morpholinopyridin-2-yl; 10) 5-(4-methylpiperazin-1-yl)pyridin-2-yl; 1P) 3,5-difluoropyridin-2-yl; or 1Q) 5-methoxypyridin-2-yl.

With respect to the ring A embodiments 1A to 1Q, $R^2$ may be, in any combination with 1A to 1Q: 2A) H; 2B) aliphatic; 2C) heteroaliphatic; 2D) heterocycloaliphatic; 2E) $C_{1-6}$alkyl; 2F) methyl; 2G) isopropyl; 2H) 2-morpholinoethyl; 21) 2-(4-methylpiperazin-1-yl)ethyl; 2J) 2-hydroxyethyl; 2K) 2-(2-methoxyethoxy)ethyl; 2L) 2-methoxycyclobut-1-yl; 2M) 4-tetrahydropyran; 2N) 2-methoxyethyl; 20) 3-methoxypropyl; 2P) (1r,4r)-4-ethoxycyclohex-1-yl; 2Q) oxetan-3-yl; 3R) 1,3-dihydroxypropan-2-yl; or 2S) 2-(N,N-diethylamino)ethyl.

A person of ordinary skill in the art will understand that any of 2A to 2S may be combined with any of 1A to 1Q to form any and all combinations between such substituents.

Each $Z^1$, $Z^2$, $Z^3$, and $Z^4$, independently is N or $CR^3$, wherein at least one of $Z^1$, $Z^2$, $Z^3$, and $Z^4$ is N. Each $R^3$ independently is H, aliphatic, or heteroaliphatic, and may be H or alkyl, such as H or $C_{1-6}$alkyl. In certain embodiments, each $R^3$ is H. In some embodiments, one of $Z^1$, $Z^2$, $Z^3$, and $Z^4$ is N and the remainder are $CR^3$. In other embodiments, two of $Z^1$, $Z^2$, $Z^3$, and $Z^4$ are N and the remainder are $CR^3$. In certain embodiments, the

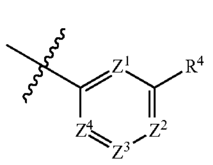

moiety is pyridinyl, pyrimidinyl, or pyrazinyl. In particular embodiments, $Z^1$ is N, and $Z^2$, $Z^3$, and $Z^4$ are $CR^3$; both $Z^1$ and $Z^2$ are N, and $Z^3$ and $Z^4$ are $CR^3$; both $Z^1$ and $Z^3$ are N, and $Z^2$ and $Z^4$ are $CR^3$; both $Z^1$ and $Z^4$ are N, and $Z^2$ and $Z^3$ are $CR^3$; or $Z^3$ is N, and $Z^1$, $Z^2$, and $Z^4$ are $CR^3$. In any of these embodiments, ring A is pyridinyl, pyrazinyl, or heterocycloaliphatic, such as pyrrolidinyl, piperidinyl, or morpholino; $R^1$ is H; and $R^2$ is H, heteroaliphatic, such as 3- to 10-membered heteroaliphatic, tetrahydropyranyl, oxetanyl, cyclobutyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic.

In particular embodiments, $Z^1$ is N, and $Z^2$, $Z^3$, and $Z^4$ are $CR^3$; both $Z^1$ and $Z^2$ are N, and $Z^3$ and $Z^4$ are $CR^3$; both $Z^1$ and $Z^3$ are N, and $Z^2$ and $Z^4$ are $CR^3$; both $Z^1$ and $Z^4$ are N, and $Z^2$ and $Z^3$ are $CR^3$; or $Z^3$ is N, and $Z^1$, $Z^2$, and $Z^4$ are $CR^3$. In any of these embodiments, ring A is pyridinyl, pyrazinyl, or heterocycloaliphatic, such as pyrrolidinyl, piperidinyl, or morpholino; $R^1$ is H; $R^2$ is H, heteroaliphatic, such as 3- to 10-membered heteroaliphatic, tetrahydropyranyl, oxetanyl, cyclobutyl, cyclobutyl substituted with alkoxy and/or hydroxy, cycloheyxyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic; and each $R^3$ is H.

In any embodiments of formula 1, $R^4$ may be halogen, heterocycloaliphatic, or aromatic, such as aryl, heteroaryl, —NH-heteroaryl, or —O-heteroaryl. $R^4$ may be halogen, such as Br; 5- to 10-membered heteroaryl, 3- to 6-membered heterocycloaliphatic, 6- to 10-membered aryl, —NH-(5- to 10-membered heteroaryl), or —O-(5- to 10-membered heteroaryl). And in some embodiments, $R^4$ is halogen, pyridinyl, pyrimidinyl, pyrazolyl, —NH— pyrazolyl, pyrrolyl, —O-pyridinyl, —NH-pyridinyl, indolyl, furanyl, —NH-benzopyrazolyl, pyrrolopyridinyl, phenyl, tetrahydropyridinyl, piperidinyl, or 2-oxo-1,2-dihydropyridinyl.

In some embodiments, $R^4$ is $R^a$, $R^b$, $R^a$ substituted with $R^b$, or $R^a$ substituted with $R^c$. $R^4$ may be Br,

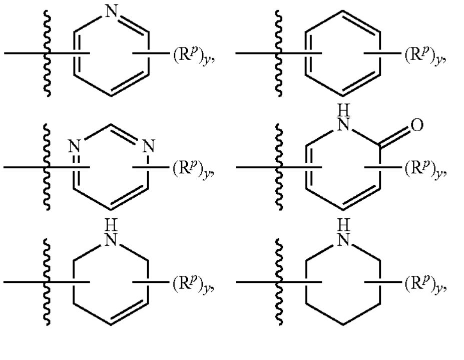

-continued

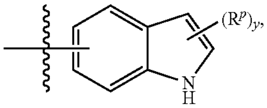
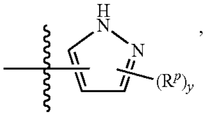
,
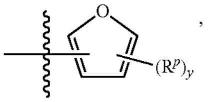
,
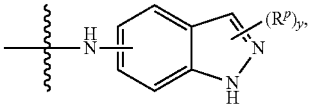
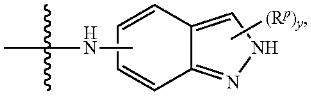
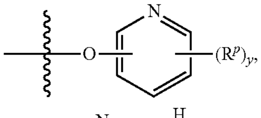
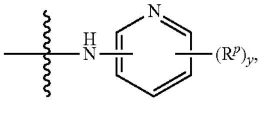
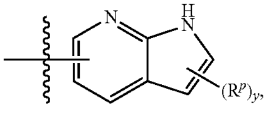
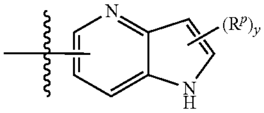
,
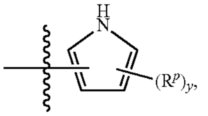
or
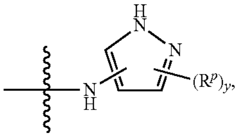

where y is 0, 1 or 2, and each $R^p$ independently is $R^a$, $R^b$, $R^a$ substituted with $R^b$, or $R^a$ substituted with $R^c$. In certain embodiments, each $R^p$ independently is —$CH_3$, —$OCH_3$, —$NH_2$, —$CF_3$, F, —CN,

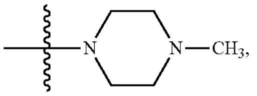
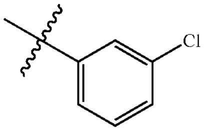
,
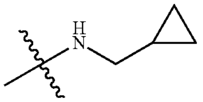
,
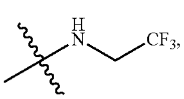
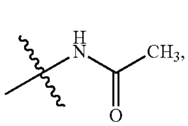
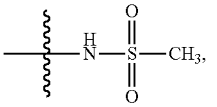
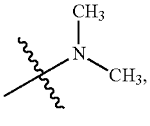
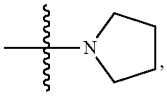
,
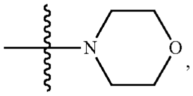
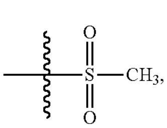
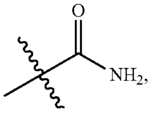
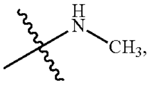
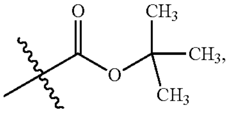
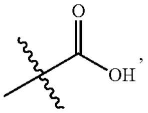
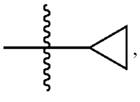
,
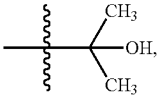
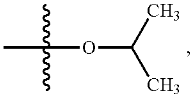
, -continued

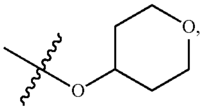
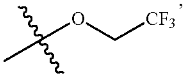
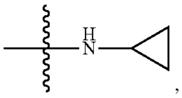
,
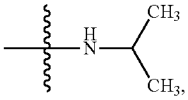
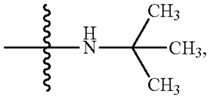
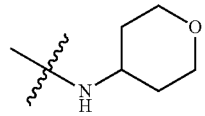
,
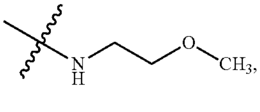
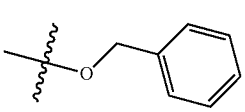
,
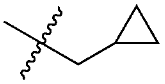
, or
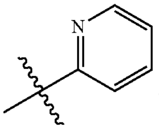
.

In particular embodiments, $Z^1$ is N, and $Z^2$, $Z^3$, and $Z^4$ are $CR^3$; both $Z^1$ and $Z^2$ are N, and $Z^3$ and $Z^4$ are $CR^3$; both $Z^1$ and $Z^3$ are N, and $Z^2$ and $Z^4$ are $CR^3$; both $Z^1$ and $Z^4$ are N, and $Z^2$ and $Z^3$ are $CR^3$; or $Z^3$ is N, and $Z^1$, $Z^2$, and $Z^4$ are $CR^3$. In any of these embodiments, ring A is pyridinyl, pyrazinyl, or heterocycloaliphatic, such as pyrrolidinyl, piperidinyl, or morpholino; $R^1$ is H; $R^2$ is H, heteroaliphatic, such as 3- to 10-membered heteroaliphatic, tetrahydropyranyl, oxetanyl, cyclobutyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic; each $R^3$ is H; and $R^4$ is Br; unsubstituted pyridinyl; pyridinyl substituted with $C_{1-6}$alkyl, haloalkyl, amino, heterocycloaliphatic, cycloalkyl, —CN, alkoxy, —O-heterocycloaliphatic, —NH-heterocycloaliphatic, halogen, sulfonamide, —O-benzyl, carboxyl, sulfonyl, —NH— cycloalkyl, or amide; unsubstituted pyrimidinyl; unsubstituted pyrazolyl; pyrazolyl substituted with $C_{1-6}$alkyl; unsubstituted —NH-pyrazolyl; —NH-pyrazolyl substituted with $C_{1-6}$alkyl, or heteroaryl; pyrrolyl; unsubstituted —O—pyridinyl; —O-pyridinyl substituted with amino; —NH-pyridinyl substituted with $C_{1-6}$alkyl, haloalkyl, or heterocycloaliphatic; unsubstituted indolyl; indolyl substituted with alkoxy; furanyl; —NH-benzopyrazolyl; pyrrolopyridinyl; unsubstituted phenyl; phenyl substituted with halogen, $C_{1-6}$alkyl, alkoxy, —CN, amino, or sulfonamide; unsubstituted tetrahydropyridinyl; tetrahydropyridinyl substituted with tert-butoxycarbonyl; piperidinyl; or 2-oxo-1,2-dihydropyridinyl.

With respect to formula 1, $R^4$ may be, in any combination with the ring A embodiments 1A to 1Q, the $R^2$ embodiments 2A to 2S, and with $R^1$ being H: 3A) halogen; 3B) heterocyclyl; 3C) aryl; 3D) heteroaryl; 3E) heterocycloaliphatic; 3F) 5-membered heteroaryl; 3G) 6-membered heteroaryl; 3H) pyridinyl; 31) pyrimidinyl; 3J) pyrazolyl; 3K) pyrrolyl; 3L) indolyl; 3M) pyrazolopyridinyl; 3N) furanyl; 3O) —NH-heteroaryl; 3P) —O-heteroaryl; 3Q) tetrahydropyridinyl; 3R) bromo; 3S) pyridin-3-yl; 3T) 3-fluoropyridin-3-yl; 3U) 5-cyanopyridin-3-yl; 3V) pyrimidin-5-yl; 3W) 1H-pyrazol-5-yl; 3X) 3-methyl-1H-pyrazol-5-yl; 3Y) 1-methyl-1H-pyrazol-4-yl; 3Z) 1H-pyrazol-4-yl; 3AA)

1H-pyrrol-2-yl; 3AB) 1H-pyrrol-3-yl; 3AC) 5-methylpyridin-3-yl; 3AD) 5-cyclopropylpyridin-3-yl; 3AE) 5-trifluoromethylpyridin-3-yl; 3AF) 2-trifluoromethylpyridin-4-yl; 3AG) 5-methoxypyridin-3-yl; 3AH) 2-methoxypyridin-5-yl; 3AI) 2-methoxypyridin-4-yl; 3AJ) 5-isopropoxypyridin-3-yl; 3AK) 5-((tetrahydro-2H-pyran)oxy)pyridin-3-yl; 3AL) 5-(2,2,2-trifluoroethoxy)pyridin-3-yl; 3AM) 5-aminopyridin-3-yl; 3AN) 5-(methylamino)pyridin-3-yl; 3AO) 5-(cyclopropylamino)pyridin-3-yl; 3AP) 5-(isopropylamino) pyridin-3-yl; 3AQ) 5-(tert-butylamino)pyridin-3-yl; 3AR) 5-((tetrahydro-2H-pyran)amino)pyridin-3-yl; 3AS) 5-((2-methoxyethyl)amino)pyridin-3-yl; 3AT) 5-((cyclopropylmethyl)amino)pyridin-3-yl; 3AU) 5-((2,2,2-trifluoroethyl) amino)pyridin-3-yl; 3AV) 5-(methylsulfonamido)pyridin-3-yl; 3AW) 5-(dimethylamino)pyridin-3-yl; 3AX) 5-(pyrrolidin-1-yl)pyridin-3-yl; 3AY) 5-(morpholino)pyridin-3-yl; 3AZ) 5-(4-methylpiperazin-1-yl)pyridin-3-yl; 3BA) 5-methylsulfonylpyridin-3-yl; 3BB) 5-carbamoylpyridin-3-yl; 3BC) 2-carbamoylpyridin-4-yl; 3BD) 2-cyano-pyridin-4-yl; 3BE) 6-aminopyridin-3-yl; 3BF) 1H-pyrrolo [2,3-b]pyridin-5-yl; 3BG) 1H-pyrrolo[3,2-b]pyridin-6-yl; 3BH) 1H-indol-5-yl; 3BI) 1H-indol-6-yl; 3BJ) phenyl; 3BK) m-tolyl; 3BL) p-tolyl; 3BM) 3-methoxyphenyl; 3BN) 4-methoxyphenyl; 3BO) 3-cyanophenyl; 3BP) 4-cyanophenyl; 3BQ) 3-fluorophenyl; 3BR) 4-fluorophenyl; 3BS) 3-aminophenyl; 3BT) 3-(methylamino)phenyl; 3BU) 3-(dimethylamino)phenyl; 3BV) 3-(methylsulfonamido)phenyl; 3BW) 1'-(tert-butoxycarbonyl)-1',2',3',6'-tetrahydropyridin-4-yl; 3BX) 1',2',3',6'-tetrahydropyridin-4-yl; 3BY) piperazin-4-yl; 3BZ) 1'-(tert-butoxycarbonyl)-1',2',3',6'-tetrahydropyridin-3-yl; 3CA) 1',2',3',6'-tetrahydropyridin-3-yl; 3CB) 3-methyl-1H-pyrazol-4-yl; 6CC) pyridin-4-yl; 3CD) pyridin-4-yloxy; 3CE) 2-oxo-1,2-dihydropyridin-4-yl; 3CF) 6-oxo-1,6-dihydropyridin-3-yl; 3CG) 6-acetamidopyridin-3-yl; 3CH) 1-(cyclopropylmethyl)-1H-pyrazol-4-yl; 3CI) 1H-pyrazol-3-yl; 3CJ) (1-methyl-3-(pyridin-2-yl)-1H-pyrazol-4-yl)amino; 3CK) (1H-pyrazol-3-yl)amino; 3CL) (3-methyl-1H-pyrazol-4-yl)amino; 3CM) 5-carboxypyridin-3-yl; 3CN) 3-fluoropyridin-4-yl; 3CO) 3-methylpyridin-4-yl; 3CP) 2-methylpyridin-4-yl; 3CQ) 6-methoxy-1H-indol-2-yl; 3CR) furan-3-yl; 3CS) furan-2-yl; 3CT) (1H-indazol-5-yl)amino; 3CU) (2H-indazol-5-yl)amino; 3CV) 5-(2-hydroxypropan-2-yl)pyridin-3-yl; 3CW) 2-methylpyridin-4-yl; 3CX) 2-methylpyridin-5-yl; 3CY) (2-aminopyridin-4-yl)oxy; 3CZ) (2,5-dimethylpyridin-4-yl)amino; 3DA) (6-(4-methylpiperazin-1-yl)-5-(trifluoromethyl)pyridin-3-yl) amino; 3DB) 2-((cyclopropylmethyl)amino)pyridin-4-yl; or 3DC) 2-((2,2,2-trifluoroethyl)amino)pyridin-4-yl.

A person of ordinary skill in the art will understand that any of 3A to 3DC may be combined with any of 1A to 1Q, any of 2A to 2FS, and $R^1$ being H, to form any and all combinations between such substituents.

With respect to the ring A embodiments 1A to 1Q, the $R^2$ embodiments 2A to 2S, the $R^4$ embodiments 3A to 3DC, and $R^1$ being hydrogen, $Z^1$, $Z^2$, $Z^3$ and $Z^4$ may be, in any combination with 1A to 1Q, 2A to 2S, and 3A to 3DC: 4A) $Z^1$ is N and $Z^2$, $Z^3$ and $Z^4$ are CH; 4B) $Z^1$ and $Z^2$ are N and $Z^3$ and $Z^4$ are CH; 4C) $Z^1$ and $Z^3$ are N and $Z^2$ and $Z^4$ are CH; 4D) $Z^1$ and $Z^4$ are N and $Z^2$ and $Z^3$ are CH; or 4E) $Z^3$ is N and $Z^1$, $Z^2$ and $Z^4$ are CH.

A person of ordinary skill in the art will understand that any of 4A to 4E may be combined with any of 1A to 1Q, any of 2A to 2S, any of 3A to 3DC, and $R^1$ being H, to form any and all combinations between such substituents.

In some embodiments of formula 1, the compound has a formula 2

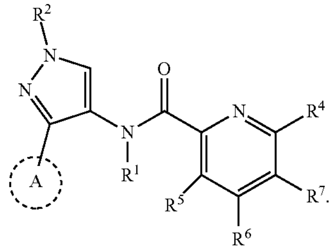

2

With reference to formula 2, $R^1$, $R^2$, $R^4$ and ring A are as defined for formula 1. Each of $R^5$, $R^6$, and $R^7$ independently is H or alkyl, such as $C_{1-6}$alkyl, and in certain embodiments, each of $R^5$, $R^6$, and $R^7$ is H.

In particular embodiments of formula 2, ring A is pyridin-2-yl, pyrazine-2-yl, pyrrolidin-1-yl, piperidin-1-yl, or morpholino; $R^1$ is H; $R^2$ is H, heteroaliphatic, such as 3- to 10-membered heteroaliphatic, tetrahydropyranyl, oxetanyl, cyclobutyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic; each $R^3$ is H; and $R^4$ is Br; unsubstituted pyridinyl; pyridinyl substituted with $C_{1-6}$alkyl, haloalkyl, amino, heterocycloaliphatic, cycloalkyl, —CN, alkoxy, —O-heterocycloaliphatic, —NH-heterocycloaliphatic, halogen, sulfonamide, —O-benzyl, carboxyl, sulfonyl, —NH-cycloalkyl, or amide; unsubstituted pyrimidinyl; unsubstituted pyrazolyl; pyrazolyl substituted with $C_{1-6}$alkyl; unsubstituted —NH—pyrazolyl; —NH-pyrazolyl substituted with $C_{1-6}$alkyl, or heteroaryl; pyrrolyl; unsubstituted —O-pyridinyl; —O—pyridinyl substituted with amino; —NH-pyridinyl substituted with $C_{1-6}$alkyl, haloalkyl, or heterocycloaliphatic; unsubstituted indolyl; indolyl substituted with alkoxy; furanyl; —NH-benzopyrazolyl; pyrrolopyridinyl; unsubstituted phenyl; phenyl substituted with halogen, $C_{1-6}$alkyl, alkoxy, —CN, amino, or sulfonamide; unsubstituted tetrahydropyridinyl; tetrahydropyridinyl substituted with tert-butoxycarbonyl; piperidinyl; or 2-oxo-1,2-dihydropyridinyl.

With respect to formula 2, a person of ordinary skill in the art will understand that when $R^1$, $R^5$, $R^6$, and $R^7$ are H, any of the ring A embodiments 1A to 1Q, may be combined with any of the $R^2$ embodiments 2A to 2S and any of the $R^4$ embodiments 3A to 3DC to form any and all combinations between such substituents.

In some embodiments of formulas 1 and 2, ring A is pyridinyl, such as pyridin-2-yl; pyrazinyl, such as pyrazine-2-yl; pyrrolidinyl, such as pyrrolidin-1-yl; morpholino; or piperidinyl, such as piperidin-1-yl. In particular embodiments, such compounds, or salts, solvates, hydrates, have a formula 3

3

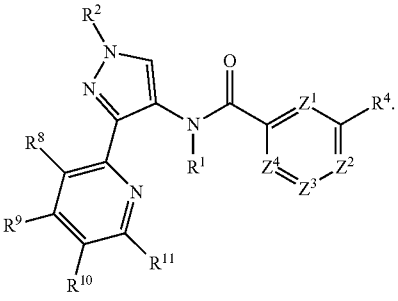

With respect to formula 3, $R^1$, $R^2$, $R^3$, $R^4$, $Z^1$, $Z^2$, $Z^3$, and $Z^4$ are as defined for formulas 1 and 2. Each of $R^8$, $R^9$, $R^{10}$ and $R^{11}$ independently is H, aliphatic, halogen, heterocycloaliphatic, alkoxy, or —O-heterocycloaliphatic. Each of $R^8$, $R^9$, $R^{10}$ and $R^{11}$ independently may be H, halogen, 3- to 6-membered heterocycloaliphatic, alkoxy, or —O-(3- to 6-membered heterocycloaliphatic). In some embodiments, $R^9$ and $R^{11}$ are H, $R^8$ is H or halogen, such as F, and $R^{10}$ is halogen, such as F, 3- to 6-membered heterocycloaliphatic, such as morpholino or N-methylpiperidinyl, alkoxy, such as methoxy or 2-hydroxy-2-methylpropoxy, or —O-oxetanyl. In some embodiments, each of $R^8$, $R^9$, $R^{10}$ and $R^{11}$ is H. In other embodiments, $R^8$, $R^9$, and $R^1$ are H and $R^{10}$ is 3- to 6-membered heterocycloaliphatic, such as morpholino or N-methylpiperidin-1-yl; alkoxy, such as methoxy or 2-hydroxy-2-methylpropoxy; or —O-oxetanyl. In certain other embodiments, $R^9$ and $R^{11}$ are H, and $R^8$ and $R^{10}$ are F.

In particular embodiments, $Z^1$ is N, and $Z^2$, $Z^3$, and $Z^4$ are $CR^3$; both $Z^1$ and $Z^2$ are N, and $Z^3$ and $Z^4$ are $CR^3$; both $Z^1$ and $Z^3$ are N, and $Z^2$ and $Z^4$ are $CR^3$; both $Z^1$ and $Z^4$ are N, and $Z^2$ and $Z^3$ are $CR^3$; or $Z^3$ is N, and $Z^1$, $Z^2$, and $Z^4$ are $CR^3$. In any of these embodiments, $R^1$ is H; $R^2$ is H, heteroaliphatic, such as 3- to 10-membered heteroaliphatic, tetrahydropyranyl, oxetanyl, cyclobutyl. cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic; each $R^3$ is H; $R^8$ is H or F; $R^9$ is H; $R^{10}$ is H, F, 3- to 6-membered heterocycloaliphatic, such as morpholino or N-methylpiperidinyl, alkoxy, such as methoxy or 2-hydroxy-2-methylpropoxy, or —O-oxetanyl; and $R^1$ is H.

In some embodiments of formula 3, the compound has a formula 4

4

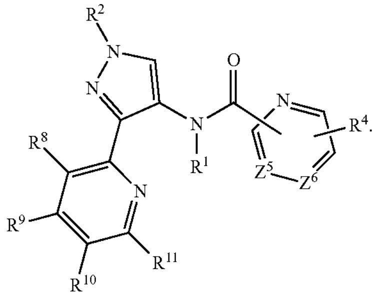

With respect to formula 4, $R^1$, $R^2$, $R^3$, $R^4$, $R^8$, $R^9$, $R^{10}$ and $R^{11}$ are as defined for formula 3, and $Z^5$ and $Z^6$ independently are N or $CR^3$, with the proviso that at least one of $Z^5$ and $Z^6$ is $CR^3$. In some embodiments, both $Z^5$ and $Z^6$ are $CR^3$. In other embodiments, $Z^5$ is N and $Z^6$ is $CR^3$, and in alternative embodiments, $Z^5$ is $CR^3$ and $Z^6$ is N. In certain embodiments, the compound has a formula selected from Formula 5

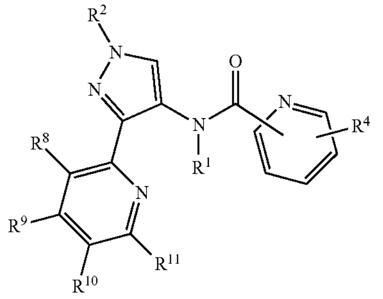

Formula 6

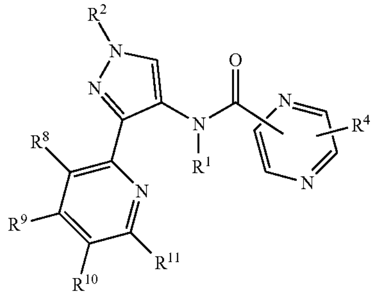

Formula 7

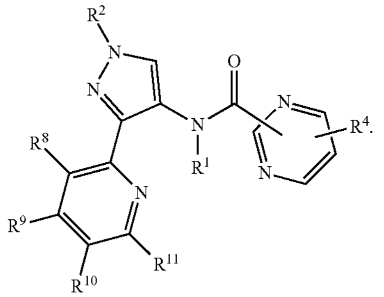

With respect to formulas 5, 6 and 7, $R^1$, $R^2$, $R^4$, $R^8$, $R^9$, $R^{10}$ and $R^{11}$ are as defined for formula 4.

In certain embodiments of formula 3, the compound has a formula 8

8

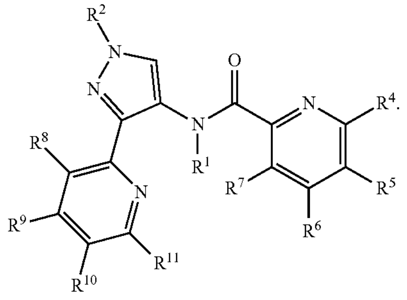

With reference to formula 8, $R^1$, $R^2$, $R^4$, $R^8$, $R^9$, $R^{10}$, and $R^{11}$ are as defined for formula 3, and each of $R^5$, $R^6$, and $R^7$ independently is H or alkyl, such as $C_{1-6}$alkyl. In certain embodiments, each of $R^5$, $R^6$, and $R^7$ is H, leading to compounds having formula 9

9

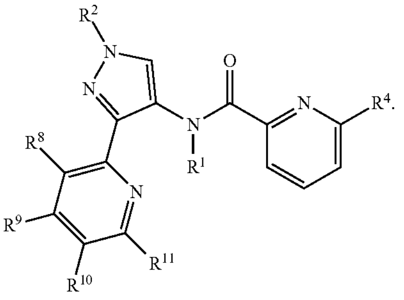

In particular embodiments of formulas 8 and 9, $R^1$ is H; $R^2$ is H, heteroaliphatic, such as 3- to 10-membered heteroaliphatic, tetrahydropyranyl, oxetanyl, cyclobutyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic; $R^4$ is Br; unsubstituted pyridinyl; pyridinyl substituted with $C_{1-6}$alkyl, haloalkyl, amino, heterocycloaliphatic, cycloalkyl, —CN, alkoxy, —O-heterocycloaliphatic, —NH-heterocycloaliphatic, halogen, sulfonamide, —O-benzyl, carboxyl, sulfonyl, —NH-cycloalkyl, or amide; unsubstituted pyrimidinyl; unsubstituted pyrazolyl; pyrazolyl substituted with $C_{1-6}$alkyl; unsubstituted —NH— pyrazolyl; —NH-pyrazolyl substituted with $C_{1-6}$alkyl, or heteroaryl; pyrrolyl; unsubstituted —O-pyridinyl; —O— pyridinyl substituted with amino; —NH-pyridinyl substituted with $C_{1-6}$alkyl, haloalkyl, or heterocycloaliphatic; unsubstituted indolyl; indolyl substituted with alkoxy; furanyl; —NH-benzopyrazolyl; pyrrolopyridinyl; unsubstituted phenyl; phenyl substituted with halogen, $C_{1-6}$alkyl, alkoxy, —CN, amino, or sulfonamide; unsubstituted tetrahydropyridinyl; tetrahydropyridinyl substituted with tert-butoxycarbonyl; piperidinyl; or 2-oxo-1,2-dihydropyridinyl; $R^8$ is H or F; $R^9$ and $R^{11}$ are H; and $R^{10}$ is H; F; 3- to 6-membered heterocycloaliphatic, such as morpholino or N-methylpiperidinyl; alkoxy, such as methoxy or 2-hydroxy-2-methylpropoxy; or —O-oxetanyl. And in certain embodiments, each of $R^8$, $R^9$, $R^{10}$ and $R^{11}$ is H; $R^8$, $R^9$, and $R^{11}$ are H and $R^{10}$ is 3- to 6-membered heterocycloaliphatic, such as morpholino or N-methylpiperidinyl, alkoxy, such as methoxy or 2-hydroxy-2-methylpropoxy, or —O-oxetanyl, or $R^8$ and $R^{10}$ are F, and $R^9$ and $R^{11}$ are H.

Certain disclosed exemplary compounds within the scope of one or more of general formulas 1-9 include:

I-1

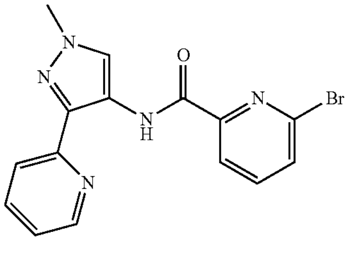

-continued

I-2

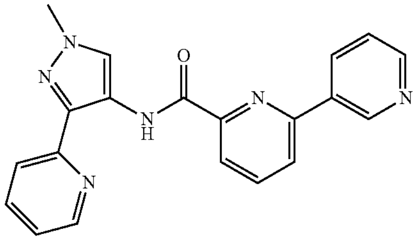

I-3

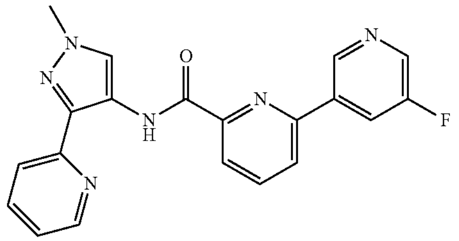

I-4

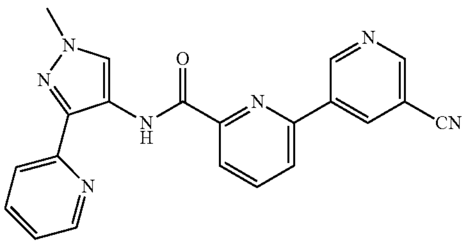

I-5

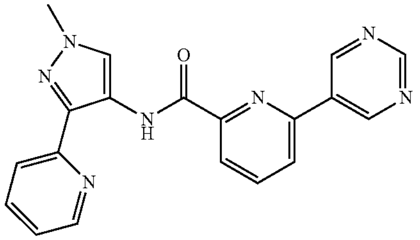

I-6

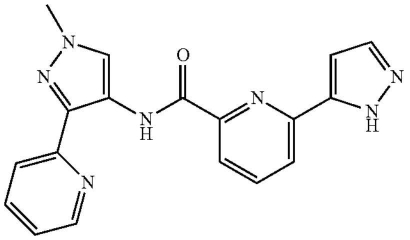

I-7

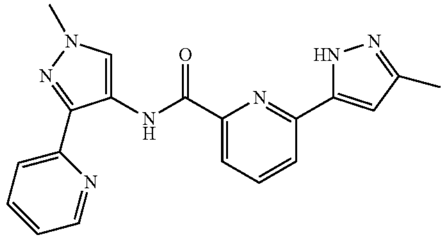

-continued
I-8
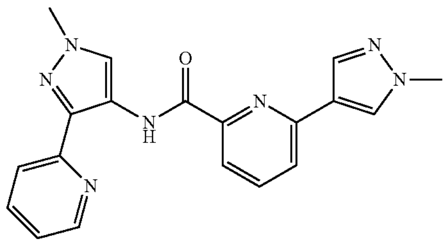
I-9
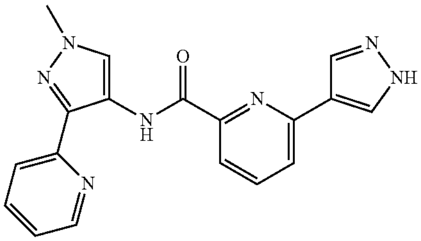
I-10
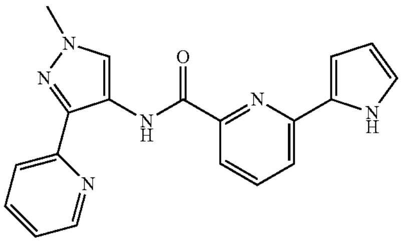
I-11
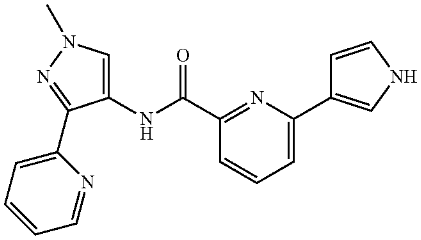
I-12
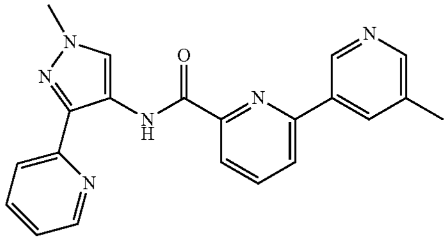
I-13
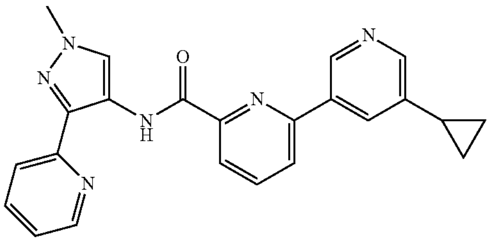
-continued
I-14
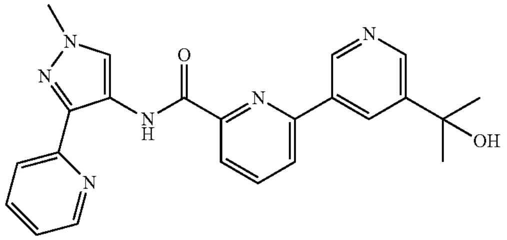
I-15
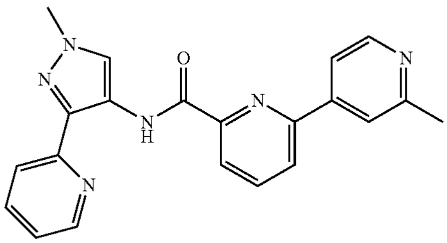
I-16
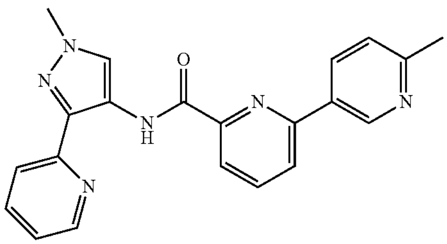
I-17
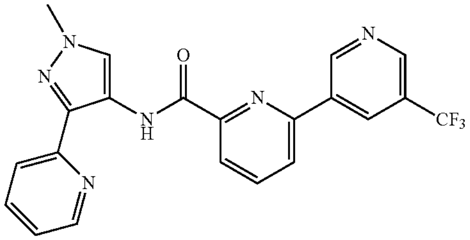
I-18
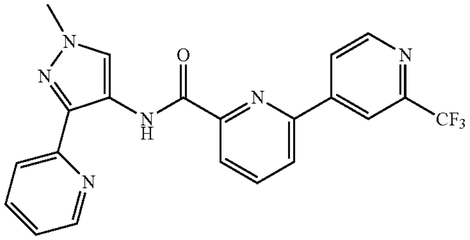
I-19
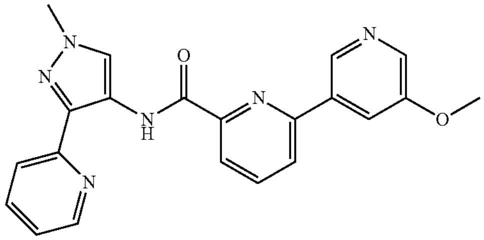

-continued
I-20
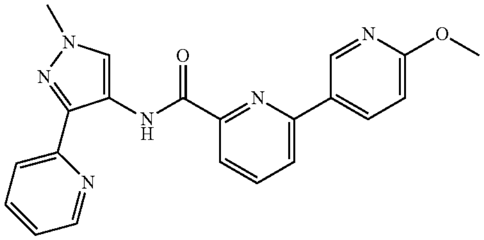
I-21
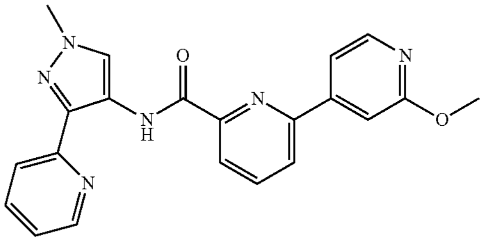
I-22
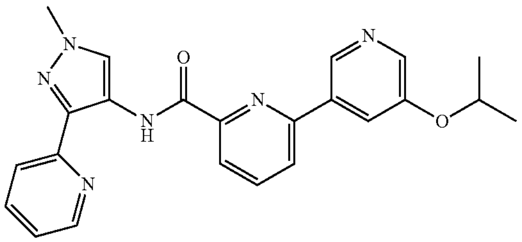
I-23
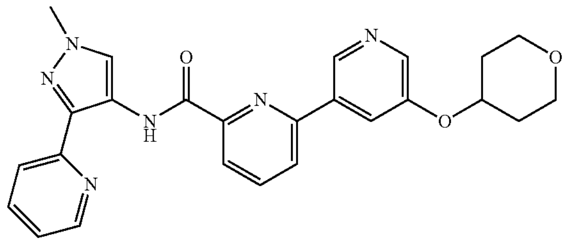
I-24
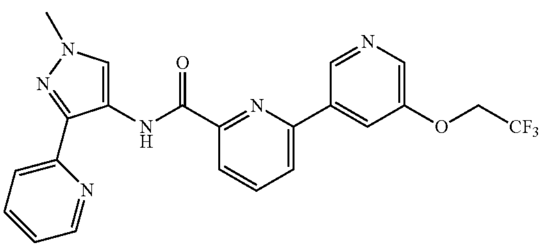
I-25
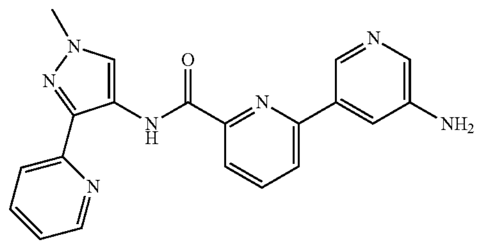
-continued
I-26
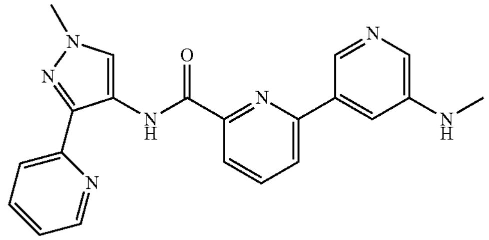
I-27
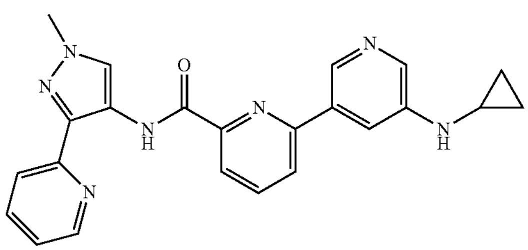
I-28
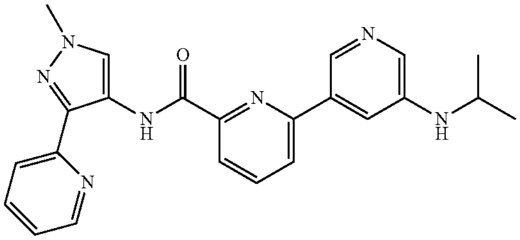
I-29
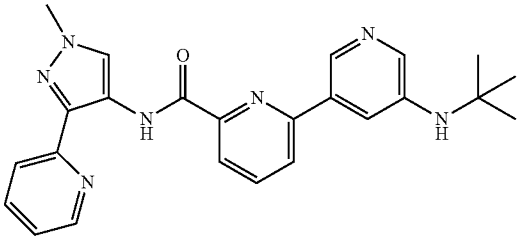
I-30
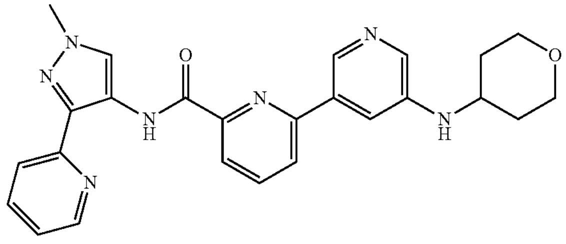
I-31
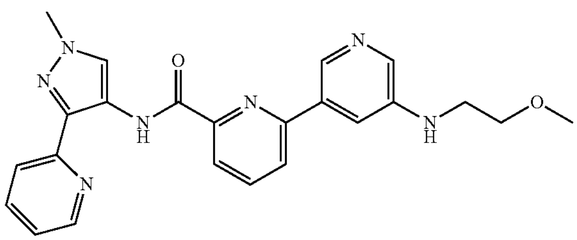

-continued
I-32
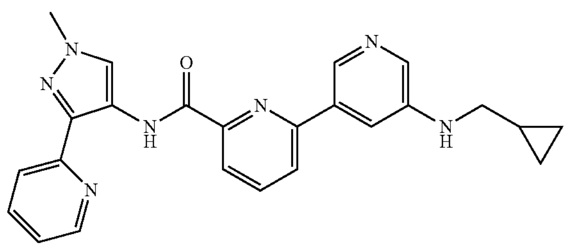
I-33
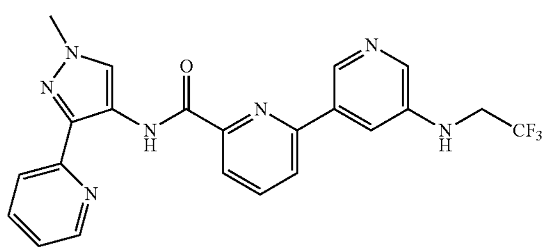
I-34
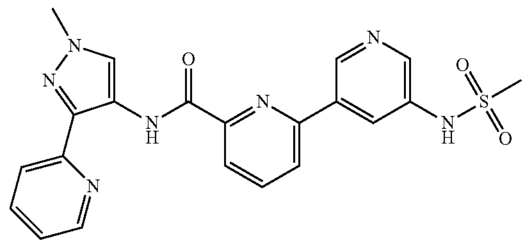
I-35
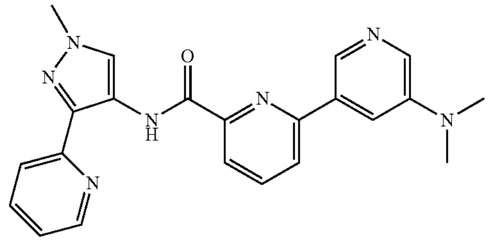
I-36
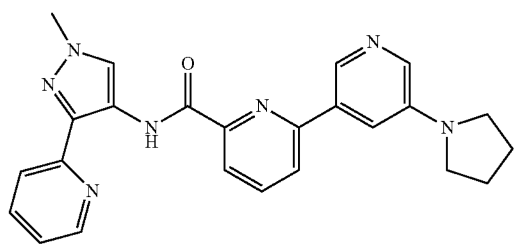
I-37
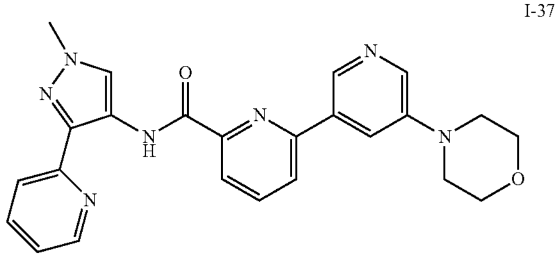
-continued
I-38
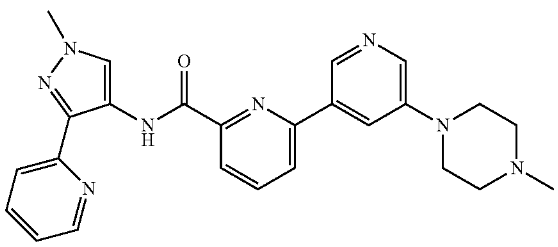
I-39
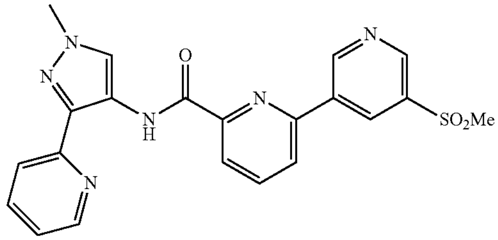
I-40
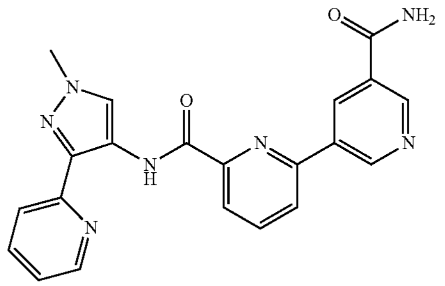
I-41
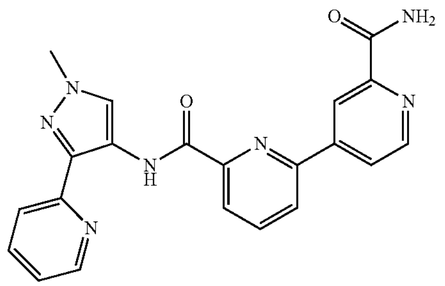
I-42
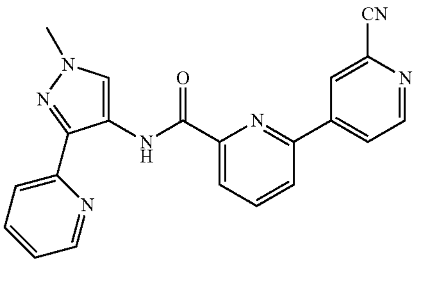
I-43
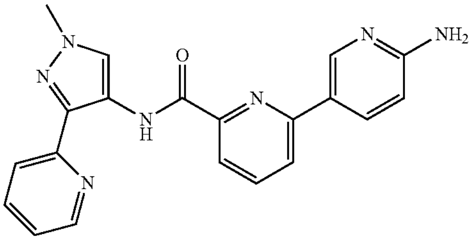

-continued
I-44
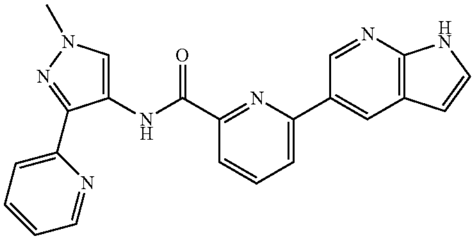
I-45
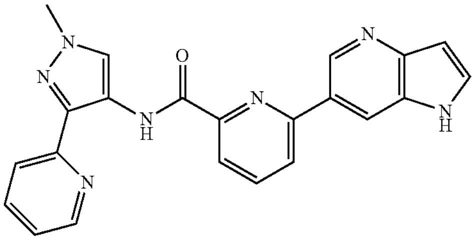
I-46
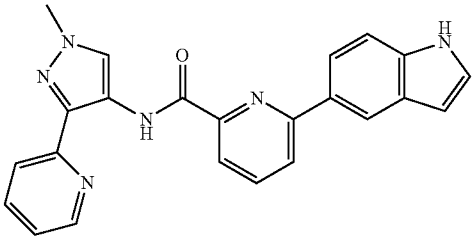
I-47
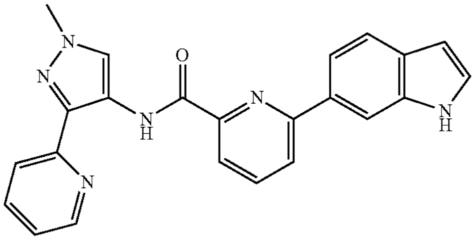
I-48
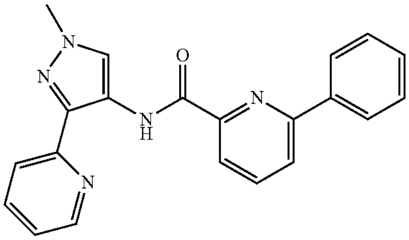
I-49
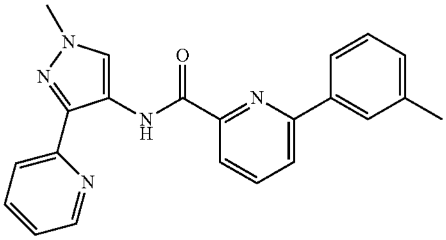
-continued
I-50
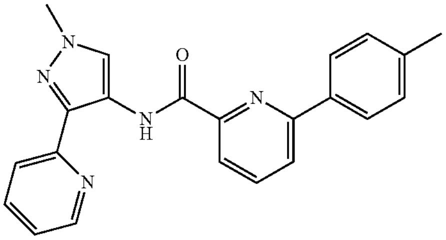
I-51
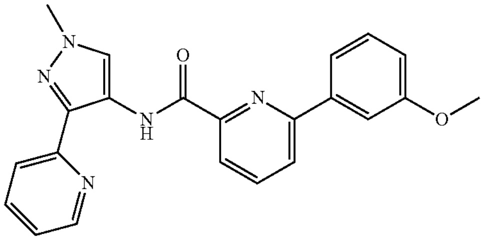
I-52
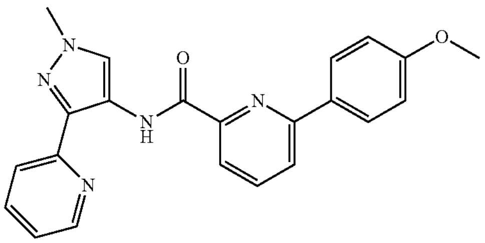
I-53
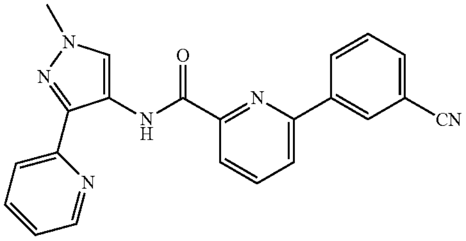
I-54
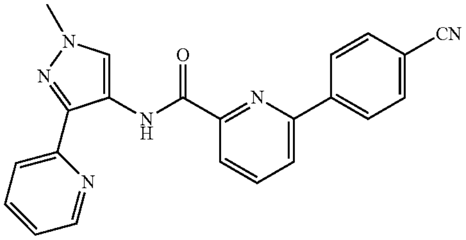
I-55
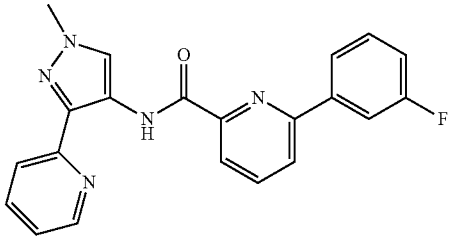

-continued
I-56
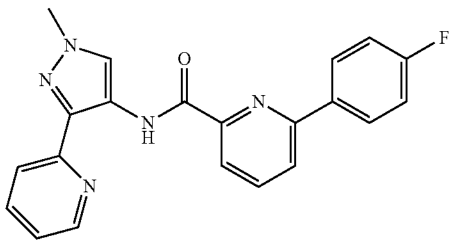
I-57
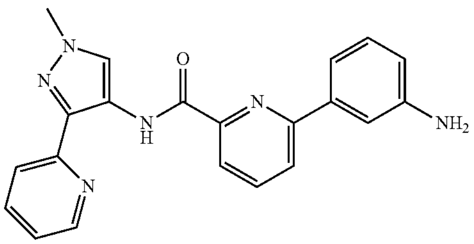
I-58
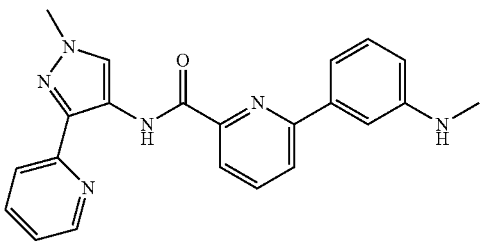
I-59
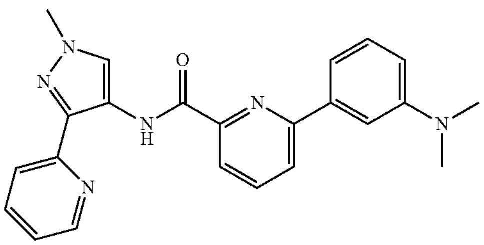
I-60
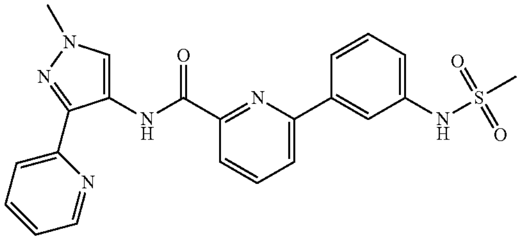
I-61
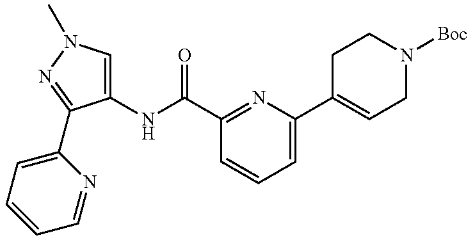
-continued
I-62
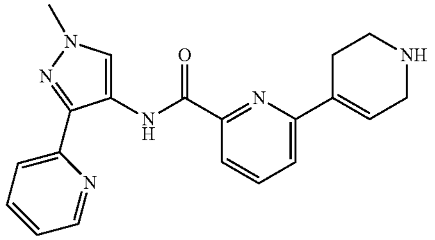
I-63
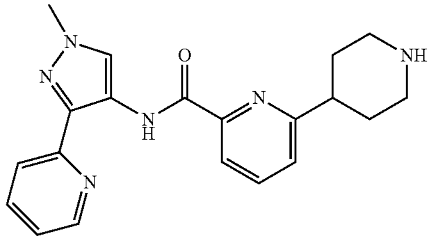
I-64
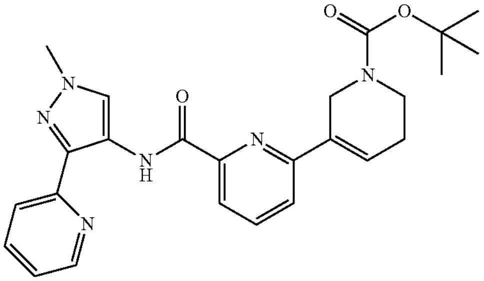
I-65
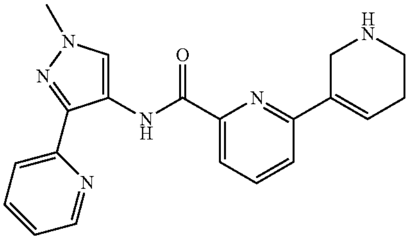
I-66
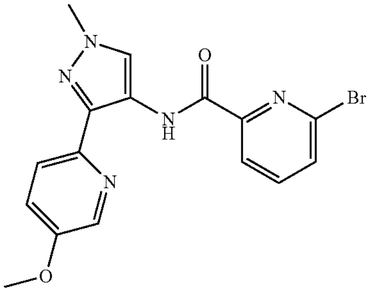
I-67
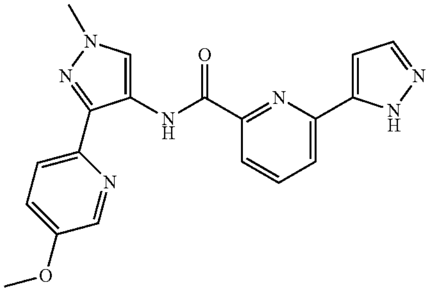

-continued
I-68
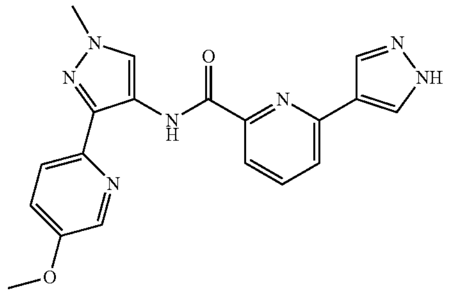
I-69
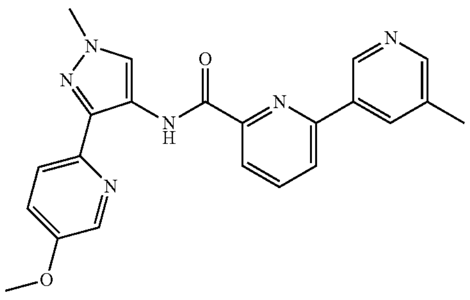
I-70
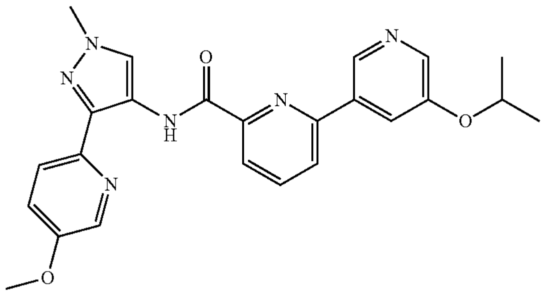
I-71
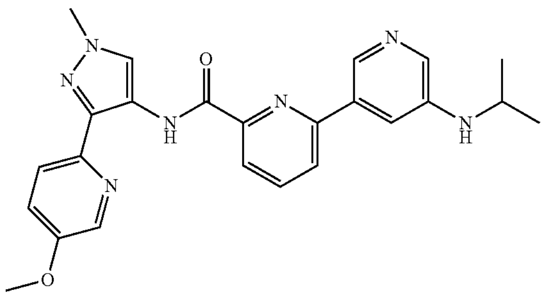
I-72
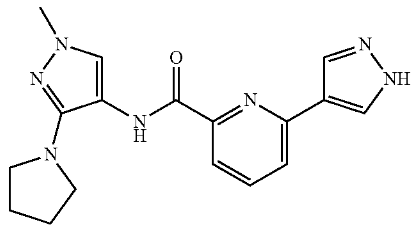
-continued
I-73
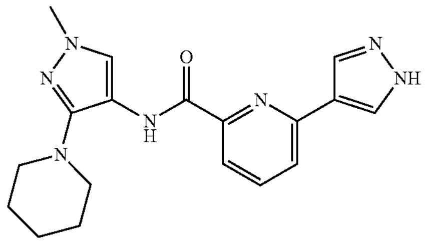
I-74
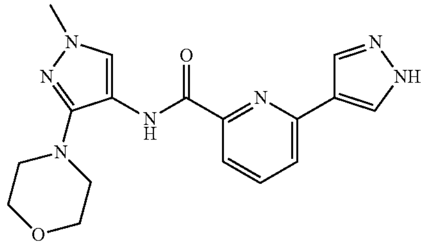
I-75
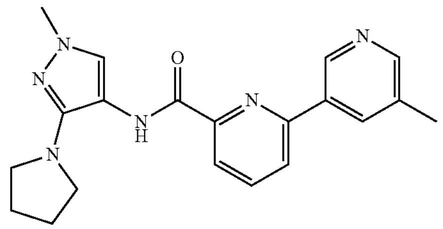
I-76
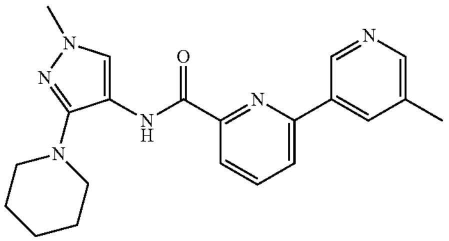
I-77
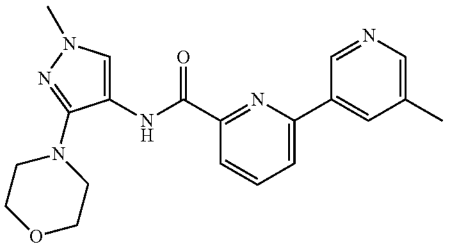
I-78
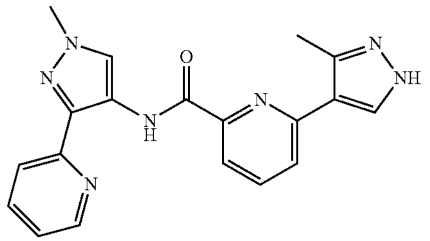

-continued
I-79
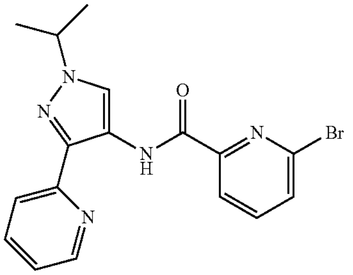
I-80
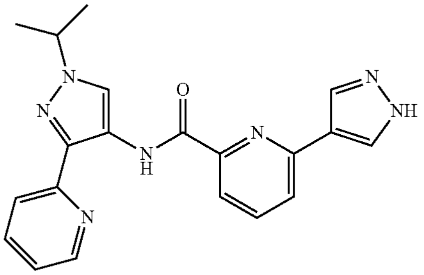
I-81
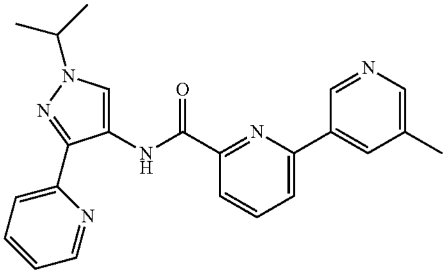
I-82
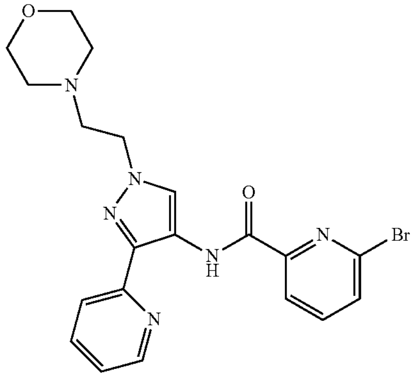
I-83
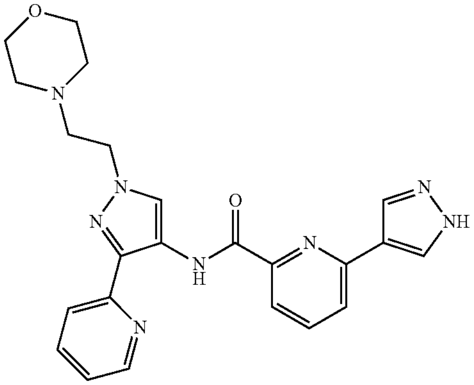
-continued
I-84
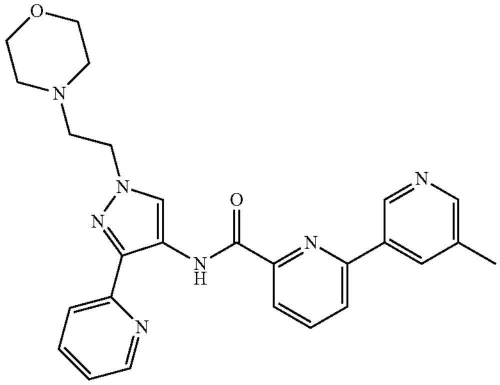
I-85
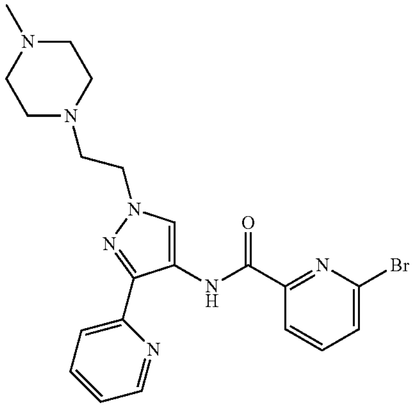
I-86
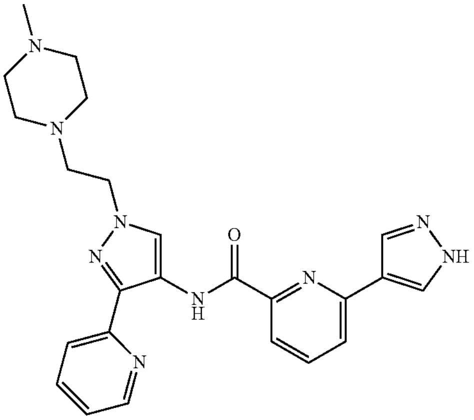
I-87
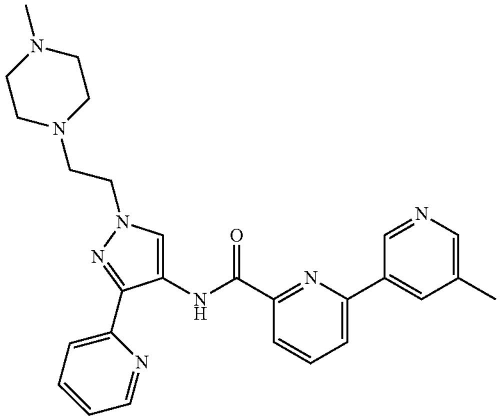

-continued
I-88
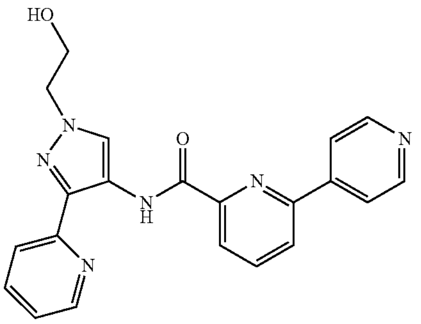
I-89
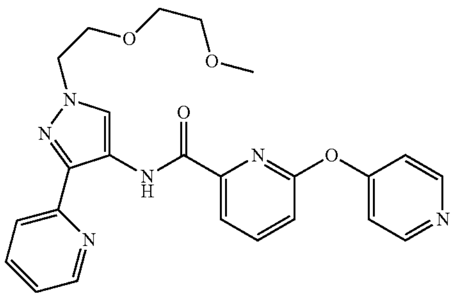
I-90
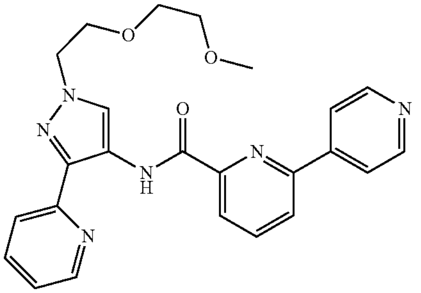
I-91
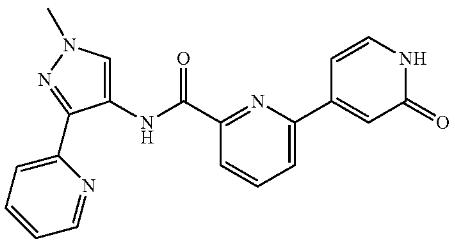
I-92
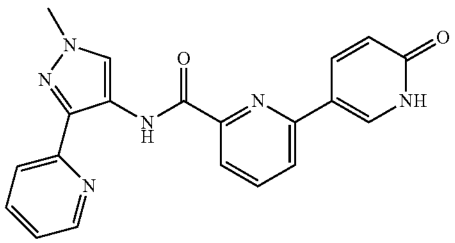
-continued
I-93
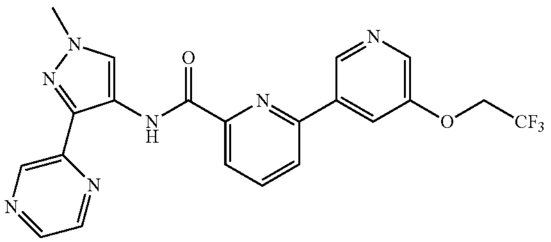
I-94
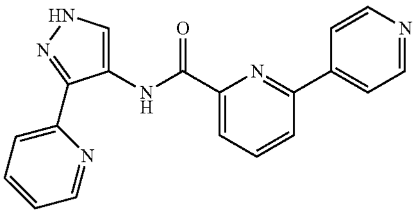
I-95
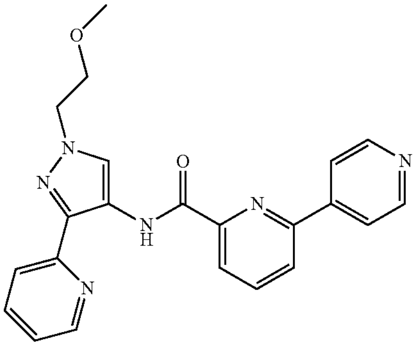
I-96
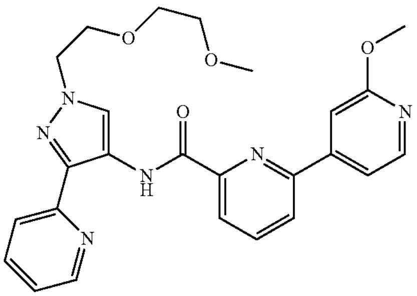
I-97
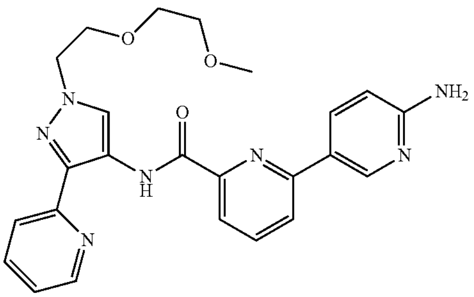

-continued
I-98
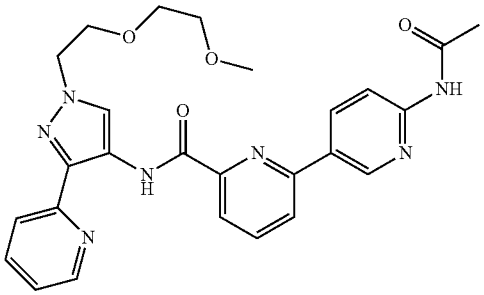
I-99
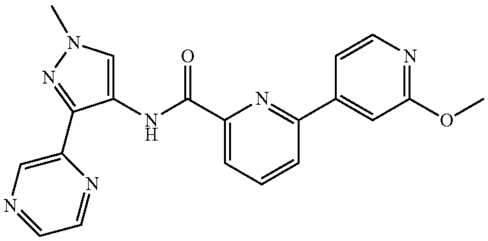
I-100
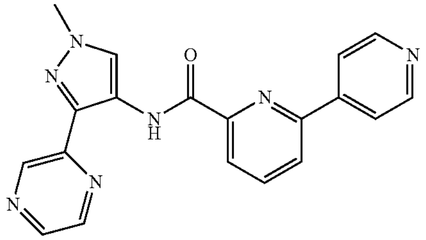
I-101
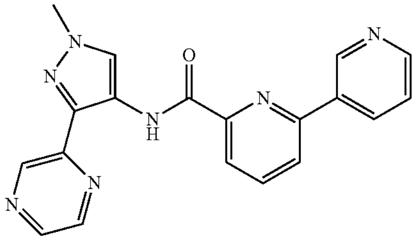
I-102
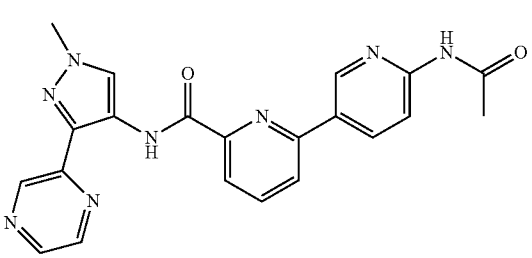
I-103
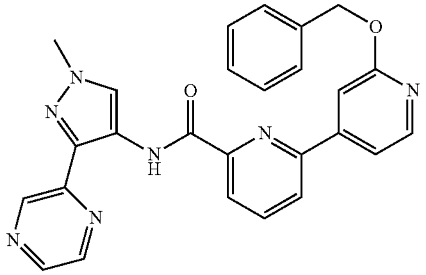
-continued
I-104
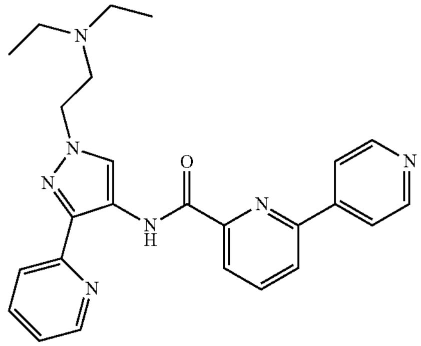
I-105
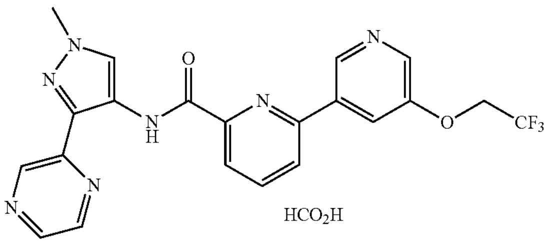
$HCO_2H$
I-106
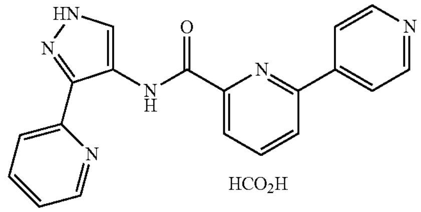
$HCO_2H$
I-107
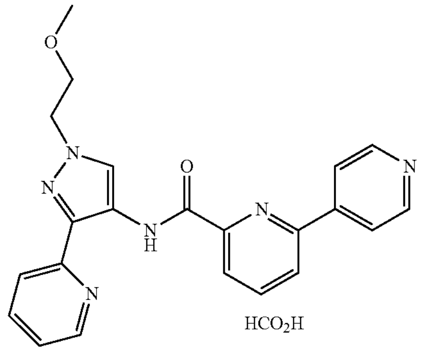
$HCO_2H$
I-108
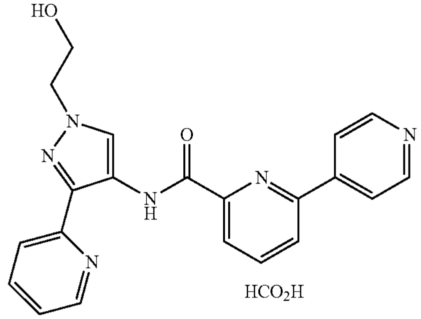
$HCO_2H$ -continued
I-109
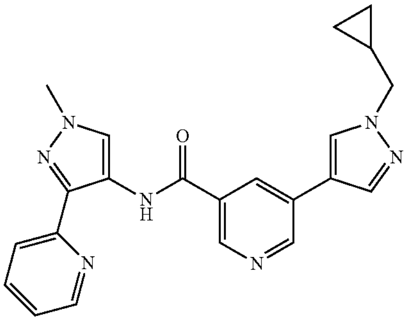
I-110
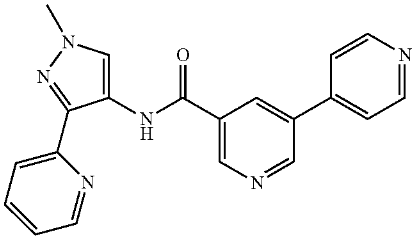
I-111
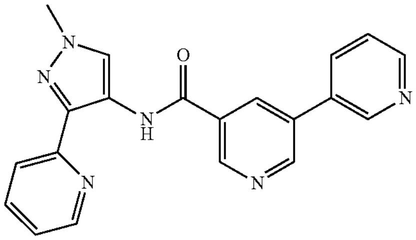
I-112
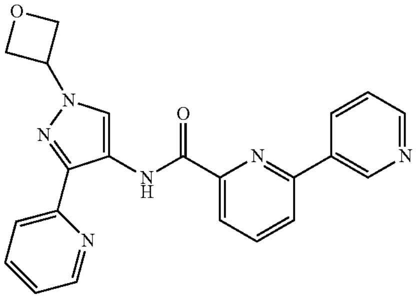
I-113
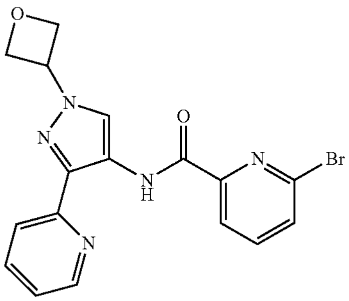
-continued
I-114
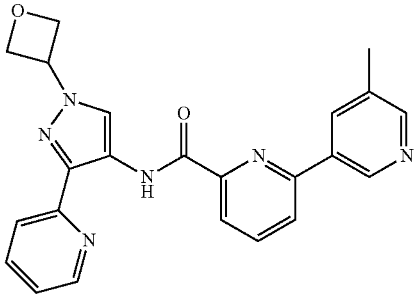
I-115
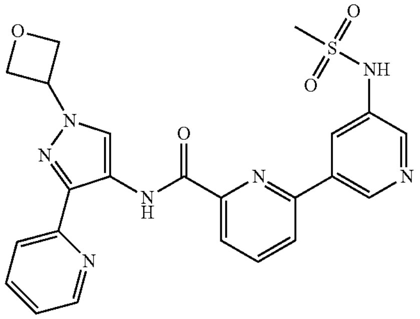
I-116
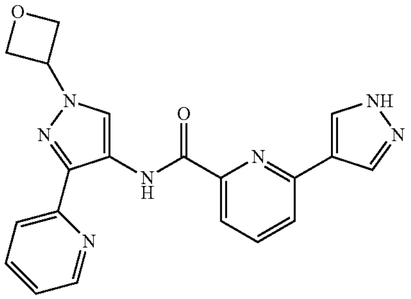
I-117
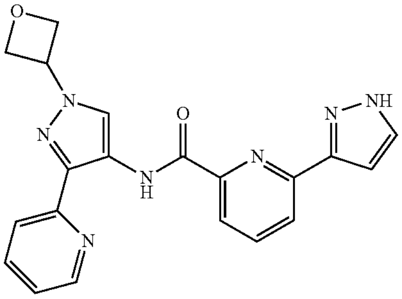
I-118
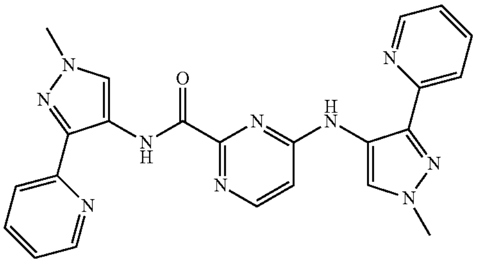

-continued
I-119
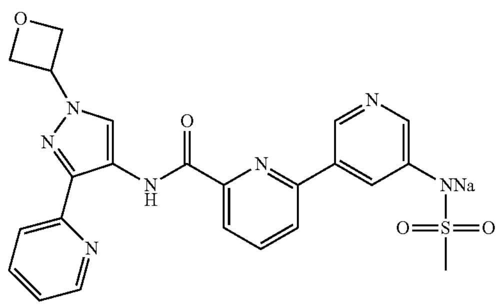
I-120
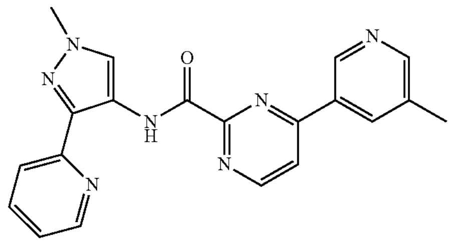
I-121
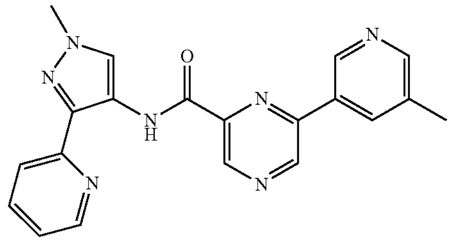
I-122
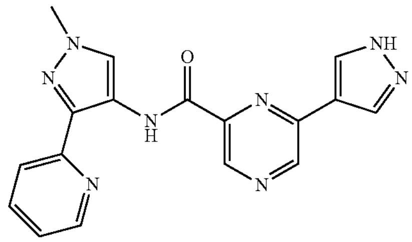
I-123
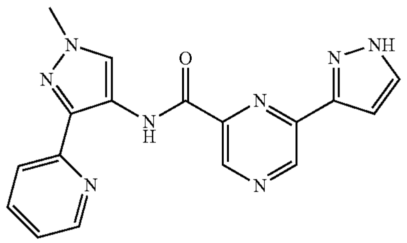
I-124
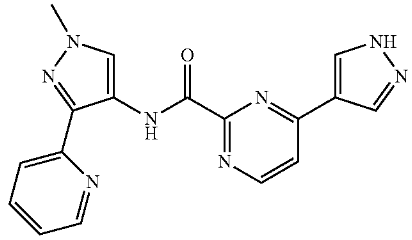
-continued
I-125
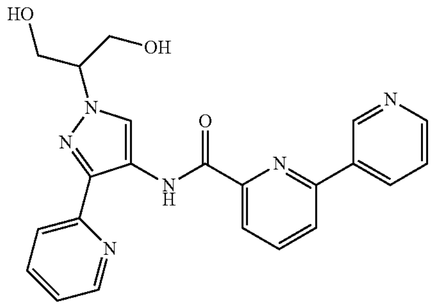
I-126
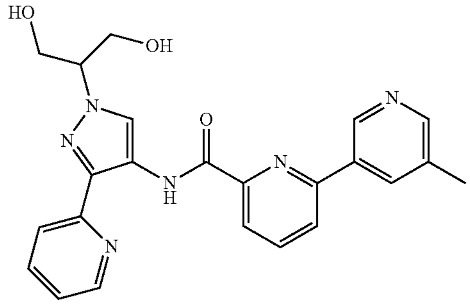
I-127
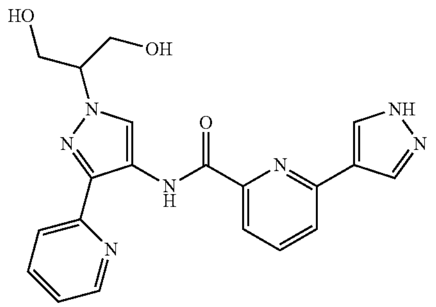
I-128
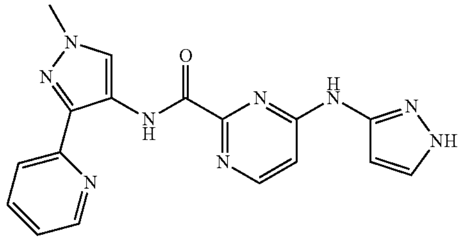
I-129
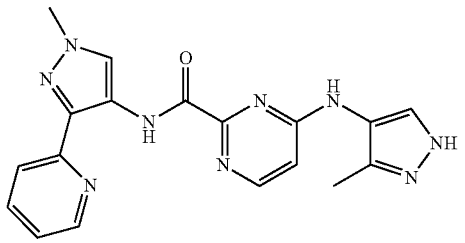

-continued
I-130
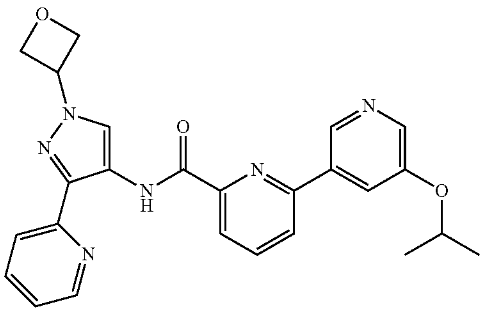
I-131
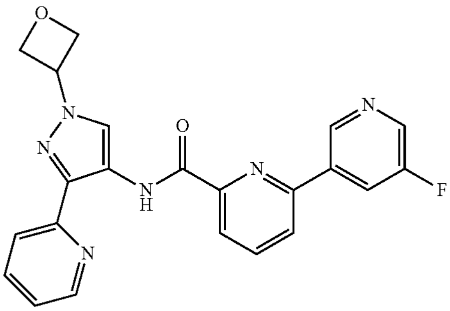
I-132
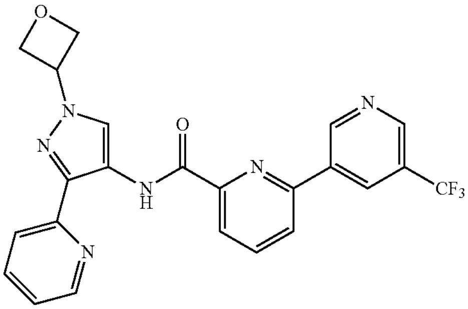
I-133
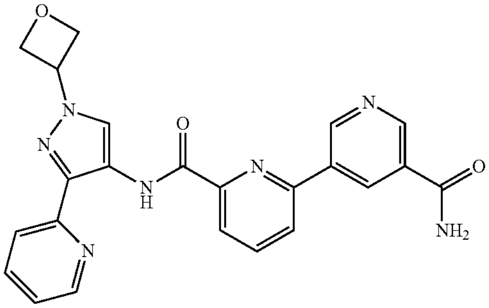
I-134
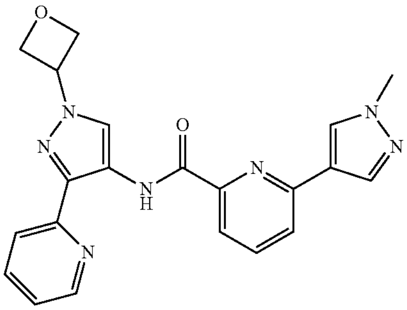
-continued
I-135
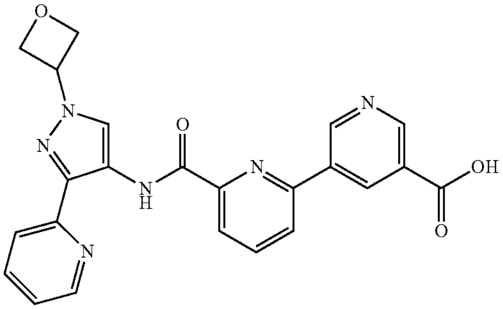
I-136
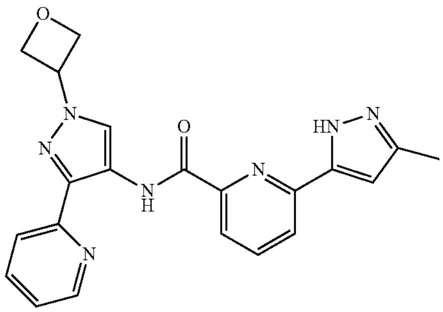
I-137
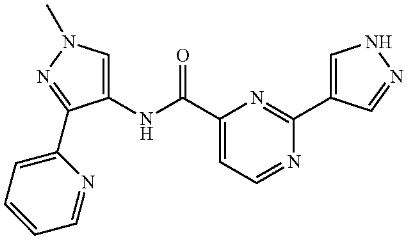
I-138
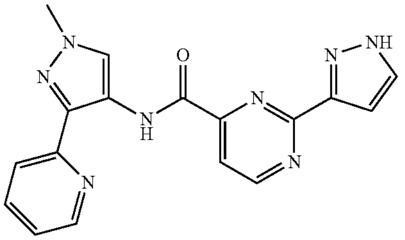
I-139
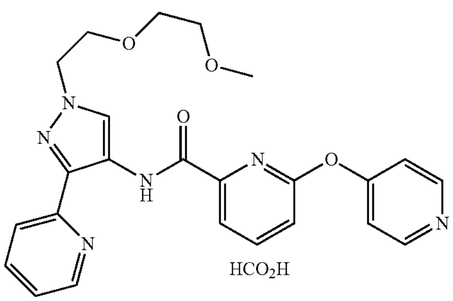
$HCO_2H$ -continued
I-140
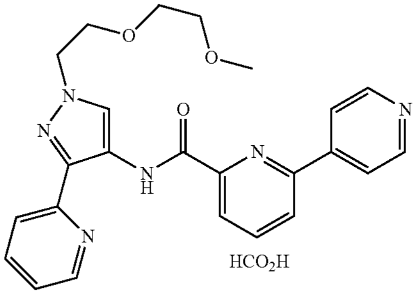
I-141
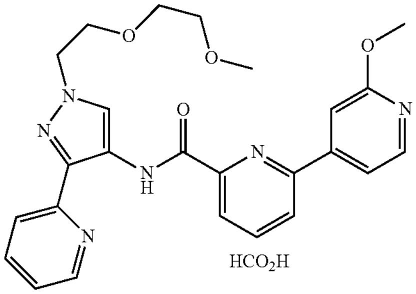
I-142
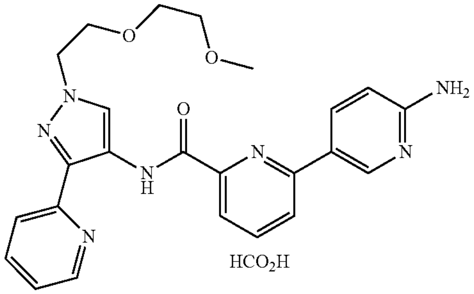
I-143
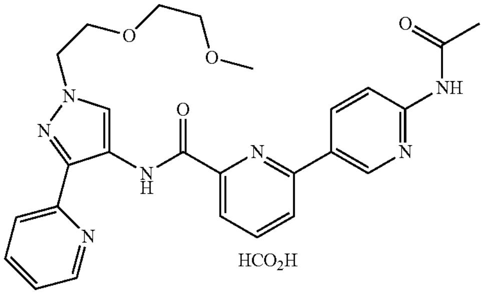
I-144
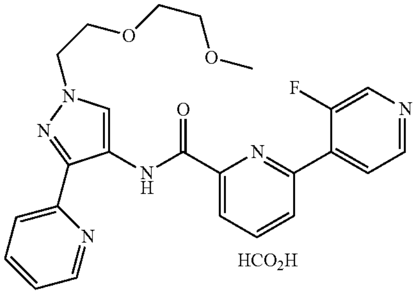
-continued
I-145
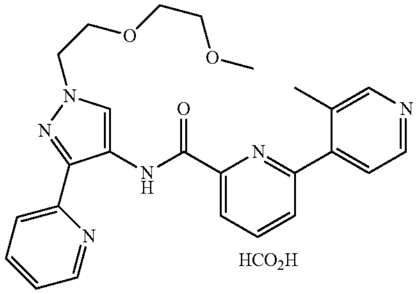
I-146
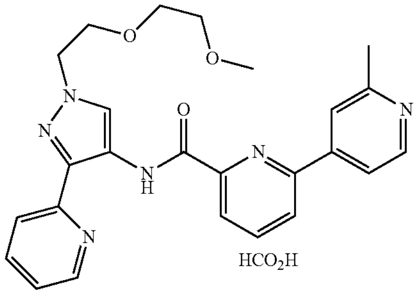
I-147
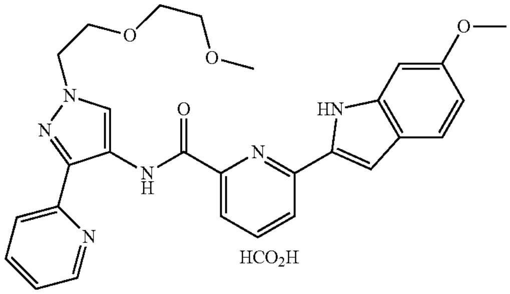
I-148
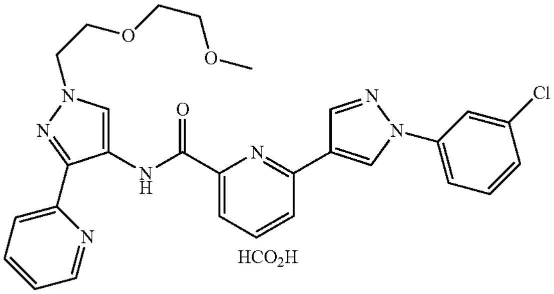
I-149
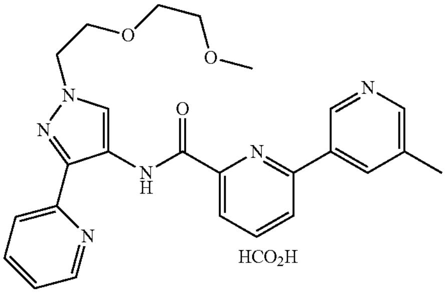

-continued
I-150
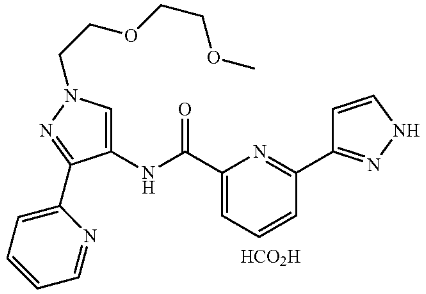
$HCO_2H$
I-151
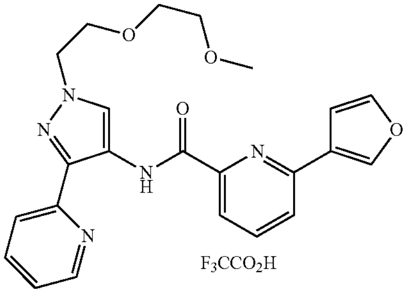
$F_3CCO_2H$
I-152
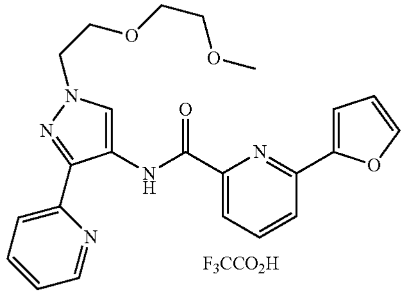
$F_3CCO_2H$
I-153
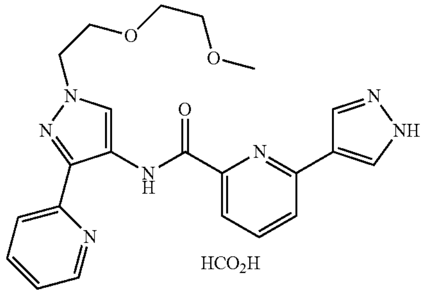
$HCO_2H$
I-154
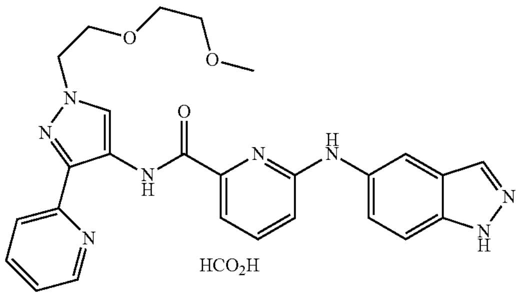
$HCO_2H$
-continued
I-155
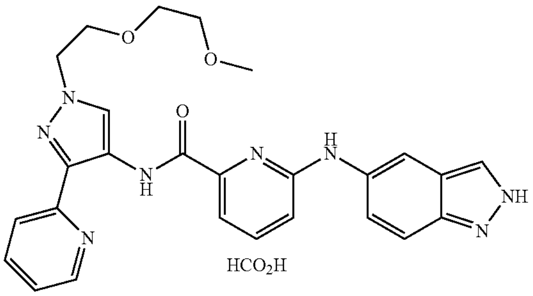
$HCO_2H$
I-156
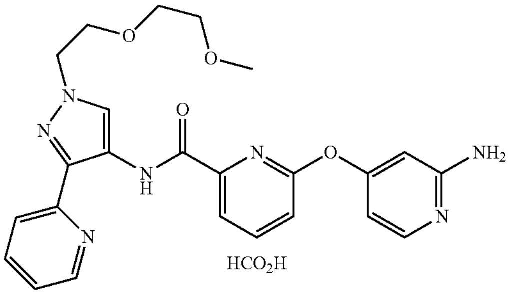
$HCO_2H$
I-157
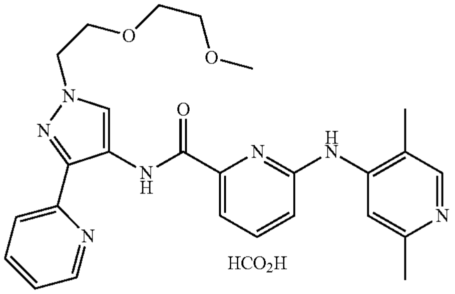
$HCO_2H$
I-158
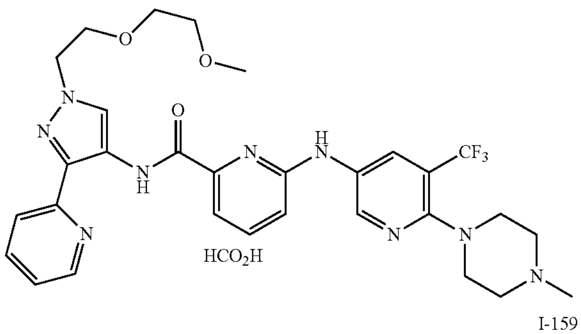
$HCO_2H$
I-159
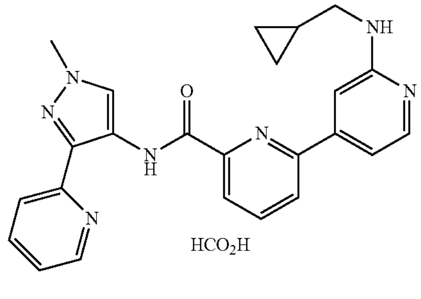
$HCO_2H$ -continued
I-160
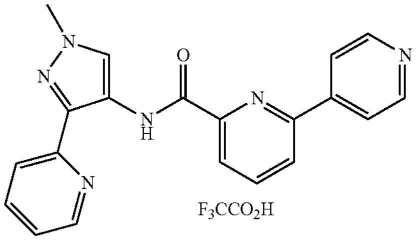
$F_3CCO_2H$
I-161
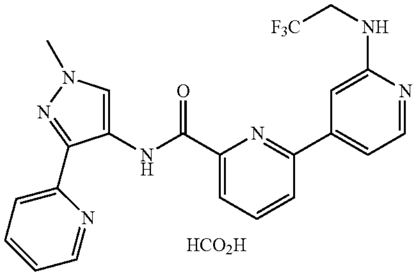
$HCO_2H$
I-162
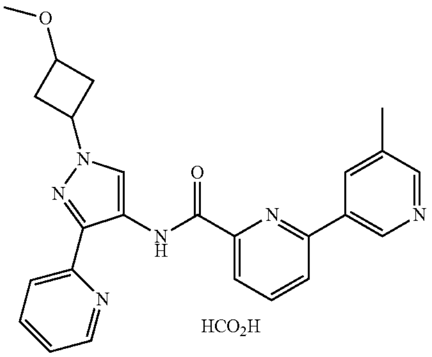
$HCO_2H$
I-163
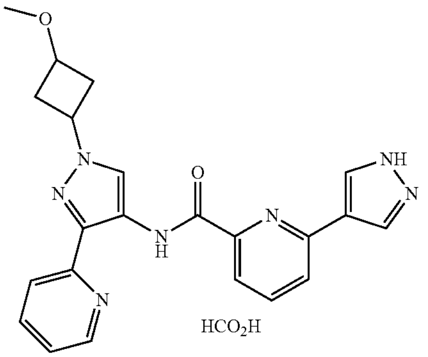
$HCO_2H$
I-164
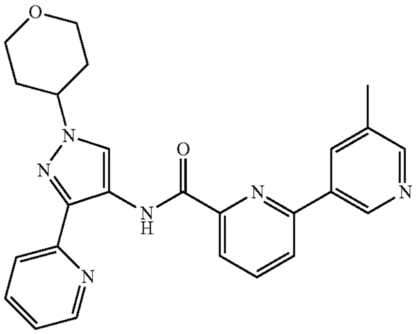
-continued
I-165
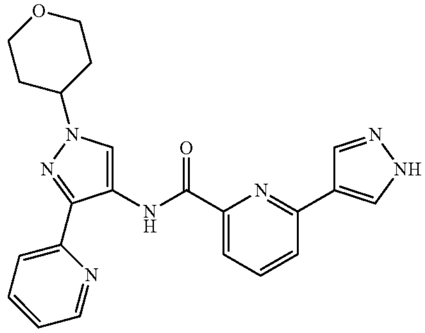
I-166
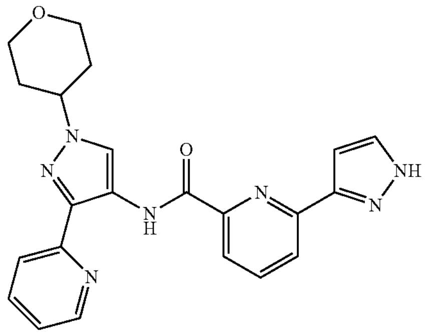
I-167
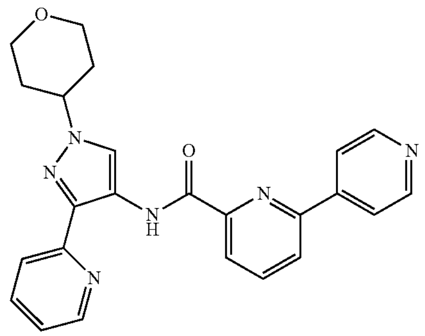
I-168
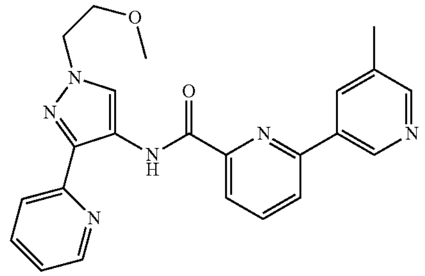
I-169
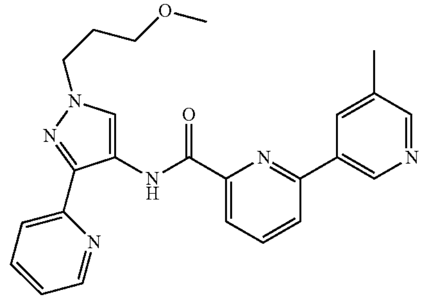

-continued
I-170
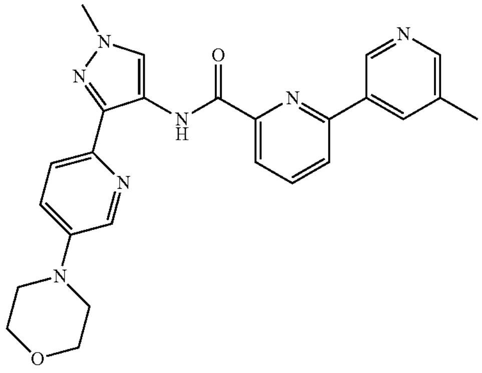
I-171
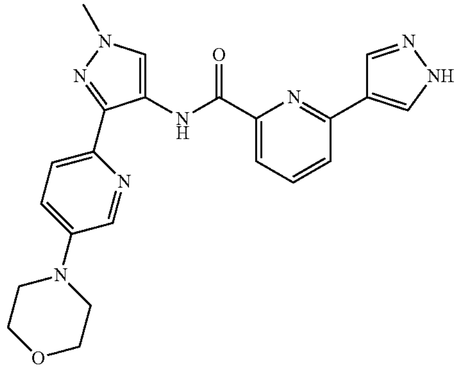
I-172
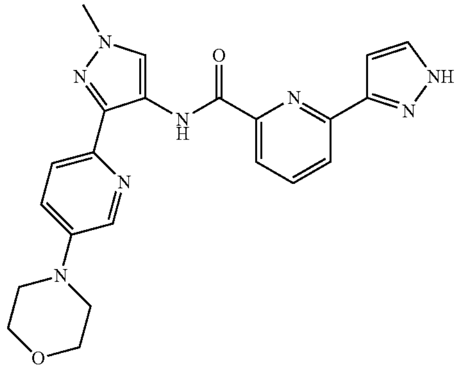
I-173
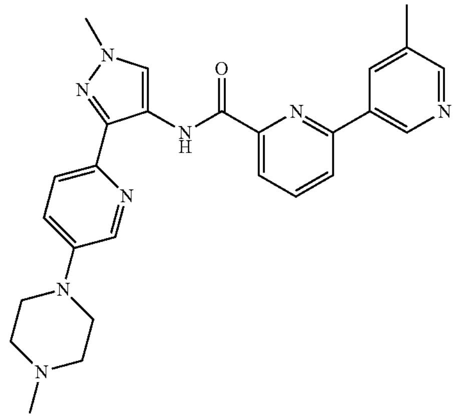
-continued
I-174
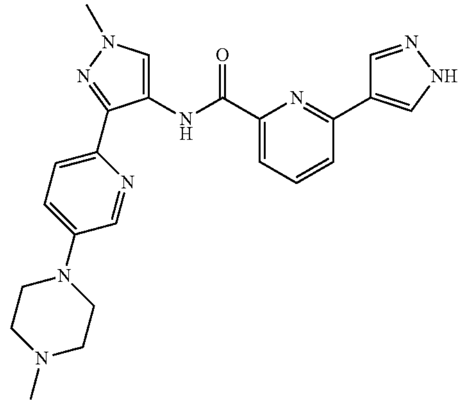
I-175
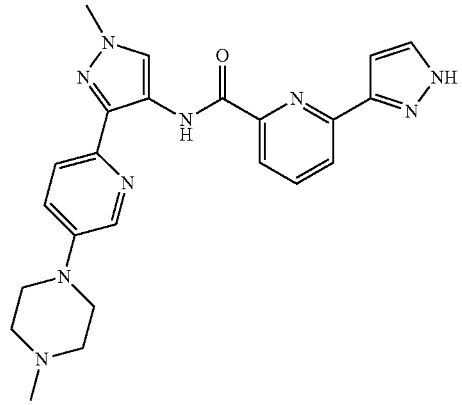
I-176
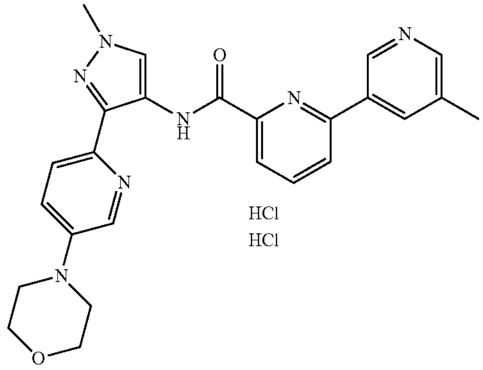
HCl
HCl
I-177
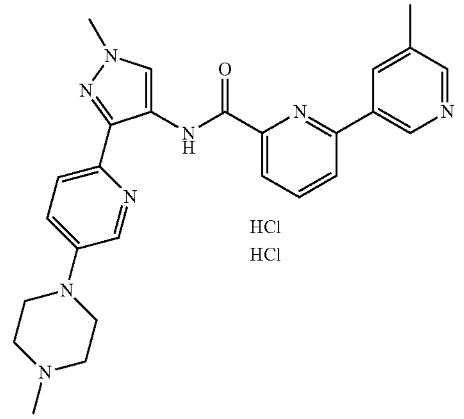
HCl
HCl -continued
I-178
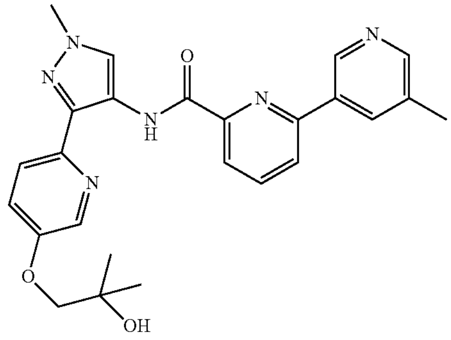
I-179
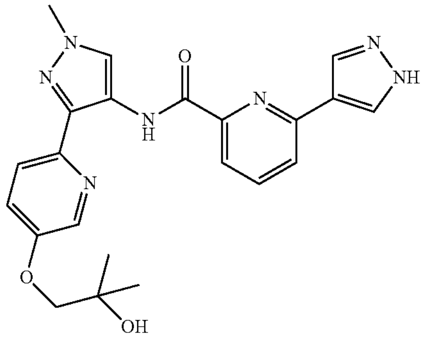
I-180
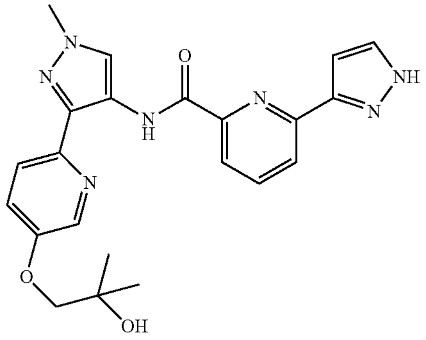
I-181
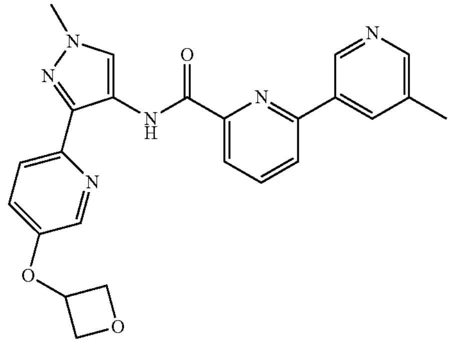
-continued
I-182
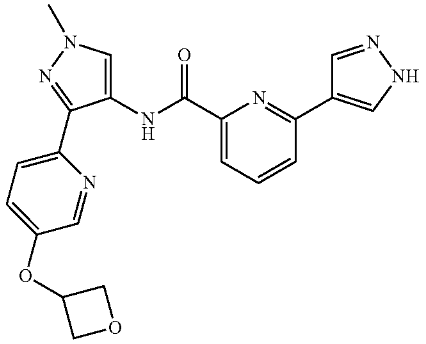
I-183
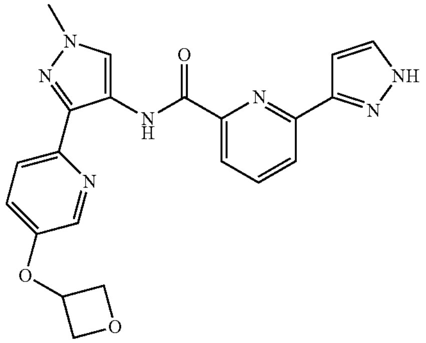
I-184
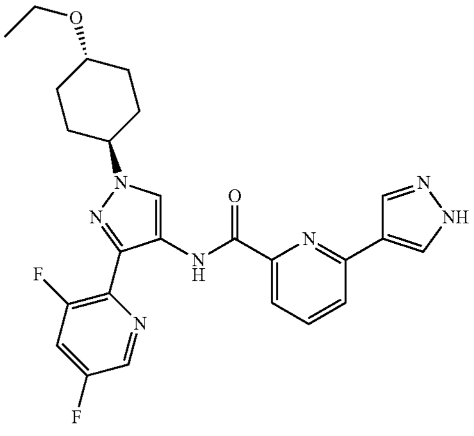
I-185
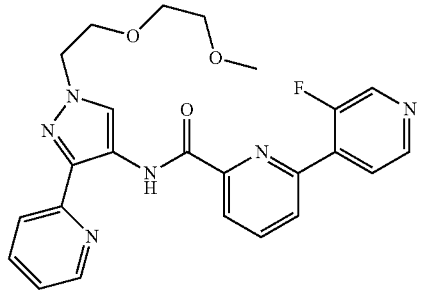

-continued
I-186
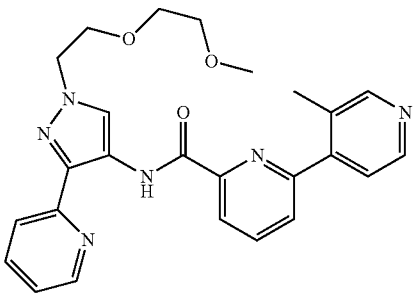
I-187
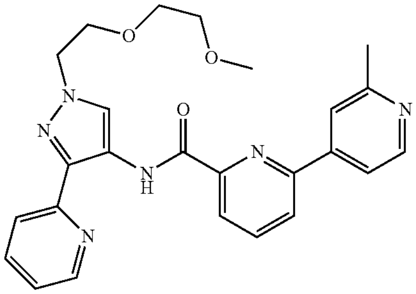
I-188
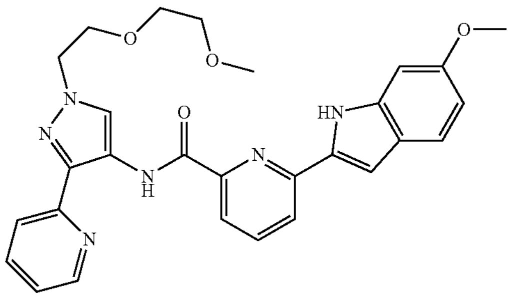
I-189
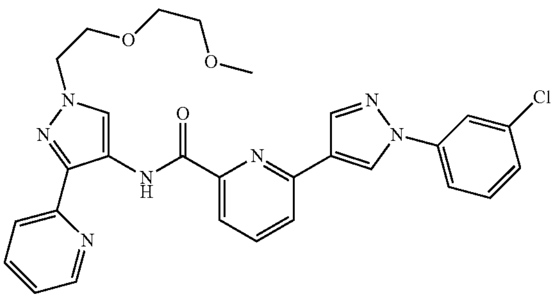
I-190
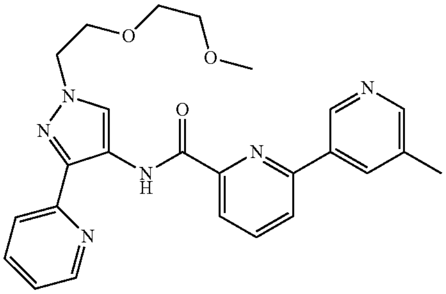
-continued
I-191
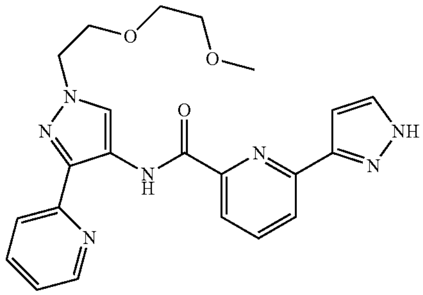
I-192
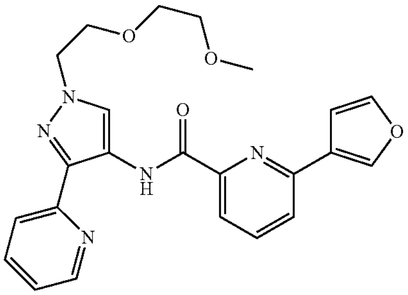
I-193
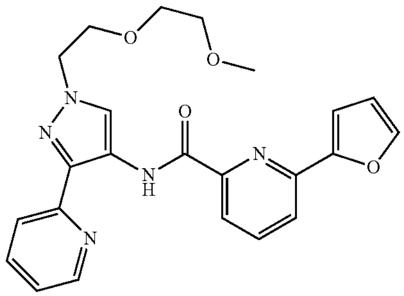
I-194
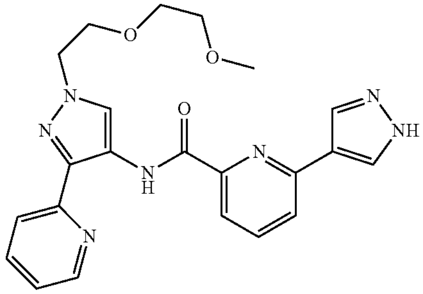
I-195
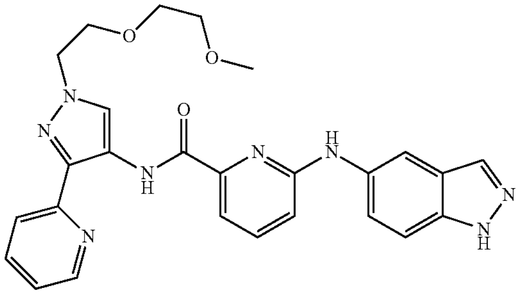

-continued
I-196
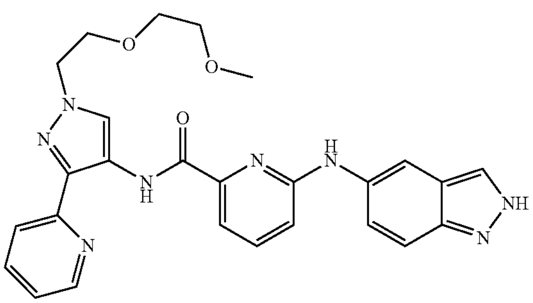
I-197
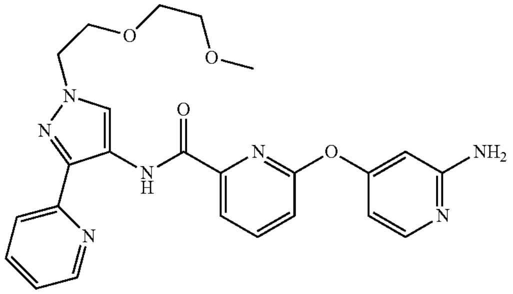
I-198
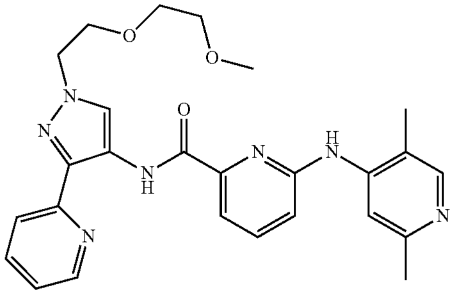
I-199
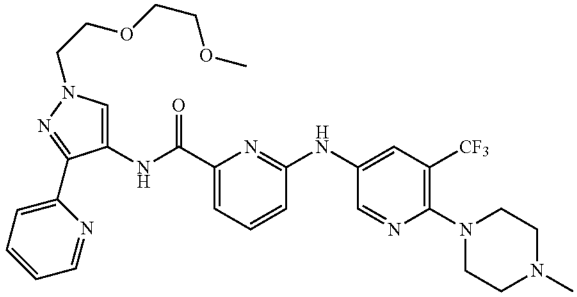
I-200
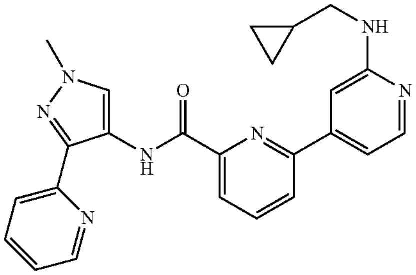
-continued
I-201
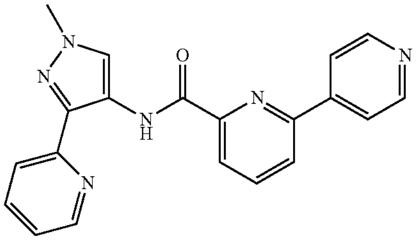
I-202
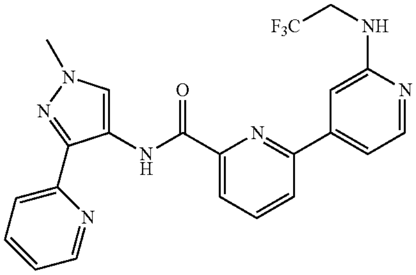
I-203
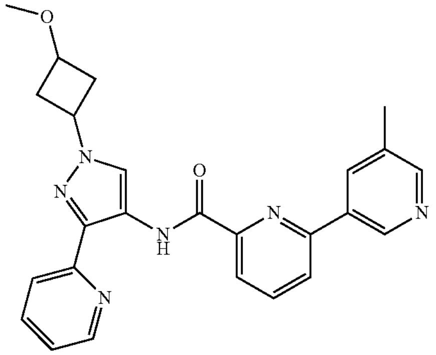
I-204
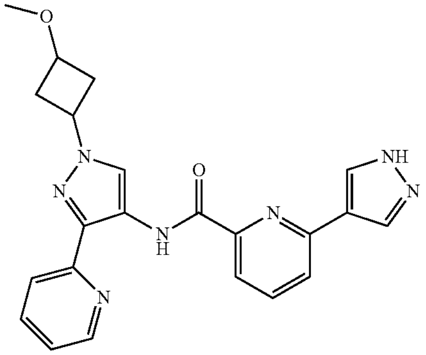

-continued

I-205

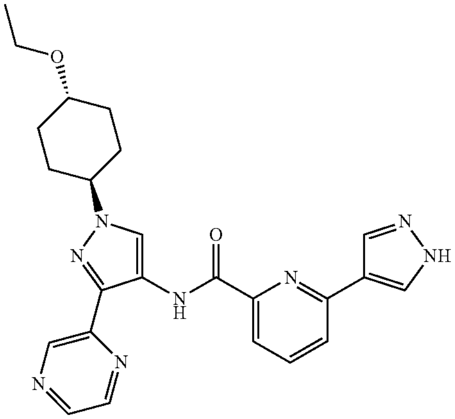

I-206

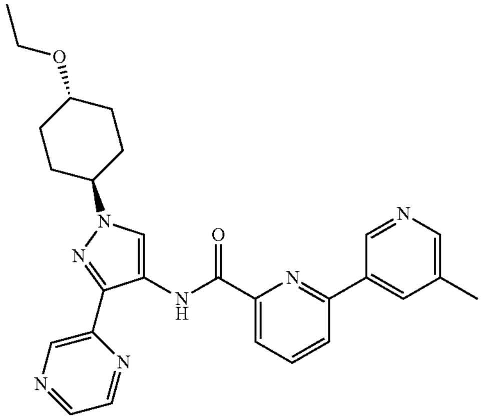

I-207

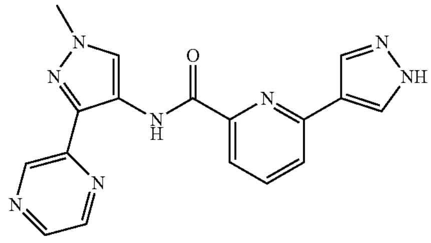

I-208

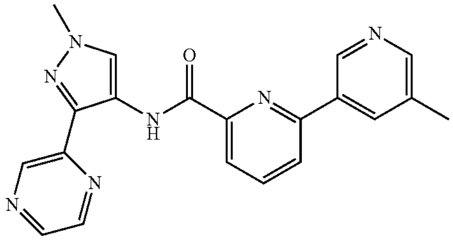

Exemplary disclosed compounds within the scope of one or more of formulas 1-9 include:

I-1: 6-bromo-N-(1-methyl-3-(pyridin-2-yl)-1H-pyrazol-4-yl)picolinamide;

I-2: N-(1-methyl-3-(pyridin-2-yl)-1H-pyrazol-4-yl)-[2,3'-bipyridine]-6-carboxamide;

I-3: 5'-fluoro-N-(1-methyl-3-(pyridin-2-yl)-1H-pyrazol-4-yl)-[2,3'-bipyridine]-6-carboxamide;

I-4: 5'-cyano-N-(1-methyl-3-(pyridin-2-yl)-1H-pyrazol-4-yl)-[2,3'-bipyridine]-6-carboxamide;

I-5: N-(1-methyl-3-(pyridin-2-yl)-1H-pyrazol-4-yl)-6-(pyrimidin-5-yl)picolinamide;

I-6: N-(1-methyl-3-(pyridin-2-yl)-1H-pyrazol-4-yl)-6-(1H-pyrazol-5-yl)picolinamide;

I-7: 6-(3-methyl-1H-pyrazol-5-yl)-N-(1-methyl-3-(pyridin-2-yl)-1H-pyrazol-4-yl)picolinamide;

I-8: 6-(1-methyl-1H-pyrazol-4-yl)-N-(1-methyl-3-(pyridin-2-yl)-1H-pyrazol-4-yl)picolinamide;

I-9: N-(1-methyl-3-(pyridin-2-yl)-1H-pyrazol-4-yl)-6-(1H-pyrazol-4-yl)picolinamide;

I-10: N-(1-methyl-3-(pyridin-2-yl)-1H-pyrazol-4-yl)-6-(1H-pyrrol-2-yl)picolinamide;

I-11: N-(1-methyl-3-(pyridin-2-yl)-1H-pyrazol-4-yl)-6-(1H-pyrrol-3-yl)picolinamide;

I-12: 5'-methyl-N-(1-methyl-3-(pyridin-2-yl)-1H-pyrazol-4-yl)-[2,3'-bipyridine]-6-carboxamide;

I-13: 5'-cyclopropyl-N-(1-methyl-3-(pyridin-2-yl)-1H-pyrazol-4-yl)-[2,3'-bipyridine]-6-carboxamide;

I-14: 5'-(2-hydroxypropan-2-yl)-N-(1-methyl-3-(pyridin-2-yl)-1H-pyrazol-4-yl)-[2,3'-bipyridine]-6-carboxamide;

I-15: 2'-methyl-N-(1-methyl-3-(pyridin-2-yl)-1H-pyrazol-4-yl)-[2,4'-bipyridine]-6-carboxamide;

I-16: 6'-methyl-N-(1-methyl-3-(pyridin-2-yl)-1H-pyrazol-4-yl)-[2,3'-bipyridine]-6-carboxamide;

I-17: N-(1-methyl-3-(pyridin-2-yl)-1H-pyrazol-4-yl)-5'-(trifluoromethyl)-[2,3'-bipyridine]-6-carboxamide;

I-18: N-(1-methyl-3-(pyridin-2-yl)-1H-pyrazol-4-yl)-2'-(trifluoromethyl)-[2,4'-bipyridine]-6-carboxamide;

I-19: 5'-methoxy-N-(1-methyl-3-(pyridin-2-yl)-1H-pyrazol-4-yl)-[2,3'-bipyridine]-6-carboxamide;

I-20: 6'-methoxy-N-(1-methyl-3-(pyridin-2-yl)-1H-pyrazol-4-yl)-[2,3'-bipyridine]-6-carboxamide;

I-21: 2'-methoxy-N-(1-methyl-3-(pyridin-2-yl)-1H-pyrazol-4-yl)-[2,4'-bipyridine]-6-carboxamide;

I-22: 5'-isopropoxy-N-(1-methyl-3-(pyridin-2-yl)-1H-pyrazol-4-yl)-[2,3'-bipyridine]-6-carboxamide;

I-23: N-(1-methyl-3-(pyridin-2-yl)-1H-pyrazol-4-yl)-5'-((tetrahydro-2H-pyran-4-yl)oxy)-[2,3'-bipyridine]-6-carboxamide;

I-24: N-(1-methyl-3-(pyridin-2-yl)-1H-pyrazol-4-yl)-5'-(2,2,2-trifluoroethoxy)-[2,3'-bipyridine]-6-carboxamide;

I-25: 5'-amino-N-(1-methyl-3-(pyridin-2-yl)-1H-pyrazol-4-yl)-[2,3'-bipyridine]-6-carboxamide;

I-26: N-(1-methyl-3-(pyridin-2-yl)-1H-pyrazol-4-yl)-5'-(methylamino)-[2,3'-bipyridine]-6-carboxamide;

I-27: 5'-(cyclopropylamino)-N-(1-methyl-3-(pyridin-2-yl)-1H-pyrazol-4-yl)-[2,3'-bipyridine]-6-carboxamide;

I-28: 5'-(isopropylamino)-N-(1-methyl-3-(pyridin-2-yl)-1H-pyrazol-4-yl)-[2,3'-bipyridine]-6-carboxamide;

I-29: 5'-(tert-butylamino)-N-(1-methyl-3-(pyridin-2-yl)-1H-pyrazol-4-yl)-[2,3'-bipyridine]-6-carboxamide;

I-30: N-(1-methyl-3-(pyridin-2-yl)-1H-pyrazol-4-yl)-5'-((tetrahydro-2H-pyran-4-yl)amino)-[2,3'-bipyridine]-6-carboxamide;

I-31: 5'-((2-methoxyethyl)amino)-N-(1-methyl-3-(pyridin-2-yl)-1H-pyrazol-4-yl)-[2,3'-bipyridine]-6-carboxamide;

I-32: 5'-((cyclopropylmethyl)amino)-N-(1-methyl-3-(pyridin-2-yl)-1H-pyrazol-4-yl)-[2,3'-bipyridine]-6-carboxamide;

I-33: N-(1-methyl-3-(pyridin-2-yl)-1H-pyrazol-4-yl)-5'-((2,2,2-trifluoroethyl)amino)-[2,3'-bipyridine]-6-carboxamide;

I-34: N-(1-methyl-3-(pyridin-2-yl)-1H-pyrazol-4-yl)-5'-(methylsulfonamido)-[2,3'-bipyridine]-6-carboxamide;

I-35: 5'-(dimethylamino)-N-(1-methyl-3-(pyridin-2-yl)-1H-pyrazol-4-yl)-[2,3'-bipyridine]-6-carboxamide;

I-36: N-(1-methyl-3-(pyridin-2-yl)-1H-pyrazol-4-yl)-5'-(pyrrolidin-1-yl)-[2,3'-bipyridine]-6-carboxamide;

I-37: N-(1-methyl-3-(pyridin-2-yl)-1H-pyrazol-4-yl)-5'-morpholino-[2,3'-bipyridine]-6-carboxamide;
I-38: N-(1-methyl-3-(pyridin-2-yl)-1H-pyrazol-4-yl)-5'-(4-methylpiperazin-1-yl)-[2,3'-bipyridine]-6-carboxamide;
I-39: N-(1-methyl-3-(pyridin-2-yl)-1H-pyrazol-4-yl)-5'-(methylsulfonyl)-[2,3'-bipyridine]-6-carboxamide;
I-40: N6-(1-methyl-3-(pyridin-2-yl)-1H-pyrazol-4-yl)-[2,3'-bipyridine]-5',6-dicarboxamide;
I-41: N6-(1-methyl-3-(pyridin-2-yl)-1H-pyrazol-4-yl)-[2,4'-bipyridine]-2',6-dicarboxamide;
I-42: 2'-cyano-N-(1-methyl-3-(pyridin-2-yl)-1H-pyrazol-4-yl)-[2,4-bipyridine]-6-carboxamide;
I-43: 6'-amino-N-(1-methyl-3-(pyridin-2-yl)-1H-pyrazol-4-yl)-[2,3-bipyridine]-6-carboxamide;
I-44: N-(1-methyl-3-(pyridin-2-yl)-1H-pyrazol-4-yl)-6-(1H-pyrrolo[2,3-b]pyridin-5-yl)picolinamide;
I-45: N-(1-methyl-3-(pyridin-2-yl)-1H-pyrazol-4-yl)-6-(1H-pyrrolo[3,2-b]pyridin-6-yl)picolinamide;
I-46: 6-(1H-indol-5-yl)-N-(1-methyl-3-(pyridin-2-yl)-1H-pyrazol-4-yl)picolinamide;
I-47: 6-(1H-indol-6-yl)-N-(1-methyl-3-(pyridin-2-yl)-1H-pyrazol-4-yl)picolinamide;
I-48: N-(1-methyl-3-(pyridin-2-yl)-1H-pyrazol-4-yl)-6-phenylpicolinamide;
I-49: N-(1-methyl-3-(pyridin-2-yl)-1H-pyrazol-4-yl)-6-(m-tolyl)picolinamide;
I-50: N-(1-methyl-3-(pyridin-2-yl)-1H-pyrazol-4-yl)-6-(p-tolyl)picolinamide;
I-51: 6-(3-methoxyphenyl)-N-(1-methyl-3-(pyridin-2-yl)-1H-pyrazol-4-yl)picolinamide;
I-52: 6-(4-methoxyphenyl)-N-(1-methyl-3-(pyridin-2-yl)-1H-pyrazol-4-yl)picolinamide;
I-53: 6-(3-cyanophenyl)-N-(1-methyl-3-(pyridin-2-yl)-1H-pyrazol-4-yl)picolinamide;
I-54: 6-(4-cyanophenyl)-N-(1-methyl-3-(pyridin-2-yl)-1H-pyrazol-4-yl)picolinamide;
I-55: 6-(3-fluorophenyl)-N-(1-methyl-3-(pyridin-2-yl)-1H-pyrazol-4-yl)picolinamide;
I-56: 6-(4-fluorophenyl)-N-(1-methyl-3-(pyridin-2-yl)-1H-pyrazol-4-yl)picolinamide;
I-57: 6-(3-aminophenyl)-N-(1-methyl-3-(pyridin-2-yl)-1H-pyrazol-4-yl)picolinamide;
I-58: N-(1-methyl-3-(pyridin-2-yl)-1H-pyrazol-4-yl)-6-(3-(methylamino)phenyl)picolinamide;
I-59: 6-(3-(dimethylamino)phenyl)-N-(1-methyl-3-(pyridin-2-yl)-1H-pyrazol-4-yl)picolinamide;
I-60: N-(1-methyl-3-(pyridin-2-yl)-1H-pyrazol-4-yl)-6-(3-(methylsulfonamido)phenyl)picolinamide;
I-61: tert-butyl 6-((1-methyl-3-(pyridin-2-yl)-1H-pyrazol-4-yl)carbamoyl)-3',6'-dihydro-[2,4'-bipyridine]-1'(2'H)-carboxylate;
I-62: N-(1-methyl-3-(pyridin-2-yl)-1H-pyrazol-4-yl)-1',2',3',6'-tetrahydro-[2,4'-bipyridine]-6-carboxamide;
I-63: N-(1-methyl-3-(pyridin-2-yl)-1H-pyrazol-4-yl)-6-(piperidin-4-yl)picolinamide;
I-64: tert-butyl 6-((1-methyl-3-(pyridin-2-yl)-1H-pyrazol-4-yl)carbamoyl)-5',6'-dihydro-[2,3'-bipyridine]-1'(2'H)-carboxylate;
I-65: N-(1-methyl-3-(pyridin-2-yl)-1H-pyrazol-4-yl)-1',2',5',6'-tetrahydro-[2,3'-bipyridine]-6-carboxamide;
I-66: 6-bromo-N-(3-(5-methoxypyridin-2-yl)-1-methyl-1H-pyrazol-4-yl)picolinamide;
I-67: N-(3-(5-methoxypyridin-2-yl)-1-methyl-1H-pyrazol-4-yl)-6-(1H-pyrazol-5-yl)picolinamide;
I-68: N-(3-(5-methoxypyridin-2-yl)-1-methyl-1H-pyrazol-4-yl)-6-(1H-pyrazol-4-yl)picolinamide;
I-69: N-(3-(5-methoxypyridin-2-yl)-1-methyl-1H-pyrazol-4-yl)-5'-methyl-[2,3'-bipyridine]-6-carboxamide;
I-70: 5'-isopropoxy-N-(3-(5-methoxypyridin-2-yl)-1-methyl-1H-pyrazol-4-yl)-[2,3'-bipyridine]-6-carboxamide;
I-71: 5'-(isopropylamino)-N-(3-(5-methoxypyridin-2-yl)-1-methyl-1H-pyrazol-4-yl)-[2,3'-bipyridine]-6-carboxamide;
I-72: N-(1-methyl-3-(pyrrolidin-1-yl)-1H-pyrazol-4-yl)-6-(1H-pyrazol-4-yl)picolinamide;
I-73: N-(1-methyl-3-(piperidin-1-yl)-1H-pyrazol-4-yl)-6-(1H-pyrazol-4-yl)picolinamide;
I-74: N-(1-methyl-3-morpholino-1H-pyrazol-4-yl)-6-(1H-pyrazol-4-yl)picolinamide;
I-75: 5'-methyl-N-(1-methyl-3-(pyrrolidin-1-yl)-1H-pyrazol-4-yl)-[2,3'-bipyridine]-6-carboxamide;
I-76: 5'-methyl-N-(1-methyl-3-(piperidin-1-yl)-1H-pyrazol-4-yl)-[2,3'-bipyridine]-6-carboxamide;
I-77: 5'-methyl-N-(1-methyl-3-morpholino-1H-pyrazol-4-yl)-[2,3'-bipyridine]-6-carboxamide;
I-78: 6-(3-methyl-1H-pyrazol-4-yl)-N-(1-methyl-3-(pyridin-2-yl)-1H-pyrazol-4-yl)picolinamide;
I-79: 6-bromo-N-(1-isopropyl-3-(pyridin-2-yl)-1H-pyrazol-4-yl)picolinamide;
I-80: N-(1-isopropyl-3-(pyridin-2-yl)-1H-pyrazol-4-yl)-6-(1H-pyrazol-4-yl)picolinamide;
I-81: N-(1-isopropyl-3-(pyridin-2-yl)-1H-pyrazol-4-yl)-5'-methyl-[2,3'-bipyridine]-6-carboxamide;
I-82: 6-bromo-N-(1-(2-morpholinoethyl)-3-(pyridin-2-yl)-1H-pyrazol-4-yl)picolinamide;
I-83: N-(1-(2-morpholinoethyl)-3-(pyridin-2-yl)-1H-pyrazol-4-yl)-6-(1H-pyrazol-4-yl)picolinamide;
I-84: 5'-methyl-N-(1-(2-morpholinoethyl)-3-(pyridin-2-yl)-1H-pyrazol-4-yl)-[2,3'-bipyridine]-6-carboxamide;
I-85: 6-bromo-N-(1-(2-(4-methylpiperazin-1-yl)ethyl)-3-(pyridin-2-yl)-1H-pyrazol-4-yl)picolinamide;
I-86: N-(1-(2-(4-methylpiperazin-1-yl)ethyl)-3-(pyridin-2-yl)-1H-pyrazol-4-yl)-6-(1H-pyrazol-4-yl)picolinamide;
I-87: 5'-methyl-N-(1-(2-(4-methylpiperazin-1-yl)ethyl)-3-(pyridin-2-yl)-1H-pyrazol-4-yl)-[2,3'-bipyridine]-6-carboxamide;
I-88: N-(1-(2-hydroxyethyl)-3-(pyridin-2-yl)-1H-pyrazol-4-yl)-[2,4'-bipyridine]-6-carboxamide;
I-89: N-(1-(2-(2-methoxyethoxy)ethyl)-3-(pyridin-2-yl)-1H-pyrazol-4-yl)-6-(pyridin-4-yloxy)picolinamide;
I-90: N-(1-(2-(2-methoxyethoxy)ethyl)-3-(pyridin-2-yl)-1H-pyrazol-4-yl)-[2,4'-bipyridine]-6-carboxamide;
I-91: N-(1-methyl-3-(pyridin-2-yl)-1H-pyrazol-4-yl)-2'-oxo-1',2'-dihydro-[2,4'-bipyridine]-6-carboxamide;
I-92: N-(1-methyl-3-(pyridin-2-yl)-1H-pyrazol-4-yl)-6'-oxo-1',6'-dihydro-[2,3'-bipyridine]-6-carboxamide;
I-93: N-(1-methyl-3-(pyrazin-2-yl)-1H-pyrazol-4-yl)-5'-(2,2,2-trifluoroethoxy)-[2,3'-bipyridine]-6-carboxamide;
I-94: N-(3-(pyridin-2-yl)-1H-pyrazol-4-yl)-[2,4'-bipyridine]-6-carboxamide;
I-95: N-(1-(2-methoxyethyl)-3-(pyridin-2-yl)-1H-pyrazol-4-yl)-[2,4'-bipyridine]-6-carboxamide;
I-96: 2'-methoxy-N-(1-(2-(2-methoxyethoxy)ethyl)-3-(pyridin-2-yl)-1H-pyrazol-4-yl)-[2,4'-bipyridine]-6-carboxamide;
I-97: 6'-amino-N-(1-(2-(2-methoxyethoxy)ethyl)-3-(pyridin-2-yl)-1H-pyrazol-4-yl)-[2,3'-bipyridine]-6-carboxamide;
I-98: 6'-acetamido-N-(1-(2-(2-methoxyethoxy)ethyl)-3-(pyridin-2-yl)-1H-pyrazol-4-yl)-[2,3'-bipyridine]-6-carboxamide;

I-99: 2'-methoxy-N-(1-methyl-3-(pyrazin-2-yl)-1H-pyrazol-4-yl)-[2,4'-bipyridine]-6-carboxamide;
I-100: N-(1-methyl-3-(pyrazin-2-yl)-1H-pyrazol-4-yl)-[2,4'-bipyridine]-6-carboxamide;
I-101: N-(1-methyl-3-(pyrazin-2-yl)-1H-pyrazol-4-yl)-[2,3'-bipyridine]-6-carboxamide;
I-102: 6'-acetamido-N-(1-methyl-3-(pyrazin-2-yl)-1H-pyrazol-4-yl)-[2,3'-bipyridine]-6-carboxamide;
I-103: 2'-(benzyloxy)-N-(1-methyl-3-(pyrazin-2-yl)-1H-pyrazol-4-yl)-[2,4'-bipyridine]-6-carboxamide;
I-104: N-(1-(2-(diethylamino)ethyl)-3-(pyridin-2-yl)-1H-pyrazol-4-yl)-[2,4'-bipyridine]-6-carboxamide;
I-105: N-(1-methyl-3-(pyrazin-2-yl)-1H-pyrazol-4-yl)-5'-(2,2,2-trifluoroethoxy)-[2,3'-bipyridine]-6-carboxamide formate;
I-106: N-(3-(pyridin-2-yl)-1H-pyrazol-4-yl)-[2,4'-bipyridine]-6-carboxamide formate;
I-107: N-(1-(2-methoxyethyl)-3-(pyridin-2-yl)-1H-pyrazol-4-yl)-[2,4'-bipyridine]-6-carboxamide formate;
I-108: N-(1-(2-hydroxyethyl)-3-(pyridin-2-yl)-1H-pyrazol-4-yl)-[2,4'-bipyridine]-6-carboxamide formate;
I-109: 5-(1-(cyclopropylmethyl)-1H-pyrazol-4-yl)-N-(1-methyl-3-(pyridin-2-yl)-1H-pyrazol-4-yl)nicotinamide;
I-110: N-(1-methyl-3-(pyridin-2-yl)-1H-pyrazol-4-yl)-[3,4'-bipyridine]-5-carboxamide;
I-111: N-(1-methyl-3-(pyridin-2-yl)-1H-pyrazol-4-yl)-[3,3'-bipyridine]-5-carboxamide;
I-112: N-(1-(oxetan-3-yl)-3-(pyridin-2-yl)-1H-pyrazol-4-yl)-[2,3'-bipyridine]-6-carboxamide;
I-113: 6-bromo-N-(1-(oxetan-3-yl)-3-(pyridin-2-yl)-1H-pyrazol-4-yl)picolinamide;
I-114: 5'-methyl-N-(1-(oxetan-3-yl)-3-(pyridin-2-yl)-1H-pyrazol-4-yl)-[2,3'-bipyridine]-6-carboxamide;
I-115: 5'-(methylsulfonamido)-N-(1-(oxetan-3-yl)-3-(pyridin-2-yl)-1H-pyrazol-4-yl)-[2,3'-bipyridine]-6-carboxamide;
I-116: N-(1-(oxetan-3-yl)-3-(pyridin-2-yl)-1H-pyrazol-4-yl)-6-(1H-pyrazol-4-yl)picolinamide;
I-117: N-(1-(oxetan-3-yl)-3-(pyridin-2-yl)-1H-pyrazol-4-yl)-6-(1H-pyrazol-3-yl)picolinamide;
I-118: N-(1-methyl-3-(pyridin-2-yl)-1H-pyrazol-4-yl)-4-((1-methyl-3-(pyridin-2-yl)-1H-pyrazol-4-yl)amino)pyrimidine-2-carboxamide;
I-119: sodium (methylsulfonyl)(6-((1-(oxetan-3-yl)-3-(pyridin-2-yl)-1H-pyrazol-4-yl)carbamoyl)-[2,3'-bipyridin]-5'-yl)amide;
I-120: N-(1-methyl-3-(pyridin-2-yl)-1H-pyrazol-4-yl)-4-(5-methylpyridin-3-yl)pyrimidine-2-carboxamide;
I-121: N-(1-methyl-3-(pyridin-2-yl)-1H-pyrazol-4-yl)-6-(5-methylpyridin-3-yl)pyrazine-2-carboxamide;
I-122: N-(1-methyl-3-(pyridin-2-yl)-1H-pyrazol-4-yl)-6-(1H-pyrazol-4-yl)pyrazine-2-carboxamide;
I-123: N-(1-methyl-3-(pyridin-2-yl)-1H-pyrazol-4-yl)-6-(1H-pyrazol-3-yl)pyrazine-2-carboxamide;
I-124: N-(1-methyl-3-(pyridin-2-yl)-1H-pyrazol-4-yl)-4-(1H-pyrazol-4-yl)pyrimidine-2-carboxamide;
I-125: N-(1-(1,3-dihydroxypropan-2-yl)-3-(pyridin-2-yl)-1H-pyrazol-4-yl)-[2,3'-bipyridine]-6-carboxamide;
I-126: N-(1-(1,3-dihydroxypropan-2-yl)-3-(pyridin-2-yl)-1H-pyrazol-4-yl)-5'-methyl-[2,3'-bipyridine]-6-carboxamide;
I-127: N-(1-(1,3-dihydroxypropan-2-yl)-3-(pyridin-2-yl)-1H-pyrazol-4-yl)-6-(1H-pyrazol-4-yl)picolinamide;
I-128: 4-((1H-pyrazol-3-yl)amino)-N-(1-methyl-3-(pyridin-2-yl)-1H-pyrazol-4-yl)pyrimidine-2-carboxamide;
I-129: 4-((3-methyl-1H-pyrazol-4-yl)amino)-N-(1-methyl-3-(pyridin-2-yl)-1H-pyrazol-4-yl)pyrimidine-2-carboxamide;
I-130: 5'-isopropoxy-N-(1-(oxetan-3-yl)-3-(pyridin-2-yl)-1H-pyrazol-4-yl)-[2,3'-bipyridine]-6-carboxamide;
I-131: 5'-fluoro-N-(1-(oxetan-3-yl)-3-(pyridin-2-yl)-1H-pyrazol-4-yl)-[2,3'-bipyridine]-6-carboxamide;
I-132: N-(1-(oxetan-3-yl)-3-(pyridin-2-yl)-1H-pyrazol-4-yl)-5'-(trifluoromethyl)-[2,3'-bipyridine]-6-carboxamide;
I-133: N6-(1-(oxetan-3-yl)-3-(pyridin-2-yl)-1H-pyrazol-4-yl)-[2,3'-bipyridine]-5',6-dicarboxamide;
I-134: 6-(1-methyl-1H-pyrazol-4-yl)-N-(1-(oxetan-3-yl)-3-(pyridin-2-yl)-1H-pyrazol-4-yl)picolinamide;
I-135: 6-((1-(oxetan-3-yl)-3-(pyridin-2-yl)-1H-pyrazol-4-yl)carbamoyl)-[2,3'-bipyridine]-5'-carboxylic acid;
I-136: 6-(3-methyl-1H-pyrazol-5-yl)-N-(1-(oxetan-3-yl)-3-(pyridin-2-yl)-1H-pyrazol-4-yl)picolinamide;
I-137: N-(1-methyl-3-(pyridin-2-yl)-1H-pyrazol-4-yl)-2-(1H-pyrazol-4-yl)pyrimidine-4-carboxamide;
I-138: N-(1-methyl-3-(pyridin-2-yl)-1H-pyrazol-4-yl)-2-(1H-pyrazol-3-yl)pyrimidine-4-carboxamide;
I-139: N-(1-(2-(2-methoxyethoxy)ethyl)-3-(pyridin-2-yl)-1H-pyrazol-4-yl)-6-(pyridin-4-yloxy)picolinamide formate;
I-140: N-(1-(2-(2-methoxyethoxy)ethyl)-3-(pyridin-2-yl)-1H-pyrazol-4-yl)-[2,4'-bipyridine]-6-carboxamide formate;
I-141: 2'-methoxy-N-(1-(2-(2-methoxyethoxy)ethyl)-3-(pyridin-2-yl)-1H-pyrazol-4-yl)-[2,4'-bipyridine]-6-carboxamide formate;
I-142: 6'-amino-N-(1-(2-(2-methoxyethoxy)ethyl)-3-(pyridin-2-yl)-1H-pyrazol-4-yl)-[2,3'-bipyridine]-6-carboxamide formate;
I-143: 6'-acetamido-N-(1-(2-(2-methoxyethoxy)ethyl)-3-(pyridin-2-yl)-1H-pyrazol-4-yl)-[2,3'-bipyridine]-6-carboxamide formate;
I-144: 3'-fluoro-N-(1-(2-(2-methoxyethoxy)ethyl)-3-(pyridin-2-yl)-1H-pyrazol-4-yl)-[2,4'-bipyridine]-6-carboxamide formate;
I-145: N-(1-(2-(2-methoxyethoxy)ethyl)-3-(pyridin-2-yl)-1H-pyrazol-4-yl)-3'-methyl-[2,4'-bipyridine]-6-carboxamide formate;
I-146: N-(1-(2-(2-methoxyethoxy)ethyl)-3-(pyridin-2-yl)-1H-pyrazol-4-yl)-2'-methyl-[2,4'-bipyridine]-6-carboxamide formate;
I-147: 6-(6-methoxy-1H-indol-2-yl)-N-(1-(2-(2-methoxyethoxy)ethyl)-3-(pyridin-2-yl)-1H-pyrazol-4-yl)picolinamide formate;
I-148: 6-(1-(3-chlorophenyl)-1H-pyrazol-4-yl)-N-(1-(2-(2-methoxyethoxy)ethyl)-3-(pyridin-2-yl)-1H-pyrazol-4-yl)picolinamide formate;
I-149: N-(1-(2-(2-methoxyethoxy)ethyl)-3-(pyridin-2-yl)-1H-pyrazol-4-yl)-5'-methyl-[2,3'-bipyridine]-6-carboxamide formate;
I-150: N-(1-(2-(2-methoxyethoxy)ethyl)-3-(pyridin-2-yl)-1H-pyrazol-4-yl)-6-(1H-pyrazol-3-yl)picolinamide formate;
I-151: 6-(furan-3-yl)-N-(1-(2-(2-methoxyethoxy)ethyl)-3-(pyridin-2-yl)-1H-pyrazol-4-yl)picolinamide 2,2,2-trifluoroacetate;
I-152: 6-(furan-2-yl)-N-(1-(2-(2-methoxyethoxy)ethyl)-3-(pyridin-2-yl)-1H-pyrazol-4-yl)picolinamide 2,2,2-trifluoroacetate;
I-153: N-(1-(2-(2-methoxyethoxy)ethyl)-3-(pyridin-2-yl)-1H-pyrazol-4-yl)-6-(1H-pyrazol-4-yl)picolinamide formate;

I-154: 6-((1H-indazol-5-yl)amino)-N-(1-(2-(2-methoxyethoxy)ethyl)-3-(pyridin-2-yl)-1H-pyrazol-4-yl)picolinamide formate;
I-155: 6-((2H-indazol-5-yl)amino)-N-(1-(2-(2-methoxyethoxy)ethyl)-3-(pyridin-2-yl)-1H-pyrazol-4-yl)picolinamide formate;
I-156: 6-((2-aminopyridin-4-yl)oxy)-N-(1-(2-(2-methoxyethoxy)ethyl)-3-(pyridin-2-yl)-1H-pyrazol-4-yl)picolinamide formate;
I-157: 6-((2,5-dimethylpyridin-4-yl)amino)-N-(1-(2-(2-methoxyethoxy)ethyl)-3-(pyridin-2-yl)-1H-pyrazol-4-yl)picolinamide formate;
I-158: N-(1-(2-(2-methoxyethoxy)ethyl)-3-(pyridin-2-yl)-1H-pyrazol-4-yl)-6-((6-(4-methylpiperazin-1-yl)-5-(trifluoromethyl)pyridin-3-yl)amino)picolinamide formate;
I-159: 2'-((cyclopropylmethyl)amino)-N-(1-methyl-3-(pyridin-2-yl)-1H-pyrazol-4-yl)-[2,4'-bipyridine]-6-carboxamide formate;
I-160: N-(1-methyl-3-(pyridin-2-yl)-1H-pyrazol-4-yl)-[2,4'-bipyridine]-6-carboxamide 2,2,2-trifluoroacetate;
I-161: N-(1-methyl-3-(pyridin-2-yl)-1H-pyrazol-4-yl)-2'-((2,2,2-trifluoroethyl)amino)-[2,4'-bipyridine]-6-carboxamide formate;
I-162: N-(1-(3-methoxycyclobutyl)-3-(pyridin-2-yl)-1H-pyrazol-4-yl)-5'-methyl-[2,3'-bipyridine]-6-carboxamide formate;
I-163: N-(1-(3-methoxycyclobutyl)-3-(pyridin-2-yl)-1H-pyrazol-4-yl)-6-(1H-pyrazol-4-yl)picolinamide formate;
I-164: 5'-methyl-N-(3-(pyridin-2-yl)-1-(tetrahydro-2H-pyran-4-yl)-1H-pyrazol-4-yl)-[2,3'-bipyridine]-6-carboxamide;
I-165: 6-(1H-pyrazol-4-yl)-N-(3-(pyridin-2-yl)-1-(tetrahydro-2H-pyran-4-yl)-1H-pyrazol-4-yl)picolinamide;
I-166: 6-(1H-pyrazol-3-yl)-N-(3-(pyridin-2-yl)-1-(tetrahydro-2H-pyran-4-yl)-1H-pyrazol-4-yl)picolinamide;
I-167: N-(3-(pyridin-2-yl)-1-(tetrahydro-2H-pyran-4-yl)-1H-pyrazol-4-yl)-[2,4'-bipyridine]-6-carboxamide;
I-168: N-(1-(2-methoxyethyl)-3-(pyridin-2-yl)-1H-pyrazol-4-yl)-5'-methyl-[2,3'-bipyridine]-6-carboxamide;
I-169: N-(1-(3-methoxypropyl)-3-(pyridin-2-yl)-1H-pyrazol-4-yl)-5'-methyl-[2,3'-bipyridine]-6-carboxamide;
I-170: 5'-methyl-N-(1-methyl-3-(5-morpholinopyridin-2-yl)-1H-pyrazol-4-yl)-[2,3'-bipyridine]-6-carboxamide;
I-171: N-(1-methyl-3-(5-morpholinopyridin-2-yl)-1H-pyrazol-4-yl)-6-(1H-pyrazol-4-yl)picolinamide;
I-172: N-(1-methyl-3-(5-morpholinopyridin-2-yl)-1H-pyrazol-4-yl)-6-(1H-pyrazol-3-yl)picolinamide;
I-173: 5'-methyl-N-(1-methyl-3-(5-(4-methylpiperazin-1-yl)pyridin-2-yl)-1H-pyrazol-4-yl)-[2,3'-bipyridine]-6-carboxamide;
I-174: N-(1-methyl-3-(5-(4-methylpiperazin-1-yl)pyridin-2-yl)-1H-pyrazol-4-yl)-6-(1H-pyrazol-4-yl)picolinamide;
I-175: N-(1-methyl-3-(5-(4-methylpiperazin-1-yl)pyridin-2-yl)-1H-pyrazol-4-yl)-6-(1H-pyrazol-3-yl)picolinamide;
I-176: 5'-methyl-N-(1-methyl-3-(5-morpholinopyridin-2-yl)-1H-pyrazol-4-yl)-[2,3'-bipyridine]-6-carboxamide dihydrochloride;
I-177: 5'-methyl-N-(1-methyl-3-(5-(4-methylpiperazin-1-yl)pyridin-2-yl)-1H-pyrazol-4-yl)-[2,3'-bipyridine]-6-carboxamide dihydrochloride;
I-178: N-(3-(5-(2-hydroxy-2-methylpropoxy)pyridin-2-yl)-1-methyl-1H-pyrazol-4-yl)-5'-methyl-[2,3'-bipyridine]-6-carboxamide;
I-179: N-(3-(5-(2-hydroxy-2-methylpropoxy)pyridin-2-yl)-1-methyl-1H-pyrazol-4-yl)-6-(1H-pyrazol-4-yl)picolinamide;
I-180: N-(3-(5-(2-hydroxy-2-methylpropoxy)pyridin-2-yl)-1-methyl-1H-pyrazol-4-yl)-6-(1H-pyrazol-3-yl)picolinamide;
I-181: 5'-methyl-N-(1-methyl-3-(5-(oxetan-3-yloxy)pyridin-2-yl)-1H-pyrazol-4-yl)-[2,3'-bipyridine]-6-carboxamide;
I-182: N-(1-methyl-3-(5-(oxetan-3-yloxy)pyridin-2-yl)-1H-pyrazol-4-yl)-6-(1H-pyrazol-4-yl)picolinamide;
I-183: N-(1-methyl-3-(5-(oxetan-3-yloxy)pyridin-2-yl)-1H-pyrazol-4-yl)-6-(1H-pyrazol-3-yl)picolinamide;
I-184: N-(3-(3,5-difluoropyridin-2-yl)-1-((1r,4r)-4-ethoxycyclohexyl)-1H-pyrazol-4-yl)-6-(1H-pyrazol-4-yl)picolinamide;
I-185: 3'-fluoro-N-(1-(2-(2-methoxyethoxy)ethyl)-3-(pyridin-2-yl)-1H-pyrazol-4-yl)-[2,4'-bipyridine]-6-carboxamide;
I-186: N-(1-(2-(2-methoxyethoxy)ethyl)-3-(pyridin-2-yl)-1H-pyrazol-4-yl)-3'-methyl-[2,4'-bipyridine]-6-carboxamide;
I-187: N-(1-(2-(2-methoxyethoxy)ethyl)-3-(pyridin-2-yl)-1H-pyrazol-4-yl)-2'-methyl-[2,4'-bipyridine]-6-carboxamide;
I-188: 6-(6-methoxy-1H-indol-2-yl)-N-(1-(2-(2-methoxyethoxy)ethyl)-3-(pyridin-2-yl)-1H-pyrazol-4-yl)picolinamide;
I-189: 6-(1-(3-chlorophenyl)-1H-pyrazol-4-yl)-N-(1-(2-(2-methoxyethoxy)ethyl)-3-(pyridin-2-yl)-1H-pyrazol-4-yl)picolinamide;
I-190: N-(1-(2-(2-methoxyethoxy)ethyl)-3-(pyridin-2-yl)-1H-pyrazol-4-yl)-5'-methyl-[2,3'-bipyridine]-6-carboxamide;
I-191: N-(1-(2-(2-methoxyethoxy)ethyl)-3-(pyridin-2-yl)-1H-pyrazol-4-yl)-6-(1H-pyrazol-3-yl)picolinamide;
I-192: 6-(furan-3-yl)-N-(1-(2-(2-methoxyethoxy)ethyl)-3-(pyridin-2-yl)-1H-pyrazol-4-yl)picolinamide;
I-193: 6-(furan-2-yl)-N-(1-(2-(2-methoxyethoxy)ethyl)-3-(pyridin-2-yl)-1H-pyrazol-4-yl)picolinamide;
I-193: 6-(furan-2-yl)-N-(1-(2-(2-methoxyethoxy)ethyl)-3-(pyridin-2-yl)-1H-pyrazol-4-yl)picolinamide;
I-194: N-(1-(2-(2-methoxyethoxy)ethyl)-3-(pyridin-2-yl)-1H-pyrazol-4-yl)-6-(1H-pyrazol-4-yl)picolinamide;
I-195: 6-((1H-indazol-5-yl)amino)-N-(1-(2-(2-methoxyethoxy)ethyl)-3-(pyridin-2-yl)-1H-pyrazol-4-yl)picolinamide;
I-196: 6-((2H-indazol-5-yl)amino)-N-(1-(2-(2-methoxyethoxy)ethyl)-3-(pyridin-2-yl)-1H-pyrazol-4-yl)picolinamide;
I-197: 6-((2-aminopyridin-4-yl)oxy)-N-(1-(2-(2-methoxyethoxy)ethyl)-3-(pyridin-2-yl)-1H-pyrazol-4-yl)picolinamide;
I-198: 6-((2,5-dimethylpyridin-4-yl)amino)-N-(1-(2-(2-methoxyethoxy)ethyl)-3-(pyridin-2-yl)-1H-pyrazol-4-yl)picolinamide;
I-199: N-(1-(2-(2-methoxyethoxy)ethyl)-3-(pyridin-2-yl)-1H-pyrazol-4-yl)-6-((6-(4-methylpiperazin-1-yl)-5-(trifluoromethyl)pyridin-3-yl)amino)picolinamide;
I-200: 2'-((cyclopropylmethyl)amino)-N-(1-methyl-3-(pyridin-2-yl)-1H-pyrazol-4-yl)-[2,4'-bipyridine]-6-carboxamide;
I-201: N-(1-methyl-3-(pyridin-2-yl)-1H-pyrazol-4-yl)-[2,4'-bipyridine]-6-carboxamide;
I-202: N-(1-methyl-3-(pyridin-2-yl)-1H-pyrazol-4-yl)-2'-((2,2,2-trifluoroethyl)amino)-[2,4'-bipyridine]-6-carboxamide;
I-203: N-(1-(3-methoxycyclobutyl)-3-(pyridin-2-yl)-1H-pyrazol-4-yl)-5'-methyl-[2,3'-bipyridine]-6-carboxamide;

I-204: N-(1-(3-methoxycyclobutyl)-3-(pyridin-2-yl)-1H-pyrazol-4-yl)-6-(1H-pyrazol-4-yl)picolinamide;

I-205: N-(1-((1r,4r)-4-ethoxycyclohexyl)-3-(pyrazin-2-yl)-1H-pyrazol-4-yl)-6-(1H-pyrazol-4-yl)picolinamide;

I-206: N-(1-((1r,4r)-4-ethoxycyclohexyl)-3-(pyrazin-2-yl)-1H-pyrazol-4-yl)-5'-methyl-[2,3'-bipyridine]-6-carboxamide;

I-207: N-(1-methyl-3-(pyrazin-2-yl)-1H-pyrazol-4-yl)-6-(1H-pyrazol-4-yl)picolinamide; or I-208: 5'-methyl-N-(1-methyl-3-(pyrazin-2-yl)-1H-pyrazol-4-yl)-[2,3'-bipyridine]-6-carboxamide.

B. Synthesis

Disclosed amide compounds can be prepared as exemplified below, and as will be understood by a person of ordinary skill in the art of organic synthesis. An exemplary synthesis may include the following 1st reaction step according to Scheme 1.

Scheme 1

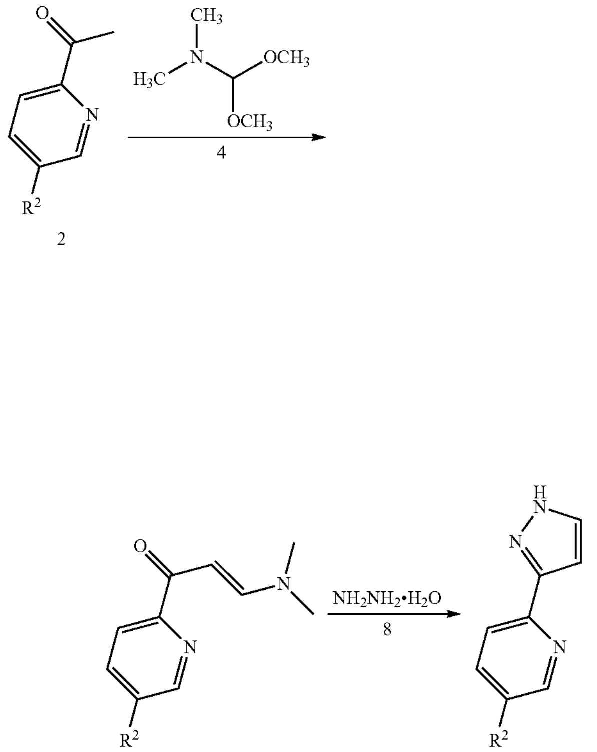

2 6 10

Acetyl compound 2 is reacted with dimethylformamide dimethylacetal 4 at a suitable reaction temperature, such as from about 85° C. to about 130° C., to form intermediate compound 6. Intermediate compound 6 is then reacted with hydrazine hydrate 8 to form pyrazole compound 10. The reaction is performed in a suitable solvent, for example, an alcohol, such as ethanol, methanol or isopropanol, and is typically heated, such as to reflux.

A 2nd reaction step in the exemplary synthesis is provided below according to Scheme 2.

Scheme 2

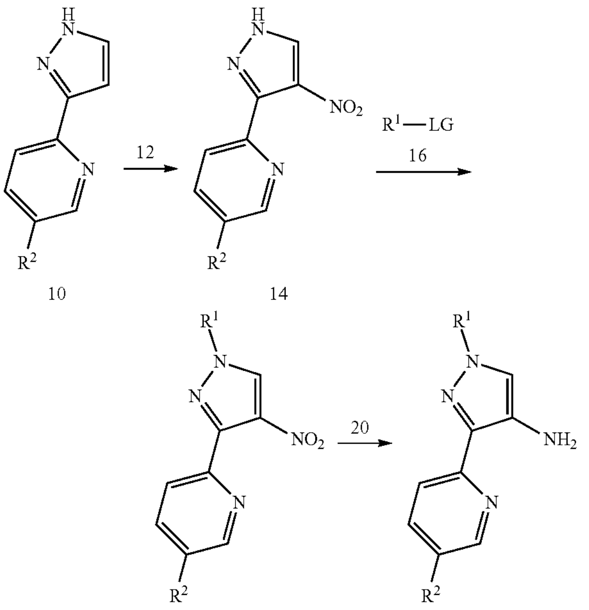

10 14 18 22

Compound 10 is nitrated using a suitable nitrating reagent or mixture of reagents 12 to form compound 14. Suitable nitrating conditions include reacting compound 10 with nitric acid, such as fuming nitric acid, optionally in the presence of sulfuric acid. Typically, compound 10 and the nitric acid are added slowly, one to the other. Cooling, such as by using an ice bath, may be used to maintain the reaction temperature within a suitable range, such as from about 0° C. to less than 50° C., from 0° C. to 20° C., or from 0 OC to 10° C. After the addition is complete the reaction is allowed to proceed until the reaction is substantially complete, and may be allowed to warm to room temperature to facilitate the reaction. Optionally, additional nitrating reagent, or mixture of nitrating reagents, may be added to facilitate the reaction proceeding to completion. The reaction is then quenched, such as by addition to water and/or ice, and the product is separated or extracted from the aqueous and purified if required. Purification techniques suitable for purifying a product from any reaction disclosed herein include, but are not limited to, crystallization, distillation and/or chromatography.

With continued reference to Scheme 2, compound 14 is then reacted with compound 16 to form compound 18. Compound 16 comprises a desired $R^1$ moiety and a suitable leaving group, LG. Suitable leaving groups include any group that will act as a leaving group to facilitate the addition of the $R^1$ moiety to compound 14. Suitable leaving groups include, but are not limited to, halogens, typically bromo, chloro or iodo, and tosylate or mesylate groups. Compound 14 is reacted with compound 16 in a suitable solvent and typically in the presence of a base. Suitable solvents include any solvent that facilitates the reaction, such as aprotic solvents. Suitable solvents include, but are not limited to, DMF (dimethylformamide), THF (tetrahydrofuran), DMSO (dimethylsulfoxide), acetonitrile, chlorinated solvents such as dichloromethane and chloroform, DMA (dimethylacetamide), dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may proceed at room temperature, or the reaction mixture may be heated, such as to 50° C., 100° C. or higher, as required. Compound 18 is then isolated from the reaction mixture and purified if required.

Compound 18 is then reacted with a reducing agent 20 suitable to reduce the nitro moiety to an amine. Suitable reducing agents include, but are not limited to: hydrogen gas in the presence of a catalyst, such as a palladium catalyst; a borohydride, such as sodium borohydride, optionally in the presence of a catalyst, such as a nickel catalyst; zinc metal in acetic acid; or iron powder in water or water and acid. In certain embodiments, hydrogen gas is used in combination with a palladium on carbon catalyst, and in a suitable solvent, such as ethyl acetate or methanol. In some embodiments, a combination of reducing agents and/or techniques are used. For example, reduction may be initially performed using a first method comprising a first reducing agent and/or technique, but result in a mixture of products. The first method may be repeated, and/or a second method may be performed, comprising a second reducing agent and/or technique. Once the reaction is complete, as indicated by an analytical technique such as LC-MS, TLC or HPLC, the product compound 22 is isolated and purified if necessary.

A 3rd step of the exemplary reaction sequence is provided below according to Scheme 3.

Scheme 3

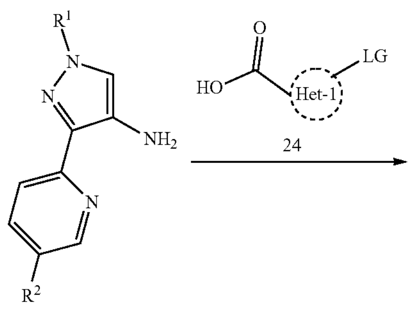

22

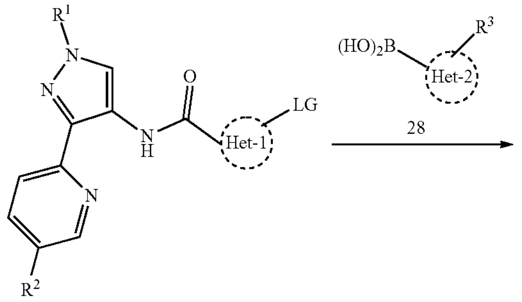

26

-continued

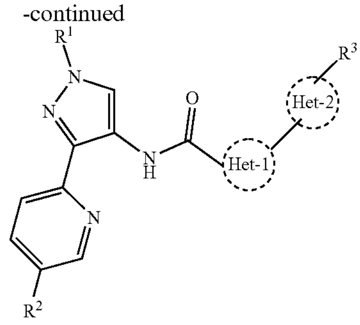

30

Compound 22 is reacted with a carboxylic acid 24 to form amide 26. The carboxylic acid 24 may be activated by any suitable method and then reacted with amine 22. Suitable activation methods include, but are not limited to: forming the acid chloride, such as by treatment with thionyl chloride; treatment with 1-[Bis(dimethylamino)methylene]-1H-1,2,3-triazolo[4,5-b]pyridinium 3-oxid hexafluorophosphate (HATU) and a base such as diisopropylethylamine (DIPEA); treatment with carbonyldiimidazole (CDI); or treatment with a carbodiimide, such as dicyclohexylcarbodiimide (DCC) or 1-ethyl-3-(3-dimethylaminopropyl)carbodiimide (EDC).

Amide 26 is then coupled with compound 28 to form compound 30 using any coupling reaction suitable to form a bond between two rings. In the example of Scheme 3, a boronic acid coupling is shown using boronic acid 28, where the leaving group LG on compound 26 is typically bromo or iodo. Other suitable coupling functional groups include trialkyl tin or boronic esters. The coupling reaction typically proceeds in the presence of a suitable catalyst. For a boronic acid coupling, the catalyst typically is a palladium catalyst, such as $PdCl_2(dppf)_2$, $Pd[P(Ph)_3]_2Cl_2$, palladium acetate and triphenyl phosphine, or tetrakis(triphenylphosphine)palladium(0). The reaction is performed in the presence of a base, such as sodium, potassium or cesium carbonate, and is performed in a suitable solvent or solvent mixture, such as dioxane, dioxane/water or DME (dimethoyethane)/ethanol/water. The reaction may be heated at a suitable temperature, such as to a temperature within the range of greater than room temperature up to the boiling point of the selected solvent, such as at a temperature of 50° C. to 125° C., typically about 100° C., and/or agitated for a suitable period of time, such as from 1 hour to 3 days, from 6 hours to 24 hours, or from 12 hours to 18 hours, to facilitate the reaction proceeding to completion. Compound 30 is then isolated from the reaction mixture and purified by a suitable technique.

An alternative exemplary synthesis may include the following 1st reaction step according to Scheme 4.

Scheme 4

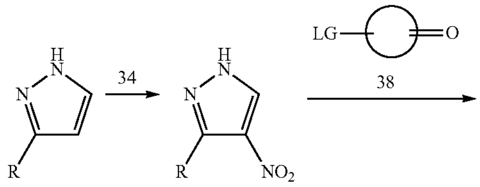

32

36

-continued

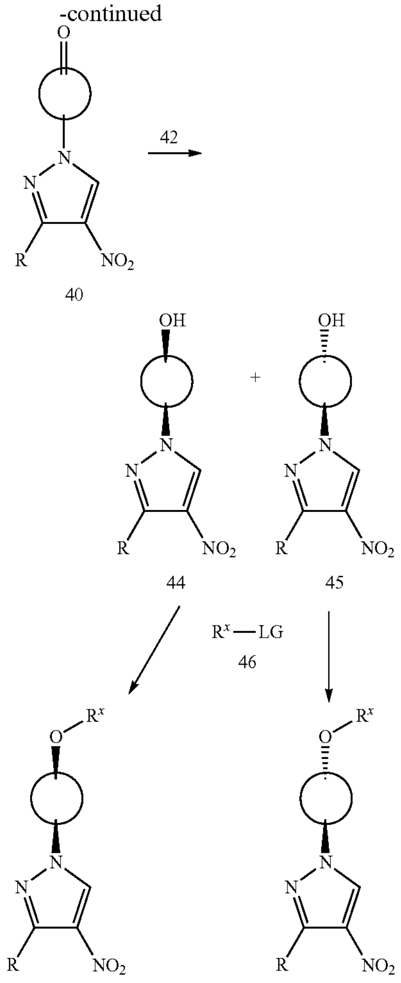

40

44 45

48 49

Compound 32 is nitrated using a suitable nitrating reagent or mixture of reagents 34 to form compound 36. Suitable nitrating conditions include reacting compound 32 with nitric acid, such as fuming nitric acid, optionally in the presence of sulfuric acid. Typically, compound 32 and the nitric acid are added slowly, one to the other. Cooling, such as by using an ice bath, may be used to maintain the reaction temperature within a suitable range, such as from about 0° C. to less than 50° C., from 0° C. to 20° C., or from 0 OC to 10° C. After the addition is complete the reaction is allowed to proceed until the reaction is substantially complete, and may be allowed to warm to room temperature to facilitate the reaction. Optionally, additional nitrating reagent, or mixture of nitrating reagents, may be added to facilitate the reaction proceeding to completion. The reaction is then quenched, such as by addition to water and/or ice, and the product is separated or extracted from an aqueous phase and purified if required. Purification techniques suitable for purifying a product from any reaction disclosed herein include, but are not limited to, crystallization, distillation and/or chromatography.

With continued reference to Scheme 4, compound 36 is then reacted with compound 38 to form compound 40. Compound 38 comprises a desired ring as discussed with reference to the general formulas, including by way of example, a cyclobutyl, cyclopentyl, or cyclohexyl ring, and a suitable leaving group, LG. Suitable leaving groups include any group that will act as a leaving group to facilitate the addition of the ring to compound 36. Suitable leaving groups include, but are not limited to, halogens, typically bromo, chloro or iodo, and tosylate or mesylate groups. Compound 36 is reacted with compound 38 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof.

Suitable bases include any base that will facilitate the reaction, such as a hydride, typically sodium hydride, or a carbonate, such as potassium carbonate, sodium carbonate, or cesium carbonate. The reaction may proceed at room temperature, or the reaction mixture may be heated, such as to a temperature within the range of greater than room temperature up to the boiling point of the selected solvent, such as at 50° C., 100° C. or higher, as required. Compound 40 is then isolated from the reaction mixture and purified if required.

Compound 40 is then reacted with a reducing agent 42 suitable to reduce the carbonyl moiety to a hydroxyl group. Suitable reducing agents include, but are not limited to, sodium borohydride, di-isobutyl aluminum hydride, or lithium aluminum hydride. The reaction is performed in a solvent suitable to facilitate the reaction, such as an alcohol, particularly methanol or ethanol, THF, or diethyl ether. The reaction may proceed at room temperature, or the reaction mixture may be heated, such as to a temperature of greater than room temperature up to the boiling point of the selected solvent, such as a temperature of 50° C., 100° C. or higher. Alternatively, the reaction mixture may be cooled as required, such as to below 20° C., below 10° C., or below 0° C. Once the reaction is complete, as indicated by an analytical technique such as LC-MS, TLC or HPLC, the product compound 44 is isolated and purified if necessary, by a suitable technique, such as column chromatography. Alternatively, or additionally, compound 45 may isolated.

Optionally, compound 44, and/or compound 45, may be reacted with compound 46 to form compound 48 and/or compound 49. Compound 46 comprises a desired $R^x$ moiety and a suitable leaving group, LG. Suitable leaving groups include any group that will act as a leaving group to facilitate the addition of the $R^x$ moiety to compound 44 and/or compound 45. Suitable leaving groups include, but are not limited to, halogens, typically bromo, chloro or iodo, and tosylate or mesylate groups. Compound 44/45 is reacted with compound 46 in a suitable solvent and typically in the presence of a base or other reagent or reagents that facilitate the reaction. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases or reagents that facilitate the reaction include, but are not limited to, silver triflate, 2,6-di-t-butylpyridine, sodium hydride, or combinations thereof. Typically, compound 46 is slowly added to the reaction mixture. Cooling, such as by an ice bath, may be used to maintain the reaction temperature within a suitable range, such as from about 0° C. to less than 50° C., from 0° C. to 20° C., or from 0 OC to 10° C. After the addition of 46 is complete the reaction is allowed to proceed until the reaction is substantially complete, and may be allowed to warm to room temperature, or the reaction may be heated to a temperature within the range of greater than room temperature up to the boiling point of the selected solvent, such as 50° C., 100° C. or higher, to facilitate the reaction. Once the reaction is complete, as may be indicated by an analytical technique such as LC-MS, TLC or HPLC, the product compound 48 and/or compound 49 is isolated and purified if necessary, by a suitable technique, such as column chromatography.

Another exemplary synthetic route to compound 48 and/or compound 49 is illustrated in Scheme 5.

Scheme 5

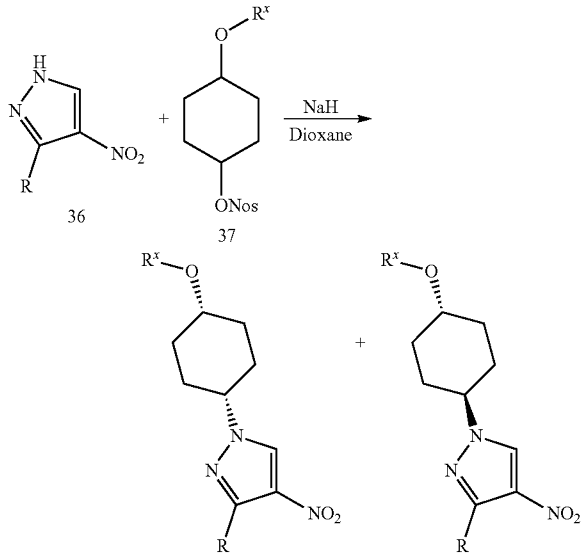

36 37

48 49

With reference to Scheme 5, compound 36 is dissolved in a suitable solvent with cooling, and treated with a base, such as sodium hydride. Suitable solvents include, but are not limited to, aprotic solvents, such as 1,4-dioxane, THF, DMF, acetonitrile, ether, or a combination thereof. Cyclohexyl compound 37 having a 4-nitrobenzenesulfone leaving group (nosyl, or Nos) is added and the reaction is heated at a temperature suitable to facilitate a reaction, such as at a temperature within a range of greater than room temperature up to the boiling point of the selected solvent, such as from 50° C. to 200° C. or higher, typically from 90° C. to 150° C. The reaction may be agitated, such as by shaking or stirring. Additional compound 37 may be added if necessary, to facilitate the reaction proceeding to completion.

The reaction mixture is quenched, such as by the addition of sodium bicarbonate solution, and the products are extracted into an organic solvent, such as ethyl acetate or chloroform. The compounds 48 and 49 can be separated and/or purified by any suitable technique, or combination of techniques, such as chromatography or trituration.

4-Nitrobenzensulfonate compound 37 may be prepared according to an exemplary synthetic route according to Scheme 6.

Scheme 6

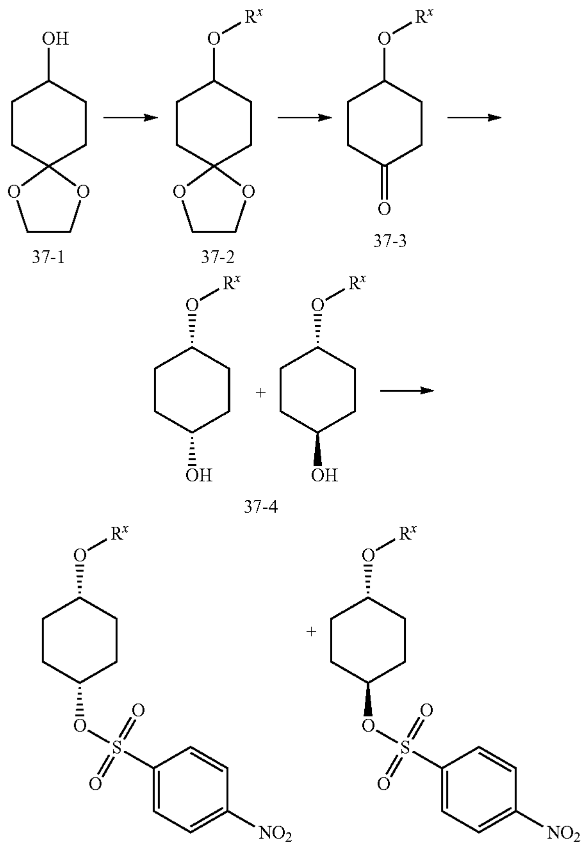

37-1 37-2 37-3

37-4

37

With reference to Scheme 6, 1,4-dioxaspiro[4.5]decan-8-ol 37-1 is treated first with a base, such as sodium hydride or potassium tert-butoxide, in a suitable solvent, and then with $R^x$-LG to form compound 37-2, where LG is a suitable leaving group, such as chloride, bromide, iodide, tosylate or mesylate. Suitable solvents include, but are not limited to, aprotic solvents, such as THF, DMF, acetonitrile, dioxane, ether, or a combination thereof. After the reaction has proceeded substantially to completion, aqueous acid, such as HCl, is added to quench the reaction and form compound 37-3.

Compound 37-3 is then treated with a reducing agent to form compound 37-4. Compound 37-4 may be substantially one isomer, or alternatively, compound 37-4 may be a mixture of cis and trans isomers, and in some embodiments, the compound 37-4 comprises about a 2:1 mixture of cis:trans isomers. The reducing agent may be any agent that can reduce the carbonyl moiety to an alcohol moiety. Suitable reducing agents include, but are not limited to, lithium aluminum hydride, diisobutylaluminum hydride, borane-THF, or a borohydride reagent, such as sodium borohydride. Solvents suitable to facilitate the reaction include, but are not limited to, THF, ether, or a combination thereof.

Compound 37-4 is then treated with 4-nitrobenzenesulfonyl chloride (nosyl) in the presence of a base, to form compound 37. The base may be any suitable base that facilitates the reaction, and may be an organic base, such as trimethylamine, 1,4-diazabicyclo[2.2.2]octane (DABCO), pyridine, or Hunig's base; or an inorganic base, such as potassium carbonate, sodium carbonate, or cesium carbonate. The reaction may proceed in a suitable solvent, typically an aprotic solvent such as pyridine, THF or a chlorinated solvent, such as dichloromethane or chloroform. Compound 37 may be substantially one isomer, or alternatively, compound 37 may be a mixture of isomers. The ratio of isomers may be modified by a suitable technique, such as chromatography or trituration. In some embodiments, the ratio of isomers is modified to about 8:1 cis to trans by trituration.

Alternatively, compound 40 may be prepared by an exemplary synthetic route according to Scheme 7.

Scheme 7

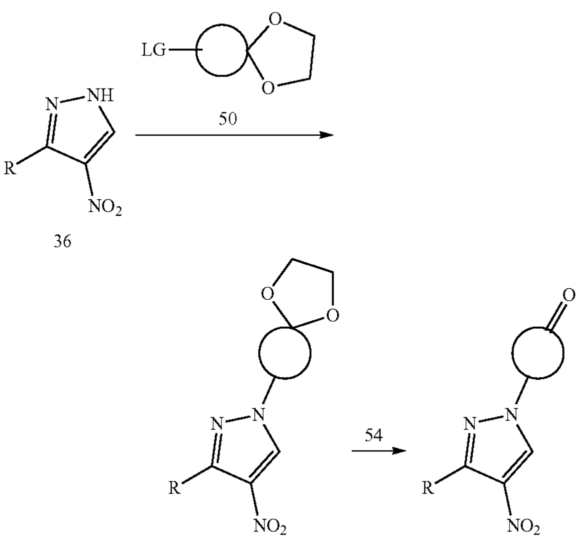

50

36

54

52

40

With respect to Scheme 7, compound 36 is reacted with compound 50 to form compound 52. Compound 50 comprises a desired ring, such as a cyclobutyl, cyclopentyl, or cyclohexyl ring, a suitable leaving group, LG, and a protected carbonyl moiety, such as an acetal or a ketal. In the example above a cyclic ketal moiety is shown. Suitable leaving groups include any group that will act as a leaving group to facilitate the addition of the ring to compound 36, and include, but are not limited to, halogens, typically bromo, chloro or iodo, and tosylate or mesylate groups. Compound 36 is reacted with compound 50 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may proceed at room temperature or alternatively the reaction mixture may be heated, such as at a temperature within the range of greater than room temperature up to the boiling point of the selected solvent, such as 50° C., 100° C. or higher, as required. Compound 52 is then isolated from the reaction mixture and purified if required by a suitable technique, such as column chromatography.

Compound 52 is then reacted with a suitable reagent 54 to form compound 40. Reagent 54 may be any reagent suitable to remove the protecting group and/or form the carbonyl moiety. In the exemplary synthesis shown in Scheme 5, the protecting group is a cyclic ketal, and suitable reagents 54 include, but are not limited to, pyridinium tosylate (PPTS), para-toluene sulfonic acid, hydrochloric acid, or acetic acid. The reaction is performed in a solvent or mixture of solvents suitable to facilitate the reaction, such as acetone, THF, acetic acid, water, or a combination thereof. The reaction may proceed at room temperature, or alternatively the reaction mixture may be heated, such as at a temperature within the range of greater than room temperature up to the boiling point of the selected solvent, such as 50° C., 100° C. or higher, as required. Compound 40 is then isolated from the reaction mixture and purified if required by a suitable technique, such as column chromatography.

A $2^{nd}$ step of the exemplary reaction sequence is provided below according to Scheme 8.

Scheme 8

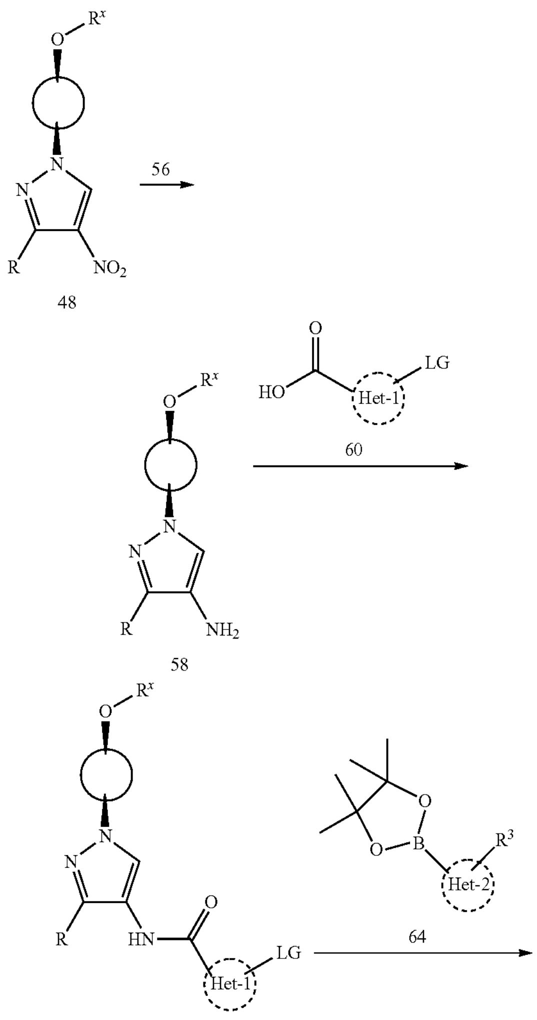

48

56

60

58

64

62

-continued

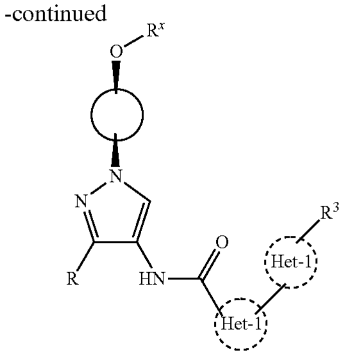

66

Compound 48 is reacted with a reducing agent 56 suitable to reduce the nitro moiety to an amine. In certain embodiments where the desired product compound comprises a hydroxyl moiety, compound 44 may be used in place of compound 48. Suitable reducing agents include, but are not limited to: hydrogen gas in the presence of a catalyst, such as a palladium catalyst; a borohydride, such as sodium borohydride, optionally in the presence of a catalyst, such as a nickel catalyst; zinc metal in acetic acid; or iron powder in water or water and acid. In certain embodiments, hydrogen gas is used, in the presence of a palladium on carbon catalyst, and in a suitable solvent, such as ethyl acetate or methanol. In some embodiments, a combination of reducing agents and/or techniques are used. For example, reduction may be initially performed using a first method comprising a first reducing agent and/or technique, but result in a mixture of products. The first method may be repeated, and/or a second method may be performed, comprising a second reducing agent and/or technique. Once the reaction is complete, as indicated by an analytical technique such as LC-MS, TLC or HPLC, the product compound 58 is isolated and purified if necessary.

Compound 58 is reacted with a carboxylic acid 60 to form amide 62. The carboxylic acid 60 is activated by any suitable method and then reacted with the amine functional group of compound 58. Suitable activation methods include, but are not limited to: forming the acid chloride by treatment with thionyl chloride; treatment with 1-[Bis(dimethylamino) methylene]-1H-1,2,3-triazolo[4,5-b]pyridinium 3-oxid hexafluorophosphate (HATU) and a base such as diisopropylethylamine (DIPEA); by treatment with carbonyldiimidazole (CDI); or treatment with a carbodiimide, such as dicyclohexylcarbodiimide (DCC) or 1-Ethyl-3-(3-dimethylaminopropyl)carbodiimide (EDC).

Compound 62 is then coupled with compound 64 to form compound 66 using any coupling reaction suitable to form a bond between two rings. In the example above, a boronic ester coupling is shown, where the leaving group LG on compound 62 is typically bromo or iodo. Other suitable coupling functional groups include trialkyl tin or boronic acids. The coupling reaction typically proceeds in the presence of a suitable catalyst. For a boronic ester or boronic acid coupling, the catalyst typically is a palladium catalyst, such as $PdCl_2(dppf)_2$, $Pd[P(Ph)_3]2Cl_2$, palladium acetate and triphenyl phosphine, or tetrakis(triphenylphosphine)palladium(0). The reaction is performed in the presence of a base, such as sodium, potassium or cesium carbonate, and is performed in a suitable solvent or solvent mixture, such as dioxane, dioxane/water or DME/ethanol/water. The reaction may be heated at a suitable temperature, such as from 50° C.

to 125° C., typically about 100° C., and/or agitated for a suitable period of time, such as from 1 hour to 3 days, from 6 hours to 24 hours, or from 12 hours to 18 hours, to facilitate the reaction proceeding to completion. Compound 66 is then isolated from the reaction mixture and purified by a suitable technique.

Certain embodiments may comprise a phosphate moiety. Scheme 9 provides an exemplary synthesis of certain such embodiments.

Scheme 9

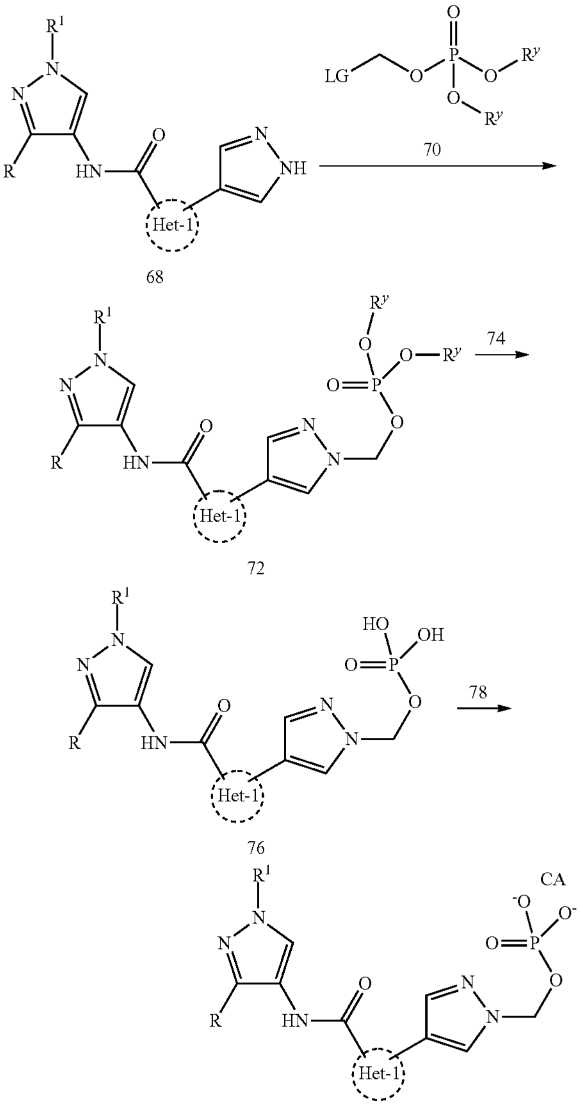

80

Compound 68 is reacted with compound 70 to form compound 72. Compound 70 comprises desired $R^y$ moieties and a suitable leaving group, LG. Typical $R^y$ moieties include, but are not limited to aliphatic, such as alkyl, typically methyl, ethyl, propyl, isopropyl or t-butyl; aryl; heteroaliphatic; or heterocyclic. The two $R^y$ moieties may be the same or different. Suitable leaving groups include, but are not limited to, halogens, typically bromo, chloro or iodo, and tosylate or mesylate groups. Compound 68 is reacted with compound 70 in a suitable solvent and typically in the presence of a base. Suitable solvents include any solvent that facilitates the reaction, such as aprotic solvents. Suitable solvents include, but are not limited to, DMF, THF, DMSO, acetonitrile, chlorinated solvents such as dichloromethane and chloroform, DMA, dioxane, N-methyl pyrrolidone, or combinations thereof. Suitable bases include any base that will facilitate the reactions, such as a hydride, typically sodium hydride, or a carbonate, such as potassium carbonate, sodium carbonate, or cesium carbonate. The reaction may proceed at room temperature, or alternatively the reaction mixture may be heated, such as at a temperature within the range of greater than room temperature up to the boiling point of the selected solvent, such as 50° C., 100° C. or higher, as required. Compound 72 is then isolated from the reaction mixture and purified if required.

Compound 72 is then reacted with compound 74 to form compound 76. Compound 74 may be any compound suitable to form the acid moieties in compound 76. Compound 74 may be an acidic reagent, such as trifluoroacetic acid, hydrochloride acid, or hydrobromic acid, or it may be a basic reagent, such as sodium hydroxide, lithium hydroxide or potassium hydroxide. Suitable solvents include, but are not limited to, chlorinated solvents such as dichloromethane and chloroform, alcohols such as methanol and ethanol, water, or combinations thereof. The reaction may proceed at room temperature, or alternatively the reaction mixture may be heated, such as at a temperature within the range of greater than room temperature up to the boiling point of the selected solvent, such as 50° C., 100° C. or higher, as required. The reaction mixture also may be cooled, such as to below 20° C., below 10° C., below 0° C. or lower. Once the reaction is complete, as indicated by an analytical technique such as LC-MS, TLC or HPLC, the product compound 76 is isolated and purified if necessary, by a suitable technique, such as by agitating, such as by stirring or sonication, in a suitable solvent or solvent system. Suitable solvents or solvent systems include, but are not limited to, acetone/water, acetone, diethyl ether, or alcohol/water.

Compound 76 is then reacted with compound 78 to form the salt compound 80. Compound 78 can be any compound that will provide a suitable counterion (CI) for the salt compound 80, such as calcium hydroxide, sodium hydroxide, potassium hydroxide, lithium hydroxide, ammonia, trimethylamine, tris(hydroxymethyl)aminomethane, or an amino acid such as lysine or arginine. A person of ordinary skill in the art will appreciate that if counter ion CI has a single positive charge, as in $Na^+$, $K^+$, $Li^+$, or $NH_4^+$, then compound 80 will comprise two CI ions, whereas if counter ion CI has two positive charges, as in $CI^{2+}$ compound 80 will comprise one CI ion.

C. Combinations of Therapeutic Agents

The amide compounds of the present invention may be used alone, in combination with one another, or as an adjunct to, or in combination with, other established therapies. In another aspect, the compounds of the present invention may be used in combination with other therapeutic agents useful for the disorder or condition being treated. These compounds may be administered simultaneously, sequentially in any order, by the same route of administration, or by a different route.

In some embodiments, the second therapeutic agent is an analgesic, an antibiotic, an anticoagulant, an antibody, an anti-inflammatory agent, an immunosuppressant, a guanylate cyclase-C agonist, an intestinal secretagogue, an antiviral, anticancer, antifungal, or a combination thereof. The anti-inflammatory agent may be a steroid or a nonsteroidal anti-inflammatory agent. In certain embodiments, the nonsteroidal anti-inflammatory agent is selected from aminosalicylates, cyclooxygenase inhibitors, diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin, or a combination thereof. In some embodiments, the immunosuppressant is mercaptopurine, a corticosteroid, an alkylating agent, a calcineurin inhibitor, an inosine monophosphate dehydrogenase inhibitor, antilymphocyte globulin, antithymocyte globulin, an anti-T-cell antibody, or a combination thereof. In one embodiment, the antibody is infliximab.

In some embodiments, the present compounds may be used with other anti-cancer or cytotoxic agents. Various classes of anti-cancer and anti-neoplastic compounds include, but are not limited to, alkylating agents, antimetabolites, BCL-2 inhibitors, vinca alkyloids, taxanes, antibiotics, enzymes, cytokines, platinum coordination complexes, proteasome inhibitors, substituted ureas, kinase inhibitors, hormones and hormone antagonists, and hypomethylating agents, for example DNMT inhibitors, such as azacitidine and decitabine. Exemplary alkylating agents include, without limitation, mechlorothamine, cyclophosphamide, ifosfamide, melphalan, chlorambucil, ethyleneimines, methylmelamines, alkyl sulfonates (e.g., busulfan), and carmustine. Exemplary antimetabolites include, by way of example and not limitation, folic acid analog methotrexate; pyrimidine analog fluorouracil, cytosine arbinoside; purine analogs mercaptopurine, thioguanine, and azathioprine. Exemplary vinca alkyloids include, by way of example and not limitation, vinblastine, vincristine, paclitaxel, and colchicine. Exemplary antibiotics include, by way of example and not limitation, actinomycin D, daunorubicin, and bleomycin. An exemplary enzyme effective as an antineoplastic agent includes L-asparaginase. Exemplary coordination compounds include, by way of example and not limitation, cisplatin and carboplatin. Exemplary hormones and hormone related compounds include, by way of example and not limitation, adrenocorticosteroids prednisone and dexamethasone; aromatase inhibitors amino glutethimide, formestane, and anastrozole; progestin compounds hydroxyprogesterone caproate, medroxyprogesterone; and anti-estrogen compound tamoxifen.

These and other useful anti-cancer compounds are described in Merck Index, 13th Ed. (O'Neil M. J. et al., ed.) Merck Publishing Group (2001) and Goodman and Gilman's The Pharmacological Basis of Therapeutics, 12th Edition, Brunton L.L. ed., Chapters 60-63, McGraw Hill, (2011), both of which are incorporated by reference herein.

Among the CTLA 4 antibodies that can be used in combination with the presently disclosed inhbitors is ipilimumab, marketed as YERVOY® by Bristol-Myers Squibb.

Other chemotherapeutic agents for combination include immunooncology agents, such as checkpoint pathway inhibitors, for example, PD-1 inhibitors, such as nivolumab and lambrolizumab, and PD-L1 inhibitors, such as pembrolizumab, MEDI-4736 and MPDL3280A/RG7446. Additional checkpoint inhibitors for combination with the compounds disclosed herein include, Anti-LAG-3 agents, such as BMS-986016 (MDX-1408).

Further chemotherapeutic agents for combination with the presently disclosed inhibitors include Anti-SLAMF7 agents, such as the humanized monoclonal antibody elotuzumab (BMS-901608), anti-KIR agents, such as the anti-KIR monoclonal antibody lirilumab (BMS-986015), and anti- CD137 agents, such as the fully human monoclonal antibody urelumab (BMS-663513).

Additional anti-proliferative compounds useful in combination with the compounds of the present invention include, by way of example and not limitation, antibodies directed against growth factor receptors (e.g., anti-Her2); and cytokines such as interferon-α and interferon-γ, interleukin-2, and GM-CSF.

Additional chemotherapeutic agents useful in combination with the present amide compounds include proteasome inhibitors, such as bortezomib, carfilzomib, marizomib and the like.

Examples of kinase inhibitors that are useful in combination with the presently disclosed compounds, particularly in treating malignancies include, Btk inhibitors, such as ibrutinib, CDK inhibitors, such as palbociclib, EGFR inhibitors, such as afatinib, erlotinib, gefitinib, lapatinib, osimertinib and vandetinib, Mek inhibitors, such as trametinib, Raf inhibitors, such as dabrafenib, sorafenib and vemurafenib, VEGFR inhibitors, such as axitinib, lenvatinib, nintedanib, pazopanib, BCR-Abl inhibitors, such as bosutinib, dasatinib, imatinib and nilotinib, Syk inhibitors, such as fostamatinib, and JAK inhibitors, such as ruxolitinib, In other embodiments, the second therapeutic agent may be selected from any of the following:

analgesics-morphine, fentanyl, hydromorphone, oxycodone, codeine, acetaminophen, hydrocodone, buprenorphine, tramadol, venlafaxine, flupirtine, meperidine, pentazocine, dextromoramide, dipipanone;

antibiotics-aminoglycosides (e.g., amikacin, gentamicin, kanamycin, neomycin, netilmicin, tobramycin, and paromycin), carbapenems (e.g., ertapenem, doripenem, imipenem, cilastatin, and meropenem), cephalosporins (e.g., cefadroxil, cefazolin, cefalotin, cephalexin, cefaclor, cefamandole, cefoxitin, cefprozil, cefuroxime, cefixime, cefdinir, cefditoren, cefoperazone, cefotaxime, cefpodoxime, ceftazidime, ceftibuten, ceftizoxime, ceftriaxone, cefepime, and cefobiprole), glycopeptides (e.g., teicoplanin, vancomycin, and telavancin), lincosamides (e.g., clindamycin and incomysin), lipopeptides) e.g., daptomycin), macrolides (azithromycin, clarithromycin, dirithromycin, erythromycin, roxithromycin, troleandomycin, telithromycin, and spectinomycin), monobactams (e.g., aztreonam), nitrofurans (e.g., furazolidone and nitrofurantoin), penicilllins (e.g., amoxicillin, ampicillin, azlocillin, carbenicillin, cloxacillin, dicloxacillin, flucloxacillin, mezlocillin, methicillin, nafcillin, oxacillin, penicillin G, penicillin V, piperacillin, temocillin, and ticarcillin), penicillin combinations (e.g., amoxicillin/clavulanate, ampicillin/sulbactam, piperacillin/tazobactam, and ticarcillin/clavulanate), polypeptides (e.g., bacitracin, colistin, and polymyxin B), quinolones (e.g., ciprofloxacin, enoxacin, gatifloxacin, levofloxacin, lomefloxacin, moxifloxacin, nalidixic acid, norfloxacin, ofloxacin, trovafloxacin, grepafloxacin, sparfloxacin, and temafloxacin), sulfonamides (e.g., mafenide, sulfonamidochrysoidine, sulfacetamide, sulfadiazine, silver sulfadiazine, sulfamethizole, sulfamethoxazole, sulfanilimide, sulfasalazine, sulfisoxazole, trimethoprim, and trimethoprim-sulfamethoxaxzole), tetracyclines (e.g., demeclocycline, doxycycline, minocycline, oxytetracycline, and tetracycline), antimycobacterial compounds (e.g., clofazimine, dapsone, capreomycin, cycloserine, ethambutol, ethionamide, isoniazid, pyrazinamide, rifampicin (rifampin), rifabutin, rifapentine, and streptomycin), and others, such as arsphenamine, chloramphenicol, fosfomycin, fusidic acid, linezolid, metronidazole, mupirocin, platensimycin, quinuprisin/dalfopristin, rifaximin, thiamphenicol, tigecycline, and timidazole;

antibodies-anti-TNF-α antibodies, e.g., infliximab (Remicader™), adalimumab, golimumab, certolizumab; anti-B cell antibodies, e.g., rituximab; anti-IL-6 antibodies, e.g., tocilizumab; anti-IL-1 antibodies, e.g., anakinra; anti PD-1 and/or anti-PD-L1 antibodies, e.g. nivolumab, pembrolizumab, pidilizumab, BMS-936559, MPDL3280A, AMP-224, MEDI4736; ixekizumab, brodalumab, ofatumumab, sirukumab, clenoliximab, clazakiumab, fezakinumab, fletikumab, mavrilimumab, ocrelizumab, sarilumab, secukinumab, toralizumab, zanolimumab;

anticoagulants-warfarin (Coumadin™), acenocoumarol, phenprocoumon, atromentin, phenindione, heparin, fondaparinux, idraparinux, rivaroxaban, apixaban, hirudin, lepirudin, bivalirudin, argatrobam, dabigatran, ximelagatran, batroxobin, hementin;

anti-inflammatory agents-steroids, e.g., budesonide, nonsteroidal anti-inflammatory agents, e.g., aminosalicylates (e.g., sulfasalazine, mesalamine, olsalazine, and balsalazide), cyclooxygenase inhibitors (COX-2 inhibitors, such as rofecoxib, celecoxib), diclofenac, etodolac, famotidine, fenoprofen, flurbiprofen, ketoprofen, ketorolac, ibuprofen, indomethacin, meclofenamate, mefenamic acid, meloxicam, nambumetone, naproxen, oxaprozin, piroxicam, salsalate, sulindac, tolmetin;

immunosuppressants-mercaptopurine, corticosteroids such as dexamethasone, hydrocortisone, prednisone, methylprednisolone and prednisolone, alkylating agents such as cyclophosphamide, calcineurin inhibitors such as cyclosporine, sirolimus and tacrolimus, inhibitors of inosine monophosphate dehydrogenase (IMPDH) such as mycophenolate, mycophenolate mofetil and azathioprine, and agents designed to suppress cellular immunity while leaving the recipient's humoral immunologic response intact, including various antibodies (for example, antilymphocyte globulin (ALG), antithymocyte globulin (ATG), monoclonal anti-T-cell antibodies (OKT3)) and irradiation. Azathioprine is currently available from Salix Pharmaceuticals, Inc. under the brand name Azasan; mercaptopurine is currently available from Gate Pharmaceuticals, Inc. under the brand name Purinethol; prednisone and prednisolone are currently available from Roxane Laboratories, Inc.; Methyl prednisolone is currently available from Pfizer; sirolimus (rapamycin) is currently available from Wyeth-Ayerst under the brand name Rapamune; tacrolimus is currently available from Fujisawa under the brand name Prograf; cyclosporine is current available from Novartis under the brand name Sandimmune and Abbott under the brand name Gengraf; IMPDH inhibitors such as mycophenolate mofetil and mycophenolic acid are currently available from Roche under the brand name Cellcept and Novartis under the brand name Myfortic; azathioprine is currently available from Glaxo Smith Kline under the brand name Imuran; and antibodies are currently available from Ortho Biotech under the brand name Orthoclone, Novartis under the brand name Simulect (basiliximab) and Roche under the brand name Zenapax (daclizumab); and Guanylate cyclase-C receptor agonists or intestinal secretagogues—for example linaclotide, sold under the name Linzess.

These various agents can be used in accordance with their standard or common dosages, as specified in the prescribing information accompanying commercially available forms of the drugs (see also, the prescribing information in the 2006

Edition of The Physician's Desk Reference), the disclosures of which are incorporated herein by reference.

D. Compositions Comprising Amide Compounds

The disclosed amide compounds may be used alone, in any combination, and in combination with, or adjunctive to, at least one second therapeutic agent, and further the amide compounds, and the at least one second therapeutic, may be used in combination with any suitable additive useful for forming compositions for administration to a subject. Additives can be included in pharmaceutical compositions for a variety of purposes, such as to dilute a composition for delivery to a subject, to facilitate processing of the formulation, to provide advantageous material properties to the formulation, to facilitate dispersion from a delivery device, to stabilize the formulation (e.g., antioxidants or buffers), to provide a pleasant or palatable taste or consistency to the formulation, or the like. Typical additives include, by way of example and without limitation: pharmaceutically acceptable excipients; pharmaceutically acceptable carriers; and/or adjuvants, such as mono-, di-, and polysaccharides, sugar alcohols and other polyols, such as, lactose, glucose, raffinose, melezitose, lactitol, maltitol, trehalose, sucrose, mannitol, starch, or combinations thereof; surfactants, such as sorbitols, diphosphatidyl choline, and lecithin; bulking agents; buffers, such as phosphate and citrate buffers; anti-adherents, such as magnesium stearate; binders, such as saccharides (including disaccharides, such as sucrose and lactose,), polysaccharides (such as starches, cellulose, microcrystalline cellulose, cellulose ethers (such as hydroxypropyl cellulose), gelatin, synthetic polymers (such as polyvinylpyrrolidone, polyalkylene gylcols); coatings (such as cellulose ethers, including hydroxypropylmethyl cellulose, shellac, corn protein zein, and gelatin); release aids (such as enteric coatings); disintegrants (such as crospovidone, crosslinked sodium carboxymethyl cellulose, and sodium starch glycolate); fillers (such as dibasic calcium phosphate, vegetable fats and oils, lactose, sucrose, glucose, mannitol, sorbitol, calcium carbonate, and magnesium stearate); flavors and sweeteners (such as mint, cherry, anise, peach, apricot or licorice, raspberry, and vanilla; lubricants (such as minerals, exemplified by talc or silica, fats, exemplified by vegetable stearin, magnesium stearate or stearic acid); preservatives (such as antioxidants exemplified by vitamin A, vitamin E, vitamin C, retinyl palmitate, and selenium, amino acids, exemplified by cysteine and methionine, citric acid and sodium citrate, parabens, exemplified by methyl paraben and propyl paraben); colorants; compression aids; emulsifying agents; encapsulation agents; gums; granulation agents; and combinations thereof.

III. Methods of Use

A. Diseases/Disorders

The disclosed amide compounds, as well as combinations and/or compositions thereof, may be used to ameliorate, treat or prevent a variety of diseases and/or disorders. In particular embodiments, the amide compound, combinations of amide compounds, or compositions thereof, may be useful for treating conditions in which inhibition of an interleukin-1 receptor-associated kinase (IRAK) pathway is therapeutically useful. In some embodiments, the compounds directly inhibit an IRAK protein, such as IRAK1, IRAK2, IRAK3, IRAK4, or a combination thereof. In certain embodiments, disclosed amide compounds are useful for treating, preventing or ameliorating auto-immune diseases, inflammatory disorders, cardiovascular diseases, nerve disorders, neurodegenerative disorders, allergic disorders, asthma, pancreatitis, multi-organ failure, kidney diseases, platelet aggregation, cancer, transplantation, sperm motility, erythrocyte deficiency, graft rejection, lung injuries, respiratory diseases, ischemic conditions, and bacterial and viral infections.

In some embodiments, the amide compound, combinations of amide compounds, or compositions thereof, may be used to treat or prevent allergic diseases, amyotrophic lateral sclerosis (ALS), systemic lupus erythematosus, rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, Wegener's granulomatosis, ichthyosis, Graves ophthalmyopathy or asthma.

The amide compound, combinations of amide compounds, or compositions thereof, may also be useful for ameliorating, treating or preventing immune regulatory disorders related to bone marrow or organ transplant rejection or graft-versus-host disease. Examples of inflammatory and immune regulatory disorders that can be treated with the present compounds include, but are not limited to, transplantation of organs or tissue, graft-versus-host diseases brought about by transplantation, autoimmune syndromes including rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, celiac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjdgren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic liver disease, including alcoholic cirrhosis, non-alcoholic steatohepatitis (NASH), hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, Parkinson's disease, trauma, or chronic bacterial infection.

In certain embodiments the present compounds are useful for treating nerve pain, including neuropathic pain and inflammation induced pain.

In certain embodiments, the amide compound, combinations of amide compounds, or compositions thereof, are useful for treating and/or preventing rheumatoid arthritis, psoriatic arthritis, osteoarthritis, systemic lupus erythematosus, lupus nephritis, ankylosing spondylitis, osteoporosis, systemic sclerosis, multiple sclerosis, psoriasis, in particular pustular psoriasis, type I diabetes, type II diabetes, inflammatory bowel disease (Crohn's disease and ulcerative colitis), hyperimmunoglobulinemia d and periodic fever syndrome, cryopyrin-associated periodic syndromes, Schnitzler's syndrome, systemic juvenile idiopathic arthritis, adult's onset Still's disease, gout, gout flares, pseudogout, sapho syndrome, Castleman's disease, sepsis, stroke, atherosclerosis, celiac disease, DIRA (deficiency of I1-1 receptor antagonist), Alzheimer's disease, Parkinson's disease.

Proliferative diseases that may be treated by the amide compound, combinations of amide compounds, or compositions thereof, include benign or malignant tumors, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, IL-1 driven disorders, a MyD88 driven disorder (such as ABC diffuse large B-cell lymphoma (DLBCL), Waldenström's macroglobulinemia, Hodgkin's lymphoma, primary cutaneous T-cell lymphoma or chronic lymphocytic leukemia), smoldering or indolent multiple myeloma, or hematological malignancies (including leukemia, acute myeloid leukemia (AML), DLBCL, ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, myelodysplastic syndromes (MDS), myelofibrosis, polycythemia vera, Kaposi's sarcoma, Waldenström's macroglobulinemia (WM), splenic marginal zone lymphoma, multiple myeloma, plasmacytoma, intravascular large B-cell lymphoma). In particular, the presently disclosed compounds are useful in treating drug resistant malignancies, such as those resistant to JAK inhibitors ibrutinib resistant malignancies, including ibrutinib resistant hematological malignancies, such as ibrutinib resistant CLL and ibrutinib resistant Waldenström's macroglobulinemia.

Examples of allergic disorders that may be treated using the amide compound, combinations of amide compounds, or compositions thereof, include, but are not limited to, asthma (e.g. atopic asthma, allergic asthma, atopic bronchial IgE-mediated asthma, non-atopic asthma, bronchial asthma, non-allergic asthma, essential asthma, true asthma, intrinsic asthma caused by pathophysiologic disturbances, essential asthma of unknown or unapparent cause, emphysematous asthma, exercise-induced asthma, emotion-induced asthma, extrinsic asthma caused by environmental factors, cold air induced asthma, occupational asthma, infective asthma caused by or associated with bacterial, fungal, protozoal, or viral infection, incipient asthma, wheezy infant syndrome, bronchiolitis, cough variant asthma or drug-induced asthma), allergic bronchopulmonary aspergillosis (ABPA), allergic rhinitis, perennial allergic rhinitis, perennial rhinitis, vasomotor rhinitis, post-nasal drip, purulent or non-purulent sinusitis, acute or chronic sinusitis, and ethmoid, frontal, maxillary, or sphenoid sinusitis.

As another example, rheumatoid arthritis (RA) typically results in swelling, pain, loss of motion and tenderness of target joints throughout the body. RA is characterized by chronically inflamed synovium that is densely crowded with lymphocytes. The synovial membrane, which is typically one cell layer thick, becomes intensely cellular and assumes a form similar to lymphoid tissue, including dendritic cells, T-, B- and NK cells, macrophages and clusters of plasma cells. This process, as well as a plethora of immunopathological mechanisms including the formation of antigen-immunoglobulin complexes, eventually result in destruction of the integrity of the joint, resulting in deformity, permanent loss of function and/or bone erosion at or near the joint. The amide compound, combinations of amide compounds, or compositions thereof, may be used to treat, ameliorate or prevent any one, several or all of these symptoms of RA. Thus, in the context of RA, the compounds are considered to provide therapeutic benefit when a reduction or amelioration of any of the symptoms commonly associated with RA is achieved, regardless of whether the treatment results in a concomitant treatment of the underlying RA and/or a reduction in the amount of circulating rheumatoid factor ("RF").

The American College of Rheumatology (ACR) has developed criteria for defining improvement and clinical remission in RA. Once such parameter, the ACR20 (ACR criteria for 20% clinical improvement), requires a 20% improvement in the tender and swollen joint count, as well as a 20% improvement in 3 of the following 5 parameters: patient's global assessment, physician's global assessment, patient's assessment of pain, degree of disability, and level of acute phase reactant. These criteria have been expanded for 50% and 70% improvement in ACR50 and ACR70, respectively. Other criteria include Paulu's criteria and radiographic progression (e.g. Sharp score).

In some embodiments, therapeutic benefit in patients suffering from RA is achieved when the patient exhibits an ACR20. In specific embodiments, ACR improvements of ACRC50 or even ACR70 may be achieved.

B. Formulations and Administration

Pharmaceutical compositions comprising one or more active amide compounds of the invention (or prodrugs thereof) may be manufactured by mixing, dissolving, granulating, dragee-making, levigating, emulsifying, encapsulating, entrapping or lyophilization processes. The compositions may be formulated using one or more physiologically acceptable excipients, diluents, carriers, adjuvants or auxiliaries to provide preparations which can be used pharmaceutically.

The active compound(s) or prodrug(s) may be formulated in the pharmaceutical compositions per se, or in the form of a hydrate, solvate, N-oxide or pharmaceutically acceptable salt. Typically, such salts are more soluble in aqueous solutions than the corresponding free acids and bases, but salts having lower solubility than the corresponding free acids and bases may also be formed.

Pharmaceutical compositions of the invention may take a form suitable for virtually any mode of administration, including, for example, topical, ocular, oral, buccal, systemic, nasal, injection, such as i.v. or i.p., transdermal, rectal, vaginal, etc., or a form suitable for administration by inhalation or insufflation.

For topical administration, the active compound(s), hydrate, solvate, N-oxide or pharmaceutically acceptable salt or prodrug(s) may be formulated as solutions, gels, ointments, creams, suspensions, etc. as are well-known in the art.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the active compound(s) in aqueous or oily vehicles. The compositions may also contain formulating agents, such as suspending, stabilizing and/or dispersing agent. The formulations for injection may be presented in unit dosage form, e.g., in ampules or in multidose containers, and may contain added preservatives.

Alternatively, the injectable formulation may be provided in powder form for reconstitution with a suitable vehicle, including but not limited to sterile, pyrogen-free water, buffer, dextrose solution, etc., before use. To this end, the active compound(s) maybe dried by any art-known technique, such as lyophilization, and reconstituted prior to use.

For transmucosal administration, penetrants appropriate to the barrier to be permeated are used in the formulation. Such penetrants are known in the art.

For oral administration, the pharmaceutical compositions may take the form of, for example, lozenges, tablets or capsules prepared by conventional means with pharmaceutically acceptable excipients, such as: binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); and/or wetting agents (e.g., sodium lauryl sulfate). The tablets may be coated by methods well known in the art with, for example, sugars, films or enteric coatings.

Liquid preparations for oral administration may take the form of, for example, elixirs, solutions, syrups or suspensions, or they may be presented as a dry product for constitution with water or other suitable vehicle before use. Such liquid preparations may be prepared by conventional means with pharmaceutically acceptable additives such as: suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol, Cremophore™ or fractionated vegetable oils); and preservatives (e.g., methyl or propyl-p-hydroxybenzoates or sorbic acid). The preparations may also contain buffer salts, preservatives, flavoring, coloring and sweetening agents as appropriate.

Preparations for oral administration may be suitably formulated to give controlled release of the active compound or prodrug, as is well known.

For buccal administration, the compositions may take the form of tablets or lozenges formulated in conventional manner.

For rectal and vaginal routes of administration, the active compound(s) may be formulated as solutions (for retention enemas) suppositories or ointments containing conventional suppository bases, such as cocoa butter or other glycerides.

For nasal administration or administration by inhalation or insufflation, the active compound(s), hydrate, solvate, N-oxide, pharmaceutically acceptable salt or prodrug(s) can be conveniently delivered in the form of an aerosol spray from pressurized packs or a nebulizer with the use of a suitable propellant, e.g.,) dichlorodifluoromethane, trichlorofluoromethane, dichlorotetrafluoroethane, fluorocarbons, carbon dioxide or other suitable gas. In the case of a pressurized aerosol, the dosage unit may be determined by providing a valve to deliver a metered amount. Capsules and cartridges for use in an inhaler or insufflator (for example capsules and cartridges comprised of gelatin) may be formulated containing a powder mix of the compound and a suitable powder base such as lactose or starch.

A specific example of an aqueous suspension formulation suitable for nasal administration using commercially-available nasal spray devices includes the following ingredients: active compound or prodrug (0.5 20 mg/ml); benzalkonium chloride (0.1 0.2 mg/mL); polysorbate 80 (TWEEN® 80; 0.5 5 mg/ml); carboxymethylcellulose sodium or microcrystalline cellulose (115 mg/ml); phenylethanol (14 mg/ml); and dextrose (20 50 mg/ml). The pH of the final suspension can be adjusted to range from about pH 5 to pH 7, with a pH of about pH 5.5 being typical.

Another specific example of an aqueous suspension suitable for administration of the compounds via inhalation contains 20 mg/mL of the amide compound(s) or prodrug(s), 1% (v/v) polysorbate 80 (TWEEN® 80), 50 mM citrate and/or 0.9% sodium chloride.

For ocular administration, the active amide compound(s) or prodrug(s) may be formulated as a solution, emulsion, suspension, etc. suitable for administration to the eye. A variety of vehicles suitable for administering compounds to the eye are known in the art. Specific non-limiting examples are described in U.S. Pat. Nos. 6,261,547; 6,197,934; 6,056,950; 5,800,807; 5,776,445; 5,698,219; 5,521,222; 5,403,841; 5,077,033; 4,882,150; and 4,738,851, which are incorporated herein by reference.

For prolonged delivery, the active amide compound(s) or prodrug(s) can be formulated as a depot preparation for administration by implantation or intramuscular injection.

The active ingredient maybe formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch which slowly releases the active compound(s) for percutaneous absorption may be used. To this end, permeation enhancers may be used to facilitate transdermal penetration of the active compound(s). Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475, which are incorporated herein by reference.

Alternatively, other pharmaceutical delivery systems may be employed. Liposomes and emulsions are well-known examples of delivery vehicles that may be used to deliver active compound(s) or prodrug(s). Certain organic solvents, such as dimethylsulfoxide (DMSO), may also be employed, although usually at the cost of greater toxicity.

The pharmaceutical compositions may, if desired, be presented in a pack or dispenser device which may contain one or more unit dosage forms containing the active compound(s). The pack may, for example, comprise metal or plastic foil, such as a blister pack. The pack or dispenser device may be accompanied by instructions for administration.

C. Dosages

The amide compound or combinations of amide compounds will generally be used in an amount effective to achieve the intended result, for example, in an amount effective to treat, prevent or ameliorate a particular condition. The amide compound(s), or compositions thereof, can be administered therapeutically to achieve therapeutic benefit or prophylactically to achieve a prophylactic benefit. Therapeutic benefit means eradication or amelioration of the underlying disorder being treated and/or eradication or amelioration of one or more of the symptoms associated with the underlying disorder such that the patient reports an improvement in feeling or condition, notwithstanding that the patient may still be afflicted with the underlying disorder. For example, administration of a compound to a patient suffering from an allergy provides therapeutic benefit not only when the underlying allergic response is eradicated or ameliorated, but also when the patient reports a decrease in the severity or duration of the symptoms associated with the allergy following exposure to the allergen. As another example, therapeutic benefit in the context of asthma includes an improvement in respiration following the onset of an asthmatic attack or a reduction in the frequency or severity of asthmatic episodes. Therapeutic benefit also includes halting or slowing the progression of the disease, regardless of whether improvement is realized.

As known by those of ordinary skill in the art, the preferred dosage of amide compounds may depend on various factors, including the age, weight, general health, and severity of the condition of the patient or subject being treated. Dosage also may need to be tailored to the sex of the individual and/or the lung capacity of the individual, when administered by inhalation. Dosage may also be tailored to individuals suffering from more than one condition or those individuals who have additional conditions that affect lung capacity and the ability to breathe normally, for example, emphysema, bronchitis, pneumonia, and respiratory infections. Dosage, and frequency of administration of the amide compound(s) or compositions thereof, will also depend on whether the amide compound(s) are formulated for treatment of acute episodes of a condition or for the prophylactic treatment of a disorder. A person or ordinary skill in the art will be able to determine the optimal dose for a particular individual.

For prophylactic administration, the amide compound, combinations of amide compounds, or compositions thereof, can be administered to a patient or subject at risk of developing one of the previously described conditions. For example, if it is unknown whether a patient or subject is allergic to a particular drug, the amide compound, combinations of amide compounds, or compositions thereof, can be administered prior to administration of the drug to avoid or ameliorate an allergic response to the drug. Alternatively, prophylactic administration can be used to avoid or ameliorate the onset of symptoms in a patient diagnosed with the underlying disorder. For example, an amide compound(s), or composition thereof, can be administered to an allergy sufferer prior to expected exposure to the allergen. An amide compound, combinations of amide compounds, or compositions thereof, can also be administered prophylactically to healthy individuals who are repeatedly exposed to agents known to one of the above-described maladies to prevent the onset of the disorder. For example, an amide compound, combinations of amide compounds, or compositions thereof, can be administered to a healthy individual who is repeatedly exposed to an allergen known to induce allergies, such as latex, in an effort to prevent the individual from developing an allergy. Alternatively, an amide compound, combinations of amide compounds, or compositions thereof, can be administered to a patient suffering from asthma prior to partaking in activities which trigger asthma attacks to lessen the severity of, or avoid altogether, an asthmatic episode.

Effective dosages can be estimated initially from in vitro assays. For example, an initial dosage for use in subjects can be formulated to achieve a circulating blood or serum concentration of active compound that is at or above an $IC_{50}$ or $EC_{50}$ of the particular compound as measured in an in vitro assay. Dosages can be calculated to achieve such circulating blood or serum concentrations taking into account the bioavailability of the particular compound. Fingl & Woodbury, "General Principles," In: Goodman and Gilman's The Pharmaceutical Basis of Therapeutics, Chapter 1, pages 1-46, Pergamon Press, and the references cited therein, provide additional guidance concerning effective dosages.

In some embodiments, the disclosed compounds have an $EC_{50}$ from greater than 0 to 20 μM, such as from greater than 0 to 10 μM, from greater than 0 to 5 μM, from greater than 0 to 1 μM, from greater than 0 to 0.5 μM, from greater than 0 to 0.1 μM, or from greater than 0 to 0.05 μM.

Initial dosages can also be estimated from in vivo data, such as animal models. Animal models useful for testing the efficacy of compounds to treat or prevent the various diseases described above are well-known in the art. Suitable animal models of hypersensitivity or allergic reactions are described in Foster, (1995) Allergy 50(21Suppl):6-9, discussion 34-38 and Tumas et al., (2001), J. Allergy Clin. Immunol. 107(6):1025-1033. Suitable animal models of allergic rhinitis are described in Szelenyi et al., (2000), Arzneimittelforschung 50(11):1037-42; Kawaguchi et al., (1994), Clin. Exp. Allergy 24(3):238-244 and Sugimoto et al., (2000), Immunopharmacology 48(1):1-7. Persons of ordinary skill in the art can adapt such information to determine dosages suitable for human administration.

Dosage amounts of disclosed amide compounds will typically be in the range of from about greater than 0 mg/kg/day, such as 0.0001 mg/kg/day or 0.001 mg/kg/day or 0.01 mg/kg/day, up to at least about 100 mg/kg/day. More typically, the dosage (or effective amount) may range from about 0.0025 mg/kg to about 1 mg/kg administered at least once per day, such as from 0.01 mg/kg to about 0.5 mg/kg or from about 0.05 mg/kg to about 0.15 mg/kg. The total daily dosage typically ranges from about 0.1 mg/kg to about 5 mg/kg or to about 20 mg/kg per day, such as from 0.5 mg/kg to about 10 mg/kg per day or from about 0.7 mg/kg per day to about 2.5 mg/kg/day. Dosage amounts can be higher or lower depending upon, among other factors, the activity of the amide compound, its bioavailability, the mode of administration, and various factors discussed above.

Dosage amount and dosage interval can be adjusted for individuals to provide plasma levels of the amide compound that are sufficient to maintain therapeutic or prophylactic effect. For example, the compounds can be administered once per day, multiple times per day, once per week, multiple times per week (e.g., every other day), one per month, multiple times per month, or once per year, depending upon, amongst other things, the mode of administration, the specific indication being treated, and the judgment of the prescribing physician. Persons of ordinary skill in the art will be able to optimize effective local dosages without undue experimentation.

Compositions comprising one or more of the disclosed amide compounds typically comprise from greater than 0 up to 99% of the amide compound, or compounds, and/or other therapeutic agent by total weight percent. More typically, compositions comprising one or more of the disclosed amide compounds comprise from about 1 to about 20 total weight percent of the amide compound and other therapeutic agent, and from about 80 to about 99 weight percent of a pharmaceutically acceptable additive.

Preferably, the amide compound, combinations of amide compounds, or compositions thereof, will provide therapeutic or prophylactic benefit without causing substantial toxicity. Toxicity of the amide compound can be determined using standard pharmaceutical procedures. The dose ratio between toxic and therapeutic (or prophylactic) effect is the therapeutic index. Amide compounds that exhibit high therapeutic indices are preferred.

IV. Examples

Example 1

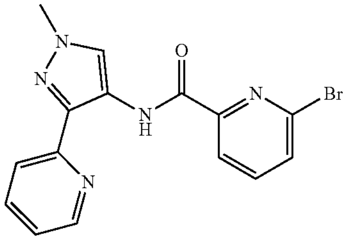 [SMILES: Cn1cc(NC(=O)c2cccc(Br)n2)c(-c2ccccn2)n1]

6-bromo-N-(1-methyl-3-(pyridin-2-yl)-1H-pyrazol-4-yl)picolinamide (I-1)

A $CH_2Cl_2$ (40 mL) solution of 6-bromopicolinic acid (2.02 g, 10 mmol), 1-methyl-3-(pyridin-2-yl)-1H-pyrazol-4-amine di-hydrochloric acid (2.52 g, 10.2 mmol), HATU (4.56 g, 12 mmol) and DIPEA (5.4 mL, 31 mmol) was stirred at room temperature for 15 hours. The reaction went to completion as monitored by LC-MS. To the reaction mixture, a saturated aqueous solution of $NaHCO_3$ (about 100 mL) was added, mixed well, two layers were separated; the aqueous layer was extracted with $CH_2Cl_2$ (20 mL×2). Organic layers were combined, dried ($Na_2SO_4$), filtered, solvent was removed in vacuo. The crude product was further treated with a saturated aqueous solution of $NaHCO_3$ (about 80 mL), mixed well, and the precipitate was collected by filtration, washing with $H_2O$ (about 10 mL×5), further dried in vacuo. Compound 6-bromo-N-(1-methyl-3-(pyridin-2-yl)-1H-pyrazol-4-yl)picolinamide was obtained as a light beige color solid: 2.70 g (75% yield); $^1$H NMR (300 MHz, Chloroform-d) δ 13.09 (s, 1H), 8.84 (ddd, J=4.9, 1.8, 1.0 Hz, 1H), 8.36 (s, 1H), 8.21 (dd, J=7.5, 1.0 Hz, 1H), 8.04 (ddd, J=8.1, 1.1, 1.1 Hz, 1H), 7.77 (ddd, J=8.1, 7.5, 1.8 Hz, partially overlapped, 1H), 7.78-7.73 (m, partially overlapped, 1H), 7.65 (dd, J=7.9, 1.0 Hz, 1H), 7.26-7.22 (m, partially overlapped with $CHCl_3$, 1H), 3.98 (s, 3H); LRMS (M+H) m/z 358.45, 360.33.

Example 2

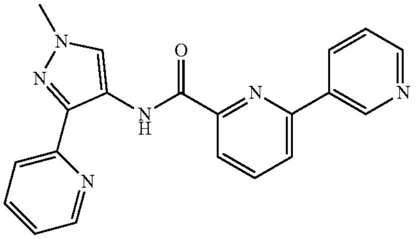 [SMILES: Cn1cc(NC(=O)c2cccc(-c3cccnc3)n2)c(-c2ccccn2)n1]

N-(1-methyl-3-(pyridin-2-yl)-1H-pyrazol-4-yl)-[2,3'-bipyridine]-6-carboxamide (I-2)

0.1 mmol scale, with pyridin-3-ylboronic acid, 16.1 mg, 45% yield. $^1$H NMR (300 MHz, DMSO-$d_6$) δ 12.53 (s, 1H), 9.71 (d, J=2.0 Hz, 1H), 8.82-8.80 (m, 2H), 8.69 (ddd, J=8.0, 1.7, 1.7 Hz, 1H), 8.55 (s, 1H), 8.37 (dd, J=7.2, 1.7 Hz, 1H), 8.25-8.17 (m, 2H), 8.06 (d, J=8.0 Hz, 1H), 7.95 (ddd, J=7.9, 7.9, 1.7 Hz, 1H), 7.72 (dd, J=7.9, 4.8 Hz, 1H), 7.45 (ddd, J=7.3, 5.0, 1.1 Hz, 1H), 4.00 (s, 3H); LRMS (M+H) m/z 357.56.

Example 3

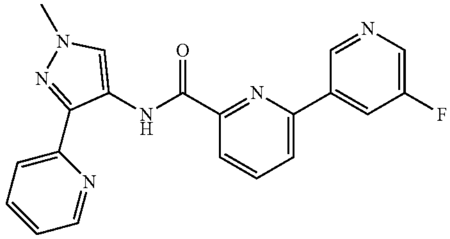 [SMILES: Cn1cc(NC(=O)c2cccc(-c3cncc(F)c3)n2)c(-c2ccccn2)n1]

5'-fluoro-N-(1-methyl-3-(pyridin-2-yl)-1H-pyrazol-4-yl)-[2,3'-bipyridine]-6-carboxamide (I-3)

A 1,4-dioxane (3 mL) solution of 6-bromo-N-(1-methyl-3-(pyridin-2-yl)-1H-pyrazol-4-yl)picolinamide (71.6 mg, 0.2 mmol), (5-fluoropyridin-3-yl)boronic acid (42.3 mg, 0.3 mmol), $Pd(PPh_3)_4$(23.1 mg, 0.02 mmol), and 2M aqueous solution of $Na_2CO_3$ (0.3 mL, 0.6 mmol) was microwaved at 150° C. for 60 minutes. Solvent was removed in vacuo, and after silica gel chromatography; 5'-fluoro-N-(1-methyl-3-(pyridin-2-yl)-1H-pyrazol-4-yl)-[2,3'-bipyridine]-6-carboxamide was obtained as a light grey solid: 328.8 mg (88% yield); $^1$H NMR (300 MHz, DMSO-$d_6$) δ 12.48 (s, 1H), 9.60 (s, 1H), 8.83-8.80 (m, 2H), 8.61 (ddd, J=9.9, 2.1, 2.1 Hz, 1H), 8.56 (s, 1H), 8.45 (dd, J=7.1, 1.6 Hz, 1H), 8.28-8.21 (m, 2H), 8.08 (d, J=7.9 Hz, 1H), 7.96 (td, J=7.9, 1.6 Hz, 1H), 7.46-7.42 (m, 1H), 3.99 (s, 4H); LRMS (M+H) m/z 375.62.

Example 4

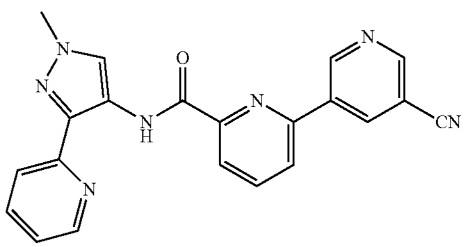 [SMILES: Cn1cc(NC(=O)c2cccc(-c3cncc(C#N)c3)n2)c(-c2ccccn2)n1]

5'-cyano-N-(1-methyl-3-(pyridin-2-yl)-1H-pyrazol-4-yl)-[2,3'-bipyridine]-6-carboxamide (I-4)

0.1 mmol scale, with (5-fluoropyridin-3-yl)boronic acid, 2.6 mg, 6.8% yield. $^1$H NMR (300 MHz, DMSO-$d_6$) δ 12.54 (s, 1H), 9.97 (s, 1H), 9.28 (d, J=1.9 Hz, 1H), 9.18 (dd, J=2.1, 2.1 Hz, 1H), 8.85 (br d, J=5.0 Hz, 1H), 8.59 (s, 1H), 8.52 (dd, J=7.0, 1.8 Hz, 1H), 8.35-8.27 (m, 2H), 8.10 (br d, J=7.9 Hz, 1H), 7.99 (ddd, J=7.9, 7.9, 1.7 Hz, 1H), 7.46 (ddd, J=7.4, 5.0, 1.3 Hz, 1H), 4.02 (s, 3H); LRMS (M+H) m/z 382.65.

Example 5

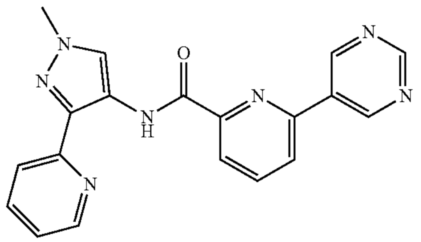 [SMILES: Cn1cc(NC(=O)c2cccc(-c3cncnc3)n2)c(-c2ccccn2)n1]

N-(1-methyl-3-(pyridin-2-yl)-1H-pyrazol-4-yl)-6-(pyrimidin-5-yl)picolinamide (I-5)

0.1 mmol scale, with pyrimidin-5-ylboronic acid, 5.8 mg, 16% yield. $^1$H NMR (300 MHz, DMSO-$d_6$) δ 12.52 (s, 1H), 9.80 (s, 2H), 9.43 (s, 1H), 8.81 (d, J=5.7 Hz, 1H), 8.56 (s, 1H), 8.49 (dd, J=7.4, 1.3 Hz, 1H), 8.32-8.23 (m, 2H), 8.08 (d, J=8.9 Hz, 1H), 7.97 (ddd, J=8.1, 8.1, 1.7 Hz, 1H), 7.47 (ddd, J=7.4, 5.0, 1.1 Hz, 1H), 4.01 (s, 4H); LRMS (M+H) m/z 358.58.

Example 6

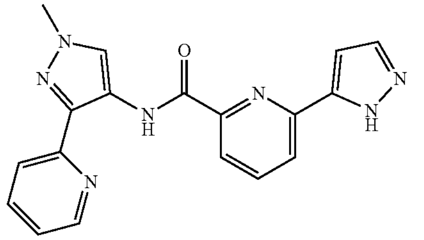 [SMILES: Cn1cc(NC(=O)c2cccc(-c3ccn[nH]3)n2)c(-c2ccccn2)n1]

N-(1-methyl-3-(pyridin-2-yl)-1H-pyrazol-4-yl)-6-(1H-pyrazol-5-yl)picolinamide (I-6)

0.1 mmol scale, with (1H-pyrazol-5-yl)boronic acid, 12.2 mg, 35% yield. $^1$H NMR (300 MHz, DMSO-$d_6$) δ 13.28 (s, 1H), 12.48 (s, 1H), 8.83 (s, 1H), 8.58 (s, 1H), 8.23 (dd, J=6.9, 2.2 Hz, 1H), 8.17-8.04 (m, 4H), 7.97 (ddd, J=7.8, 7.8, 1.7 Hz, 1H), 7.45 (ddd, J=7.3, 5.0, 1.0 Hz, 1H), 7.20 (d, J=2.2 Hz, 1H), 4.01 (s, 3H); LRMS (M+H) m/z 346.57.

Example 7

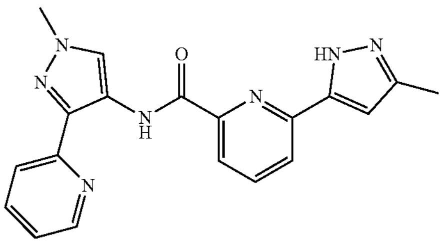 [SMILES: Cc1cc(-c2cccc(C(=O)Nc3cn(C)nc3-c3ccccn3)n2)[nH]n1]

6-(3-methyl-1H-pyrazol-5-yl)-N-(1-methyl-3-(pyridin-2-yl)-1H-pyrazol-4-yl)picolinamide (I-7)

Example 8

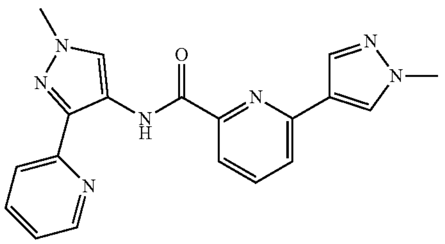 [SMILES: Cn1cc(-c2cccc(C(=O)Nc3cn(C)nc3-c3ccccn3)n2)cn1]

6-(1-methyl-1H-pyrazol-4-yl)-N-(1-methyl-3-(pyridin-2-yl)-1H-pyrazol-4-yl)picolinamide (I-8)

0.1 mmol scale, with (1-methyl-1H-pyrazol-4-yl)boronic acid, 5.6 mg, 16% yield. $^1$H NMR (300 MHz, DMSO-$d_6$) δ 12.38 (s, 1H), 8.75 (br d, J=4.9 Hz, 1H), 8.57 (s, 1H), 8.48 (s, 1H), 8.29 (s, 1H), 8.10-8.05 (m, 2H), 8.01-7.96 (m, 2H), 7.93 (dd, J=7.7, 1.2 Hz, 1H), 7.51-7.46 (m, 1H), 4.03 (s, 3H), 4.01 (s, 3H); LRMS (M+H) m/z 360.65.

Example 9

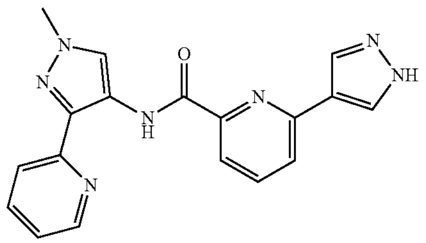 [SMILES: Cn1cc(NC(=O)c2cccc(-c3cn[nH]c3)n2)c(-c2ccccn2)n1]

N-(1-methyl-3-(pyridin-2-yl)-1H-pyrazol-4-yl)-6-(1H-pyrazol-4-yl)picolinamide (I-9)

A dioxane (4.5 mL) solution of 6-bromo-N-(1-methyl-3-(pyridin-2-yl)-1H-pyrazol-4-yl)picolinamide (107.5 mg, 0.3 mmol), (1H-pyrazol-4-yl)boronic acid (50.4 mg, 0.45 mmol), $Pd(PPh_3)_4$(34.7 mg, 0.03 mmol), and 2M aqueous solution of $Na_2CO_3$ (0.45 mL, 0.9 mmol) was microwaved at 150° C. for 45 minutes. Solid was removed by filtration through a celite pad, washing with MeOH. Filtrate was collected, solvent was removed in vacuo, after silica gel chromatography, N-(1-methyl-3-(pyridin-2-yl)-1H-pyrazol-4-yl)-6-(1H-pyrazol-4-yl)picolinamid was obtained as a pale yellow solid: 93.4 mg (90% yield):

$^1$H NMR (300 MHz, DMSO-$d_6$) δ 13.31 (s, 1H), 12.38 (s, 1H), 8.76 (ddd, J=5.0, 1.7, 1.0 Hz, 1H), 8.58 (s, 1H), 8.56 (d, J=1.3 Hz, 1H), 8.36 (d, J=1.7 Hz, 1H), 8.12-8.05 (m, 2H), 8.02-7.96 (m, 3H), 7.47 (ddd, J=7.4, 5.0, 1.3 Hz, 1H), 4.01 (s, 3H); LRMS (M+H) m/z 346.59.

Example 10

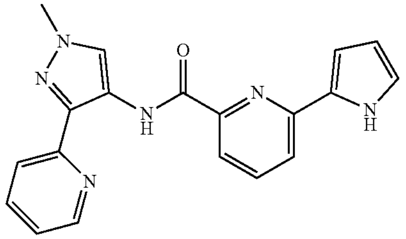 [SMILES: Cn1cc(NC(=O)c2cccc(-c3ccc[nH]3)n2)c(-c2ccccn2)n1]

N-(1-methyl-3-(pyridin-2-yl)-1H-pyrazol-4-yl)-6-(1H-pyrrol-2-yl)picolinamide (I-10)

0.08 mmol scale, with (1H-pyrrol-2-yl)boronic acid, 19.5 mg, 71% yield. $^1$H NMR (300 MHz, DMSO-$d_6$) δ 12.42 (s, 1H), 11.56 (s, 1H), 8.74 (ddd, J=5.0, 1.7, 0.9 Hz, 1H), 8.56 (s, 1H), 8.09-8.03 (m, 2H), 8.00-7.90 (m, 3H), 7.46 (ddd, J=7.4, 5.0, 1.3 Hz, 1H), 7.15-7.12 (m, 2H), 6.37 (ddd, J=3.3, 2.4, 2.4 Hz, 1H), 4.01 (s, 3H); LRMS (M+H) m/z 345.56.

Example 11

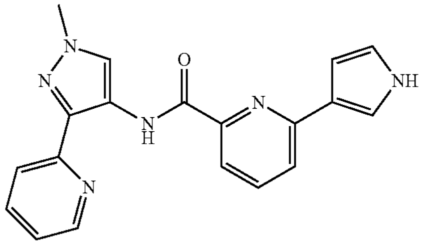 [SMILES: Cn1cc(NC(=O)c2cccc(-c3cc[nH]c3)n2)c(-c2ccccn2)n1]

N-(1-methyl-3-(pyridin-2-yl)-1H-pyrazol-4-yl)-6-(1H-pyrrol-3-yl)picolinamide (I-11)

0.08 mmol scale, with (1H-pyrrol-3-yl)boronic acid, 9.4 mg, 34% yield. $^1$H NMR (300 MHz, DMSO-$d_6$) δ 12.37 (s, 1H), 11.33 (s, 1H), 8.82 (ddd, J=5.0, 1.7, 1.0 Hz, 1H), 8.58 (s, 1H), 8.09 (ddd, J=8.1, 1.1, 1.1 Hz, 1H), 8.01-7.95 (m, 2H), 7.90-7.87 (m, 2H), 7.74 (ddd, J=2.8, 1.8, 1.8 Hz, 1H), 7.45 (ddd, J=7.4, 5.0, 1.3 Hz, 1H), 7.02 (dd, J=2.5, 2.5 Hz, 1H), 6.95 (ddd, J=2.6, 1.6, 1.6 Hz, 1H), 4.01 (s, 3H); LRMS (M+H) m/z 345.60.

Example 12

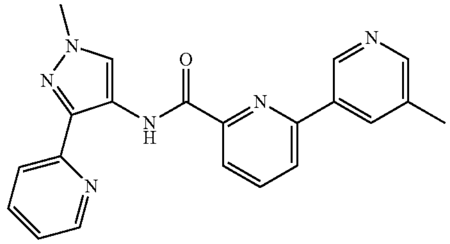 [SMILES: Cc1cncc(-c2cccc(C(=O)Nc3cn(C)nc3-c3ccccn3)n2)c1]

5'-methyl-N-(1-methyl-3-(pyridin-2-yl)-1H-pyrazol-4-yl)-[2,3'-bipyridine]-6-carboxamide (I-12)

0.3 mmol scale, with (5-methylpyridin-3-yl)boronic acid, 95.7 mg, 86% yield. $^1$H NMR (300 MHz, DMSO-$d_6$) δ 12.62 (s, 1H), 9.55 (s, 1H), 8.81 (ddd, J=4.9, 1.6, 1.0 Hz, 1H), 8.66 (d, J=1.9 Hz, 1H), 8.58 (s, 1H), 8.48 (dd, J=1.6, 1.6 Hz, 1H), 8.38 (dd, J=7.1, 1.8 Hz, 1H), 8.27-8.19 (m, 2H), 8.09 (ddd, J=8.1, 1.0, 1.0 Hz, 1H), 7.98 (ddd, J=7.7, 7.7, 1.8 Hz, 1H), 7.47 (ddd, J=7.4, 5.0, 1.3 Hz, 1H), 4.02 (s, 3H), 2.51 (s, 3H); LRMS (M+H) m/z 371.64.

Example 13

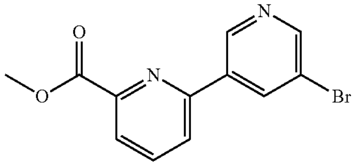 [SMILES: COC(=O)c1cccc(-c2cncc(Br)c2)n1]

methyl 5'-bromo-[2,3'-bipyridine]-6-carboxylate

A dioxane/$H_2O$ (15/1.5 mL) solution of methyl 6-bromopicolinate (648.1 mg, 3 mmol), (5-bromopyridin-3-yl) boronic acid (726.5 mg, 3.6 mmol), $Pd(PPh_3)_4$(173.2 mg, 0.15 mmol), and 2M aqueous solution of $Na_2CO_3$ (0.795 mL, 7.5 mmol) was microwaved at 150° C. for 60 minutes. Solvent was removed in vacuo, after silica gel chromatography, fractions with desired product was further triturated from Hexanes-EtOAc (about 9:0.5). Title compound was obtained as an off-white solid: 582.3 mg (66% yield): $^1H$ NMR (300 MHz, Chloroform-d) δ 9.12 (d, J=1.9 Hz, 1H), 8.75 (d, J=2.2 Hz, 1H), 8.59 (dd, J=2.1, 2.1 Hz, 1H), 8.15 (dd, J=7.4, 1.4 Hz, 1H), 7.98 (dd, J=7.9, 7.4 Hz, 1H), 7.92 (dd, J=7.9, 1.4 Hz, 1H), 4.05 (s, 3H); LRMS (M+H) m/z 295.28.

Example 14

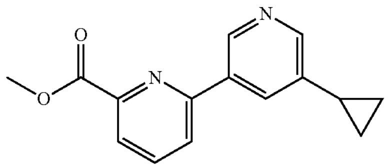 [SMILES: COC(=O)c1cccc(-c2cncc(C3CC3)c2)n1]

methyl 5'-cyclopropyl-[2,3'-bipyridine]-6-carboxylate

A toluene/$H_2O$ (3/0.3 mL) solution of methyl methyl 5'-bromo-[2,3'-bipyridine]-6-carboxylate (35.2 mg, 0.12 mmol), cyclopropylboronic acid MIDA ester (35.5 mg, 0.18 mmol), $Pd(OAc)_2$ (1.3 mg, 0.006 mmol), tricyclohexylphosphine (3.4 mg, 0.012 mmol) and potassium phophosphate (89.2 mg, 0.42 mmol) was microwaved at 150° C. for 30 minutes, followed by another 39 hours at 100° C., after additional MIDA ester and catalysts, until reaction went to completion as monitored by LC-MS. Solvent was removed in vacuo, after silica gel chromatography, title compound was obtained as light yellow sticky solid: $^1H$ NMR (300 MHz, Chloroform-d) δ 8.96 (d, J=2.1 Hz, 1H), 8.47 (d, J=2.2 Hz, 1H), 8.11 (dd, J=7.1, 1.7 Hz, 1H), 8.04 (ddd, J=2.2, 2.2, 0.5 Hz, 1H), 7.95 (dd, J=7.9, 7.1 Hz, 1H), 7.90 (dd, J=7.9, 1.7 Hz, 1H), 4.04 (s, 3H), 2.06-1.97 (m, 1H), 1.11-1.05 (m, 2H), 0.87-0.82 (m, 2H); LRMS (M+H) m/z 255.36.

Example 15

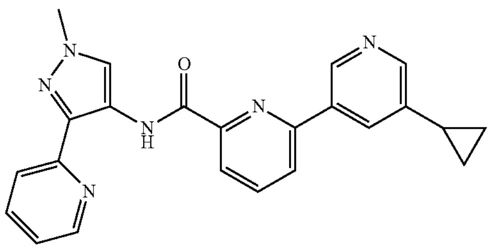 [SMILES: Cn1cc(NC(=O)c2cccc(-c3cncc(C4CC4)c3)n2)c(-c2ccccn2)n1]

5'-cyclopropyl-N-(1-methyl-3-(pyridin-2-yl)-1H-pyrazol-4-yl)-[2,3'-bipyridine]-6-carboxamide (I-13)

A MeOH (0.5 mL) solution of methyl 5'-cyclopropyl-[2,3'-bipyridine]-6-carboxylate (~0.12 mmol) and NaOH aqueous solution (1N, 126 μL) was stirred at 50° C. for 1 hour. The reaction went to completion as monitored by LC-MS, volatiles were removed in vacuo and crude product was directly used in next reaction without further purification. A $CH_2Cl_2$ (2 mL) solution of the acid, 1-methyl-3-(pyridin-2-yl)-1H-pyrazol-4-amine di-hydrochloric acid (29.7 mg, 0.12 mmol), HATU (55 mg, 0.14 mmol) and DIPEA (63 μL, 0.36 mmol) was stirred at room temperature for 1 hour, the reaction went to completion as monitored by LC-MS. Solvent was removed in vacuo, after silica gel chromatography, product was further triturated from Hexanes-EtOAc. Title compound was obtained as a white solid: 7.9 mg (17% yield over 3 steps); $^1H$ NMR (300 MHz, DMSO-$d_6$) δ 12.61 (s, 1H), 9.55 (s, 1H), 8.84 (d, J=4.9 Hz, 1H), 8.61 (d, J=2.1 Hz, 1H), 8.57 (s, 1H), 8.40 (dd, J=7.0, 1.9 Hz, 1H), 8.26-8.18 (m, 3H), 8.08 (d, J=8.0 Hz, 1H), 7.97 (ddd, J=7.8, 7.8, 1.7 Hz, 1H), 7.45 (ddd, J=7.3, 5.0, 1.2 Hz, 1H), 4.01 (s, 3H), 2.18-2.09 (m, 1H), 1.15-1.09 (m, 2H), 0.98-0.95 (m, 2H); LRMS (M+H) m/z 397.59.

Example 16

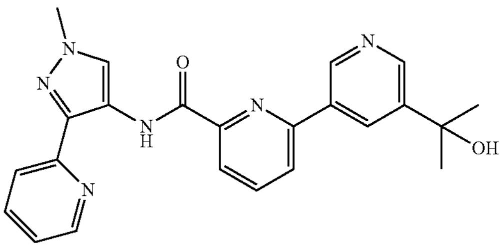 [SMILES: Cn1cc(NC(=O)c2cccc(-c3cncc(C(C)(C)O)c3)n2)c(-c2ccccn2)n1]

5'-(2-hydroxypropan-2-yl)-N-(1-methyl-3-(pyridin-2-yl)-1H-pyrazol-4-yl)-[2,3'-bipyridine]-6-carboxamide (1-14)

0.1 mmol scale, with 2-(5-(4,4,5,5-tetramethyl-1,3,2-dioxaborolan-2-yl)pyridin-3-yl)propan-2-ol, 29.8 mg, 72% yield. $^1H$ NMR (300 MHz, DMSO-$d_6$) δ 12.62 (s, 1H), 9.64 (s, 1H), 8.93 (d, J=2.1 Hz, 1H), 8.91 (ddd, J=5.0, 1.7, 1.0 Hz, 1H), 8.59-8.58 (m, 2H), 8.39 (dd, J=6.9, 2.1 Hz, 1H), 8.28-8.21 (m, 2H), 8.08 (ddd, J=8.1, 8.1, 1.1 Hz, 1H), 7.97 (ddd, J=7.8, 7.8, 1.8 Hz, 1H), 7.45 (ddd, J=7.4, 5.0, 1.3 Hz, 1H), 5.41 (s, 1H), 4.02 (s, 3H), 1.61 (s, 6H); LRMS (M+H) m/z 415.66.

Example 17

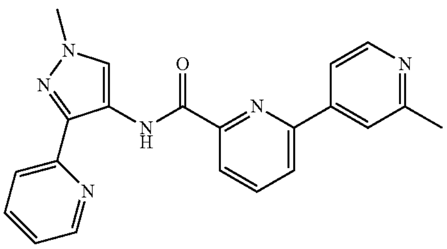 [SMILES: Cc1cc(-c2cccc(C(=O)Nc3cn(C)nc3-c3ccccn3)n2)ccn1]

2'-methyl-N-(1-methyl-3-(pyridin-2-yl)-1H-pyrazol-4-yl)-[2,4'-bipyridine]-6-carboxamide (I-15)

0.08 mmol scale, with 2-methyl-4-(4,4,5,5-tetramethyl-1,3,2-dioxaborolan-2-yl)pyridine, 10.8 mg, 36% yield. $^1$H NMR (300 MHz, DMSO-$d_6$) δ 12.57 (s, 1H), 8.78 (d, J=5.1 Hz, 1H), 8.66 (br d, J=4.7 Hz, 1H), 8.55 (s, 1H), 8.41-8.36 (m, 1H), 8.25 (d, J=0.8 Hz, 1H), 8.24 (s, 1H), 8.15-8.12 (m, 2H), 8.06 (d, J=8.0 Hz, 1H), 7.96 (ddd, J=7.7, 7.7, 1.7 Hz, 1H), 7.46 (ddd, J=7.3, 5.0, 1.3 Hz, 1H), 4.01 (s, 3H), 2.67 (s, 3H); LRMS (M+H) m/z 371.64.

Example 18

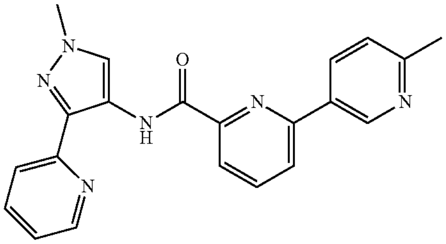 [SMILES: Cc1ccc(-c2cccc(C(=O)Nc3cn(C)nc3-c3ccccn3)n2)cn1]

6'-methyl-N-(1-methyl-3-(pyridin-2-yl)-1H-pyrazol-4-yl)-[2,3'-bipyridine]-6-carboxamide (I-16)

0.08 mmol scale, with (6-methylpyridin-3-yl)boronic acid, 20.4 mg, 69% yield. $^1$H NMR (300 MHz, DMSO-$d_6$) δ 12.55 (s, 1H), 9.58 (s, 1H), 8.84 (ddd, J=5.0, 1.7, 0.9 Hz, 1H), 8.63 (dd, J=8.1, 2.4 Hz, 1H), 8.59 (s, 1H), 8.37 (dd, J=7.2, 1.8 Hz, 1H), 8.25-8.17 (m, 2H), 8.10 (ddd, J=8.1, 1.1, 1.1 Hz, 1H), 7.99 (ddd, J=7.8, 7.8, 1.8 Hz, 1H), 7.60 (d, J=8.2 Hz, 1H), 7.49 (ddd, J=7.4, 5.0, 1.3 Hz, 1H), 4.02 (s, 3H), 2.67 (s, 3H); LRMS (M+H) m/z 371.67.

Example 19

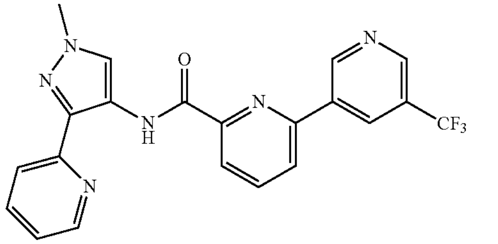 [SMILES: Cn1cc(NC(=O)c2cccc(-c3cncc(C(F)(F)F)c3)n2)c(-c2ccccn2)n1]

N-(1-methyl-3-(pyridin-2-yl)-1H-pyrazol-4-yl)-5'-(trifluoromethyl)-[2,3'-bipyridine]-6-carboxamide (I-17)

0.08 mmol scale, with (5-(trifluoromethyl)pyridin-3-yl) boronic acid, 24.6 mg, 72% yield.

$^1$H NMR (300 MHz, DMSO-$d_6$) δ 12.43 (s, 1H), 9.95 (s, 1H), 9.16 (s, 1H), 8.90 (s, 1H), 8.69 (d, J=4.8 Hz, 1H), 8.49-8.47 (m, 2H), 8.24-8.16 (m, 2H), 8.01 (d, J=8.0 Hz, 1H), 7.90 (ddd, J=7.9, 7.9, 1.5 Hz, 1H), 7.36-7.32 (m, 1H), 3.98 (s, 3H); LRMS (M+H) m/z 425.62.

Example 20

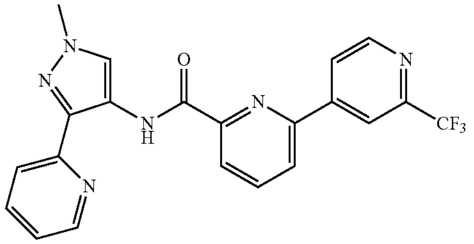 [SMILES: Cn1cc(NC(=O)c2cccc(-c3ccnc(C(F)(F)F)c3)n2)c(-c2ccccn2)n1]

N-(1-methyl-3-(pyridin-2-yl)-1H-pyrazol-4-yl)-2'-(trifluoromethyl)-[2,4'-bipyridine]-6-carboxamide (I-18)

0.08 mmol scale, with (2-(trifluoromethyl)pyridin-4-yl) boronic acid, 17.2 mg, 51% yield.

$^1$H NMR (300 MHz, DMSO-$d_6$) δ 12.47 (s, 1H), 9.09 (d, J=5.0 Hz, 1H), 8.63-8.60 (m, 2H), 8.55-8.50 (m, 3H), 8.27-8.26 (m, 2H), 8.02 (d, J=8.0 Hz, 1H), 7.92 (ddd, J=7.8, 7.8, 1.7 Hz, 1H), 7.37 (ddd, J=7.2, 5.0, 1.2 Hz, 1H), 3.99 (s, 3H); LRMS (M+H) m/z 425.67.

Example 21

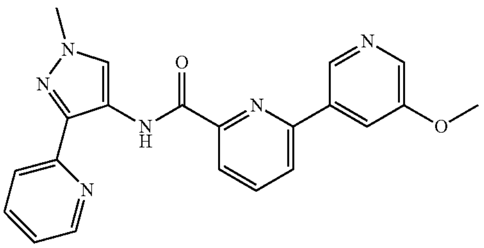 [SMILES: COc1cncc(-c2cccc(C(=O)Nc3cn(C)nc3-c3ccccn3)n2)c1]

5'-methoxy-N-(1-methyl-3-(pyridin-2-yl)-1H-pyrazol-4-yl)-[2,3'-bipyridine]-6-carboxamide (I-19)

0.08 mmol scale, with (5-methoxypyridin-3-yl)boronic acid, 21.5 mg, 70% yield. $^1$H NMR (300 MHz, DMSO-$d_6$) δ 12.58 (s, 1H), 9.38 (d, J=1.8 Hz, 1H), 8.88 (ddd, J=5.0, 1.7, 1.0 Hz, 1H), 8.59 (s, 1H), 8.56 (d, J=2.8 Hz, 1H), 8.45 (dd, J=7.1, 1.8 Hz, 1H), 8.28-8.20 (m, 3H), 8.09 (ddd, J=8.1, 1.1, 1.1 Hz, 1H), 7.98 (ddd, J=8.1, 7.5, 1.8 Hz, 1H), 7.46 (ddd, J=7.4, 5.0, 1.3 Hz, 1H), 4.03 (s, 3H), 4.02 (s, 3H); LRMS (M+H) m/z 387.62.

Example 22

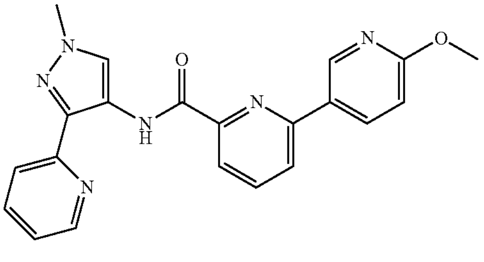 [SMILES: COc1ccc(-c2cccc(C(=O)Nc3cn(C)nc3-c3ccccn3)n2)cn1]

6'-methoxy-N-(1-methyl-3-(pyridin-2-yl)-1H-pyrazol-4-yl)-[2,3'-bipyridine]-6-carboxamide (I-20)

0.08 mmol scale with (6-methoxypyridin-3-yl)boronic acid, 20.4 mg, 66% yield. $^{1}$H NMR (300 MHz, DMSO-$d_6$) δ 12.55 (s, 1H), 9.27 (dd, J=2.5, 0.6 Hz, 1H), 8.80 (ddd, J=5.0, 1.7, 1.0 Hz, 1H), 8.69 (dd, J=8.7, 2.5 Hz, 1H), 8.58 (s, 1H), 8.30 (dd, J=7.6, 1.4 Hz, 1H), 8.19 (dd, J=7.6, 7.6 Hz, 1H), 8.14 (dd, J=7.6, 1.4 Hz, 1H), 8.08 (ddd, J=8.1, 1.1, 1.1 Hz, 1H), 7.97 (ddd, J=8.1, 7.5, 1.8 Hz, 1H), 7.48 (ddd, J=7.4, 5.0, 1.3 Hz, 1H), 7.18 (dd, J=8.7, 0.6 Hz, 1H), 4.05 (s, 3H), 4.01 (s, 3H); LRMS (M+H) m/z 387.61.

Example 23

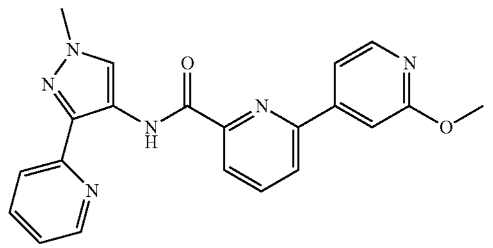 [SMILES: COc1cc(-c2cccc(C(=O)Nc3cn(C)nc3-c3ccccn3)n2)ccn1]

2'-methoxy-N-(1-methyl-3-(pyridin-2-yl)-1H-pyrazol-4-yl)-[2,4'-bipyridine]-6-carboxamide (I-21)

0.08 mmol scale, with (2-methoxypyridin-4-yl)boronic acid, 16 mg, 52% yield. $^{1}$H NMR (300 MHz, DMSO-$d_6$) δ 12.52 (s, 1H), 8.86 (ddd, J=5.0, 1.7, 1.0 Hz, 1H), 8.58 (s, 1H), 8.50 (dd, J=5.4, 0.6 Hz, 1H), 8.43 (dd, J=5.5, 3.5 Hz, 1H), 8.27 (s, 1H), 8.26 (d, J=2.2 Hz, 1H), 8.08 (ddd, J=8.1, 1.1, 1.1 Hz, 1H), 7.99 (dd, J=7.4, 1.8 Hz, 1H), 7.94 (dd, J=5.4, 1.5 Hz, 1H), 7.84 (dd, J=1.4, 0.7 Hz, 1H), 7.47 (ddd, J=7.4, 5.0, 1.3 Hz, 1H), 4.05 (s, 3H), 4.01 (s, 3H); LRMS (M+H) m/z 387.52.

Example 24

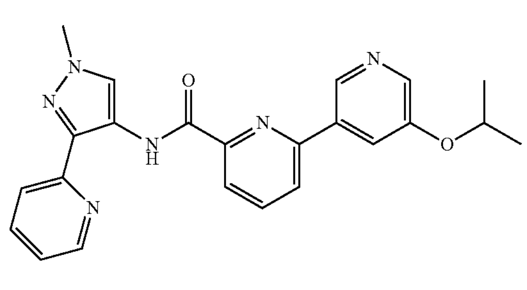 [SMILES: CC(C)Oc1cncc(-c2cccc(C(=O)Nc3cn(C)nc3-c3ccccn3)n2)c1]

5'-isopropoxy-N-(1-methyl-3-(pyridin-2-yl)-1H-pyrazol-4-yl)-[2,3'-bipyridine]-6-carboxamide (I-22)

0.3 mmol scale, with (5-isopropoxypyridin-3-yl)boronic acid, 99.3 mg, 80% yield. $^{1}$H NMR (300 MHz, DMSO-$d_6$) δ 12.54 (s, 1H), 9.31 (d, J=1.8 Hz, 1H), 8.93 (ddd, J=4.9, 1.6, 0.9 Hz, 1H), 8.59 (s, 1H), 8.54 (d, J=2.7 Hz, 1H), 8.45 (dd, J=6.6, 2.3 Hz, 1H), 8.27-8.21 (m, 3H), 8.10 (ddd, J=8.1, 0.9, 0.9 Hz, 1H), 7.98 (ddd, J=7.7, 7.7, 1.8 Hz, 1H), 7.44 (ddd, J=7.4, 5.0, 1.2 Hz, 1H), 4.97 (hept, J=6.0 Hz, 1H), 4.02 (s, 3H), 1.41 (d, J=6.0 Hz, 6H); LRMS (M+H) m/z 415.67.

Example 25

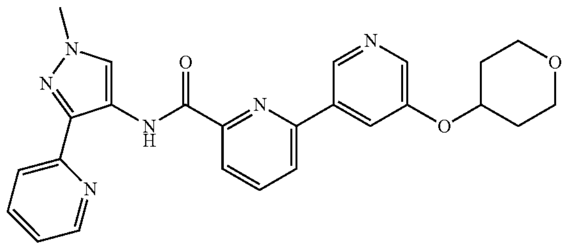 [SMILES: Cn1cc(NC(=O)c2cccc(-c3cncc(OC4CCOCC4)c3)n2)c(-c2ccccn2)n1]

N-(1-methyl-3-(pyridin-2-yl)-1H-pyrazol-4-yl)-5'-((tetrahydro-2H-pyran-4-yl)oxy)-[2,3'-bipyridine]-6-carboxamide (I-23)

0.3 mmol scale, with (5-((tetrahydro-2H-pyran-4-yl)oxy)pyridin-3-yl)boronic acid, 110.4 mg, 81% yield. $^{1}$H NMR (300 MHz, DMSO-$d_6$) δ 12.55 (s, 1H), 9.34 (d, J=1.7 Hz, 1H), 8.92 (ddd, J=5.0, 1.6, 0.9 Hz, 1H), 8.61 (d, J=2.7 Hz, 1H), 8.60 (s, 1H), 8.46 (dd, J=6.8, 2.1 Hz, 1H), 8.31-8.29 (m, 1H), 8.28-8.21 (m, 2H), 8.10 (br d, J=8.0 Hz, 1H), 7.99 (ddd, J=7.7, 7.7, 1.7 Hz, 1H), 7.44 (ddd, J=7.4, 5.0, 1.2 Hz, 1H), 4.92 (tt, J=8.5, 4.1 Hz, 1H), 4.02 (s, 3H), 3.94 (dt, J=11.7, 4.2 Hz, 2H), 3.55 (ddd, J=11.7, 9.5, 2.6 Hz, 2H), 2.15-2.10 (m, 2H), 1.71 (dtd, J=13.0, 9.5, 4.1 Hz, 2H); LRMS (M+H) m/z 457.61.

Example 26

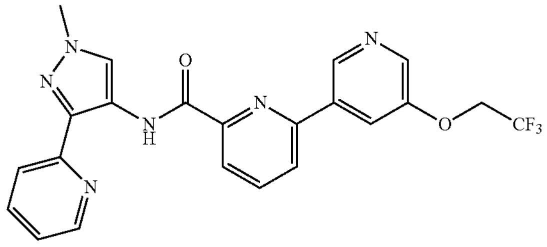 [SMILES: Cn1cc(NC(=O)c2cccc(-c3cncc(OCC(F)(F)F)c3)n2)c(-c2ccccn2)n1]

N-(1-methyl-3-(pyridin-2-yl)-1H-pyrazol-4-yl)-5'-(2,2,2-trifluoroethoxy)-[2,3'-bipyridine]-6-carboxamide (I-24)

0.1 mmol scale, with (5-(2,2,2-trifluoroethoxy)pyridin-3-yl)boronic acid, 30.8 mg, 68% yield. $^{1}$H NMR (300 MHz, DMSO-$d_6$) δ 12.55 (s, 1H), 9.29 (d, J=2.4 Hz, 1H), 8.81-8.77 (m, 2H), 8.58 (s, 1H), 8.35 (dd, J=7.5, 1.3 Hz, 1H), 8.22 (dd, J=7.6, 7.6 Hz, 1H), 8.17 (dd, J=7.9, 1.1 Hz, 1H), 8.09 (d, J=8.2 Hz, 1H), 7.98 (ddd, J=7.7, 7.7, 1.6 Hz, 1H), 7.49 (ddd, J=6.7, 4.7, 1.0 Hz, 1H), 7.38 (d, J=8.7 Hz, 1H), 5.21 (q, J=9.1 Hz, 2H), 4.01 (s, 3H); LRMS (M+H) m/z 455.53.

Example 27

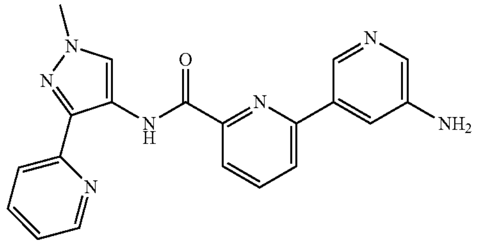 [SMILES: Cn1cc(NC(=O)c2cccc(-c3cncc(N)c3)n2)c(-c2ccccn2)n1]

5'-amino-N-(1-methyl-3-(pyridin-2-yl)-1H-pyrazol-4-yl)-[2,3'-bipyridine]-6-carboxamide (I-25)

0.08 mmol scale, with 5-(4,4,5,5-tetramethyl-1,3,2-dioxaborolan-2-yl)pyridin-3-amine, 13.3 mg, 45% yield. $^1$H NMR (300 MHz, DMSO-$d_6$) δ 12.67 (s, 1H), 8.86 (d, J=1.9 Hz, 1H), 8.81 (ddd, J=5.0, 1.7, 0.9 Hz, 1H), 8.58 (s, 1H), 8.24-8.15 (m, 4H), 8.07 (ddd, J=8.1, 1.1, 1.1 Hz, 1H), 7.97 (ddd, J=7.7, 7.7, 1.8 Hz, 1H), 7.73-7.71 (m, 1H), 7.43 (ddd, J=7.4, 5.0, 1.3 Hz, 1H), 5.60 (s, 2H), 4.03 (s, 3H); LRMS (M+H) m/z 372.64.

Example 28

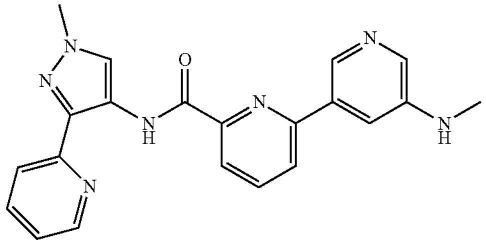

N-(1-methyl-3-(pyridin-2-yl)-1H-pyrazol-4-yl)-5'-(methylamino)-[2,3'-bipyridine]-6-carboxamide (I-26)

An NMP (1 mL) solution of 5'-fluoro-N-(1-methyl-3-(pyridin-2-yl)-1H-pyrazol-4-yl)-[2,3'-bipyridine]-6-carboxamide (22.5 mg, 0.06 mmol), methylamine hydrochloride (>5 eq.) and $NaHCO_3$ (>2 eq) was heated at 150-180° C. for 20 days until >50% of desired product was formed, as monitored by LC-MS. Solvent was removed in vacuo, after silica gel chromatography, title compound was obtained as a beige color solid: 14 mg (61% yield); $^1$H NMR (300 MHz, DMSO-$d_6$) δ 12.66 (s, 1H), 8.97 (d, J=1.9 Hz, 1H), 8.81 (ddd, J=5.0, 1.7, 1.0 Hz, 1H), 8.58 (s, 1H), 8.29 (dd, J=7.1, 2.0 Hz, 1H), 8.25-8.17 (m, 3H), 8.08 (ddd, J=8.1, 1.1, 1.1 Hz, 1H), 7.97 (ddd, J=8.1, 7.5, 1.8 Hz, 1H), 7.61-7.60 (m, 1H), 7.44 (ddd, J=7.4, 5.0, 1.3 Hz, 1H), 6.18 (q, J=5.0 Hz, 1H), 4.02 (s, 3H), 2.85 (d, J=5.0 Hz, 3H); LRMS (M+H) m/z 386.68.

Example 29

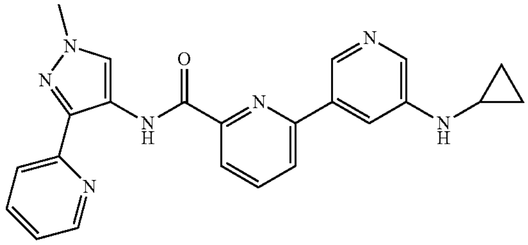 [SMILES: Cn1cc(NC(=O)c2cccc(-c3cncc(NC4CC4)c3)n2)c(-c2ccccn2)n1]

5'-(cyclopropylamino)-N-(1-methyl-3-(pyridin-2-yl)-1H-pyrazol-4-yl)-[2,3'-bipyridine]-6-carboxamide (I-27)

An NMP (1 mL) solution of 5'-fluoro-N-(1-methyl-3-(pyridin-2-yl)-1H-pyrazol-4-yl)-[2,3'-bipyridine]-6-carboxamide (22.5 mg, 0.06 mmol), cyclopropanamine (>5 eq.) and $NaHCO_3$ (>2 eq) was heated at 140-150° C. for 12 days until >50% of desired product was formed, as monitored by LC-MS. Solvent was removed in vacuo, after silica gel chromatography and further trituration from Hexanes-EtOAc, title compound was obtained as an off-white solid: 1.8 mg (7% yield); $^1$H NMR (300 MHz, DMSO-$d_6$) δ 12.67 (s, 1H), 9.00 (d, J=1.9 Hz, 1H), 8.80 (ddd, J=5.0, 1.7, 0.9 Hz, 1H), 8.58 (s, 1H), 8.30 (d, J=2.6 Hz, 1H), 8.24-8.19 (m, 3H), 8.08 (ddd, J=8.1, 1.1, 1.1 Hz, 1H), 7.97 (ddd, J=7.7, 7.7, 1.8 Hz, 1H), 7.76-7.75 (m, 1H), 7.42 (ddd, J=7.3, 5.0, 1.2 Hz, 1H), 6.62 (d, J=1.7 Hz, 1H), 4.02 (s, 3H), 3.35-3.33 (m, overlapped with $H_2O$, 1H), 0.84-0.78 (m, 2H), 0.52-0.48 (m, 2H); LRMS (M+H) m/z 412.73.

Example 30

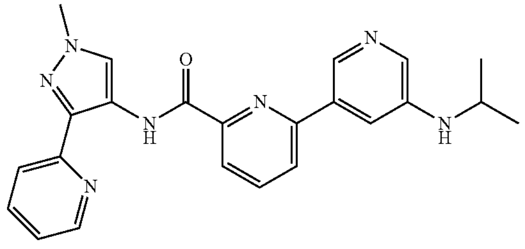 [SMILES: CC(C)Nc1cncc(-c2cccc(C(=O)Nc3cn(C)nc3-c3ccccn3)n2)c1]

5'-(isopropylamino)-N-(1-methyl-3-(pyridin-2-yl)-1H-pyrazol-4-yl)-[2,3'-bipyridine]-6-carboxamide (I-28)

An NMP (1 mL) solution of 5'-fluoro-N-(1-methyl-3-(pyridin-2-yl)-1H-pyrazol-4-yl)-[2,3'-bipyridine]-6-carboxamide (22.5 mg, 0.06 mmol) and propan-2-amine (>5 eq.) was heated at 120-150° C. for 24 days until >50% of desired product was formed. Solvent was removed in vacuo, after silica gel chromatography and further trituration from Hexanes-EtOAc, title compound was obtained as a light beige color solid: 7.1 mg (29% yield); $^1$H NMR (300 MHz, DMSO-$d_6$) δ 12.66 (s, 1H), 8.90 (d, J=1.9 Hz, 1H), 8.80 (ddd, J=5.0, 1.7, 1.0 Hz, 1H), 8.58 (s, 1H), 8.27-8.16 (m, 4H), 8.08 (ddd, J=8.1, 1.1, 1.1 Hz, 1H), 7.97 (ddd, J=7.7, 7.7, 1.8 Hz, 1H), 7.66-7.64 (m, 1H), 7.43 (ddd, J=7.4, 5.0, 1.3 Hz, 1H), 5.95 (d, J=8.3 Hz, 1H), 4.01 (s, 3H), 3.84-3.73 (m, 1H), 1.22 (d, J=6.3 Hz, 6H); LRMS (M+H) m/z 414.73.

Example 31

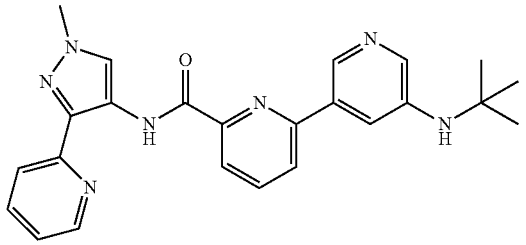 [SMILES: Cn1cc(NC(=O)c2cccc(-c3cncc(NC(C)(C)C)c3)n2)c(-c2ccccn2)n1]

5'-(tert-butylamino)-N-(1-methyl-3-(pyridin-2-yl)-1H-pyrazol-4-yl)-[2,3'-bipyridine]-6-carboxamide (I-29)

0.1 mmol scale, with N-(tert-butyl)-5-(4,4,5,5-tetramethyl-1,3,2-dioxaborolan-2-yl)pyridin-3-amine, 15.2 mg, 36% yield. $^1$H NMR (300 MHz, DMSO-$d_6$) δ 12.65 (s, 1H), 8.94 (d, J=1.6 Hz, 1H), 8.82 (d, J=4.4 Hz, 1H), 8.58 (s, 1H), 8.32 (d, J=2.6 Hz, 1H), 8.22-8.19 (m, 3H), 8.08 (br d, J=8.0 Hz, 1H), 7.97 (ddd, J=7.8, 7.8, 1.7 Hz, 1H), 7.81-7.79 (m, 1H), 7.43 (ddd, J=7.3, 5.0, 1.0 Hz, 1H), 5.84 (br s, 1H), 4.02 (s, 3H), 1.42 (s, 9H); LRMS (M+H) m/z 428.66.

Example 32

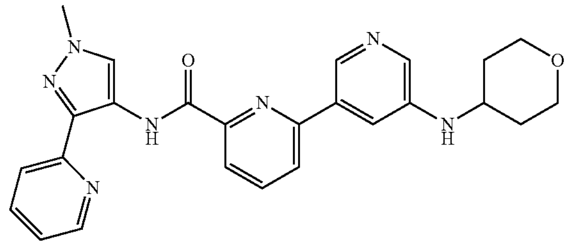 [SMILES: Cn1cc(NC(=O)c2cccc(-c3cncc(NC4CCOCC4)c3)n2)c(-c2ccccn2)n1]

N-(1-methyl-3-(pyridin-2-yl)-1H-pyrazol-4-yl)-5'-((tetrahydro-2H-pyran-4-yl)amino)-[2,3'-bipyridine]-6-carboxamide (I-30)

An NMP (1.5 mL) solution of 5'-fluoro-N-(1-methyl-3-(pyridin-2-yl)-1H-pyrazol-4-yl)-[2,3'-bipyridine]-6-carboxamide (30 mg, 0.08 mmol) and tetrahydro-2H-pyran-4-amine 40 mg, 0.4 mmol) was heated at 150° C. for 19 days until >50% of desired product was formed, as monitored by LC-MS. Solvent was removed in vacuo, after silica gel chromatography and further trituration from Hexanes-EtOAc, title compound was obtained as a light beige color solid: 5 mg (14% yield); $^1$H NMR (300 MHz, DMSO-$d_6$) δ 12.66 (s, 1H), 8.93 (d, J=1.8 Hz, 1H), 8.80 (ddd, J=5.0, 1.7, 0.9 Hz, 1H), 8.58 (s, 1H), 8.30-8.17 (m, 4H), 8.08 (ddd, J=8.1, 1.0, 1.0 Hz, 1H), 7.97 (ddd, J=7.7, 7.7, 1.8 Hz, 1H), 7.72-7.71 (m, 1H), 7.43 (ddd, J=7.4, 5.0, 1.3 Hz, 1H), 6.10 (d, J=8.3 Hz, 1H), 4.02 (s, 3H), 3.91 (ddd, J=11.3, 3.2, 3.2 Hz, 2H), 3.75-3.63 (m, 1H), 3.47-3.36 (m, partially overlapped with $H_2O$, 2H), 2.00-1.95 (m, 2H), 1.63 (s, 1H), 1.53-1.40 (m, 2H); LRMS (M+H) m/z 456.46.

Example 33

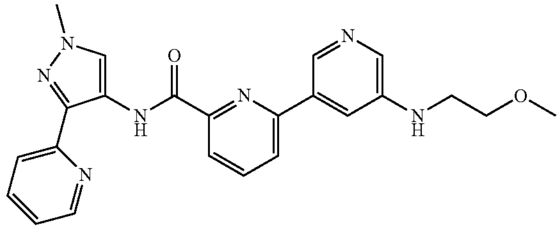 [SMILES: COCCNc1cncc(-c2cccc(C(=O)Nc3cn(C)nc3-c3ccccn3)n2)c1]

5'-((2-methoxyethyl)amino)-N-(1-methyl-3-(pyridin-2-yl)-1H-pyrazol-4-yl)-[2,3'-bipyridine]-6-carboxamide (1-31)

An NMP (1.2 mL) solution of 5'-fluoro-N-(1-methyl-3-(pyridin-2-yl)-1H-pyrazol-4-yl)-[2,3'-bipyridine]-6-carboxamide (22.5 mg, 0.06 mmol) and 2-methoxyethan-1-amine (>5 eq) was heated at 140-150° C. for 13 days until reaction went to completion, as monitored by LC-MS. Solvent was removed in vacuo, after silica gel chromatography and further trituration from Hexanes-EtOAc, title compound was obtained as a tan color solid: 14 mg (54% yield); $^1$H NMR (300 MHz, DMSO-$d_6$) δ 12.64 (s, 1H), 8.97 (d, J=1.7 Hz, 1H), 8.82 (ddd, J=5.0, 1.6, 0.9 Hz, 1H), 8.57 (s, 1H), 8.28-8.16 (m, 4H), 8.07 (br d, J=8.0 Hz, 1H), 7.96 (ddd, J=7.8, 7.8, 1.7 Hz, 1H), 7.70-7.68 (m, 1H), 7.43 (ddd, J=7.4, 5.0, 1.2 Hz, 1H), 6.13 (t, J=5.7 Hz, 1H), 4.01 (s, 3H), 3.59 (t, J=5.5 Hz, 2H), 3.41-3.36 (m, partially overlapped with $H_2O$, 2H), 3.34 (s, 3H); LRMS (M+H) m/z 430.72.

Example 34

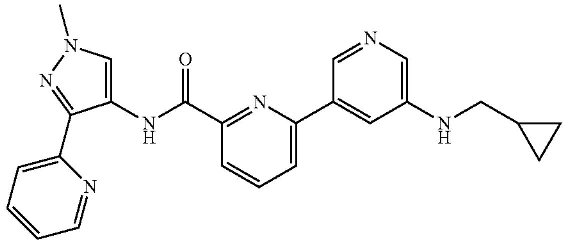 [SMILES: Cn1cc(NC(=O)c2cccc(-c3cncc(NCC4CC4)c3)n2)c(-c2ccccn2)n1]

5'-((cyclopropylmethyl)amino)-N-(1-methyl-3-(pyridin-2-yl)-1H-pyrazol-4-yl)-[2,3'-bipyridine]-6-carboxamide (1-32)

A mixture of 5'-fluoro-N-(1-methyl-3-(pyridin-2-yl)-1H-pyrazol-4-yl)-[2,3'-bipyridine]-6-carboxamide (22.5 mg, 0.06 mmol) and cyclopropylmethanamine (1 mL) was heated at 150-180° C. for 20 days until >50% of desired product was formed, as monitored by LC-MS. Solvent was removed in vacuo, after silica gel chromatography and further trituration from Hexanes-EtOAc, title compound was obtained as a beige color solid: 8.6 mg (34% yield); $^1$H NMR (300 MHz, DMSO-$d_6$) δ 12.65 (s, 1H), 8.94 (d, J=1.7 Hz, 1H), 8.81 (br d, J=5.0 Hz, 1H), 8.58 (s, 1H), 8.28-8.16

(m, 4H), 8.08 (br d, J=8.2 Hz, 1H), 7.96 (ddd, J=7.5, 7.5, 1.3 Hz, 1H), 7.66 (dd, J=2.1 Hz, 1H), 7.45-7.41 (m, 1H), 6.21 (t, J=5.4 Hz, 1H), 4.01 (s, 3H), 3.09-3.05 (m, 2H), 1.20-1.07 (m, 1H), 0.57-0.51 (m, 2H), 0.30-0.26 (m, 2H); LRMS (M+H) m/z 426.75.

Example 35

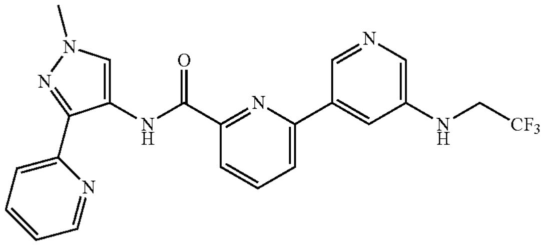 [SMILES: Cn1cc(NC(=O)c2cccc(-c3cncc(NCC(F)(F)F)c3)n2)c(-c2ccccn2)n1]

N-(1-methyl-3-(pyridin-2-yl)-1H-pyrazol-4-yl)-5'-((2,2,2-trifluoroethyl)amino)-[2,3'-bipyridine]-6-carboxamide (I-33)

$^1$H NMR (300 MHz, DMSO-$d_6$) δ 12.64 (s, 1H), 9.10 (d, J=1.7 Hz, 1H), 8.84 (br d, J=4.9 Hz, 1H), 8.58 (s, 1H), 8.36 (d, J=2.6 Hz, 1H), 8.32 (dd, J=7.5, 1.5 Hz, 1H), 8.25 (dd, J=7.5, 7.5 Hz, 1H), 8.20 (dd, J=7.5, 1.6 Hz, 1H), 8.08 (d, J=8.1 Hz, 1H), 7.97 (ddd, J=7.7, 7.7, 1.7 Hz, 1H), 7.89 (dd, J=2.1, 2.1 Hz, 1H), 7.43 (ddd, J=7.3, 5.0, 1.2 Hz, 1H), 6.79 (t, J=6.9 Hz, 1H), 4.26-4.14 (m, 2H), 4.02 (s, 3H); LRMS (M+H) m/z 454.69.

Example 36

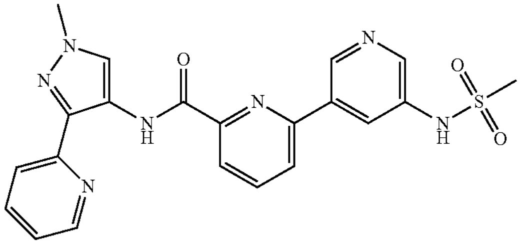 [SMILES: Cn1cc(NC(=O)c2cccc(-c3cncc(NS(C)(=O)=O)c3)n2)c(-c2ccccn2)n1]

N-(1-methyl-3-(pyridin-2-yl)-1H-pyrazol-4-yl)-5'-(methylsulfonamido)-[2,3'-bipyridine]-6-carboxamide (I-34)

0.08 mmol scale, with N-(5-(4,4,5,5-tetramethyl-1,3,2-dioxaborolan-2-yl)pyridin-3-yl)methanesulfonamide, 21.3 mg, 59% yield. $^1$H NMR (300 MHz, DMSO-$d_6$) δ 12.63 (s, 1H), 10.27 (s, 1H), 9.48 (d, J=2.0 Hz, 1H), 8.83 (ddd, J=5.0, 1.7, 1.0 Hz, 1H), 8.69 (d, J=2.4 Hz, 1H), 8.59 (s, 1H), 8.36-8.35 (m, 1H), 8.31-8.23 (m, 3H), 8.08 (ddd, J=8.1, 1.1, 1.1 Hz, 1H), 7.97 (ddd, J=8.1, 7.5, 1.8 Hz, 1H), 7.43 (ddd, J=7.4, 5.0, 1.3 Hz, 1H), 4.02 (s, 3H), 3.20 (s, 3H); LRMS (M+H) m/z 450.67.

Example 37

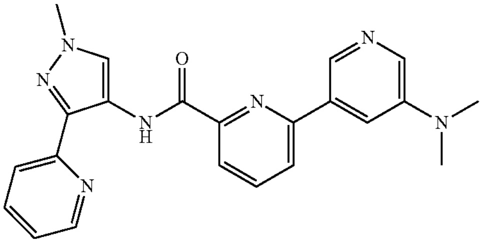 [SMILES: CN(C)c1cncc(-c2cccc(C(=O)Nc3cn(C)nc3-c3ccccn3)n2)c1]

5'-(dimethylamino)-N-(1-methyl-3-(pyridin-2-yl)-1H-pyrazol-4-yl)-[2,3'-bipyridine]-6-carboxamide (I-35)

An NMP (1 mL) solution of 5'-fluoro-N-(1-methyl-3-(pyridin-2-yl)-1H-pyrazol-4-yl)-[2,3'-bipyridine]-6-carboxamide (22.5 mg, 0.06 mmol), dimethylamine hydrochloride (>5 eq.) and $NaHCO_3$ (>2 eq) was heated at 120-150° C. for 11 days until >50% of desired product was formed, as monitored by LC-MS. Solvent was removed in vacuo, after silica gel chromatography and further trituration from Hexanes-EtOAc, title compound was obtained as a tan color solid: 4.3 mg (18% yield); $^1$H NMR (300 MHz, DMSO-$d_6$) δ 12.65 (s, 1H), 9.12 (d, J=1.7 Hz, 1H), 8.83 (br d, J=4.9 Hz, 1H), 8.58 (s, 1H), 8.40 (dd, J=7.2, 1.8 Hz, 1H), 8.35 (d, J=2.8 Hz, 1H), 8.26-8.18 (m, 2H), 8.09 (d, J=8.0 Hz, 1H), 7.97 (ddd, J=7.7, 7.7, 1.8 Hz, 1H), 7.80-7.79 (m, 1H), 7.44 (ddd, J=7.4, 5.0, 1.2 Hz, 1H), 4.02 (s, 3H), 3.08 (s, 6H); LRMS (M+H) m/z 400.66.

Example 38

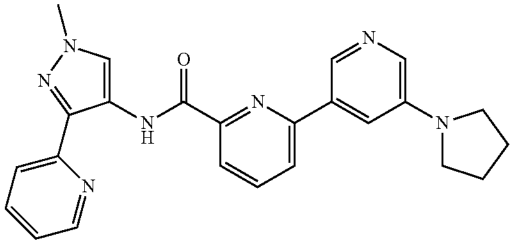 [SMILES: Cn1cc(NC(=O)c2cccc(-c3cncc(N4CCCC4)c3)n2)c(-c2ccccn2)n1]

N-(1-methyl-3-(pyridin-2-yl)-1H-pyrazol-4-yl)-5'-(pyrrolidin-1-yl)-[2,3'-bipyridine]-6-carboxamide (I-36)

An NMP (1 mL) solution of 5'-fluoro-N-(1-methyl-3-(pyridin-2-yl)-1H-pyrazol-4-yl)-[2,3'-bipyridine]-6-carboxamide (22.5 mg, 0.06 mmol) and pyrrolidine (0.1 mL) was heated at 120-150° C. for 4 days until reaction went to completion, as monitored by LC-MS. Solvent was removed in vacuo, after silica gel chromatography and further trituration from Hexanes-EtOAc, title compound was obtained as a yellow solid: 14.9 mg (58% yield); $^1$H NMR (300 MHz, DMSO-$d_6$) δ 12.66 (s, 1H), 9.06 (d, J=1.8 Hz, 1H), 8.81 (ddd, J=5.0, 1.7, 0.9 Hz, 1H), 8.58 (s, 1H), 8.37 (dd, J=7.2, 1.8 Hz, 1H), 8.25-8.17 (m, 3H), 8.08 (ddd, J=8.1, 1.1, 1.1 Hz, 1H), 7.97 (ddd, J=7.7, 7.7, 1.8 Hz, 1H), 7.60-7.59 (m, 1H), 7.44 (ddd, J=7.4, 5.0, 1.3 Hz, 1H), 4.02 (s, 3H), 3.44-3.39 (m, 4H), 2.05-2.01 (m, 4H); LRMS (M+H) m/z 426.69.

Example 39

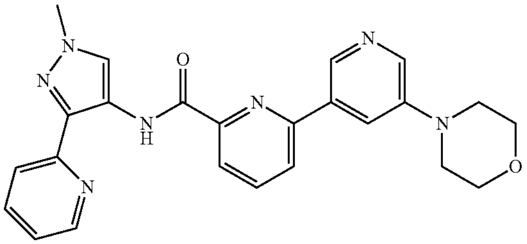 [SMILES: Cn1cc(NC(=O)c2cccc(-c3cncc(N4CCOCC4)c3)n2)c(-c2ccccn2)n1]

N-(1-methyl-3-(pyridin-2-yl)-1H-pyrazol-4-yl)-5'-morpholino-[2,3'-bipyridine]-6-carboxamide (I-37)

An NMP (1 mL) solution of 5'-fluoro-N-(1-methyl-3-(pyridin-2-yl)-1H-pyrazol-4-yl)-[2,3'-bipyridine]-6-carboxamide (22.5 mg, 0.06 mmol) and morpholine (0.1 mL) was heated at 120-150° C. for 11 days until reaction went to completion, as monitored by LC-MS. Solvent was removed in vacuo, after silica gel chromatography and further trituration from Hexanes-EtOAc, title compound was obtained as an off-white solid: 21.4 mg (87% yield); $^1$H NMR (300 MHz, DMSO-$d_6$) δ 12.64 (s, 1H), 9.23 (d, J=1.7 Hz, 1H), 8.82 (br d, J=5.0 Hz, 1H), 8.58 (s, 1H), 8.54 (d, J=2.7 Hz, 1H), 8.42 (dd, J=7.2, 1.7 Hz, 1H), 8.26-8.18 (m, 2H), 8.10-8.07 (m, 2H), 7.98 (ddd, J=7.7, 7.7, 1.7 Hz, 1H), 7.46 (ddd, J=7.4, 5.0, 1.2 Hz, 1H), 4.02 (s, 3H), 3.84-3.81 (m, 4H), 3.37-3.34 (m, partially overlapped with $H_2O$, 4H); LRMS (M+H) m/z 442.59.

Example 40

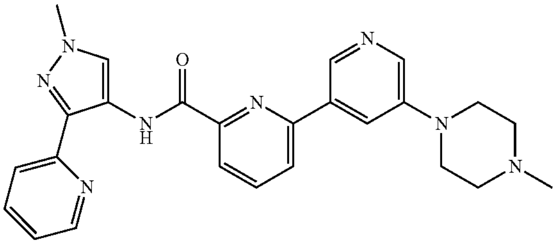 [SMILES: CN1CCN(c2cncc(-c3cccc(C(=O)Nc4cn(C)nc4-c4ccccn4)n3)c2)CC1]

N-(1-methyl-3-(pyridin-2-yl)-1H-pyrazol-4-yl)-5'-(4-methylpiperazin-1-yl)-[2,3'-bipyridine]-6-carboxamide (1-38)

An NMP (1 mL) solution of 5'-fluoro-N-(1-methyl-3-(pyridin-2-yl)-1H-pyrazol-4-yl)-[2,3'-bipyridine]-6-carboxamide (22.5 mg, 0.06 mmol) and 1-methylpiperazine (0.1 mL) was heated at 120-150° C. for 11 days until >50% desired product formed, as monitored by LC-MS. Solvent was removed in vacuo, after silica gel chromatography and further trituration from Hexanes-EtOAc, title compound was obtained as a light tan color solid: 12.4 mg (45% yield); $^1$H NMR (300 MHz, DMSO-$d_6$) δ 12.64 (s, 1H), 9.19 (d, J=1.7 Hz, 1H), 8.81 (ddd, J=4.9, 1.6, 0.9 Hz, 1H), 8.58 (s, 1H), 8.53 (d, J=2.7 Hz, 1H), 8.41 (dd, J=7.0, 1.9 Hz, 1H), 8.26-8.18 (m, 2H), 8.10-8.07 (m, 2H), 7.98 (ddd, J=7.7, 7.7, 1.8 Hz, 1H), 7.45 (ddd, J=7.4, 5.0, 1.3 Hz, 1H), 4.02 (s, 3H), 3.38-3.35 (m, partially overlapped with $H_2O$, 4H), 2.56-2.52 (m, overlapped with DMSO, 4H), 2.28 (s, 3H); LRMS (M+H) m/z 455.77.

Example 41

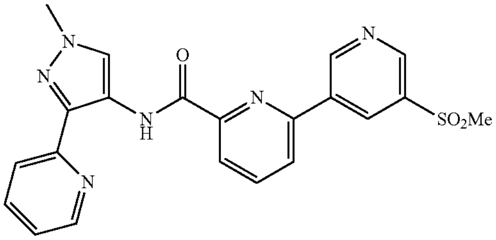 [SMILES: Cn1cc(NC(=O)c2cccc(-c3cncc(S(C)(=O)=O)c3)n2)c(-c2ccccn2)n1]

N-(1-methyl-3-(pyridin-2-yl)-1H-pyrazol-4-yl)-5'-(methylsulfonyl)-[2,3'-bipyridine]-6-carboxamide (I-39)

0.1 mmol scale, with (5-(methylsulfonyl)pyridin-3-yl) boronic acid, 26.1 mg, 45% yield. $^1$H NMR (300 MHz, DMSO-$d_6$) δ 12.58 (s, 1H), 10.02 (d, J=2.1 Hz, 1H), 9.31 (d, J=2.1 Hz, 1H), 9.05 (dd, J=2.1, 2.1 Hz, 1H), 8.83 (ddd, J=5.0, 1.7, 1.0 Hz, 1H), 8.59 (s, 1H), 8.54 (dd, J=6.7, 2.2 Hz, 1H), 8.35-8.28 (m, 2H), 8.08 (ddd, J=8.1, 1.1, 1.1 Hz, 1H), 7.97 (ddd, J=7.8, 7.8, 1.8 Hz, 1H), 7.43 (ddd, J=7.4, 5.0, 1.3 Hz, 1H), 4.02 (s, 3H), 3.50 (s, 3H); LRMS (M+H) m/z 435.45.

Example 42

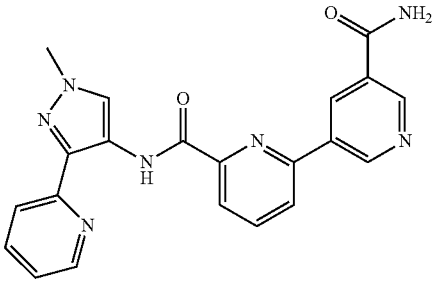 [SMILES: Cn1cc(NC(=O)c2cccc(-c3cncc(C(N)=O)c3)n2)c(-c2ccccn2)n1]

N6-(1-methyl-3-(pyridin-2-yl)-1H-pyrazol-4-yl)-[2,3'-bipyridine]-5',6-dicarboxamide (I-40)

Example 43

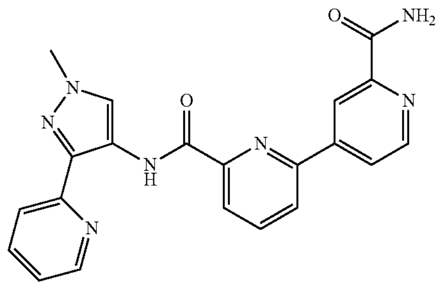 [SMILES: Cn1cc(NC(=O)c2cccc(-c3ccnc(C(N)=O)c3)n2)c(-c2ccccn2)n1]

N6-(1-methyl-3-(pyridin-2-yl)-1H-pyrazol-4-yl)-[2,4'-bipyridine]-2',6-dicarboxamide (I-41)

Example 44

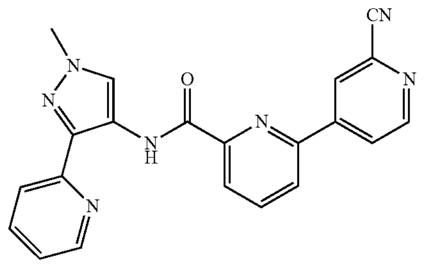 [SMILES: Cn1cc(NC(=O)c2cccc(-c3ccnc(C#N)c3)n2)c(-c2ccccn2)n1]

2'-cyano-N-(1-methyl-3-(pyridin-2-yl)-1H-pyrazol-4-yl)-[2,4'-bipyridine]-6-carboxamide (I-42)

Example 45

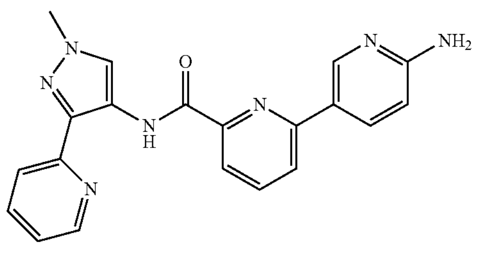 [SMILES: Cn1cc(NC(=O)c2cccc(-c3ccc(N)nc3)n2)c(-c2ccccn2)n1]

6'-amino-N-(1-methyl-3-(pyridin-2-yl)-1H-pyrazol-4-yl)-[2,3'-bipyridine]-6-carboxamide (I-43)

0.1 mmol scale, with (6-aminopyridin-3-yl)boronic acid, 18.8 mg, 51% yield. $^1$H NMR (300 MHz, DMSO-$d_6$) δ 12.49 (s, 1H), 9.14 (d, J=2.2 Hz, 1H), 8.84 (br d, J=4.9 Hz, 1H), 8.58 (s, 1H), 8.36 (dd, J=8.7, 2.5 Hz, 1H), 8.14 (dd, J=7.8, 1.6 Hz, 1H), 8.13-7.94 (m, 4H), 7.44 (ddd, J=7.4, 5.0, 1.2 Hz, 1H), 6.70 (d, J=8.7 Hz, 1H), 6.53 (s, 2H), 4.01 (s, 3H); LRMS (M+H) m/z 372.50.

Example 46

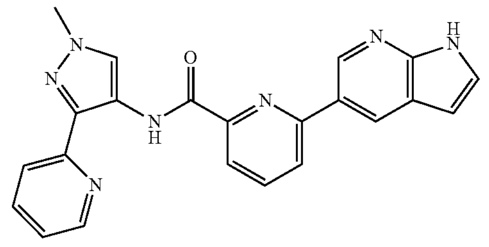 [SMILES: Cn1cc(NC(=O)c2cccc(-c3cnc4[nH]ccc4c3)n2)c(-c2ccccn2)n1]

N-(1-methyl-3-(pyridin-2-yl)-1H-pyrazol-4-yl)-6-(1H-pyrrolo[2,3-b]pyridin-5-yl)picolinamide (I-44)

0.1 mmol scale, with (1H-pyrrolo[2,3-b]pyridin-5-yl)boronic acid, 26.1 mg, 66% yield. $^1$H NMR (300 MHz, DMSO-$d_6$) δ 12.64 (s, 1H), 12.06 (s, 1H), 9.46 (d, J=2.1 Hz, 1H), 8.95 (ddd, J=5.0, 1.7, 0.9 Hz, 1H), 8.92 (d, J=2.0 Hz, 1H), 8.60 (s, 1H), 8.39 (dd, J=7.7, 1.2 Hz, 1H), 8.20 (dd, J=7.7, 7.7 Hz, 1H), 8.15 (d, J=1.2 Hz, 1H), 8.11 (d, J=8.2 Hz, 1H), 8.00 (ddd, J=7.7, 7.7, 1.8 Hz, 1H), 7.66 (dd, J=3.3, 2.6 Hz, 1H), 7.46 (ddd, J=7.4, 5.0, 1.3 Hz, 1H), 6.67 (dd, J=3.4, 1.8 Hz, 1H), 4.03 (s, 3H); LRMS (M+H) m/z 396.57.

Example 47

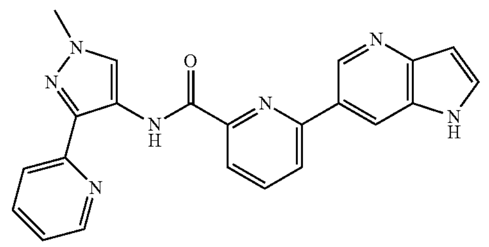 [SMILES: Cn1cc(NC(=O)c2cccc(-c3cnc4cc[nH]c4c3)n2)c(-c2ccccn2)n1]

N-(1-methyl-3-(pyridin-2-yl)-1H-pyrazol-4-yl)-6-(1H-pyrrolo[3,2-b]pyridin-6-yl)picolinamide (I-45)

0.1 mmol scale, with 6-(4,4,5,5-tetramethyl-1,3,2-dioxaborolan-2-yl)-1H-pyrrolo[3,2-b]pyridine, 9.7 mg, 25% yield. $^1$H NMR (300 MHz, DMSO-$d_6$) δ 12.67 (s, 1H), 11.68 (s, 1H), 9.60 (d, J=2.0 Hz, 1H), 8.93 (ddd, J=5.0, 1.6, 0.9 Hz, 1H), 8.60-8.59 (m, 2H), 8.38 (dd, J=7.6, 1.3 Hz, 1H), 8.21 (dd, J=7.6, 7.6 Hz, 1H), 8.15 (dd, J=7.6, 1.3 Hz, 1H), 8.10 (ddd, J=8.1, 1.1, 1.1 Hz, 1H), 7.98 (ddd, J=7.7, 7.7, 1.8 Hz, 1H), 7.87-7.85 (m, 1H), 7.47 (ddd, J=7.4, 5.0, 1.3 Hz, 1H), 6.78-6.77 (m, 1H), 4.03 (s, 3H); LRMS (M+H) m/z 396.59.

Example 48

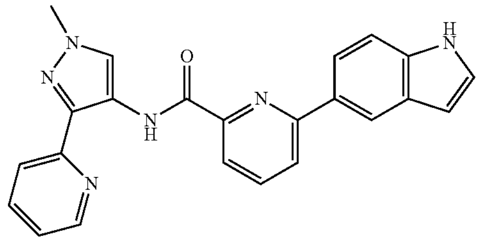 [SMILES: Cn1cc(NC(=O)c2cccc(-c3ccc4[nH]ccc4c3)n2)c(-c2ccccn2)n1]

6-(1H-indol-5-yl)-N-(1-methyl-3-(pyridin-2-yl)-1H-pyrazol-4-yl)picolinamide (I-46)

0.1 mmol scale, with (1H-indol-5-yl)boronic acid, 27.9 mg, 70% yield. $^{1}$H NMR (300 MHz, DMSO-$d_6$) δ 12.67 (s, 1H), 11.40 (s, 1H), 8.85 (ddd, J=5.0, 1.6, 0.9 Hz, 1H), 8.65 (d, J=1.3 Hz, 1H), 8.60 (s, 1H), 8.29 (dd, J=7.7, 1.3 Hz, 1H), 8.20 (dd, J=8.6, 1.7 Hz, 1H), 8.16-8.07 (m, 3H), 8.00 (ddd, J=7.7, 7.7, 1.8 Hz, 1H), 7.68 (d, J=8.6 Hz, 1H), 7.54-7.52 (m, 1H), 7.46 (ddd, J=7.4, 5.0, 1.2 Hz, 1H), 6.65-6.64 (m, 1H), 4.02 (s, 3H); LRMS (M+H) m/z 395.57.

Example 49

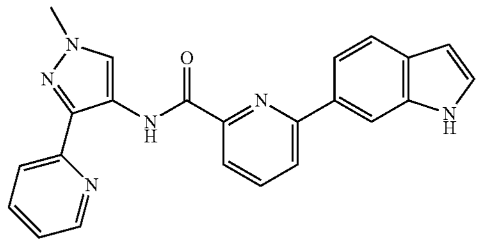 [SMILES: Cn1cc(NC(=O)c2cccc(-c3ccc4cc[nH]c4c3)n2)c(-c2ccccn2)n1]

6-(1H-indol-6-yl)-N-(1-methyl-3-(pyridin-2-yl)-1H-pyrazol-4-yl)picolinamide (I-47)

0.1 mmol scale, with (1H-indol-6-yl)boronic acid, 37.8 mg, 96% yield. $^{1}$H NMR (300 MHz, DMSO-$d_6$) δ 12.69 (s, 1H), 11.44 (s, 1H), 8.76 (br d, J=4.9 Hz, 1H), 8.60 (s, 1H), 8.32 (s, 1H), 8.27 (dd, J=7.6, 1.4 Hz, 1H), 8.20-8.07 (m, 4H), 7.98 (ddd, J=7.7, 7.7, 1.7 Hz, 1H), 7.87 (d, J=8.3 Hz, 1H), 7.56 (dd, J=2.7, 2.7 Hz, 1H), 7.45 (ddd, J=7.3, 5.0, 1.2 Hz, 1H), 6.61-6.60 (m, 1H), 4.02 (s, 3H); LRMS (M+H) m/z 395.54.

Example 50

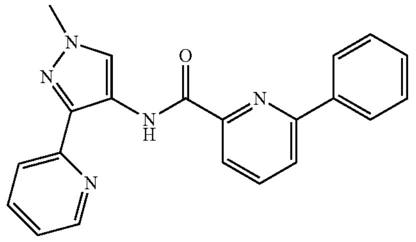 [SMILES: Cn1cc(NC(=O)c2cccc(-c3ccccc3)n2)c(-c2ccccn2)n1]

N-(1-methyl-3-(pyridin-2-yl)-1H-pyrazol-4-yl)-6-phenylpicolinamide (I-48)

0.08 mmol scale, with phenylboronic acid, 20.5 mg, 72% yield. $^{1}$H NMR (300 MHz, DMSO-$d_6$) δ 12.58 (s, 1H), 8.75 (ddd, J=5.0, 1.7, 1.0 Hz, 1H), 8.59 (s, 1H), 8.45-8.42 (m, 2H), 8.32 (dd, J=6.9, 2.1 Hz, 1H), 8.24-8.17 (m, 2H), 8.09 (ddd, J=8.0, 1.1, 1.1 Hz, 1H), 7.98 (ddd, J=7.7, 7.7, 1.8 Hz, 1H), 7.75-7.70 (m, 2H), 7.66-7.61 (m, 1H), 7.49 (ddd, J=7.4, 5.0, 1.3 Hz, 1H), 4.02 (s, 3H); LRMS (M+H) m/z 356.59.

Example 51

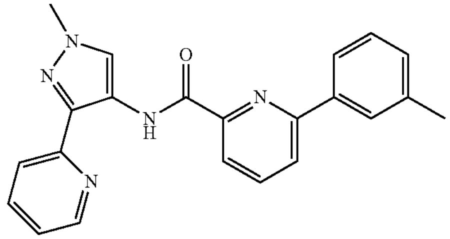 [SMILES: Cc1cccc(-c2cccc(C(=O)Nc3cn(C)nc3-c3ccccn3)n2)c1]

N-(1-methyl-3-(pyridin-2-yl)-1H-pyrazol-4-yl)-6-(m-tolyl)picolinamide (I-49)

0.08 mmol scale, with m-tolylboronic acid, 15.8 mg, 71% yield. $^{1}$H NMR (300 MHz, DMSO-$d_6$) δ 12.63 (s, 1H), 8.67 (br d, J=4.9 Hz, 1H), 8.58 (s, 1H), 8.29-8.17 (m, 4H), 8.12 (s, 1H), 8.07 (d, J=8.1 Hz, 1H), 7.97 (ddd, J=7.7, 7.7, 1.8 Hz, 1H), 7.61 (dd, J=7.6, 7.6 Hz, 1H), 7.48-7.43 (m, 2H), 4.02 (s, 3H), 2.51 (s, 3H); LRMS (M+H) m/z 370.63.

Example 52

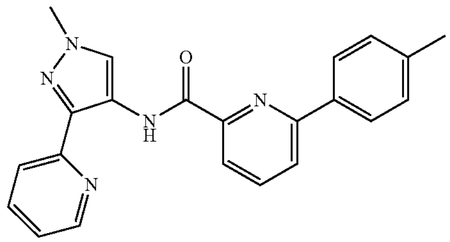 [SMILES: Cc1ccc(-c2cccc(C(=O)Nc3cn(C)nc3-c3ccccn3)n2)cc1]

N-(1-methyl-3-(pyridin-2-yl)-1H-pyrazol-4-yl)-6-(p-tolyl)picolinamide (I-50)

0.08 mmol scale, with p-tolylboronic acid, 22.1 mg, 75% yield. $^{1}$H NMR (300 MHz, DMSO-$d_6$) δ 12.64 (s, 1H), 8.68 (br d, J=4.9 Hz, 1H), 8.58 (s, 1H), 8.28 (dd, J=6.7, 2.4 Hz, 1H), 8.25-8.17 (m, 3H), 8.13 (s, 1H), 8.08 (d, J=8.1 Hz, 1H), 7.98 (ddd, J=7.7, 7.7, 1.8 Hz, 1H), 7.62 (dd, J=7.6, 7.6 Hz, 1H), 7.48-7.43 (m, 2H), 4.02 (s, 3H), 2.51 (s, 3H); LRMS (M+H) m/z 370.18.

Example 53

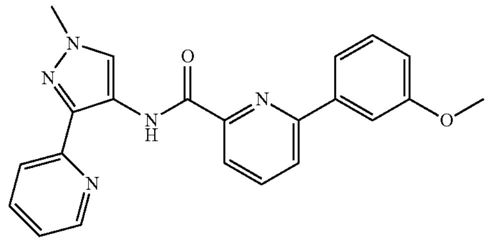 [SMILES: COc1cccc(-c2cccc(C(=O)Nc3cn(C)nc3-c3ccccn3)n2)c1]

6-(3-methoxyphenyl)-N-(1-methyl-3-(pyridin-2-yl)-1H-pyrazol-4-yl)picolinamide (I-51)

0.08 mmol scale, with (3-methoxyphenyl)boronic acid, 2.2 mg, 7% yield. $^1$H NMR (300 MHz, DMSO-$d_6$) δ 12.58 (s, 1H), 8.82 (br d, J=5.0 Hz, 1H), 8.59 (s, 1H), 8.33 (dd, J=6.4, 2.7 Hz, 1H), 8.23-8.17 (m, 2H), 8.08 (d, J=8.0 Hz, 1H), 8.01-7.94 (m, 3H), 7.65 (dd, J=8.0, 8.0 Hz, 1H), 7.48-7.44 (m, 1H), 7.23 (dd, J=8.1, 2.6 Hz, 1H), 4.02 (s, 3H), 3.95 (s, 3H); LRMS (M+H) m/z 386.58.

Example 54

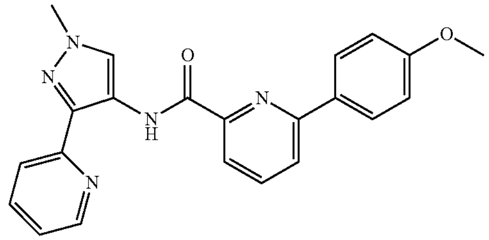 [SMILES: COc1ccc(-c2cccc(C(=O)Nc3cn(C)nc3-c3ccccn3)n2)cc1]

6-(4-methoxyphenyl)-N-(1-methyl-3-(pyridin-2-yl)-1H-pyrazol-4-yl)picolinamide (I-52)

0.08 mmol scale, with (4-methoxyphenyl)boronic acid, 16 mg, 52% yield. $^1$H NMR (300 MHz, DMSO-$d_6$) δ 12.54 (s, 1H), 8.77-8.75 (m, 1H), 8.58 (s, 1H), 8.40-8.37 (m, 2H), 8.24 (dd, J=7.5, 1.6 Hz, 1H), 8.17-8.07 (m, 3H), 7.98 (ddd, J=7.5, 7.5, 1.7 Hz, 1H), 7.51 (ddd, J=7.4, 5.0, 1.3 Hz, 1H), 7.27-7.24 (m, 2H), 4.01 (s, 3H), 3.94 (s, 3H); LRMS (M+H) m/z 386.64.

Example 55

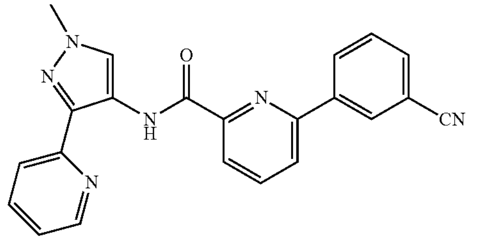 [SMILES: Cn1cc(NC(=O)c2cccc(-c3cccc(C#N)c3)n2)c(-c2ccccn2)n1]

6-(3-cyanophenyl)-N-(1-methyl-3-(pyridin-2-yl)-1H-pyrazol-4-yl)picolinamide (I-53)

0.08 mmol scale, with (3-cyanophenyl)boronic acid, 21 mg, 69% yield. $^1$H NMR (300 MHz, DMSO-$d_6$) δ 12.46 (s, 1H), 8.73-8.66 (m, 3H), 8.53 (s, 1H), 8.37 (dd, J=6.1, 2.7 Hz, 1H), 8.24-8.17 (m, 2H), 8.07-8.03 (m, 2H), 7.97-7.86 (m, 2H), 7.41-7.37 (m, 1H), 4.00 (s, 3H); LRMS (M+H) m/z 381.61.

Example 56

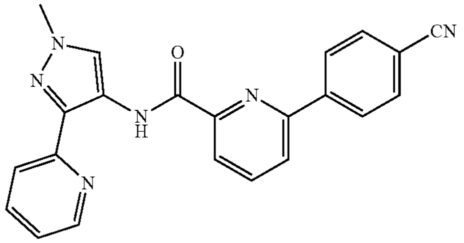 [SMILES: Cn1cc(NC(=O)c2cccc(-c3ccc(C#N)cc3)n2)c(-c2ccccn2)n1]

6-(4-cyanophenyl)-N-(1-methyl-3-(pyridin-2-yl)-1H-pyrazol-4-yl)picolinamide (I-54)

0.08 mmol scale, with (3-cyanophenyl)boronic acid, 9.1 mg, 30% yield. $^1$H NMR (300 MHz, DMSO-$d_6$) δ 12.50 (s, 1H), 8.72 (br d, J=5.2 Hz, 1H), 8.60-8.57 (m, 2H), 8.43-8.36 (m, 1H), 8.27-8.19 (m, 3H), 8.08 (d, J=7.9 Hz, 1H), 8.00-7.96 (m, 1H), 7.69-7.58 (m, 2H), 7.53-7.49 (m, 1H), 4.02 (s, 3H); LRMS (M+H) m/z 381.56.

Example 57

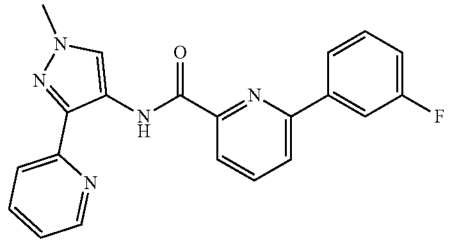 [SMILES: Cn1cc(NC(=O)c2cccc(-c3cccc(F)c3)n2)c(-c2ccccn2)n1]

6-(3-fluorophenyl)-N-(1-methyl-3-(pyridin-2-yl)-1H-pyrazol-4-yl)picolinamide (I-55)

0.08 mmol scale, with (3-fluorophenyl)boronic acid, 20.7 mg, 69% yield. $^1$H NMR (300 MHz, DMSO-$d_6$) δ 12.51 (s, 1H), 8.75 (ddd, J=5.0, 1.7, 1.0 Hz, 1H), 8.59 (s, 1H), 8.37 (dd, J=6.3, 2.7 Hz, 1H), 8.27-8.21 (m, 4H), 8.09 (ddd, J=8.1, 1.1, 1.1 Hz, 1H), 7.98 (ddd, J=8.1, 7.5, 1.8 Hz, 1H), 7.79-7.72 (m, 1H), 7.50-7.43 (m, 2H), 4.02 (s, 3H); LRMS (M+H) m/z 374.64.

Example 58

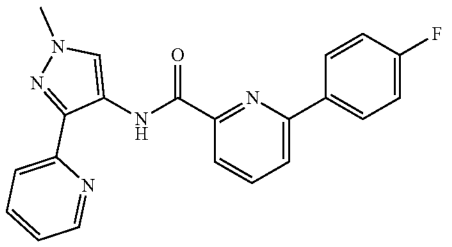 [SMILES: Cn1cc(NC(=O)c2cccc(-c3ccc(F)cc3)n2)c(-c2ccccn2)n1]

6-(4-fluorophenyl)-N-(1-methyl-3-(pyridin-2-yl)-1H-pyrazol-4-yl)picolinamide (I-56)

0.08 mmol scale, with (4-fluorophenyl)boronic acid, 22 mg, 74% yield. $^1$H NMR (300 MHz, DMSO-$d_6$) δ 12.52 (s, 1H), 8.72 (ddd, J=5.0, 1.6, 0.9 Hz, 1H), 8.58 (s, 1H), 8.49-8.44 (m, 2H), 8.30 (dd, J=7.0, 2.0 Hz, 1H), 8.22-8.15 (m, 2H), 8.08 (br d, J=8.0 Hz, 1H), 7.98 (ddd, J=7.7, 7.7, 1.8 Hz, 1H), 7.60-7.54 (m, 2H), 7.50 (ddd, J=7.3, 5.0, 1.3 Hz, 1H), 4.01 (s, 3H); LRMS (M+H) m/z 374.64.

Example 59

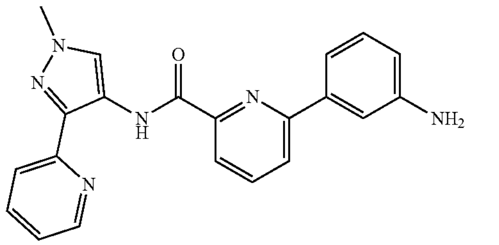 [SMILES: Cn1cc(NC(=O)c2cccc(-c3cccc(N)c3)n2)c(-c2ccccn2)n1]

6-(3-aminophenyl)-N-(1-methyl-3-(pyridin-2-yl)-1H-pyrazol-4-yl)picolinamide (I-57)

0.08 mmol scale, with (3-aminophenyl)boronic acid, 18 mg, 61% yield. $^1$H NMR (300 MHz, DMSO-$d_6$) δ 12.68 (s, 1H), 8.75 (br d, J=4.8 Hz, 1H), 8.58 (s, 1H), 8.19-8.05 (m, 4H), 7.96 (ddd, J=7.7, 7.7, 1.7 Hz, 1H), 7.56 (br d, J=7.7 Hz, 1H), 7.47 (dd, J=1.9, 1.9 Hz, 1H), 7.42 (ddd, J=7.4, 5.0, 1.2 Hz, 1H), 7.36 (dd, J=7.8, 7.8 Hz, 1H), 6.83 (dd, J=7.6, 1.7 Hz, 1H), 5.33 (s, 2H), 4.01 (s, 3H); LRMS (M+H) m/z 371.60.

Example 60

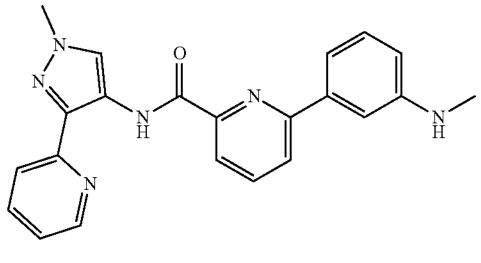 [SMILES: CNc1cccc(-c2cccc(C(=O)Nc3cn(C)nc3-c3ccccn3)n2)c1]

N-(1-methyl-3-(pyridin-2-yl)-1H-pyrazol-4-yl)-6-(3-(methylamino)phenyl)picolinamide (I-58)

$^1$H NMR (300 MHz, DMSO-$d_6$) δ 12.68 (s, 1H), 8.68 (br d, J=4.9 Hz, 1H), 8.58 (s, 1H), 8.18-8.13 (m, 3H), 8.06 (br d, J=8.0 Hz, 1H), 7.96 (ddd, J=7.7, 7.7, 1.7 Hz, 1H), 7.64 (d, J=7.7 Hz, 1H), 7.47-7.41 (m, 2H), 7.36 (dd, J=1.8, 1.8 Hz, 1H), 6.79 (dd, J=7.7, 1.9 Hz, 1H), 5.88-5.86 (m, 1H), 4.01 (s, 3H), 2.80 (d, J=4.2 Hz, 3H); LRMS (M+H) m/z 385.68.

Example 61

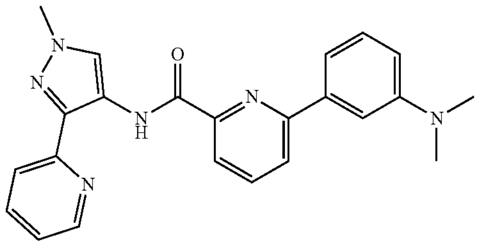 [SMILES: CN(C)c1cccc(-c2cccc(C(=O)Nc3cn(C)nc3-c3ccccn3)n2)c1]

6-(3-(dimethylamino)phenyl)-N-(1-methyl-3-(pyridin-2-yl)-1H-pyrazol-4-yl)picolinamide (I-59)

0.08 mmol scale, with (3-(dimethylamino)phenyl)boronic acid, 13.2 mg, 41% yield. $^1$H NMR (300 MHz, DMSO-$d_6$) δ 12.66 (s, 1H), 8.65 (ddd, J=4.9, 1.7, 0.9 Hz, 1H), 8.58 (s, 1H), 8.28 (dd, J=6.8, 2.3 Hz, 1H), 8.20-8.14 (m, 2H), 8.07 (ddd, J=8.1, 1.0, 1.0 Hz, 1H), 7.97 (ddd, J=7.7, 7.7, 1.8 Hz, 1H), 7.78 (br d, J=7.8 Hz, 1H), 7.57-7.51 (m, 2H), 7.43 (ddd, J=7.3, 5.0, 1.3 Hz, 1H), 6.98 (dd, J=8.0, 2.2 Hz, 1H), 4.02 (s, 3H), 3.03 (s, 6H); LRMS (M+H) m/z 399.64.

Example 62

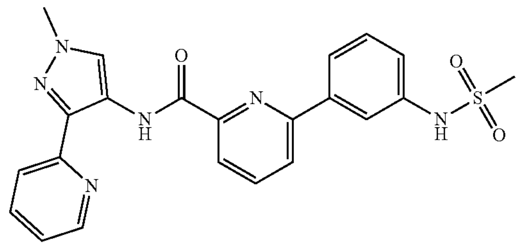 [SMILES: Cn1cc(NC(=O)c2cccc(-c3cccc(NS(C)(=O)=O)c3)n2)c(-c2ccccn2)n1]

N-(1-methyl-3-(pyridin-2-yl)-1H-pyrazol-4-yl)-6-(3-(methylsulfonamido)phenyl)picolinamide (I-60)

0.08 mmol scale, with (3-(methylsulfonamido)phenyl) boronic acid, 21.7 mg, 41% yield. $^1$H NMR (300 MHz, DMSO-$d_6$) δ 12.64 (s, 1H), 9.99 (s, 1H), 8.72 (ddd, J=5.0, 1.7, 0.9 Hz, 1H), 8.58 (s, 1H), 8.26-8.21 (m, 4H), 8.07 (ddd, J=8.1, 1.1, 1.1 Hz, 1H), 8.03 (dd, J=1.8, 1.8 Hz, 1H), 7.97 (ddd, J=7.7, 7.7, 1.8 Hz, 1H), 7.72 (dd, J=7.9, 7.9 Hz, 1H), 7.49 (ddd, J=8.0, 2.1, 0.9 Hz, 1H), 7.42 (ddd, J=7.4, 5.0, 1.3 Hz, 1H), 4.02 (s, 3H), 3.11 (s, 3H); LRMS (M+H) m/z 449.45.

Example 63

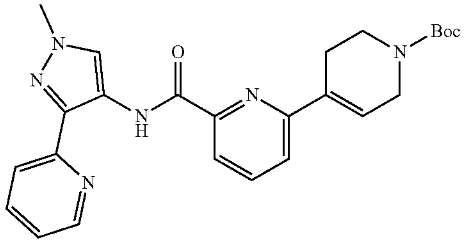 [SMILES: Cn1cc(NC(=O)c2cccc(C3=CCN(C(=O)OC(C)(C)C)CC3)n2)c(-c2ccccn2)n1]

tert-butyl 6-((1-methyl-3-(pyridin-2-yl)-1H-pyrazol-4-yl)carbamoyl)-3',6'-dihydro-[2,4'-bipyridine]-1'(2'H)-carboxylate (1-61)

0.15 mmol scale, with tert-butyl 4-(4,4,5,5-tetramethyl-1,3,2-dioxaborolan-2-yl)-3,6-dihydropyridine-1(2H)-carboxylate, 33.1 mg, 48% yield. $^{1}$H NMR (300 MHz, Chloroform-d) δ 12.40 (s, 1H), 8.60 (ddd, J=5.0, 1.8, 0.9 Hz, 1H), 8.49 (s, 1H), 8.15 (dd, J=7.7, 0.9 Hz, 1H), 8.10 (ddd, J=8.1, 1.1, 1.1 Hz, 1H), 7.86 (dd, J=7.8, 7.8 Hz, 1H), 7.76 (ddd, J=8.1, 7.5, 1.8 Hz, 1H), 7.58 (d, J=7.8 Hz, 1H), 7.22 (ddd, J=7.5, 5.0, 1.2 Hz, 1H), 6.93 (br s, 1H), 4.26 (br s, 2H), 3.99 (s, 3H), 3.78 (t, J=5.6 Hz, 2H), 2.90 (br s, 2H), 1.53 (s, 9H); LRMS (M+H) m/z 461.80.

Example 64

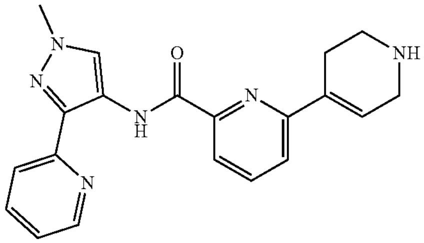 [SMILES: Cn1cc(NC(=O)c2cccc(C3=CCNCC3)n2)c(-c2ccccn2)n1]

N-(1-methyl-3-(pyridin-2-yl)-1H-pyrazol-4-yl)-1',2',3',6'-tetrahydro-[2,4'-bipyridine]-6-carboxamide (I-62)

$^{1}$H NMR (300 MHz, Chloroform-d) δ 12.41 (s, 1H), 8.59 (ddd, J=5.0, 1.8, 0.9 Hz, 1H), 8.48 (s, 1H), 8.12 (dd, J=7.7, 0.9 Hz, 1H), 8.09 (ddd, J=8.1, 1.1, 1.1 Hz, 1H), 7.83 (dd, J=7.8, 7.8z Hz, 1H), 7.75 (ddd, J=8.0, 7.6, 1.8 Hz, 1H), 7.55 (dd, J=8.0, 0.9 Hz, 1H), 7.20 (ddd, J=7.5, 5.0, 1.2 Hz, 1H), 7.04-7.00 (m, 1H), 3.98 (s, 3H), 3.73-3.70 (m, 2H), 3.25 (t, J=5.7 Hz, 2H), 2.83-2.79 (m, 2H), 2.06 (s, 1H); LRMS (M+H) m/z 361.48.

Example 65

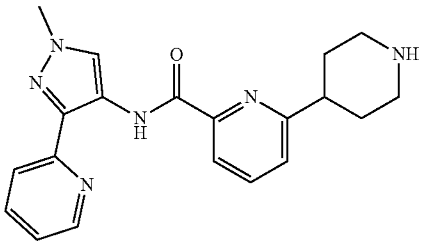 [SMILES: Cn1cc(NC(=O)c2cccc(C3CCNCC3)n2)c(-c2ccccn2)n1]

N-(1-methyl-3-(pyridin-2-yl)-1H-pyrazol-4-yl)-6-(piperidin-4-yl)picolinamide (I-63)

$^{1}$H NMR (300 MHz, Chloroform-d) δ 12.46 (s, 1H), 8.60 (ddd, J=5.0, 1.7, 0.9 Hz, 1H), 8.45 (s, 1H), 8.17 (dd, J=7.7, 0.7 Hz, 1H), 8.08 (ddd, J=8.1, 1.0, 1.0 Hz, 1H), 7.88 (dd, J=7.8, 7.8 Hz, 1H), 7.75 (ddd, J=7.8, 7.8, 1.8 Hz, 1H), 7.40 (d, J=7.3 Hz, 1H), 7.29-7.25 (m, partially overlapped with chloroform, 1H), 3.98 (s, 3H), 3.70 (dt, J=12.8, 3.0 Hz, 2H), 3.24-3.15 (m, 3H), 2.52-2.32 (m, 4H); LRMS (M+H) m/z 363.63.

Example 66

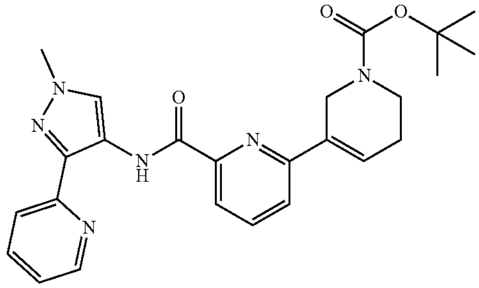 [SMILES: Cn1cc(NC(=O)c2cccc(C3=CCCN(C(=O)OC(C)(C)C)C3)n2)c(-c2ccccn2)n1]

tert-butyl 6-((1-methyl-3-(pyridin-2-yl)-1H-pyrazol-4-yl)carbamoyl)-5',6'-dihydro-[2,3'-bipyridine]-1'(2'H)-carboxylate (1-64)

Example 67

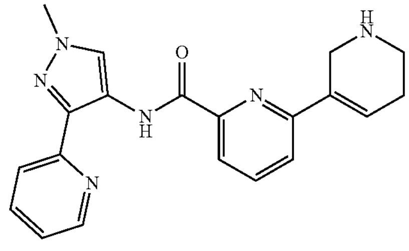 [SMILES: Cn1cc(NC(=O)c2cccc(C3=CCCNC3)n2)c(-c2ccccn2)n1]

N-(1-methyl-3-(pyridin-2-yl)-1H-pyrazol-4-yl)-1',2',5',6'-tetrahydro-[2,3'-bipyridine]-6-carboxamide (I-65)

Example 68

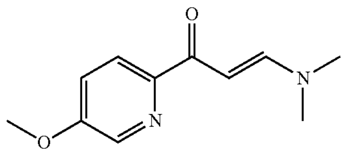

(E)-3-(dimethylamino)-1-(5-methoxypyridin-2-yl)prop-2-en-1-one

A 1,1-dimethoxy-N,N-dimethylmethanamine (1.4 mL, 10 mmol) solution of 1-(5-methoxypyridin-2-yl)ethan-1-one (755.8 mg, 5 mmol) was stirred at 110° C. After 16 hours, the reaction went to completion monitored by LC-MS. Solvent was removed in vacuo, title compound was obtained as a brown solid: $^1$H NMR (300 MHz, Chloroform-d) δ 8.30 (dd, J=2.9, 0.6 Hz, 1H), 8.15 (dd, J=8.7, 0.6 Hz, 1H), 7.87 (d, J=12.7 Hz, 1H), 7.28-7.24 (m, partially overlapped with $CHCl_3$, 1H), 6.42 (d, J=12.7 Hz, 1H), 3.90 (s, 3H), 3.16 (br s, 3H), 2.95 (br s, 3H); LRMS (M+H) m/z 207.37.

Example 69

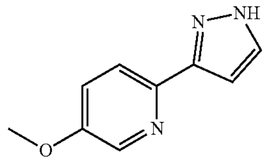

5-methoxy-2-(1H-pyrazol-3-yl)pyridine

An EtOH (5 mL) solution of (E)-3-(dimethylamino)-1-(5-methoxypyridin-2-yl)prop-2-en-1-one (about 5 mmol) and hydrazine hydrate (0.32 mL, 6.5 mmol) was stirred at 85° C. for 2 hours. The reaction went to completion as monitored by LC-MS. After cooling to room temperature, $H_2O$ (about 10 mL) was added, and most organic solvent was removed in vacuo. The mixture was extracted with EtOAc (15 mL×2), organic layers were combined, washed with $H_2O$, dried ($Na_2SO_4$), filtered, solvent was removed in vacuo. Title compound was obtained as a brown solid: 801.5 mg (91% yield over 2 steps): $^1$H NMR (300 MHz, Chloroform-d) δ 10.89 (v br s, 1H), 8.31 (dd, J=3.0, 0.7 Hz, 1H), 7.66 (d, J=8.7 Hz, 1H), 7.63 (d, J=2.0 Hz, 1H), 7.26 (dd, J=8.7, 3.0 Hz, 1H), 6.69 (d, J=2.0 Hz, 1H), 3.90 (s, 3H); LRMS (M+H) m/z 176.30.

Example 70

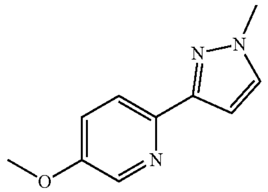

5-methoxy-2-(1-methyl-1H-pyrazol-3-yl)pyridine

Over ice bath, to a THF (20 mL) solution of 5-methoxy-2-(1H-pyrazol-3-yl)pyridine (801 mg, 4.58 mmol), was added NaH (60% dispersion in mineral oil, 274.5 mg, 6.87 mmol) portion-wise. The reaction was maintained at 0° C. for 30 minutes, then allowed to warm to room temperature for 20 minutes. After cooling back to 0° C., MeI (0.3 mL, 4.81 mmol) was added dropwise. The reaction was then allowed to warm to room temperature, then was heated at 50° C. overnight. By LC-MS, the reaction went to completion. The reaction was cooled to room temperature, quenched by a saturated aqueous solution of $NH_4Cl$ (about 50 mL). Most of the THF was removed by rotary evaporation, and the mixture was extracted with EtOAc (50 mL×2). Organic layers were combined, dried ($Na_2SO_4$), filtered, solvent was removed in vacuo. Title compound was obtained as a brown oil (contains mineral oil): $^1$H NMR (300 MHz, Chloroform-d) δ 8.32 (dd, J=3.0, 0.7 Hz, 1H), 7.84 (dd, J=8.7, 0.7 Hz, 1H), 7.39 (d, J=2.3 Hz, 1H), 7.24 (dd, J=8.7, 3.0 Hz, 1H), 6.77 (d, J=2.3 Hz, 1H), 3.96 (s, 3H), 3.89 (s, 3H); LRMS (M+H) m/z 190.35.

Example 71

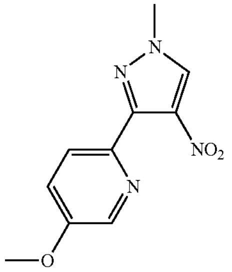 [SMILES: COc1ccc(-c2nn(C)cc2[N+](=O)[O-])nc1]

5-methoxy-2-(1-methyl-4-nitro-1H-pyrazol-3-yl)pyridine

Over ice bath, to a $H_2SO_4$ (5 mL) solution of 5-methoxy-2-(1-methyl-1H-pyrazol-3-yl)pyridine (about 4.58 mmol), $HNO_3$ (90% aq. solution, 0.252 mL) was added dropwise. After the addition, the reaction was allowed to warm up to room temperature. After 17 hours, the reaction was quenched by pouring onto ice, then basified with solid NaOH and $Na_2CO_3$ until about pH=8. Precipitate was collected by filtration (unreacted SM and desired product <about 1:1> which don't separate on silica column, was removed), and was further purified by silica gel chromatography to remove di-nitro-by-product. Title compound was obtained as a tan color solid: 663.2 mg (62% yield over 2 steps); $^1$H NMR (300 MHz, Chloroform-d) δ 8.43 (dd, J=3.0, 0.7 Hz, 1H), 8.23 (d, J=0.5 Hz, 1H), 7.75 (dd, J=8.7, 0.6 Hz, 1H), 7.29 (dd, J=8.7, 3.0 Hz, 1H), 4.01 (s, 3H), 3.92 (s, 3H); LRMS (M+H) m/z 235.42. The structure was confirmed, in terms of regioselectivity, by 1D-NOE experiment: NOE was observed between methyl group and the proton on the pyrazole.

The other regioisomer was also isolated:

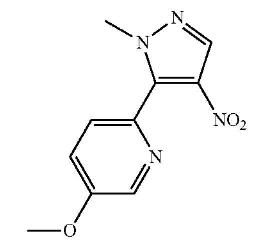 [SMILES: COc1ccc(-c2c([N+](=O)[O-])cnn2C)nc1]

5-methoxy-methyl-4-nitro-1H-pyrazol-5-yl)pyridine $^1$H NMR (300 MHz, Chloroform-d) δ 8.24 (d, J=0.4 Hz, 1H), 8.01 (d, J=8.6 Hz, 1H), 7.61 (d, J=8.6 Hz, 1H), 4.04 (s, 3H), 4.03 (d, J=0.4 Hz, 2H).

Example 72

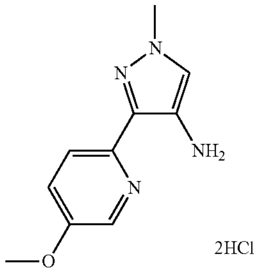

3-(5-methoxypyridin-2-yl)-1-methyl-1H-pyrazol-4-amine dihydrogen chloride

An EtOAc (20 mL) solution of 5-methoxy-2-(1-methyl-4-nitro-1H-pyrazol-3-yl)pyridine (663 mg, 2.83 mmol) and Pd—C(10% on C, 50% wet, 100 mg), was shaken in a Parr flask under 30 psi of hydrogen. After 21 hours, the reaction went to completion as monitored by LC-MS. Solid was removed by filtration through a celite pad, washed with EtOAc and MeOH, and the filtrate was collected in a flask with 4M HCl-dioxane solution (1.5 mL). Precipitate formed and was collected by filtration, washing with EtOAc, and was further dried in vacuo. Title compound was obtained as di-HCl salt: 703.8 mg (90% yield); $^1$H NMR (300 MHz, DMSO-$d_6$) δ 10.06 (br s, 2H), 8.37 (dd, J=3.0, 0.7 Hz, 1H), 8.04 (d, J=3.7 Hz, 1H), 7.94 (dd, J=8.8, 0.7 Hz, 1H), 7.60 (dd, J=8.8, 3.0 Hz, 1H), 3.96 (s, 3H), 3.93 (s, 3H), 3.64 (br s, 2H); LRMS (M+H) m/z 205.32.

Example 73

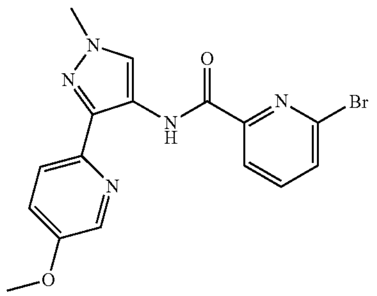 [SMILES: COc1ccc(-c2nn(C)cc2NC(=O)c2cccc(Br)n2)nc1]

6-bromo-N-(3-(5-methoxypyridin-2-yl)-1-methyl-1H-pyrazol-4-yl)picolinamide (I-66)

0.8 mmol scale, with 6-bromopicolinic acid, 239.9 mg, 77% yield. $^1$H NMR (300 MHz, Chloroform-d) δ 12.98 (s, 1H), 8.56 (dd, J=3.0, 0.7 Hz, 1H), 8.33 (s, 1H), 8.20 (dd, J=7.5, 1.0 Hz, 1H), 7.98 (dd, J=8.8, 0.7 Hz, 1H), 7.75 (dd, J=7.9, 7.5 Hz, 1H), 7.65 (dd, J=7.9, 1.0 Hz, 1H), 7.32 (dd, J=8.8, 3.0 Hz, 1H), 3.96 (s, 3H), 3.94 (s, 3H); LRMS (M+H) m/z 390.60.

Example 74

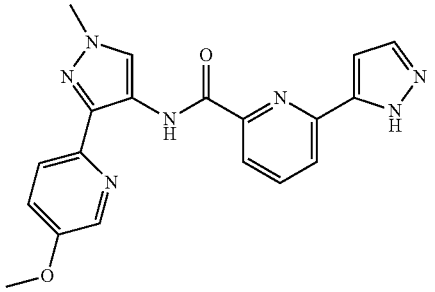 [SMILES: COc1ccc(-c2nn(C)cc2NC(=O)c2cccc(-c3ccn[nH]3)n2)nc1]

N-(3-(5-methoxypyridin-2-yl)-1-methyl-1H-pyrazol-4-yl)-6-(1H-pyrazol-5-yl)picolinamide (I-67)

0.08 mmol scale, 22.3 mg, 71% yield. $^1$H NMR (300 MHz, DMSO-$d_6$) δ 13.29 (s, 1H), 12.40 (s, 1H), 8.52 (s, 1H), 8.46 (d, J=2.4 Hz, 1H), 8.23 (dd, J=6.8, 2.0 Hz, 1H), 8.15-8.08 (m, 3H), 8.01 (d, J=8.8 Hz, 1H), 7.59 (dd, J=8.9, 2.9 Hz, 1H), 7.20 (br s, 1H), 3.98 (s, 3H), 3.95 (s, 3H); LRMS (M+H) m/z 376.61.

Example 75

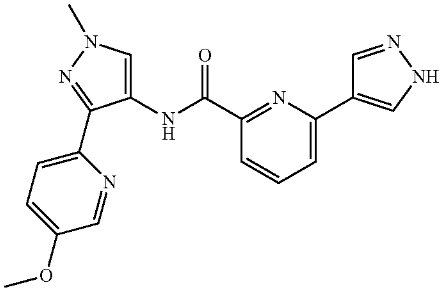 [SMILES: COc1ccc(-c2nn(C)cc2NC(=O)c2cccc(-c3cn[nH]c3)n2)nc1]

N-(3-(5-methoxypyridin-2-yl)-1-methyl-1H-pyrazol-4-yl)-6-(1H-pyrazol-4-yl)picolinamide (I-68)

0.08 mmol scale, 11.1 mg, 37% yield. $^1$H NMR (300 MHz, DMSO-$d_6$) δ 13.34 (s, 1H), 12.32 (s, 1H), 8.55 (s, 1H), 8.53 (s, 1H), 8.43 (d, J=2.6 Hz, 1H), 8.37 (s, 1H), 8.19-7.96 (m, 4H), 7.62 (dd, J=8.9, 3.0 Hz, 1H), 3.98 (s, 3H), 3.97 (s, 3H); LRMS (M+H) m/z 376.60.

Example 76

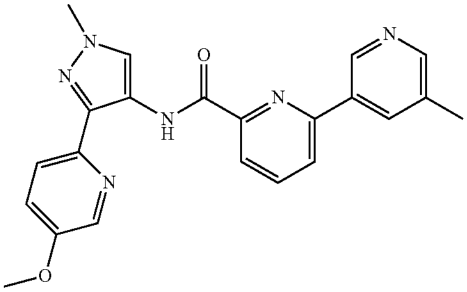

N-(3-(5-methoxypyridin-2-yl)-1-methyl-1H-pyrazol-4-yl)-5'-methyl-[2,3'-bipyridine]-6-carboxamide (I-69)

0.08 mmol scale, 28.2 mg, 88% yield. $^1$H NMR (300 MHz, DMSO-$d_6$) δ 12.48 (s, 1H), 9.53 (s, 1H), 8.59 (dd, J=2.0, 0.7 Hz, 1H), 8.49 (br d, J=2.9 Hz, 1H), 8.48 (s, 1H), 8.39 (ddd, J=2.1, 2.1, 0.7 Hz, 1H), 8.30 (dd, J=7.4, 1.6 Hz, 1H), 8.21-8.12 (m, 2H), 7.97 (dd, J=8.9, 0.5 Hz, 1H), 7.55 (dd, J=8.9, 3.0 Hz, 1H), 3.93 (s, 3H), 3.91 (s, 3H), 2.44 (s, 3H); LRMS (M+H) m/z 401.66.

Example 77

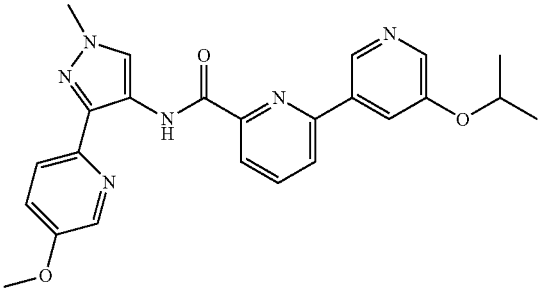 [SMILES: COc1ccc(-c2nn(C)cc2NC(=O)c2cccc(-c3cncc(OC(C)C)c3)n2)nc1]

5'-isopropoxy-N-(3-(5-methoxypyridin-2-yl)-1-methyl-1H-pyrazol-4-yl)-[2,3'-bipyridine]-6-carboxamide (I-70)

0.08 mmol scale, 24.1 mg, 68% yield. $^1$H NMR (300 MHz, DMSO-$d_6$) δ 12.41 (s, 1H), 9.31 (d, J=1.8 Hz, 1H), 8.57 (br d, J=2.9 Hz, 1H), 8.49-8.48 (m, 2H), 8.37 (dd, J=7.0, 2.0 Hz, 1H), 8.21-8.13 (m, 3H), 7.98 (dd, J=8.9, 0.5 Hz, 1H), 7.56 (dd, J=8.9, 3.0 Hz, 1H), 4.92 (hept, J=6.0 Hz, 1H), 3.97 (s, 3H), 3.94 (s, 3H), 1.38 (d, J=6.0 Hz, 6H); LRMS (M+H) m/z 445.73.

Example 78

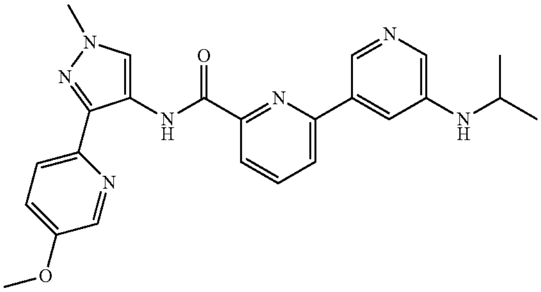 [SMILES: COc1ccc(-c2nn(C)cc2NC(=O)c2cccc(-c3cncc(NC(C)C)c3)n2)nc1]

5'-(isopropylamino)-N-(3-(5-methoxypyridin-2-yl)-1-methyl-1H-pyrazol-4-yl)-[2,3'-bipyridine]-6-carboxamide (1-71)

$^1$H NMR (300 MHz, DMSO-$d_6$) δ 12.60 (s, 1H), 8.92 (d, J=1.8 Hz, 1H), 8.54-8.53 (m, 2H), 8.27-8.16 (m, 4H), 8.01 (d, J=8.8 Hz, 1H), 7.63-7.62 (m, 1H), 7.59 (dd, J=8.9, 3.0 Hz, 1H), 5.95 (d, J=8.2 Hz, 1H), 3.99 (s, 3H), 3.97 (s, 3H), 3.83-3.72 (m, 1H), 1.21 (d, J=6.3 Hz, 6H); LRMS (M+H) m/z 444.80.

Example 79

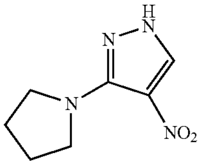 [SMILES: O=[N+]([O-])c1c[nH]nc1N1CCCC1]

4-nitro-3-(pyrrolidin-1-yl)-1H-pyrazole

A BuOH (5 mL) solution of 5-chloro-4-nitro-1-((2-(trimethylsilyl)ethoxy)methyl)-1H-pyrazole (1.39 g, 5 mmol) and pyrrolidine (0.575 mL, 7 mmol) was stirred at 120° C. for 15 hours, after which LC-MS indicated that the reaction had gone to completion. Volatiles were removed in vacuo, and crude reaction mixture was treated with EtOH (10 mL) and 6N HCl (aq., 3 mL), and stirred at 70° C. for 3 hours. Volatiles were removed in vacuo. After trituration from EtOH-EtOAc, title compound was obtained as an orange color solid: 631 mg as HCl salt; $^1$H NMR (300 MHz, DMSO-$d_6$) δ 8.09 (s, 1H), 3.49-3.45 (m, 4H), 1.97-1.92 (m, 4H); LRMS (M+H) m/z 183.24.

Example 80

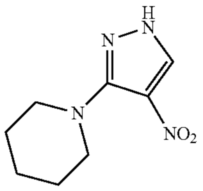 [SMILES: O=[N+]([O-])c1c[nH]nc1N1CCCCC1]

1-(4-nitro-1H-pyrazol-3-yl)

5 mmol scale, with piperidine, 667.1 mg. $^1$H NMR (300 MHz, DMSO-$d_6$) δ 8.40 (s, 1H), 3.25-3.21 (m, 4H), 1.70-1.60 (m, 6H); LRMS (M+H) m/z 197.33.

Example 81

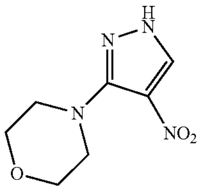 [SMILES: O=[N+]([O-])c1c[nH]nc1N1CCOCC1]

4-(4-nitro-1H-pyrazol-3-yl)morpholine 5 mmol scale, with morpholine, 540 mg. $^1$H NMR (300 MHz, DMSO-$d_6$) δ 8.58 (s, 1H), 3.78-3.75 (m, 4H), 3.27-3.23 (m, 4H); LRMS (M+H) m/z 199.26.

Example 82

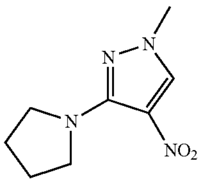

1-methyl-4-nitro-3-(pyrrolidin-1-yl)-1H-pyrazole 397.2 mg, 40% yield over 3 step. $^1$H NMR (300 MHz, Chloroform-d) δ 8.03 (s, 1H), 3.76 (s, 3H), 3.38-3.33 (m, 4H), 2.08-2.04 (m, 4H); LRMS (M+H) m/z 197.34. Structure was confirmed by 1D-NOE experiment: NOE was observed between protons of methyl group and the proton on pyrazole.

Example 83

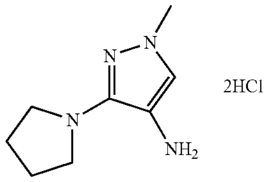

1-methyl-3-(pyrrolidin-1-yl)-1H-pyrazol-4-amine 0.34 g as 2 HCl salt. $^1$H NMR (300 MHz, Chloroform-d) δ 7.98 (q, J=0.6 Hz, 1H), 3.76 (d, J=0.5 Hz, 3H), 3.48-3.43 (m, 4H), 1.96-1.91 (m, 4H); LRMS (M+H) m/z 167.28.

Example 84

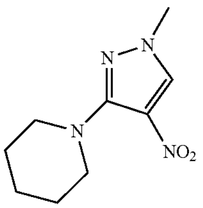

1-(1-methyl-4-nitro-1H-pyrazol-3-yl)piperidine 460.1 mg, 44% yield over 3 steps. $^1$H NMR (300 MHz, Chloroform-d) δ 8.04 (d, J=0.6 Hz, 1H), 3.78 (d, J=0.5 Hz, 4H), 3.22-3.19 (m, 4H), 1.75-1.68 (m, 4H), 1.64-1.56 (m, 2H); LRMS (M+H) m/z 211.36. Structure was confirmed by 1D-NOE experiment: NOE was observed between protons of methyl group and the proton on pyrazole.

The other regioisomer was also isolated and characterized:

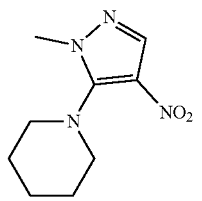

1-(1-methyl-4-nitro-1H-pyrazol-5-yl)piperidine $^1$H NMR (300 MHz, Chloroform-d) δ 8.01 (s, 1H), 3.75 (s, 3H), 3.16-3.13 (m, 4H), 1.73-1.67 (m, 6H).

Example 85

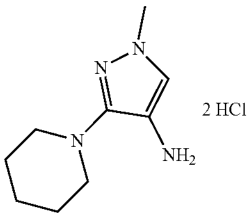

1-methyl-3-(piperidin-1-yl)-1H-pyrazol-4-amine dihydrogen chloride 317.1 mg, as 2HCl salt, 91% yield. $^1$H NMR (300 MHz, DMSO-$d_6$) δ 9.75 (br s, 2H), 7.74 (s, 1H), 3.73 (s, 3H), 3.66 (s, 2H), 3.02-2.98 (m, 4H), 1.69-1.61 (m, 4H), 1.58-1.52 (m, 2H); LRMS (M+H) m/z 181.38.

Example 86

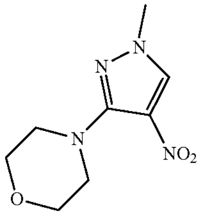

4-(1-methyl-4-nitro-1H-pyrazol-3-yl)morpholine 337 mg, 37% yield over 3 steps. $^1$H NMR (300 MHz, Chloroform-d) δ 8.07 (d, J=0.5 Hz, 1H), 3.88-3.85 (m, 4H), 3.81 (d, J=0.5 Hz, 3H), 3.32-3.29 (m, 4H); LRMS (M+H) m/z 213.34.
Structure was confirmed by 1D-NOE experiment: NOE was observed between protons of methyl group and the proton on pyrazole.

Example 87

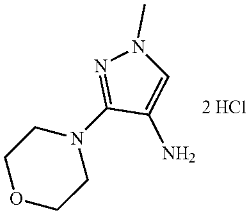

1-methyl-3-morpholino-1H-pyrazol-4-amine 328.7 mg as 2HCl salt, 81% yield. $^1$H NMR (300 MHz, DMSO-$d_6$) δ 10.00 (br s, 2H), 7.80 (d, J=0.9 Hz, 1H), 5.31 (br s, 2H), 3.75-3.72 (m, 7H), 3.05-3.02 (m, 4H); LRMS (M+H) m/z 183.30.

Example 88

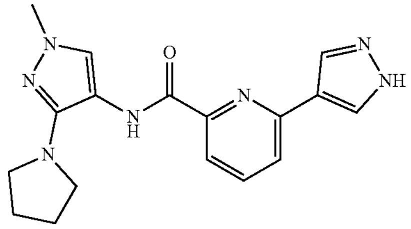 [SMILES: Cn1cc(NC(=O)c2cccc(-c3cn[nH]c3)n2)c(N2CCCC2)n1]

N-(1-methyl-3-(pyrrolidin-1-yl)-1H-pyrazol-4-yl)-6-(1H-pyrazol-4-yl)picolinamide (I-72)

0.08 mmol scale, 20.7 mg, 77% yield. $^1$H NMR (300 MHz, Chloroform-d) δ 10.47 (br s, 1H), 9.85 (s, 1H), 8.14 (s, 2H), 8.09 (dd, J=7.8, 1.0 Hz, 1H), 7.95 (s, 1H), 7.88 (dd, J=7.8, 7.8 Hz, 1H), 7.65 (dd, J=7.8, 1.0 Hz, 1H), 3.78 (s, 3H), 3.49-3.45 (m, 4H), 2.02-1.97 (m, 4H); LRMS (M+H) m/z 338.60.

Example 89

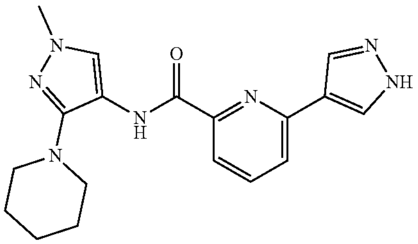 [SMILES: Cn1cc(NC(=O)c2cccc(-c3cn[nH]c3)n2)c(N2CCCCC2)n1]

N-(1-methyl-3-(piperidin-1-yl)-1H-pyrazol-4-yl)-6-(1H-pyrazol-4-yl)picolinamide (I-73)

0.08 mmol scale, 13.1 mg, 47% yield. $^1$H NMR (300 MHz, Chloroform-d) δ 10.52 (br s, 1H), 9.82 (s, 1H), 8.20 (s, 2H), 8.09 (dd, J=7.8, 1.0 Hz, 1H), 8.05 (s, 1H), 7.88 (dd, J=7.8, 7.8 Hz, 1H), 7.65 (dd, J=7.8, 1.0 Hz, 1H), 3.81 (s, 3H), 3.12-3.09 (m, 4H), 1.83-1.75 (m, 4H), 1.66-1.59 (m, partially overlapped with $H_2O$, 2H); LRMS (M+H) m/z 352.52.

Example 90

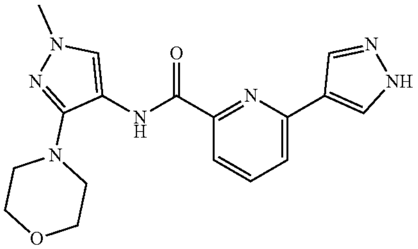 [SMILES: Cn1cc(NC(=O)c2cccc(-c3cn[nH]c3)n2)c(N2CCOCC2)n1]

N-(1-methyl-3-morpholino-1H-pyrazol-4-yl)-6-(1H-pyrazol-4-yl)picolinamide (I-74)

0.08 mmol scale, 22 mg, 78% yield. $^1$H NMR (300 MHz, Chloroform-d) δ 10.61 (br s, 1H), 9.81 (s, 1H), 8.18 (s, 2H), 8.09 (dd, J=7.8, 1.0 Hz, 1H), 8.04 (s, 1H), 7.89 (d, J=7.8, 7.8 Hz, 1H), 7.67 (dd, J=7.9, 1.0 Hz, 1H), 3.94-3.91 (m, 4H), 3.82 (s, 3H), 3.18-3.15 (m, 4H); LRMS (M+H) m/z 354.53.

Example 91

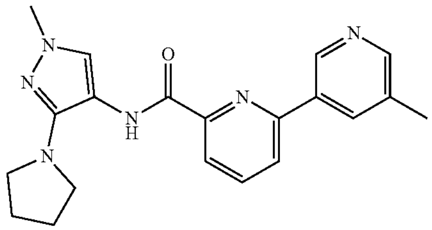 [SMILES: Cc1cncc(-c2cccc(C(=O)Nc3cn(C)nc3N3CCCC3)n2)c1]

5'-methyl-N-(1-methyl-3-(pyrrolidin-1-yl)-1H-pyrazol-4-yl)-[2,3'-bipyridine]-6-carboxamide (I-75)

0.08 mmol scale, 19.6 mg, 68% yield. $^1$H NMR (300 MHz, Chloroform-d) δ 9.90 (s, 1H), 9.04 (d, J=2.1 Hz, 1H), 8.55 (dd, J=2.1, 0.7 Hz, 1H), 8.25 (dd, J=7.6, 1.1 Hz, 1H), 8.15-8.13 (m, 1H), 8.03-7.98 (m, 2H), 7.92 (dd, J=7.9, 1.1 Hz, 1H), 3.78 (s, 3H), 3.49-3.45 (m, 4H), 2.47 (s, 3H), 2.02-1.98 (m, 4H); LRMS (M+H) m/z 363.66.

Example 92

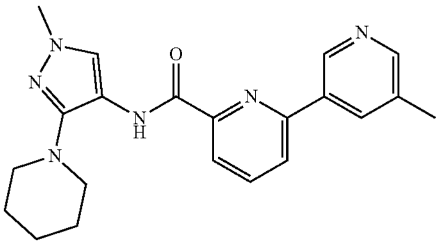 [SMILES: Cc1cncc(-c2cccc(C(=O)Nc3cn(C)nc3N3CCCCC3)n2)c1]

5'-methyl-N-(1-methyl-3-(piperidin-1-yl)-1H-pyrazol-4-yl)-[2,3'-bipyridine]-6-carboxamide (I-76)

0.08 mmol scale, 14 mg, 46% yield. $^1$H NMR (300 MHz, Chloroform-d) δ 9.87 (s, 1H), 9.07 (d, J=1.9 Hz, 1H), 8.57-8.56 (m, 1H), 8.27-8.24 (m, 2H), 8.05 (s, 1H), 8.04-7.98 (m, 1H), 7.94 (dd, J=7.9, 1.2 Hz, 1H), 3.82 (s, 3H), 3.11-3.08 (m, 5H), 2.48 (s, 3H), 1.83-1.75 (m, 4H), 1.66-1.59 (m, partially overlapped with $H_2O$, 5H); LRMS (M+H) m/z 377.71.

Example 93

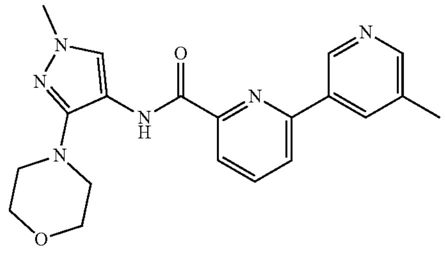 [SMILES: Cc1cncc(-c2cccc(C(=O)Nc3cn(C)nc3N3CCOCC3)n2)c1]

5'-methyl-N-(1-methyl-3-morpholino-1H-pyrazol-4-yl)-[2,3'-bipyridine]-6-carboxamide (1-77)

0.08 mmol scale, 19.4 mg, 64% yield. $^1$H NMR (300 MHz, Chloroform-d) δ 9.86 (s, 1H), 9.06 (d, J=2.1 Hz, 1H), 8.58 (dd, J=2.1, 0.7 Hz, 1H), 8.25 (dd, J=7.5, 1.2 Hz, 1H), 8.21-8.19 (m, 1H), 8.04-7.99 (m, 2H), 7.94 (dd, J=7.9, 1.2 Hz, 1H), 3.92-3.89 (m, 4H), 3.83 (s, 3H), 3.17-3.14 (m, 4H), 2.51 (br s, 3H); LRMS (M+H) m/z 379.69.

Example 94

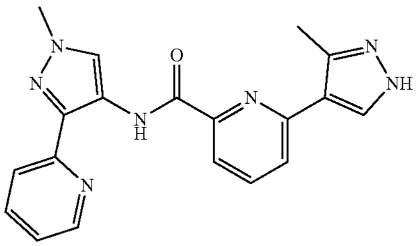 [SMILES: Cc1n[nH]cc1-c1cccc(C(=O)Nc2cn(C)nc2-c2ccccn2)n1]

6-(3-methyl-1H-pyrazol-4-yl)-N-(1-methyl-3-(pyridin-2-yl)-1H-pyrazol-4-yl)picolinamide (I-78)

0.1 mmol scale, with 3-methyl-4-(4,4,5,5-tetramethyl-1,3,2-dioxaborolan-2-yl)-1H-pyrazole, 19.1 mg, 53% yield. $^1$H NMR (300 MHz, DMSO-$d_6$) δ 12.98, 12.93 (s, s, two atropisomers, 1H), 12.25, 12.23 (s, s, two atropisomers, 1H), 8.62-8.56 (m, 2H), 8.41, 8.22 (s, s, two atropisomers, 1H), 8.10-8.05 (m, 2H), 8.00-7.93 (m, 2H), 7.87-7.83 (m, 1H), 7.45-7.40 (m, 1H), 4.01 (s, 3H), 2.66, 2.60 (s, s, two atropisomers, 3H); LRMS (M+H) m/z 360.68.

Example 95

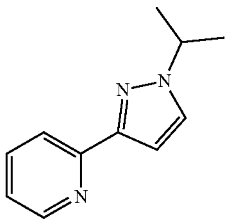

2-(1-isopropyl-1H-pyrazol-3-yl)pyridine 40 mmol scale, with 2-iodopropane, a light brown oil was used directly in next reaction.

$^{1}$H NMR (300 MHz, Chloroform-d) δ 8.62 (ddd, J=4.9, 1.8, 1.0 Hz, 1H), 7.94 (ddd, J=8.0, 1.1, 1.1 Hz, 1H), 7.73-7.67 (m, 1H), 7.48 (d, J=2.4 Hz, 1H), 7.17 (ddd, J=7.5, 4.9, 1.2 Hz, 1H), 6.87 (d, J=2.4 Hz, 1H), 4.60 (hept, J=6.7 Hz, 1H), 1.56 (d, J=6.7 Hz, 6H); LRMS (M+H) m/z 188.22.

Example 96

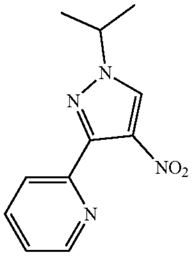 [SMILES: CC(C)n1cc([N+](=O)[O-])c(-c2ccccn2)n1]

2-(1-isopropyl-4-nitro-H-pyrazol-3-yl)pyridine 40 mmol scale, after silica gel chromatography, a yellow solid: 8.79 g, 95% yield over 2 steps. $^{1}$H NMR (300 MHz, Chloroform-d) δ 8.75 (ddd, J=4.9, 1.7, 1.0 Hz, 1H), 8.29 (s, 1H), 7.84-7.72 (m, 2H), 7.36 (ddd, J=7.4, 4.9, 1.4 Hz, 1H), 4.62 (hept, J=6.7 Hz, 1H), 1.61 (d, J=6.7 Hz, 6H); LRMS (M+H) m/z 233.28.

Example 97

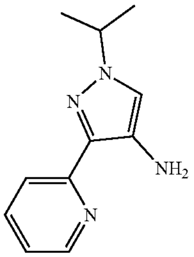

1-isopropyl-3-(pyridin-2-yl)-1H-pyrazol-4-amine, di-hydrogen chloride

Obtained as di-HCl salt, a light yellow solid: 9.99 g, 96% yield. $^{1}$H NMR (300 MHz, Chloroform-d) δ 8.52 (ddd, J=5.0, 1.8, 1.0 Hz, 1H), 7.97 (ddd, J=8.1, 1.1, 1.1 Hz, 1H), 7.66 (ddd, J=8.1, 7.5, 1.8 Hz, 1H), 7.09-7.05 (m, 2H), 4.43 (hept, J=6.7 Hz, 1H), 4.07 (br s, 2H), 1.49 (d, J=6.7 Hz, 6H); LRMS (M+H) m/z 203.28.

Example 98

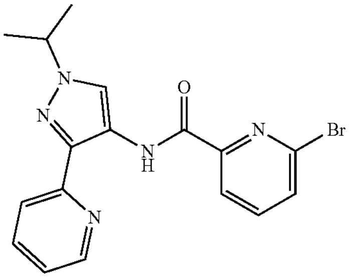 [SMILES: CC(C)n1cc(NC(=O)c2cccc(Br)n2)c(-c2ccccn2)n1]

6-bromo-N-(1-isopropyl-3-(pyridin-2-yl)-1H-pyrazol-4-yl)picolinamide (I-79)

1.0 mmol scale, with 6-bromopicolinic acid, 244.7 mg, 63% yield. $^{1}$H NMR (300 MHz, Chloroform-d) δ 13.11 (s, 1H), 8.84 (ddd, J=4.9, 1.8, 1.0 Hz, 1H), 8.41 (s, 1H), 8.20 (dd, J=7.5, 1.0 Hz, 1H), 8.07 (ddd, J=8.1, 1.1, 1.1 Hz, 1H), 7.79-7.73 (m, 2H), 7.65 (dd, J=7.9, 1.0 Hz, 1H), 7.22 (ddd, J=7.5, 4.9, 1.1 Hz, 1H), 4.56 (hept, J=6.7 Hz, 1H), 1.58 (d, J=6.7 Hz, 6H); LRMS (M+H) m/z 386.58, 388.49.

Example 99

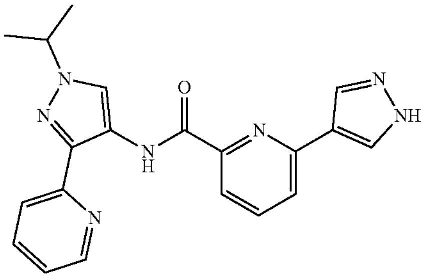 [SMILES: CC(C)n1cc(NC(=O)c2cccc(-c3cn[nH]c3)n2)c(-c2ccccn2)n1]

N-(1-isopropyl-3-(pyridin-2-yl)-1H-pyrazol-4-yl)-6-(1H-pyrazol-4-yl)picolinamide (I-80)

0.1 mmol scale, 32 mg, 86% yield. $^{1}$H NMR (300 MHz, DMSO-$d_6$) δ 13.31 (s, 1H), 12.38 (s, 1H), 8.76 (ddd, J=5.0, 1.7, 0.9 Hz, 1H), 8.61 (s, 1H), 8.56 (s, 1H), 8.36-8.35 (m, 1H), 8.13 (ddd, J=8.1, 1.1, 1.1 Hz, 1H), 8.08 (dd, J=8.0, 7.3 Hz, 1H), 8.02-7.96 (m, 3H), 7.47 (ddd, J=7.4, 5.0, 1.3 Hz, 1H), 4.69 (hept, J=6.7 Hz, 1H), 1.55 (d, J=6.7 Hz, 6H); LRMS (M+H) m/z 374.69.

Example 100

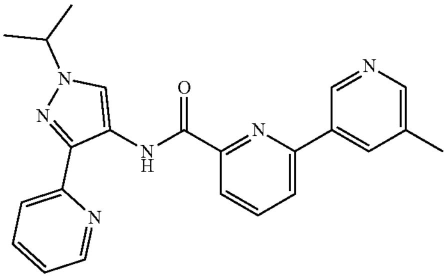 [SMILES: Cc1cncc(-c2cccc(C(=O)Nc3cn(C(C)C)nc3-c3ccccn3)n2)c1]

N-(1-isopropyl-3-(pyridin-2-yl)-1H-pyrazol-4-yl)-5'-methyl-[2,3'-bipyridine]-6-carboxamide (I-81)

0.1 mmol scale, 31.4 mg, 79% yield. $^1$H NMR (300 MHz, DMSO-$d_6$) δ 12.63 (s, 1H), 9.55 (d, J=2.1 Hz, 1H), 8.81 (ddd, J=5.0, 1.7, 0.9 Hz, 1H), 8.67-8.66 (m, 1H), 8.61 (s, 1H), 8.48 (ddd, J=2.1, 2.1, 0.7 Hz, 1H), 8.38 (dd, J=7.4, 1.6 Hz, 1H), 8.28-8.19 (m, 2H), 8.12 (ddd, J=8.1, 1.1, 1.1 Hz, 1H), 8.01-7.95 (m, 1H), 7.47 (ddd, J=7.4, 5.0, 1.2 Hz, 1H), 4.69 (hept, J=6.7 Hz, 1H), 2.51 (s, 3H), 1.56 (d, J=6.7 Hz, 6H); LRMS (M+H) m/z 399.69.

Example 101

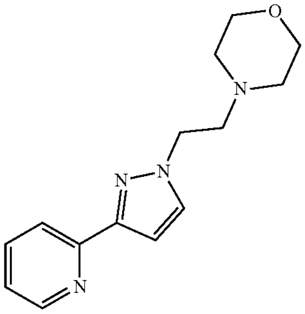 [SMILES: c1ccc(-c2ccn(CCN3CCOCC3)n2)nc1]

4-(2-(3-(pyridin-2-yl)-1H-pyrazol-1-yl)ethyl)morpholine 15 mmol scale, with 4-(2-bromoethyl)morpholine hydrogen bromide, an orange-light brown oil was used directly in next reaction. $^1$H NMR (300 MHz, Chloroform-d) δ 8.63 (ddd, J=4.9, 1.8, 1.0 Hz, 1H), 7.90 (ddd, J=8.0, 1.1, 1.1 Hz, 1H), 7.70 (ddd, J=8.0, 7.5, 1.8 Hz, 1H), 7.53 (d, J=2.3 Hz, 1H), 7.19 (ddd, J=7.5, 4.9, 1.2 Hz, 1H), 6.85 (d, J=2.3 Hz, 1H), 4.32 (t, J=6.6 Hz, 2H), 3.72-3.68 (m, 4H), 2.87 (t, J=6.6 Hz, 2H), 2.51-2.48 (m, 4H); LRMS (M+H) m/z 259.53.

Example 102

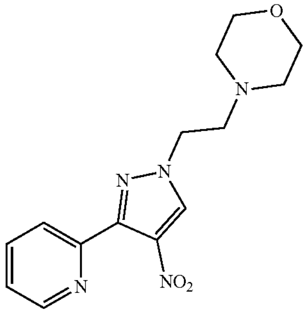 [SMILES: O=[N+]([O-])c1cn(CCN2CCOCC2)nc1-c1ccccn1]

4-(2-(4-nitro-3-(pyridin-2-yl)-1H-pyrazol-1-yl)ethyl)morpholine 15 mmol scale, 3.145 g, 69% yield. $^1$H NMR (300 MHz, Chloroform-d) δ 8.75 (ddd, J=4.9, 1.7, 1.0 Hz, 1H), 8.41 (s, 1H), 7.81 (ddd, J=7.9, 7.2, 1.7 Hz, 1H), 7.76 (ddd, J=7.9, 1.6, 1.0 Hz, 1H), 7.37 (ddd, J=7.2, 4.9, 1.6 Hz, 1H), 4.32-4.30 (m, 2H), 3.74-3.71 (m, 4H), 2.89-2.85 (m, 2H), 2.54-2.51 (m, 4H); LRMS (M+H) m/z 304.56.

A mixed fraction (1.17 g) with about 26% of the other regioisomer was obtained. Structure of title compound was confirmed by 1D-NOE experiment: NOE was observed between $CH_2$-protons connecting to pyrazole-nitrogen and the proton on pyrazole.

Example 103

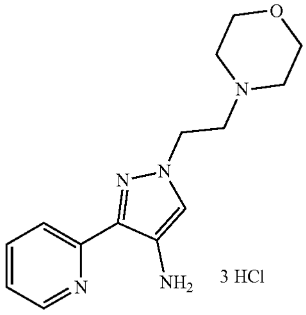 [SMILES: Nc1cn(CCN2CCOCC2)nc1-c1ccccn1]

1-(2-morpholinoethyl)-3-(pyridin-2-yl)-1H-pyrazol-4-amine tri-hydrogen chloride 10.35 mmol scale, obtained as tri-hydrogen chloride salt: 2.92 g, 74% yield. $^1$H NMR (300 MHz, DMSO-$d_6$) δ 11.55 (s, 1H), 10.26 (br s, 2H), 8.70 (ddd, J=4.9, 1.3, 1.3 Hz, 1H), 8.28 (s, 1H), 8.04-7.97 (m, 2H), 7.49 (ddd, J=5.1, 5.1, 3.5 Hz, 1H), 5.20 (br s, 3H), 4.80 (t, J=6.7 Hz, 2H), 3.98-3.88 (m, 4H), 3.70 (t, J=6.7 Hz, 2H), 3.49-3.40 (m, 2H), 3.25-3.17 (m, 2H); LRMS (M+H) m/z 274.54.

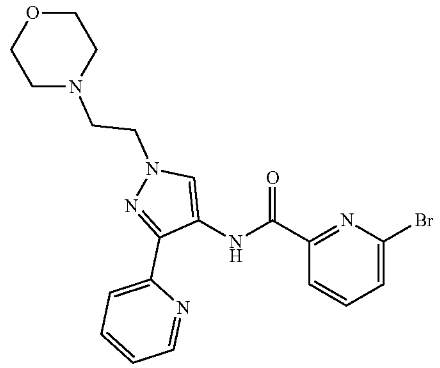 [SMILES: O=C(Nc1cn(CCN2CCOCC2)nc1-c1ccccn1)c1cccc(Br)n1]

6-bromo-N-(1-(2-morpholinoethyl)-3-(pyridin-2-yl)-1H-pyrazol-4-yl)picolinamide (I-82)

1.0 mmol scale, 323.6 g, 71% yield. $^1$H NMR (300 MHz, Chloroform-d) δ 13.05 (s, 1H), 8.86 (br d, J=4.7 Hz, 1H), 8.50 (s, 1H), 8.21 (d, J=7.4 Hz, 1H), 8.03 (d, J=8.0 Hz, 1H), 7.82-7.74 (m, 2H), 7.66 (d, J=7.9 Hz, 1H), 7.30-7.26 (m, 1H, partially overlapped with $CHCl_3$), 4.77-4.70 (m, 2H), 4.03-3.94 (m, 4H), 3.54-3.44 (m, 2H), 3.02-2.84 (m, 4H); LRMS (M+H) m/z 457.61, 459.50.

Example 105

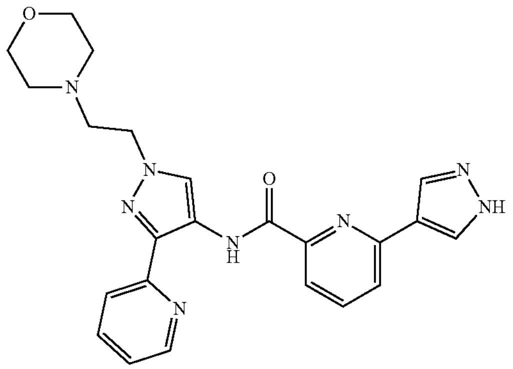 [SMILES: O=C(Nc1cn(CCN2CCOCC2)nc1-c1ccccn1)c1cccc(-c2cn[nH]c2)n1]

N-(1-(2-morpholinoethyl)-3-(pyridin-2-yl)-1H-pyrazol-4-yl)-6-(1H-pyrazol-4-yl)picolinamide (I-83)

0.1 mmol scale, 27.8 mg, 63% yield. $^1$H NMR (300 MHz, Chloroform-d) δ 12.56 (s, 1H), 10.35 (v br s, 1H), 8.73 (ddd, J=5.0, 1.8, 0.9 Hz, 1H), 8.56 (s, 1H), 8.33 (s, 2H), 8.13-8.09 (m, 2H), 7.88 (dd, J=7.8, 7.8 Hz, 1H), 7.76 (ddd, J=8.1, 7.5, 1.8 Hz, 1H), 7.65 (dd, J=7.8, 1.0 Hz, 1H), 7.23 (ddd, J=7.5, 5.0, 1.1 Hz, 1H), 4.32 (t, J=6.8 Hz, 2H), 3.74-3.71 (m, 4H), 2.92 (t, J=6.8 Hz, 2H), 2.55-2.52 (m, 4H); LRMS (M+H) m/z 445.79.

Example 106

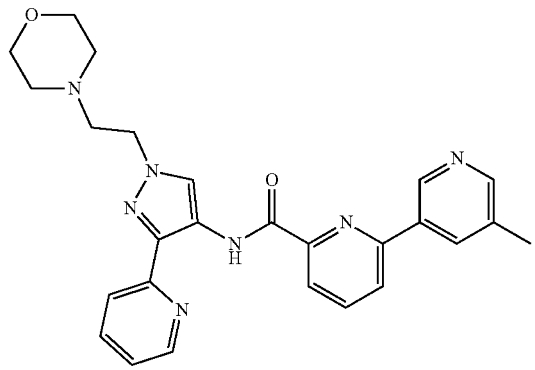 [SMILES: Cc1cncc(-c2cccc(C(=O)Nc3cn(CCN4CCOCC4)nc3-c3ccccn3)n2)c1]

5'-methyl-N-(1-(2-morpholinoethyl)-3-(pyridin-2-yl)-1H-pyrazol-4-yl)-[2,3'-bipyridine]-6-carboxamide (I-84)

0.1 mmol scale, 27.9 mg, 59% yield. $^1$H NMR (300 MHz, Chloroform-d) δ 12.83 (s, 1H), 9.38 (br d, J=2.1 Hz, 1H), 8.74 (ddd, J=5.0, 1.8, 1.0 Hz, 1H), 8.61 (dd, J=2.1, 0.7 Hz, 1H), 8.55 (s, 1H), 8.29-8.26 (m, 2H), 8.10 (ddd, J=8.1, 1.1, 1.1 Hz, 1H), 8.04-7.99 (m, 1H), 7.93 (dd, J=7.9, 1.2 Hz, 1H), 7.76 (ddd, J=8.1, 7.5, 1.8 Hz, 1H), 7.26-7.22 (m, 1H, partially overlapped with $CHCl_3$), 4.32 (s, J=6.8 Hz, 2H), 3.74-3.71 (m, 4H), 2.92 (t, J=6.8 Hz, 2H), 2.55-2.52 (m, 4H), 2.51 (br s, 3H); LRMS (M+H) m/z 470.85.

Example 107

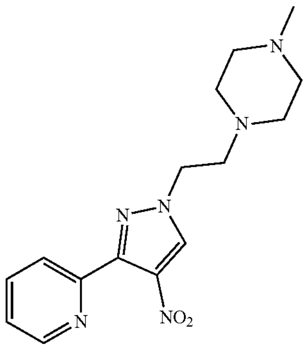 [SMILES: CN1CCN(CCn2cc([N+](=O)[O-])c(-c3ccccn3)n2)CC1]

1-methyl-4-(2-(4-nitro-3-(pyridin-2-yl)-1H-pyrazol-1-yl)ethyl)piperazine 10 mmol scale, 1$^{st}$ step: crude was used directly in next reaction; 2$^{nd}$ step: after silica gel chromatography, 1.69 g, 53% yield. $^1$H NMR (300 MHz, Chloroform-d) δ 8.75 (ddd, J=4.9, 1.7, 1.0 Hz, 1H), 8.42 (s, 1H), 7.84-7.74 (m, 2H), 7.37 (ddd, J=7.1, 4.9, 1.6 Hz, 1H), 4.33-4.29 (m, 2H), 2.89-2.85 (m, 2H), 2.60-2.39 (m, 8H), 2.31 (s, 3H); LRMS (M+H) m/z 317.63.

Example 108

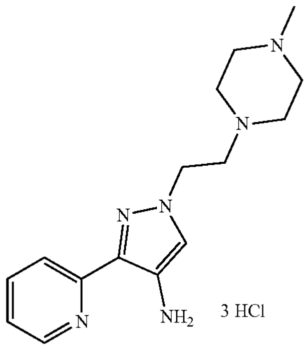 [SMILES: CN1CCN(CCn2cc(N)c(-c3ccccn3)n2)CC1]

1-(2-(4-methylpiperazin-1-yl)ethyl)-3-(pyridin-2-yl)-1H-pyrazol-4-amine tri-hydrogen chloride 5.3 mmol scale, obtained as tri-hydrogenchloride salt: 1.67 g, 79% yield; LRMS (M+H) m/z 287.55.

Example 109

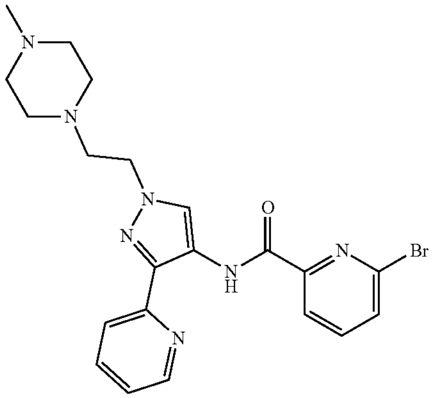 [SMILES: CN1CCN(CCn2cc(NC(=O)c3cccc(Br)n3)c(-c3ccccn3)n2)CC1]

6-bromo-N-(1-(2-(4-methylpiperazin-1-yl)ethyl)-3-(pyridin-2-yl)-1H-pyrazol-4-yl)picolinamide (I-85)

1.0 mmol, 342.1 mg, 73% yield. $^1$H NMR (300 MHz, Chloroform-d) δ 13.10 (s, 1H), 8.85 (ddd, J=4.9, 1.7, 1.0 Hz, 1H), 8.40 (s, 1H), 8.19 (dd, J=7.5, 0.9 Hz, 1H), 8.03 (ddd, J=8.1, 1.0, 1.0 Hz, 1H), 7.78 (ddd, J=7.8, 7.8, 1.8 Hz, 1H), 7.77 (dd, J=7.7, 7.7 Hz, 1H), 7.67 (dd, J=7.9, 0.9 Hz, 1H), 7.28-7.24 (m, partially overlapped with $CHCl_3$, 1H), 4.27 (t, J=5.9 Hz, 2H), 3.39-3.29 (m, 2H), 3.01 (t, J=5.9 Hz, 2H), 3.03-2.81 (m, 6H), 2.73 (s, 3H); LRMS (M+H) m/z 472.68.

Example 110

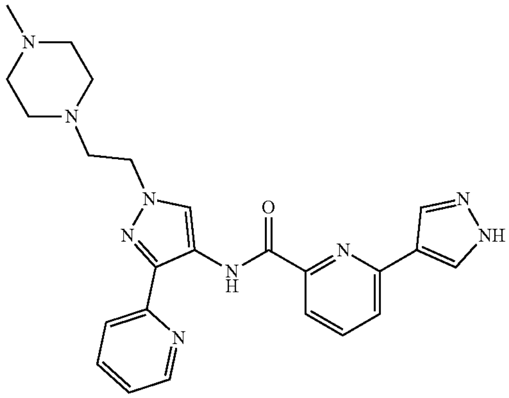 [SMILES: CN1CCN(CCn2cc(NC(=O)c3cccc(-c4cn[nH]c4)n3)c(-c3ccccn3)n2)CC1]

N-(1-(2-(4-methylpiperazin-1-yl)ethyl)-3-(pyridin-2-yl)-1H-pyrazol-4-yl)-6-(1H-pyrazol-4-yl)picolinamide (1-86)

0.1 mmol scale, 15.2 mg, 33% yield. $^1$H NMR (300 MHz, DMSO-$d_6$) δ 13.35 (br s, 1H), 12.38 (s, 1H), 8.76 (br d, J=4.9 Hz, 1H), 8.63 (s, 1H), 8.46 (br s, 2H), 8.12-8.05 (m, 2H), 8.01-7.96 (m, 3H), 7.47 (ddd, J=7.4, 5.0, 1.0 Hz, 1H), 4.38 (t, J=6.5 Hz, 2H), 3.44 (v br s, 2H), 2.85 (t, J=6.5 Hz, 2H), 2.57-2.52 (m, overlapped with DMSO, 6H), 2.29 (s, 3H); LRMS (M+H) m/z 458.81.

Example 111

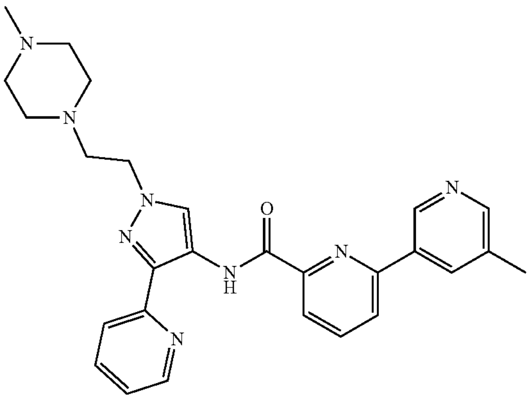 [SMILES: Cc1cncc(-c2cccc(C(=O)Nc3cn(CCN4CCN(C)CC4)nc3-c3ccccn3)n2)c1]

5'-methyl-N-(1-(2-(4-methylpiperazin-1-yl)ethyl)-3-(pyridin-2-yl)-1H-pyrazol-4-yl)-[2,3'-bipyridine]-6-carboxamide (I-87)

0.1 mmol scale, 9.1 mg, 19% yield. $^1$H NMR (300 MHz, DMSO-$d_6$) δ 12.61 (s, 1H), 9.54 (d, J=1.8 Hz, 1H), 8.80 (br d, J=4.5 Hz, 1H), 8.66 (d, J=1.0 Hz, 1H), 8.63 (s, 1H), 8.47 (s, 1H), 8.37 (dd, J=7.1, 1.8 Hz, 1H), 8.27-8.19 (m, 2H), 8.09 (br d, J=8.0 Hz, 1H), 7.98 (ddd, J=7.8, 7.8, 1.7 Hz, 1H), 7.47 (ddd, J=7.4, 5.0, 1.0 Hz, 1H), 4.39 (t, J=6.5 Hz, 2H), 3.38 (v br s, 2H), 2.84 (t, J=6.5 Hz, 2H), 2.50 (s, 3H), 2.57-2.51 (m, overlapped with DMSO, 2H), 2.42 (br s, 4H), 2.22 (s, 3H); LRMS (M+H) m/z 483.88.

Example 112

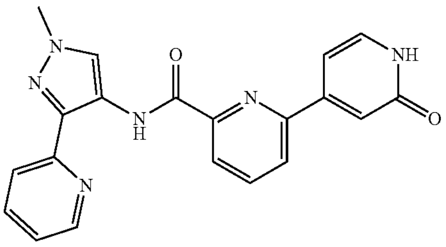 [SMILES: Cn1cc(NC(=O)c2cccc(-c3cc[nH]c(=O)c3)n2)c(-c2ccccn2)n1]

N-(1-methyl-3-(pyridin-2-yl)-1H-pyrazol-4-yl)-2‘-oxo-’,2'-dihydro-[2,4'-bipyridine]-6-carboxamide (I-91)

$^1$H NMR (300 MHz, DMSO-$d_6$) δ 12.48 (s, 1H), 11.72 (br s, 1H), 9.00 (ddd, J=5.0, 1.7, 0.9 Hz, 1H), 8.59 (s, 1H), 8.35 (dd, J=7.0, 2.0 Hz, 1H), 8.27-8.24 (m, 2H), 8.08 (ddd, J=8.1, 1.1, 1.1 Hz, 1H), 7.97 (ddd, J=7.7, 7.7, 1.7 Hz, 1H), 7.73 (d, J=6.8 Hz, 1H), 7.14 (dd, J=6.9, 1.8 Hz, 1H), 6.34 (ddd, J=9.2, 1.0, 1.0 Hz, 1H), 6.18 (ddd, J=6.5, 6.5, 1.2 Hz, 1H), 4.01 (s, 3H); LRMS (M+H) m/z 373.60.

Example 113

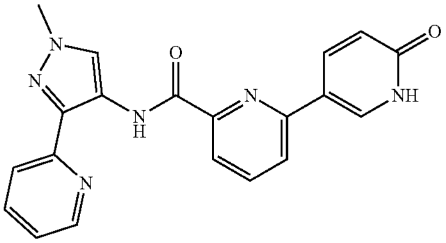 [SMILES: Cn1cc(NC(=O)c2cccc(-c3ccc(=O)[nH]c3)n2)c(-c2ccccn2)n1]

N-(1-methyl-3-(pyridin-2-yl)-1H-pyrazol-4-yl)-6‘-oxo-’,6'-dihydro-[2,3'-bipyridine]-6-carboxamide (I-92)

$^1$H NMR (300 MHz, DMSO-$d_6$) δ 12.39 (s, 1H), 12.30 (s, 1H), 8.73-8.70 (m, 1H), 8.57 (s, 1H), 8.52 (dd, J=9.6, 2.7 Hz, 1H), 8.41 (d, J=2.9 Hz, 1H), 8.16 (dd, J=7.6, 1.8 Hz, 1H), 8.12 (d, J=7.2 Hz, 1H), 8.07-8.04 (m, 2H), 7.98 (ddd, J=7.7, 7.7, 1.7 Hz, 1H), 7.48 (ddd, J=7.4, 5.0, 1.4 Hz, 1H), 6.70 (d, J=9.6 Hz, 1H), 4.01 (s, 3H); LRMS (M+H) m/z 373.62.

Example 114

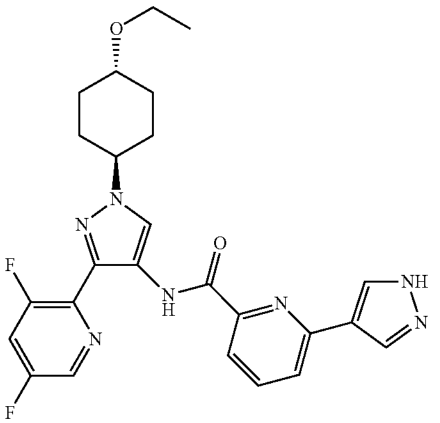 [SMILES: CCO[C@H]1CC[C@H](n2cc(NC(=O)c3cccc(-c4cn[nH]c4)n3)c(-c3ncc(F)cc3F)n2)CC1]

N-(3-(3,5-difluoropyridin-2-yl)-1-(trans-4-ethoxycyclohexyl)-1H-pyrazol-4-yl)-6-(1H-pyrazol-4-yl)picolinamide (I-184)

$^1$H NMR (300 MHz, Chloroform-d) δ 12.17 (s, 1H), 8.58 (br s, 1H), 8.47 (d, J=2.4 Hz, 1H), 8.26 (br s, 2H), 8.10 (dd, J=7.7, 1.0 Hz, 1H), 7.88 (dd, J=7.8, 7.8 Hz, 1H), 7.65 (dd, J=7.9, 1.1 Hz, 1H), 7.36 (ddd, J=10.7, 8.3, 2.4 Hz, 1H), 4.28 (tt, J=11.8, 3.8 Hz, 1H), 3.57 (q, J=7.0 Hz, 2H), 3.38 (tt, J=10.7, 4.1 Hz, 1H), 2.33-2.20 (m, 4H), 1.97-1.84 (m, 2H), 1.55-1.41 (m, 2H), 1.23 (t, J=7.0 Hz, 3H); LRMS (M+H) m/z 494.28.

Example 115

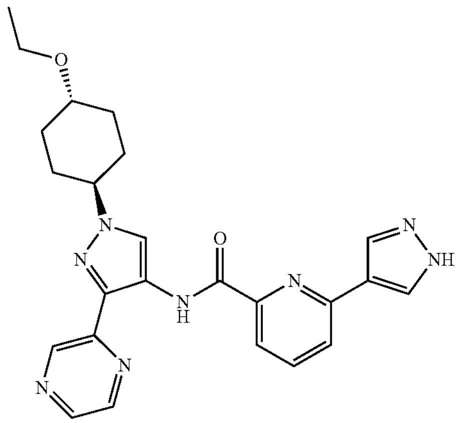 [SMILES: CCO[C@H]1CC[C@H](n2cc(NC(=O)c3cccc(-c4cn[nH]c4)n3)c(-c3cnccn3)n2)CC1]

N-(1-(trans-4-ethoxycyclohexyl)-3-(pyrazin-2-yl)-1H-pyrazol-4-yl)-6-(1H-pyrazol-4-yl)picolinamide (I-205)

$^1$H NMR (400 MHz, Chloroform-d) δ 12.19 (s, 1H), 10.57 (br s, 1H), 9.38 (d, J=1.5 Hz, 1H), 8.64 (dd, J=2.7, 1.6 Hz, 1H), 8.53 (s, 1H), 8.48 (d, J=2.6 Hz, 1H), 8.31 (s, 2H), 8.09 (dd, J=7.7, 1.0 Hz, 1H), 7.88 (dd, J=7.8, 7.8 Hz, 1H), 7.65 (dd, J=7.9, 1.0 Hz, 1H), 4.22 (tt, J=11.8, 3.9 Hz, 1H), 3.57 (q, J=7.0 Hz, 2H), 3.38 (tt, J=10.6, 4.1 Hz, 1H), 2.31-2.20

(m, 4H), 1.98-1.88 (m, 2H), 1.53-1.43 (m, 2H), 1.23 (t, J=7.0 Hz, 3H); LRMS (M+H) m/z 459.3.

Example 116

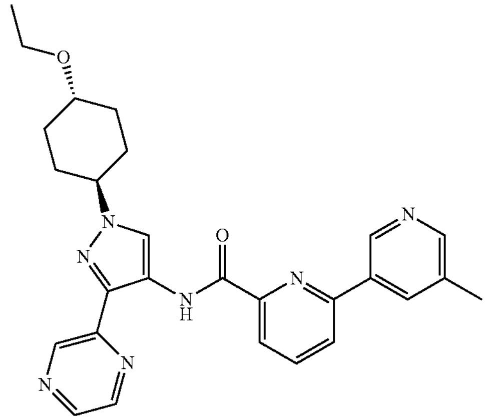 [SMILES: CCO[C@H]1CC[C@H](n2cc(NC(=O)c3cccc(-c4cncc(C)c4)n3)c(-c3cnccn3)n2)CC1]

N-(1-(trans-4-ethoxycyclohexyl)-3-(pyrazin-2-yl)-21H-pyrazo-4-yl)-methy-[2,3'-bipyridine]-6-carboxamide (1-206)

$^1$H NMR (400 MHz, Chloroform-d) δ 12.43 (s, 1H), 9.46 (dd, J=2.2, 0.7 Hz, 1H), 9.37 (d, J=1.5 Hz, 1H), 8.72 (dd, J=2.7, 1.6 Hz, 1H), 8.60 (dd, J=2.1, 0.9 Hz, 1H), 8.52 (s, 1H), 8.51 (d, J=2.7 Hz, 1H), 8.25 (dd, J=7.6, 1.0 Hz, 1H), 8.15 (ddd, J=2.1, 2.1, 0.9 Hz, 1H), 8.01 (dd, J=7.8, 7.8 Hz, 1H), 7.92 (dd, J=7.9, 1.0 Hz, 1H), 4.23 (tt, J=11.8, 3.9 Hz, 1H), 3.57 (q, J=7.0 Hz, 2H), 3.38 (tt, J=10.6, 4.1 Hz, 1H), 2.49 (br d, J=0.7 Hz, 3H), 2.32-2.21 (m, 4H), 1.98-1.88 (m, 2H), 1.53-1.43 (m, 2H), 1.23 (t, J=7.0 Hz, 3H); LRMS (M+H) m/z 484.3.

Example 117

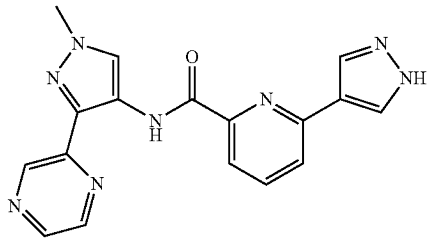 [SMILES: Cn1cc(NC(=O)c2cccc(-c3cn[nH]c3)n2)c(-c2cnccn2)n1]

N-(1-methyl-3-(pyrazin-2-yl)-1H-pyrazol-4-yl)-6-(1H-pyrazol-4-yl)picolinamide (I-207)

$^1$H NMR (400 MHz, Chloroform-d) δ 12.19 (s, 1H), 9.39 (d, J=1.6 Hz, 1H), 8.67 (dd, J=2.7, 1.6 Hz, 1H), 8.51 (d, J=2.7 Hz, 1H), 8.50 (s, 1H), 8.31 (s, 2H), 8.11 (dd, J=7.7, 1.0 Hz, 1H), 7.90 (t, J=7.8 Hz, 1H), 7.66 (dd, J=7.8, 1.0 Hz, 1H), 4.02 (s, 3H); LRMS (M+H) m/z 347.3.

Example 118

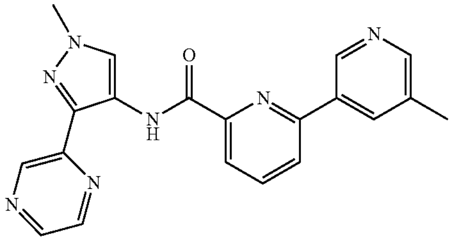 [SMILES: Cc1cncc(-c2cccc(C(=O)Nc3cn(C)nc3-c3cnccn3)n2)c1]

5'-methyl-N-(1-methyl-3-(pyrazin-2-yl)-1H-pyrazol-4-yl)-[2,3'-bipyridine]-6-carboxamide (I-208)

$^1$H NMR (400 MHz, Chloroform-d) δ 12.43 (s, 1H), 9.46 (d, J=2.0 Hz, 1H), 9.37 (d, J=1.5 Hz, 1H), 8.74 (dd, J=2.7, 1.6 Hz, 1H), 8.61 (dd, J=2.1, 0.9 Hz, 1H), 8.53 (d, J=2.6 Hz, 1H), 8.49 (s, 1H), 8.26 (dd, J=7.6, 1.0 Hz, 1H), 8.16 (ddd, J=2.1, 2.1, 0.9 Hz, 1H), 8.01 (dd, J=7.8, 7.8 Hz, 1H), 7.93 (dd, J=7.9, 1.0 Hz, 1H), 4.02 (s, 3H), 2.50 (q, J=0.7 Hz, 3H); LRMS (M+H) m/z 372.3.

Example 119

Preparation of 8-ethoxy-1,4-dioxaspiro[4.5]decane

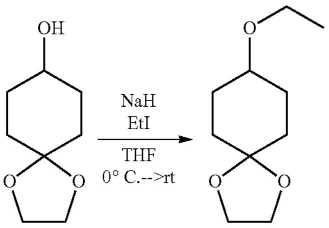

Sodium hydride (60% dispersion in mineral oil, 74.3 g, 1.858 mol) in a round bottom flask was washed four times with hexanes. A suspension in THF (1L) was prepared and cooled to 0° C. Gradually, 1,4-dioxaspiro[4.5]decan-8-ol (150 g, 929 mmol) was added and the reaction allowed to warm to room temperature. After two hours, the reaction was cooled back to 0° C. and iodoethane was added via dropping funnel over one hour. The reaction was gradually allowed warmed to room temperature whereupon a reflux condenser was fitted. The reaction was monitored by TLC (1:1 ethyl acetate in hexanes). Upon completion, the reaction was quenched with ice, the solvent was reduced in volume in vacuo, and then diluted with ethyl acetate and water. After extracting twice with ethyl acetate, the combined organic layers were washed with brine, dried over solid sodium sulfate, filtered, and concentrated in vacuo. After drying on high vacuum, 166.9 g of 8-ethoxy-1,4-dioxaspiro[4.5]decane was obtained as a yellow oil.

$^1$H NMR (300 MHz, Chloroform-d) δ 3.90 (t, J=2.2 Hz, 4H), 3.45 (q, J=7.0 Hz, 2H), 3.40-3.32 (m, 1H), 1.82-1.62 (m, 6H), 1.56-1.46 (m, 2H), 1.16 (t, J=7.0 Hz, 3H).

Example 120

Preparation of 4-ethoxycyclohexan-1-one

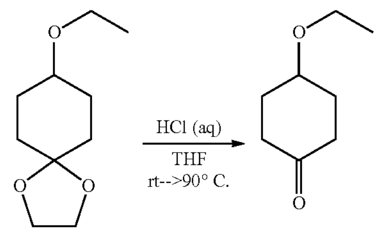

To a solution of 8-ethoxy-1,4-dioxaspiro[4.5]decane (166.9 g, 896.1 mmol) in THF (700 mL) was added a 3M aqueous solution of HCl (597 mL). The solution was heated to 90° C. with an attached reflux condenser for two hours. The reaction was monitored by TLC (1:1 ethyl acetate in hexanes) by taking aliquots quenched with aqueous NaOH and extracted in to ethyl acetate. Upon completion, the solvent volume was reduced in vacuo and was adjusted to pH 8 with 4M NaOH solution. This was extracted twice with ethyl acetate, the combined organic phases were washed with brine, dried over solid sodium sulfate, filtered, and concentrated in vacuo. After drying under high vacuum, 124.2 g of the desired 4-ethoxycyclohexan-1-one was obtained as a yellow oil.

$^1$H NMR (300 MHz, Chloroform-d) δ 3.74-3.61 (m, 1H), 3.53 (q, J=7.0 Hz, 2H), 2.63-2.46 (m, 2H), 2.30-2.15 (m, 2H), 2.12-1.82 (m, 4H), 1.21 (t, J=7.0 Hz, 3H).

Example 121

Preparation of (1s,4s)-4-ethoxycyclohexan-1-ol

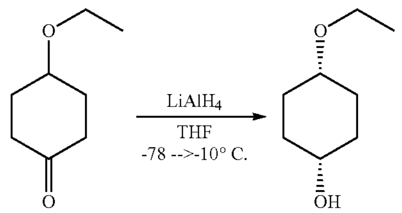

A solution of 4-ethoxycyclohexan-1-one (121.6 g, 855 mmol) in 750 mL of THF was cooled to −78° C. Solid $LiAlH_4$ (95%, 51.2 g, 1.28 mol) was added portion-wise over one hour then gradually warmed to −10° C. After an hour, an aliquot was taken and quenched for TLC analysis in 1:1 ethyl acetate in hexanes showed the reaction was complete. The reaction was cooled back to −78° C. and quenched with dropwise addition of 4M NaOH solution (641 mL). The mixture was diluted and washed three times with ethyl acetate, decanting off the solvent. The combined organic phases were washed with 1M NaOH, brine, dried over solid sodium sulfate, filtered, and concentrated in vacuo. After drying under high vacuum 117.9 g of 4-ethoxycyclohexan-1-ol (in ~2:1 ratio of 1s,4s and 2s,4s isomers) was obtained as a yellow oil.

$^1$H NMR (300 MHz, Chloroform-d) δ 3.76-3.61 (m, 1H), 3.52-3.38 (m, 2H), 3.34 (dp, J=6.3, 3.2 Hz, 1H), 3.27-3.18 (m, ~0.5H), 2.01-1.92 (m, 1H), 1.84-1.47 (m, 6H), 1.33-1.25 (m, 1H), 1.17 (td, J=7.0, 2.5 Hz, 3H).

Example 122

Preparation of (1r,4r)-4-ethoxycyclohexyl 4-nitrobenzenesulfonate

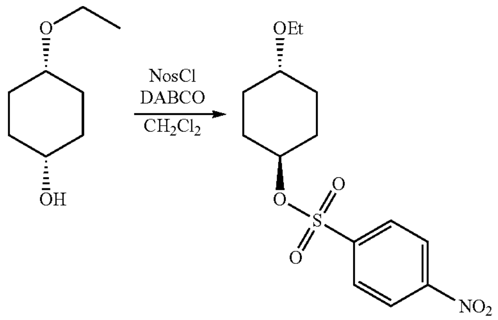

To a solution of 4-ethoxycyclohexan-1-ol (in ~2:1 ratio of 1s,4s and 2s,4s isomers; 112.9 g, 782.9 mmol) in $CH_2Cl_2$ (800 mL) cooled to 0° C. was added 1,4-diazabicyclo[2.2.2]octane (105.4 g, 939.5 mmol). Portion-wise added of 4-nitrobenzenesulfonyl chloride was added at 0° C. over 1 hour then the reaction was gradually warmed to room temperature overnight. When the reaction appeared complete by TLC analysis in 1:1 ethyl acetate in hexanes, it was quenched with addition of $NaHCO_3$ saturated aqueous solution. After further dilution with $CH_2Cl_2$ and water, the organic phase isolated and washed further with $NaHCO_3$ solution, water, and brine. After drying over solid sodium sulfate, the solution was filtered, concentrated in vacuo, and dried under high vacuum. The resulting solid was triturated from ethyl acetate and hexanes to yield 160.8 g of 4-ethoxycyclohexyl 4-nitrobenzenesulfonate (as a mixture of 1r,4r and 1s,4s) as an off-white solid.

$^1$H NMR (300 MHz, Chloroform-d) δ 8.51-8.31 (m, 2H), 8.17-8.03 (m, 2H), 4.73 (dtt, J=11.7, 8.1, 4.0 Hz, 1H), 3.44 (qd, J=7.0, 1.5 Hz, 2H), 3.34 (tt, J=6.7, 3.1 Hz, 1H), 1.99-1.87 (m, 2H), 1.81-1.53 (m, 6H), 1.16 (td, J=7.0, 2.8 Hz, 3H).

Example 123

LPS Induced IL23p19 in THP-1 Cells (with IFNγ Primed) Assay

Materials and Equipment

THP-1 Cells (ATCC, Cat# TIB-202), Dimethyl Sulfoxide (DMSO) (Sigma-Aldrich, Cat# D2650), RPMI 1640 (Cellgro, Cat#10-040-CM), Fetal Bovine Serum (Sigma, Cat# F4135), Albumin From Bovine Serum (BSA) (Sigma-Aldrich, Cat#A7906), LPS (Serotype K-235, Sigma, Product Number L 2143), IFNγ (Peprotech, Cat#300-02) Capture antibody: Human IL-23p19 ELISA (e-Bioscience, Cat. #14-7238-85), Detection antibody: Primary Mouse Biotinylated anti-human IL-12(p40/p70) (e-Bioscience, Cat. #13-7129-85), Secondary HRP-conjugated Streptavidin (R&D Systems, Cat#DY998), 1×PBST Washing Buffer (PBS-Tween tablet) (VWR International, Cat#80058-558), ELISA Blocking Buffer (PBS with 1% BSA), ELISA Dilution Buffer (PBS with 1% BSA), 384 Well Flat-Bottom, MaxiSorp Black Immuno Plates (Thermo Scientific, Cat#12-565-346), 384 Well Flat-Bottom, White Tissue Culture Plates (Thermo Scientific, Cat#12-565-343), Super Signal ELISA Pico Chemiluminescent Substrate (Thermo Scientific, Cat#37070), Cell Titer Glo reagent (Promega, Cat#G7573), Positive control, IKK2VI inhibitor (Calbiochem, Cat#401483), AquaMax 4000 plate washer (Molecular Devices), Luminometer, Wallac Victor2 1420 Multilabel Counter.

Method

THP-1 Cells Stimulation:

On day 1, 50K/well THP-1 cells were seeded and primed with IFNγ (50 ng/mL) in 384-well plates for about 18 hours in RPMI media with 10% FBS. On day 2, the compound was serially diluted in DMSO from 5 mM in 3-fold dilutions, and then diluted 1:125 in RPMI media with 10% FBS. 50 μL/well 2× compound was added to 50 μL/well THP-1 cells (with IFNγ primed) in duplicate in 384 well tissue culture plates. The cells were pre-incubated with compound for 1 hour at 37° C., 5% $CO_2$ before addition of 10 μL/well 11×LPS to give a final concentration of 1 ug/mL LPS. Day 3, after stimulation for 18 hours at 37° C., 5% $CO_2$, the assay plate was centrifuged and 70 μL/well supernatant was harvested. IL-23p19 protein in 70 μL/well of supernatant was measured by sandwich ELISA, and 25 μl/well Cell Titer Glo reagent was added to the remaining cells to measure compound toxicity.

Human IL-23p19 Sandwich ELISA:

Maxisorp immuno ELISA plates were pre-coated with 25 μL/well of anti-IL-23p19 capture antibody (2.5 ug/mL) in PBS overnight at room temperature. After washing with 1×PBST, the plates were blocked using 100 μL/well of 1% BSA in PBS for 2 hours at room temperature. The plates were washed three times with 1×PBST and 70 μL/well supernatant were added. The plates were incubated at room temperature for 2 hours with shaking and washed three times with 1×PBST. 25 μL/well of biotin labeled anti-IL-12(p40/p70) detection antibody (100 ng/mL) in PBS with 1% BSA was added and the plates were incubated at room temperature for 2 hours with shaking. After washing three times with 1×PBST, 25 μL/well of streptavidin-HRP (1:200) in PBS with 1% BSA was added and the plates were incubated at room temperature for 20 minutes with shaking. The plates were washed three times with 1×PBST and 25 μL/well of Super Signal ELISA Pico Chemiluminescent Substrate were added. The plates were read with a luminometer, and the chemiluminescence values were entered into Athena (Rigel) for curve fitting, $EC_{50}$ calculation, and database storage. The results are shown in Table 1.

Example 124

Compound Screening Using DC Cells

Materials

Human PBMC cells (All Cells, Cat No. PB002)

RPMI growth media containing 10% FBS

IFNγ (Peprotech, Cat No. 300-02)

GMCSF (Peprotech, Cat No. 300-03) and IL4 (Peprotech Cat No. 200-04)

White clear bottom 96 well plates (Fisher, Cat No. 07-200-587, Corning #3903)

LPS (Make 2.5 mg/ml Stock in PBS) from Sigma Aldrich (Cat No. L2018-5MG)

Cell Titer Glo reagent (Promega, Cat No. G7573)

Positive controls, IKK2VI inhibitor (Calbiochem, Cat No. 401483)

Protocol

I. Differentiation of PBMC's to DC Cells:

Human PBMC cells (400 million) obtained from the vendor were transferred into a T-175 flask containing 15 ml RPMI media (10% FBS) and incubate for 2 hours at 37° C. After 2 hours, the media including floating cells was aspirated out carefully and 12 ml of fresh RPMI media (10% FBS) containing GMCSF (100 ng/ml) and IL4 (20 ng/ml) was added, and the flask was kept in a 37° C. incubator for 7 days.

After 3 days, fresh GMCSF (100 ng/ml) and IL4 (20 ng/ml) were added to the flask and the incubation continued. After 7 days, the fully differentiated cells were harvested by spinning down (1200 rpm/5 min) and aspirating the media. The cells were suspended in fresh RPMI media (10% FBS) containing 50 ng/ml IFNγ (1000 U/ml) and then plated (50K/well in 100 μl) onto a white clear bottom 96 well plate and left in a 37° C. incubator for 24 hours.

II. Addition of Compounds:

After 24 hours incubation, 100 μl of RPMI media was added containing 2× concentrated test compound per well to the above cell-culture media (final concentration becomes 1×) and the plates were pre-incubated for 1 hour at 37° C. before stimulating with LPS.

After 1 hour compound pre-incubation, 10 μl per well of 20× concentrated LPS solution in RPMI media was added to give a final concentration of 1 μg/ml. The mixture was shaken and incubated the plates at 37° C. for an additional 18 hours.

155 μl of the supernatant was harvested from each well carefully (without the tip touching the bottom of the well) and to the remaining 50 μl/well of the cell culture plate was added 50 μl of Cell Titer Glo reagent. The mixture was incubated for 1-2 minutes on a shaker and the plate was read for luminescence intensity to determine the compound cytotoxicity. The cell culture supernatant collected above was used to carry out IL23 ELISA (65 μl—Supernatant) and IL10 ELISA (90 μl—Supernatant) as described below.

Example 125

Human IL-23 (p19/p40) ELISA Protocol (e-Biosciences)

Materials:

96-well high binding opaque white plates (from Pierce, Cat No. 15042);

1×PBS; 1×TBST washing buffer;

Blocking Solution: 0.5% Casein in PBS (from BDH, Cat No. 440203H);

Dilution Solution: 1% BSA in PBS (10% BSA from Fisher, Cat No. 37525);

Capture antibody: Rat anti-human IL-23 (p19) (e-Biosciences, Cat. No. 14-7238-85);

Detection antibody: Primary Mouse Biotinylated anti-human IL-12 (p40/p70) (e-biosciences, Cat No. 13-7129-85);

Secondary HRP-conjugated Streptavidin (R&D Systems, Cat No. DY998);

rHuman-IL-23 (e-biosciences, Cat No. 34-8239) (Suggested starting concentration=5 ng/ml in RPMI cell culture media);

Cell Culture Supernatant (65 μl from THP-1 cells primed with IFNγ (50 ng/ml-1000 U/ml) and stimulated with 0.01% SAC);

SuperSignal ELISA Pico Chemiluminescent substrate [Pierce, Cat No. 37069].

Coating Plates:

To 10.5 ml PBS add 50 μl of anti-IL23 (p19) was added capture antibody (2.5 g/ml). The mixture was mixed well and 100 μl of the coating solution was added to each well of the 96 well white plates from Pierce. The wells were covered and incubated overnight at 4° C.

Blocking the Plates:

The anti-IL23 (p19)-antibody-coated plates were washed 2× using TBST (use plate washer) and blocked using 200 μl of 0.5% Casein for 1.5-2 hours at room temperature with shaking.

Addition of Supernatant and Detection:

The plates were washed 2× using TBST and the supernatant was transferred (65 μl/well) to the above pre-blocked/IL23(p19)-antibody-coated 96 well plate, and incubated at room temperature for 1.5 hours with shaking.

The plates were washed 4× using TBST (plate washer) and 100 μl/well detection antibody solution prepared from 2 μl of biotin labeled anti-IL-12 (p40/p70) antibody in 11 ml 1% BSA/PBS solution (I-5000 dilution) was added. The plates were incubated for 1 hour with shaking at Room temperature.

Again, the plates were washed 4× with TBST and 100 μl of HRP labeled Streptavidin (R&D Systems) solution (10 μl/10 ml 1% BSA solution) was added, and the plates were incubated at room temperature for another 45 minutes with shaking.

After 45 minutes, the plates were washed with TBST 4× and 100 μl/well Super Signal ELISA Pico Chemiluminescent Substrate from Pierce (3.5 ml A+3.5 ml B+3.5 ml MQ water) was added. The plates were shaken for 1-2 minutes then read on a plate reader.

The $EC_{50}$ results from the assays described in Examples 123 and 125 are shown in Table 1.

TABLE 1

| Compound | IL23-p19 ELISA, Dendritic, LPS, 10 pt, $EC_{50}$ (μM) | IL23-p19 ELISA, THP1-IFNy, LPS, 10 pt $EC_{50}$ (μM) |
|---|---|---|
| I-2 | 2.722 | 1.255 |
| I-3 | 7777 | 21.54 |
| I-4 | ND* | 1901 |
| I-5 | 7777 | 40.09 |
| I-6 | 0.1617 | 0.5358 |
| I-7 | 0.3541 | 0.5329 |
| I-8 | 2.423 | 1.695 |
| I-9 | 0.1785 | 0.2809 |
| I-10 | ND* | 654.6 |
| I-11 | 4.116 | 5.896 |
| I-12 | 0.1064 | 0.2497 |
| I-13 | 0.5306 | 1.339 |
| I-14 | ND* | 1.522 |
| I-15 | ND* | 63.56 |
| I-16 | 1.202 | 6.351 |
| I-17 | ND* | 58.28 |
| I-18 | 7777 | ND* |
| I-19 | 5.633 | 2.541 |
| I-20 | ND* | 128.1 |
| I-21 | ND* | 398.2 |
| I-22 | 8.56 | 8888 |
| I-23 | 1.79 | 2.289 |
| I-24 | ND* | 101.2 |
| I-25 | 0.0347 | 0.1689 |
| I-26 | 0.2041 | 2.869 |
| I-27 | 0.3424 | 7.021 |
| I-28 | 0.5456 | 1.454 |
| I-29 | 0.9103 | 16.37 |
| I-30 | 3.208 | 0.7725 |
| I-31 | 0.4131 | Not tested |

TABLE 1-continued

| Compound | IL23-p19 ELISA, Dendritic, LPS, 10 pt, $EC_{50}$ (μM) | IL23-p19 ELISA, THP1-IFNy, LPS, 10 pt $EC_{50}$ (μM) |
|---|---|---|
| I-32 | 7.186 | 2.516 |
| I-33 | 1.024 | 3.156 |
| I-34 | 16.14 | 71.87 |
| I-35 | 0.8784 | 1.11 |
| I-36 | 0.7845 | 4.253 |
| I-37 | 1253 | 0.5869 |
| I-38 | 33.74 | 6.203 |
| I-39 | ND* | 1.392 |
| I-40 | 2.993 | ND* |
| I-41 | 7777 | 116.5 |
| I-42 | ND* | 25.47 |
| I-43 | 1.459 | 1.317 |
| I-44 | 1.765 | 0.3487 |
| I-45 | ND* | 3.461 |
| I-46 | 7777 | 3.499 |
| I-47 | 7777 | 3.599 |
| I-48 | 9.163 | ND* |
| I-49 | ND* | 72.09 |
| I-50 | ND* | 5.437 |
| I-51 | ND* | 59.11 |
| I-52 | 1.113 | 4.483 |
| I-53 | ND* | ND* |
| I-54 | ND* | ND* |
| I-55 | ND* | ND* |
| I-56 | ND* | ND* |
| I-57 | 3333 | 5.273 |
| I-58 | ND* | 15.16 |
| I-59 | 2.469 | 23.94 |
| I-60 | ND* | 14.75 |
| I-61 | ND* | 22.28 |
| I-62 | ND* | 28.03 |
| I-63 | 5000 | 26.58 |
| I-64 | ND* | 13.26 |
| I-65 | 7.876 | 77.2 |
| I-67 | 2.675 | 0.4833 |
| I-68 | 2.414 | 0.29 |
| I-69 | 1.505 | 1.203 |
| I-70 | ND* | 2.208 |
| I-71 | 0.4149 | 0.2995 |
| I-72 | 3.17 | 7.582 |
| I-73 | 2.157 | 1.772 |
| I-74 | 3.815 | 18.8 |
| I-75 | ND* | 15.88 |
| I-76 | 4.315 | 1.934 |
| I-77 | 2.163 | 33.2 |
| I-78 | 0.8317 | 0.6428 |
| I-80 | 8.786 | 2.392 |
| I-81 | 6.47 | 2.781 |
| I-83 | 82.72 | 2.006 |
| I-84 | ND* | 0.4437 |
| I-86 | 0.4069 | 0.0985 |
| I-87 | 1.998 | 0.0754 |
| I-99 | ND* | ND* |
| I-100 | 9.853 | 64.14 |
| I-101 | 1.83 | 14.52 |
| I-102 | 2.041 | 26.66 |
| I-103 | ND* | ND* |
| I-104 | ND* | 74.12 |
| I-105 | ND* | ND* |
| I-106 | ND* | 4.944 |
| I-107 | 4999 | 3.583 |
| I-108 | 4.925 | 5.965 |
| I-109 | Not tested | 10.81 |
| I-110 | ND* | ND* |
| I-111 | ND* | ND* |
| I-112 | 1.282 | 0.3251 |
| I-113 | 10.86 | 8.042 |
| I-114 | 2.328 | 1.764 |
| I-115 | 7.647 | 2.18 |
| I-116 | 0.1416 | 0.2125 |
| I-117 | 0.1002 | 0.156 |
| I-118 | ND* | 130.5 |
| I-119 | 1.003 | 1.024 |
| I-120 | 2.994 | 46.87 |

TABLE 1-continued

| Compound | IL23-p19 ELISA, Dendritic, LPS, 10 pt, $EC_{50}$ (μM) | IL23-p19 ELISA, THP1-IFNy, LPS, 10 pt $EC_{50}$ (μM) |
|---|---|---|
| I-121 | 1.806 | 1.071 |
| I-122 | 3.776 | 0.873 |
| I-123 | 0.7381 | 0.9212 |
| I-124 | 1.54 | 6.637 |
| I-125 | ND* | 3.916 |
| I-126 | 7777 | 3.354 |
| I-127 | ND* | 18.21 |
| I-128 | ND* | 24.19 |
| I-129 | ND* | 72.88 |
| I-130 | 1.649 | 8888 |
| I-131 | 12.76 | 6.616 |
| I-132 | 7.765 | 54.92 |
| I-133 | 6.54 | 11.05 |
| I-134 | 2.205 | 1.263 |
| I-135 | ND* | 41.69 |
| I-136 | 0.1983 | 0.4692 |
| I-137 | 5.057 | 4.009 |
| I-138 | 1.183 | 29.45 |
| I-139 | ND* | ND* |
| I-140 | ND* | 10.94 |
| I-141 | 2.835 | 8.431 |
| I-142 | 2.545 | 0.7613 |
| I-143 | ND* | 8888 |
| I-144 | ND* | 11.54 |
| I-145 | ND* | 56.85 |
| I-146 | 5.899 | 4.235 |
| I-147 | 10.73 | 41.12 |
| I-148 | 6.28 | 4.505 |
| I-149 | 1.423 | 1.203 |
| I-150 | 0.0662 | 3.391 |
| I-151 | 4.124 | 7.877 |
| I-152 | 14.19 | 12.43 |
| I-153 | 0.628 | 0.4632 |
| I-154 | 6.509 | 4.919 |
| I-155 | 2.407 | 6.165 |
| I-156 | 2.733 | 21.45 |
| I-157 | 10.9 | ND* |
| I-158 | ND* | ND* |
| I-159 | ND* | 14.69 |
| I-160 | ND* | 150.4 |
| I-161 | 4.201 | 7.518 |
| I-162 | 0.1673 | 0.4989 |
| I-163 | 1.063 | 0.3708 |
| I-164 | 2.887 | 1.374 |
| I-165 | 4999 | 1.532 |
| I-166 | 0.071 | 1.094 |
| I-167 | 6.504 | ND* |
| I-168 | ND* | 0.5414 |
| I-169 | 2.419 | 0.557 |
| I-170 | ND* | 568.7 |
| I-171 | 2.378 | 8888 |
| I-172 | 0.0468 | 8888 |
| I-173 | ND* | ND* |
| I-174 | 7.069 | 19.52 |
| I-175 | 6.841 | 9.012 |
| I-176 | ND* | 27.95 |
| I-177 | 12.25 | 21.68 |
| I-178 | 19.31 | 2.07 |
| I-179 | ND* | 8888 |
| I-180 | 1.189 | 0.3402 |
| I-181 | 4.175 | 1.487 |
| I-182 | ND* | 8888 |
| I-183 | 0.2159 | 0.0961 |
| I-184 | 8.248 | 0.3282 |

*ND indicates that an accurate inhibition curve may not have been produced due to compound insolubility, artifacts in the assay, and/or other factors.

V. Exemplary Embodiments

The following numbered paragraphs illustrate exemplary embodiments of the disclosed technology.

Paragraph 1. A compound, having a formula 1

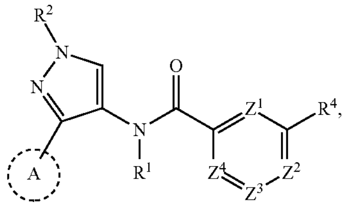

1 or a salt thereof, wherein:

ring A is aromatic or heterocycloalphatic;

$R^1$ is H, aliphatic, or heteroaliphatic;

$R^2$ is H, aliphatic, heteroaliphatic, or heterocyclyl;

each $Z^1$, $Z^2$, $Z^3$, and $Z^4$, independently is N or $CR^3$, wherein at least one of $Z^1$, $Z^2$, $Z^3$, and $Z^4$ is N;

each $R^3$ independently is H, aliphatic, or heteroaliphatic; and $R^4$ is halogen, heterocycloaliphatic, aromatic, —O-aromatic, or —NH-aromatic.

Paragraph 2. The compound of paragraph 1, wherein ring A is aryl, heteroaryl, 5-membered heterocycloaliphatic, or 6-membered heterocycloaliphatic.

Paragraph 3. The compound of paragraphs 1 or 2, wherein ring A is pyridinyl, pyrazinyl, pyrrolidinyl, piperidinyl, or morpholino.

Paragraph 4. The compound of any one of paragraphs 1-3, wherein ring A is pyridin-2-yl.

Paragraph 5. The compound of any one of paragraphs 1-4, wherein ring A is

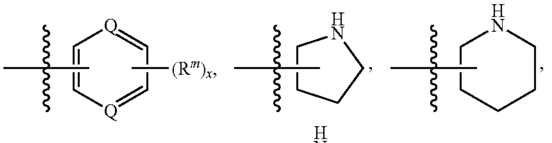

or

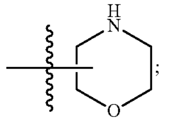

each Q independently is CH or N, wherein at least one Q is N;

$R^m$ is $R^b$;

x is 0, 1, or 2;

$R^a$ is independently for each occurrence H, D, $C_{1-6}$alkyl, $C_{3-6}$cycloalkyl, $C_{5-10}$aromatic, or $C_{3-6}$heterocycloaliphatic;

$R^b$ is independently for each occurrence —OH, —$CF_3$, —CN, —$OR^c$, —$SO_2R^c$, —$NR^dR^d$, —$N(H)SO_2R^c$, —C(O)OH, —$N(H)C(O)R^c$, —$C(O)OR^c$, —$C(O)NR^dR^d$, ═O, or halogen;

$R^c$ is independently for each occurrence $C_{1-6}$alkyl, $C_{3-6}$cycloalkyl, $C_{3-6}$heteroalicyclyl, aralkyl, $C_{1-6}$alkyl substituted with 1, 2 or 3 $R^e$, $C_{5-10}$aromatic, $C_{5-10}$aromatic substituted with 1, 2 or 3 $R^e$;

$R^d$ is independently for each occurrence H, $C_{1-6}$alkyl optionally substituted with 1, 2 or 3 $R^e$, $C_{3-6}$cycloalkyl optionally substituted with 1, 2 or 3 $R^e$, $C_{3-6}$heteroalicyclyl optionally substituted with 1, 2 or 3 $R^e$, $C_{5-10}$aromatic optionally substituted with 1, 2 or 3 $R^a$ or $R^b$, or two $R^d$ groups together with the nitrogen bound thereto form a $C_{3-6}$heteroalicyclyl moiety optionally substituted with $C_{1-6}$alkyl and optionally interrupted with one or two —O— or —$N(R^g)$ wherein $R^g$ is $R^{70}$; and $R^e$ is independently for each occurrence halogen, $C_{1-6}$alkyl, $C_{3-6}$cycloalkyl, or —$OR^a$.

Paragraph 6. The compound of any one of paragraphs 1-5, wherein ring A is

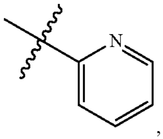
,
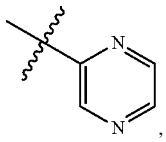
,
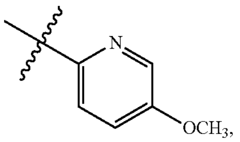

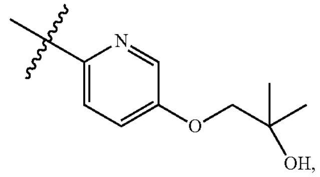
,
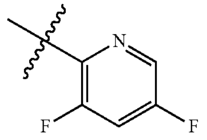

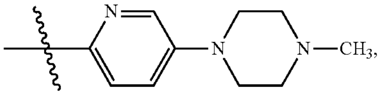

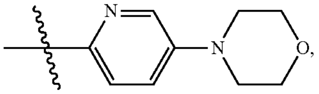

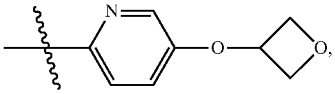

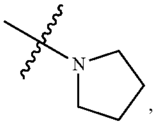
,
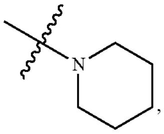
, or
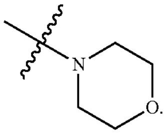

Paragraph 7. The compound of any one of paragraphs 1-6, wherein $R^1$ is H or $C_{1-6}$ alkyl.

Paragraph 8. The compound of any one of paragraphs 1-7, wherein $R^2$ is H, 3- to 10-membered heteroaliphatic, tetrahydropyranyl, oxetanyl, cyclobutyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic.

Paragraph 9. The compound of any one of paragraphs 5-8, wherein $R^2$ is $R^a$, $R^a$ substituted with $R^b$, $R^a$ substituted with 1 or 2 $R^c$, or $R^a$ substituted with $R^d$.

Paragraph 10. The compound of any one of paragraphs 1-9, wherein $R^2$ is H, $CH_3$,

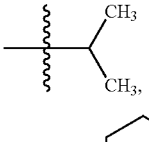

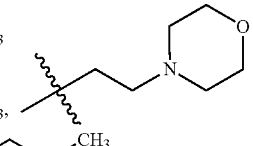
,
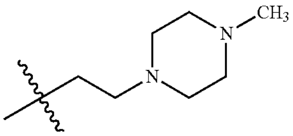
,
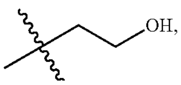

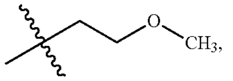

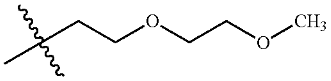
,

-continued

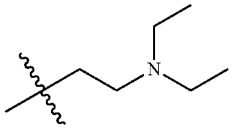
,
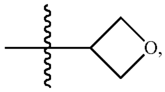

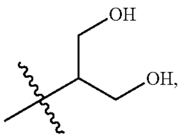

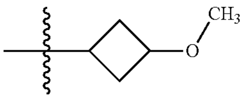
,
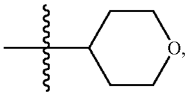
or
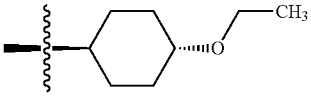
.

Paragraph 11. The compound of paragraph 1, wherein:

ring A is phenyl, pyridinyl, pyrazinyl, pyrrolidinyl, piperidinyl, or morpholino;

$R^1$ is H; and $R^2$ is H, 3- to 10-membered heteroaliphatic, tetrahydropyranyl, oxetanyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic.

Paragraph 12. The compound of paragraph 1, wherein:

each $Z^1$, $Z^2$, $Z^3$, and $Z^4$, independently is N or $CR^3$, wherein at least one of $Z^1$, $Z^2$, $Z^3$, and $Z^4$ is N;

each $R^3$ independently is H, aliphatic, or heteroaliphatic; and $R^4$ is halogen, heteroaryl, heterocycloaliphatic, aryl, —NH-heteroaryl, or —O-heteroaryl.

Paragraph 13. The compound of paragraph 12, wherein the

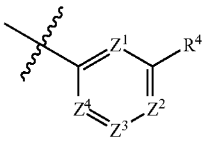

moiety is pyridinyl, pyrimidinyl, or pyrazinyl.

Paragraph 14. The compound of paragraph 12 or paragraph 13, wherein $Z^1$ is N.

Paragraph 15. The compound of any one of paragraphs 12-14, wherein $Z^1$ is N, and $Z^2$, $Z^3$, and $Z^4$ are $CR^3$.

Paragraph 16. The compound of any one of paragraphs 12-14, wherein $Z^1$ and $Z^2$ are N, and $Z^3$ and $Z^4$ are $CR^3$.

Paragraph 17. The compound of paragraph 12 or paragraph 13, wherein $Z^1$ and $Z^3$ are N, and $Z^2$ and $Z^4$ are $CR^3$.

Paragraph 18. The compound of paragraph 12 or paragraph 13, wherein $Z^1$ and $Z^4$ are N, and $Z^2$ and $Z^3$ are $CR^3$.

Paragraph 19. The compound of paragraph 12 or paragraph 13, wherein $Z^3$ is N, and $Z^1$, $Z^2$, and $Z^4$ are $CR^3$.

Paragraph 20. The compound of any one of paragraphs 12-19, wherein $R^1$ is H.

Paragraph 21. The compound of any of paragraphs 1-20, wherein $R^4$ is halogen, heterocycloaliphatic, aryl, heteroaryl, —NH-heteroaryl, or —O-heteroaryl.

Paragraph 22. The compound of paragraph 21, wherein $R^4$ is Br, 5- to 10-membered heteroaryl, 3- to 6-membered heterocycloaliphatic, 6- to 10-membered aryl, —NH-(5- to 10-membered heteroaryl), or —O-(5- to 10-membered heteroaryl).

Paragraph 23. The compound of paragraph 22, wherein $R^4$ is pyridinyl, pyrimidinyl, pyrazolyl, —NH— pyrazolyl, pyrrolyl, —O-pyridinyl, —NH-pyridinyl, indolyl, furanyl, —NH-benzopyrazolyl, pyrrolopyridinyl, phenyl, tetrahydropyridinyl, piperidinyl, or 2-oxo-1,2-dihydropyridinyl.

Paragraph 24. The compound of paragraph 21, wherein $R^4$ is Br; unsubstituted pyridinyl; pyridinyl substituted with $C_{1-6}$alkyl, haloalkyl, amino, heterocycloaliphatic, cycloalkyl, —CN, alkoxy, —O-heterocycloaliphatic, —NH-heterocycloaliphatic, halogen, sulfonamide, —O-benzyl, carboxyl, sulfonyl, —NH— cycloalkyl, or amide; unsubstituted pyrimidinyl; unsubstituted pyrazolyl; pyrazolyl substituted with $C_{1-6}$alkyl; unsubstituted —NH-pyrazolyl; —NH-pyrazolyl substituted with $C_{1-6}$alkyl, or heteroaryl; pyrrolyl; unsubstituted —O— pyridinyl; —O-pyridinyl substituted with amino; —NH-pyridinyl substituted with $C_{1-6}$alkyl, haloalkyl, or heterocycloaliphatic; unsubstituted indolyl; indolyl substituted with alkoxy; furanyl; —NH-benzopyrazolyl; pyrrolopyridinyl; unsubstituted phenyl; phenyl substituted with halogen, $C_{1-6}$alkyl, alkoxy, —CN, amino, or sulfonamide; unsubstituted tetrahydropyridinyl; tetrahydropyridinyl substituted with tert-butoxycarbonyl; piperidinyl; or 2-oxo-1,2-dihydropyridinyl.

Paragraph 25. The compound of any one of paragraphs 21-24, wherein $R^4$ is Br,

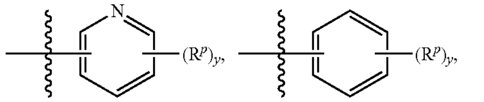

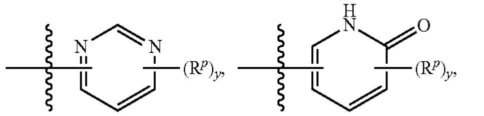

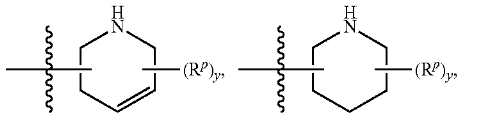

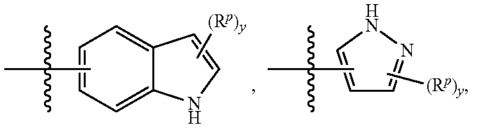

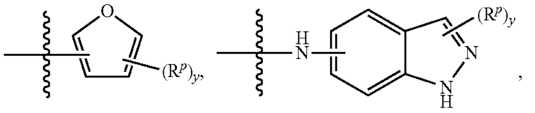

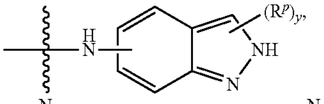

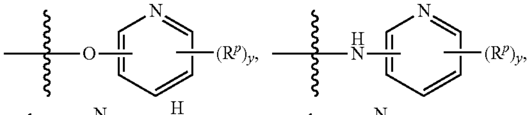

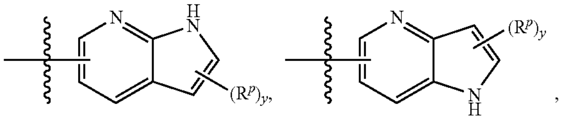

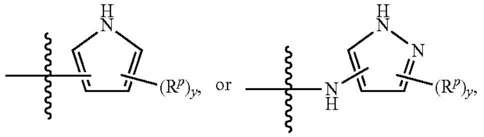

where y is 0, 1 or 2, and each $R^p$ independently is $R^a$, $R^b$, $R^a$ substituted with $R^b$, or $R^a$ substituted with $R^c$.

Paragraph 26. The compound of paragraph 25, wherein each $R^p$ independently is $—CH_3$, $—OCH_3$, $—NH_2$, $—CF_3$, F, —CN,

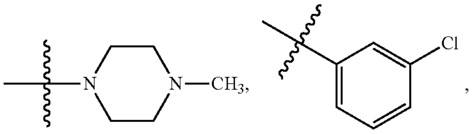

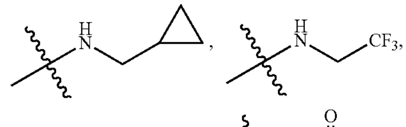

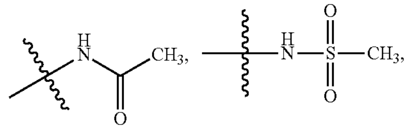

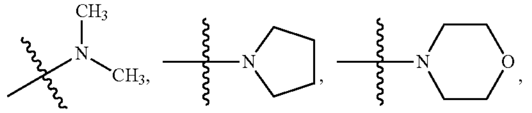

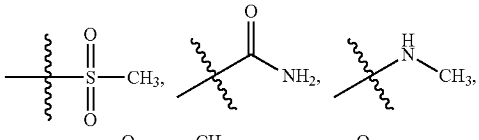

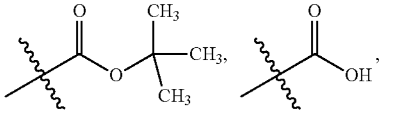

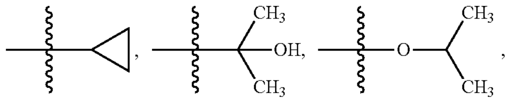

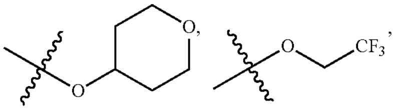

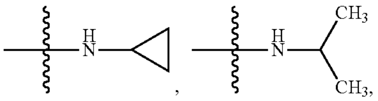

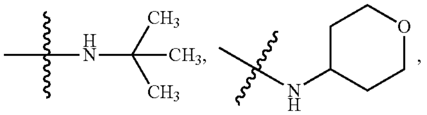

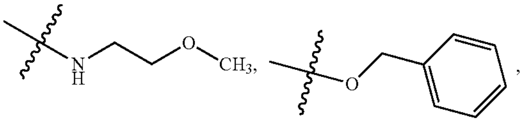

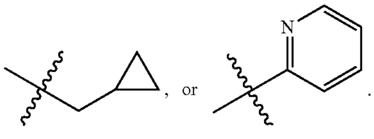 [SMILES: *CC1CC1 ; *c1ccccn1]

Paragraph 27. The compound of any one of paragraphs 21-24, wherein $R^4$ is $R^a$, $R^b$, $R^a$ substituted with $R^b$, or $R^a$ substituted with $R^c$.

Paragraph 28. The compound of any one of paragraphs 1-27, wherein the compound has a formula 2,

2

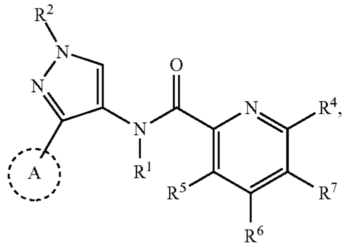

wherein each of $R^5$, $R^6$, and $R^7$ independently is H or alkyl.

Paragraph 29. The compound of paragraph 28, wherein each of $R^5$, $R^6$, and $R^7$ is H.

Paragraph 30. The compound of paragraph 28 or paragraph 29, wherein each of $R^5$, $R^6$, and $R^7$ is $C_{1-6}$ alkyl.

Paragraph 31. The compound of any one of paragraphs 28-30, wherein ring A is pyridin-2-yl, pyrazine-2-yl, pyrrolidin-1-yl, piperidin-1-yl, or morpholino.

Paragraph 32. The compound of any one of paragraphs 1-31, wherein the compound has a formula 3

3

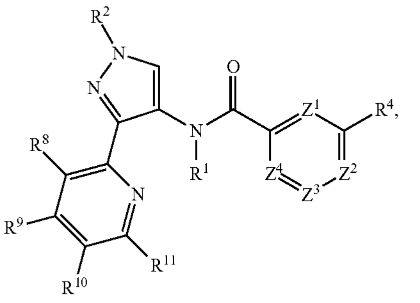

and each of $R^8$, $R^9$, $R^{10}$ and $R^{11}$ independently is H, aliphatic, halogen, heterocycloaliphatic, alkoxy, or —O-heterocycloaliphatic.

Paragraph 33. The compound of paragraph 32, wherein each of $R^8$, $R^9$, $R^{10}$ and $R^{11}$ independently is H, halogen, 3- to 6-membered heterocycloaliphatic, alkoxy, or —O-(3- to 6-membered heterocycloaliphatic).

Paragraph 34. The compound of paragraph 32 or paragraph 33, wherein $R^8$ is H or halogen.

Paragraph 35. The compound of any one of paragraphs 32-34, wherein $R^9$ and $R^{11}$ are H.

Paragraph 36. The compound of any one of paragraphs 32-35, wherein $R^{10}$ is H, F, morpholino, N-methylpiperidin-1-yl, methoxy, 2-hydroxy-2-methylpropoxy, or —O-oxetanyl.

Paragraph 37. The compound of any one of paragraphs 32-36, wherein each of $R^8$, $R^9$, and $R^{11}$ is H.

Paragraph 38. The compound of any one of paragraphs 32-37, wherein $R^9$ and $R^{11}$ are H, and $R^8$ and $R^{10}$ are F.

Paragraph 39. The compound of any one of paragraphs 32-36, wherein each of $R^8$, $R^9$, $R^{10}$ and $R^{11}$ is H.

Paragraph 40. The compound of any one of paragraphs 32-39, wherein the compound has a formula 9

9

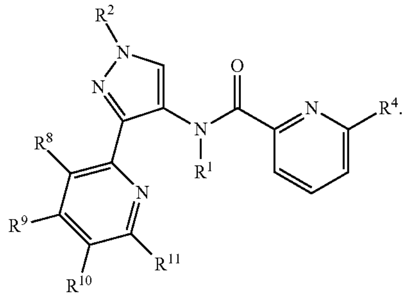

Paragraph 41. The compound of paragraph 40, wherein:

$R^1$ is H;

$R^2$ is H, 3- to 10-membered heteroaliphatic, tetrahydropyranyl, oxetanyl, cyclobutyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic;

$R^4$ is Br; unsubstituted pyridinyl; pyridinyl substituted with $C_{1-6}$alkyl, haloalkyl, amino, heterocycloaliphatic, cycloalkyl, —CN, alkoxy, —O-heterocycloaliphatic, —NH-heterocycloaliphatic, halogen, sulfonamide, —O-benzyl, carboxyl, sulfonyl, —NH-cycloalkyl, or amide; unsubstituted pyrimidinyl; unsubstituted pyrazolyl; pyrazolyl substituted with $C_{1-6}$alkyl; unsubstituted —NH-pyrazolyl; —NH-pyrazolyl substituted with $C_{1-6}$alkyl, or heteroaryl; pyrrolyl; unsubstituted —O-pyridinyl; —O-pyridinyl substituted with amino; —NH-pyridinyl substituted with $C_{1-6}$alkyl, haloalkyl, or heterocycloaliphatic; unsubstituted indolyl; indolyl substituted with alkoxy; furanyl; —NH-benzopyrazolyl; pyrrolopyridinyl; unsubstituted phenyl; phenyl substituted with halogen, $C_{1-6}$alkyl, alkoxy, —CN, amino, or sulfonamide; unsubstituted tetrahydropyridinyl; tetrahydropyridinyl substituted with tert-butoxycarbonyl; piperidinyl; or 2-oxo-1,2-dihydropyridinyl;

$R^8$ is H or F;

$R^9$ and R" are H; and $R^{10}$ is H, F, morpholino, N-methylpiperidinyl, methoxy, 2-hydroxy-2-methylpropoxy, or —O-oxetanyl.

Paragraph 42. The compound of paragraph 41, wherein each of $R^8$, $R^9$, $R^{10}$ and $R^{11}$ is H.

Paragraph 43. The compound of paragraph 41 wherein $R^8$, $R^9$, and $R^{11}$ are H and $R^{10}$ is 3- to 6-membered morpholino or N-methylpiperidinyl, methoxy, 2-hydroxy-2-methylpropoxy, or —O-oxetanyl.

Paragraph 44. The compound of paragraph 41 wherein $R^8$ and $R^{10}$ are F, and $R^9$ and R" are H.

Paragraph 45. A compound selected from the exemplary compounds disclosed herein.

Paragraph 46. A composition, comprising a compound of any one of paragraphs 1-45, and a pharmaceutically acceptable excipient.

Paragraph 47. The composition of paragraph 46, further comprising an additional therapeutic agent.

Paragraph 48. A method, comprising administering to a subject in need thereof an effective amount of a compound of any one of paragraphs 1-45, or a composition of any one of paragraphs 46-47.

Paragraph 49. The method of paragraph 48, for treating a disease or condition for which an IRAK inhibitor is indicated.

Paragraph 50. The method of paragraph 49, wherein the disease is an auto-immune disease, inflammatory disorder, cardiovascular disease, neurodegenerative disorder, allergic disorder, multi-organ failure, kidney disease, platelet aggregation, cancer, transplantation, sperm motility, erythrocyte deficiency, graft rejection, lung injury, respiratory disease, ischemic condition, bacterial infection, viral infection, immune regulatory disorder or a combination thereof.

Paragraph 51. The method of paragraph 49, wherein the disease is amyotrophic lateral sclerosis (ALS), systemic lupus erythematosus, chronic rheumatoid arthritis, type I diabetes mellitus, inflammatory bowel disease, biliary cirrhosis, uveitis, multiple sclerosis, Crohn's disease, ulcerative colitis, bullous pemphigoid, sarcoidosis, psoriasis, autoimmune myositis, pancreatitis, Kaposi's sarcoma, myelodysplastic syndrome, Wegener's granulomatosis, ichthyosis, Graves ophthalmopathy or asthma.

Paragraph 52. The method of paragraph 50, wherein the immune regulatory disorder is rheumatoid arthritis, systemic lupus erythematosus, Hashimoto's thyroiditis, multiple sclerosis, systemic sclerosis, myasthenia gravis, type I diabetes, uveitis, posterior uveitis, allergic encephalomyelitis, glomerulonephritis, postinfectious autoimmune diseases including rheumatic fever and post-infectious glomerulonephritis, inflammatory and hyperproliferative skin diseases, psoriasis, atopic dermatitis, contact dermatitis, eczematous dermatitis, seborrhoeic dermatitis, lichen planus, pemphigus, bullous pemphigoid, epidermolysis bullosa, urticaria, angioedemas, vasculitis, erythema, cutaneous eosinophilia, lupus erythematosus, acne, alopecia areata, keratoconjunctivitis, vernal conjunctivitis, uveitis associated with Behcet's disease, keratitis, herpetic keratitis, conical cornea, dystrophia epithelialis corneae, corneal leukoma, ocular pemphigus, Mooren's ulcer, scleritis, Graves' opthalmopathy, Vogt-Koyanagi-Harada syndrome, sarcoidosis, pollen allergies, reversible obstructive airway disease, bronchial asthma, allergic asthma, intrinsic asthma, extrinsic asthma, dust asthma, chronic or inveterate asthma, late asthma and airway hyper-responsiveness, bronchitis, gastric ulcers, vascular damage caused by ischemic diseases and thrombosis, ischemic bowel diseases, inflammatory bowel diseases, necrotizing enterocolitis, intestinal lesions associated with thermal burns, coeliac diseases, proctitis, eosinophilic gastroenteritis, mastocytosis, Crohn's disease, ulcerative colitis, migraine, rhinitis, eczema, interstitial nephritis, Goodpasture's syndrome, hemolytic-uremic syndrome, diabetic nephropathy, multiple myositis, Guillain-Barre syndrome, Meniere's disease, polyneuritis, multiple neuritis, mononeuritis, radiculopathy, hyperthyroidism, Basedow's disease, pure red cell aplasia, aplastic anemia, hypoplastic anemia, idiopathic thrombocytopenic purpura, autoimmune hemolytic anemia, agranulocytosis, pernicious anemia, megaloblastic anemia, anerythroplasia, osteoporosis, sarcoidosis, fibroid lung, idiopathic interstitial pneumonia, dermatomyositis, leukoderma vulgaris, ichthyosis vulgaris, photoallergic sensitivity, cutaneous T cell lymphoma, chronic lymphocytic leukemia, arteriosclerosis, atherosclerosis, aortitis syndrome, polyarteritis nodosa, myocardosis, scleroderma, Wegener's granuloma, Sjdgren's syndrome, adiposis, eosinophilic fascitis, lesions of gingiva, periodontium, alveolar bone, substantia ossea dentis, glomerulonephritis, male pattern alopecia or alopecia senilis by preventing epilation or providing hair germination and/or promoting hair generation and hair growth, muscular dystrophy, pyoderma and Sezary's syndrome, Addison's disease, ischemia-reperfusion injury of organs which occurs upon preservation, transplantation or ischemic disease, endotoxin-shock, pseudomembranous colitis, colitis caused by drug or radiation, ischemic acute renal insufficiency, chronic renal insufficiency, toxinosis caused by lung-oxygen or drugs, lung cancer, pulmonary emphysema, cataracta, siderosis, retinitis pigmentosa, senile macular degeneration, vitreal scarring, corneal alkali burn, dermatitis erythema multiforme, linear IgA ballous dermatitis and cement dermatitis, gingivitis, periodontitis, sepsis, pancreatitis, diseases caused by environmental pollution, aging, carcinogenesis, metastasis of carcinoma and hypobaropathy, disease caused by histamine or leukotriene-C4 release, Behcet's disease, autoimmune hepatitis, primary biliary cirrhosis, sclerosing cholangitis, partial liver resection, acute liver necrosis, necrosis caused by toxin, viral hepatitis, shock, or anoxia, B-virus hepatitis, non-A/non-B hepatitis, cirrhosis, alcoholic cirrhosis, hepatic failure, fulminant hepatic failure, late-onset hepatic failure, "acute-on-chronic" liver failure, augmentation of chemotherapeutic effect, cytomegalovirus infection, HCMV infection, AIDS, cancer, senile dementia, Parkinson's disease, trauma, or chronic bacterial infection.

Paragraph 53. A method for inhibiting an IRAK protein, comprising contacting the IRAK protein with an effective amount of a compound of any one of paragraphs 1-45, or a composition of any one of paragraphs 46-47.

Paragraph 54. The method of paragraph 53, wherein the compound has an $EC_{50}$ of from greater than 0 to 5 μM.

Paragraph 55. The method of paragraph 53, wherein the compound has an $EC_{50}$ of from greater than 0 to 1 μM.

Paragraph 56. The method of any one of paragraphs 53-55, wherein the IRAK protein is in a subject.

Paragraph 57. The method of any one of paragraphs 53-55, wherein contacting the IRAK protein comprises contacting the IRAK protein in vitro.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A compound, having a formula 1

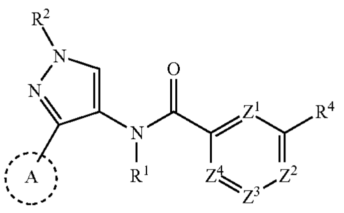

1 or a salt thereof, wherein:

ring A is heterocyclyl;

$R^1$ is H, aliphatic, or heteroaliphatic;

$R^2$ is H, aliphatic, heteroaliphatic, or heterocyclyl;

each of $Z^1$, $Z^2$, $Z^3$, and $Z^4$, independently is N or $CR^3$, wherein at least one of $Z^1$, $Z^2$, $Z^3$, and $Z^4$ is N;

each $R^3$ independently is H, aliphatic, or heteroaliphatic; and $R^4$ is halogen, heterocycloaliphatic, aromatic, —O-aromatic, or NH-aromatic.

2. The compound of claim 1, wherein ring A is heteroaryl, 5-membered heterocycloaliphatic, or 6-membered heterocycloaliphatic.

3. The compound of claim 1, wherein ring A is pyridinyl, pyrazinyl, pyrrolidinyl, piperidinyl, or morpholino.

4. The compound of claim 1, wherein ring A is

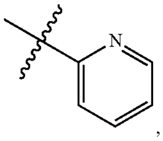
,
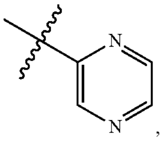
,
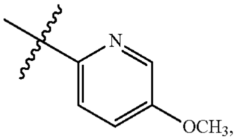

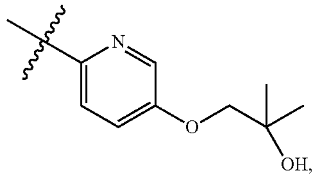

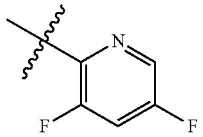
,

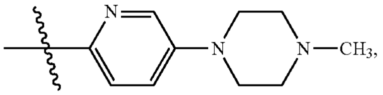

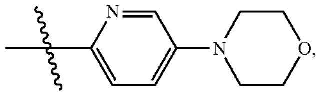

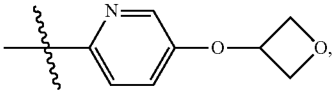

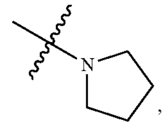
,
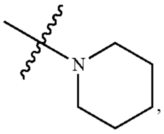
, or
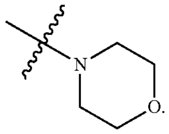

5. The compound of claim 1, wherein the compound has a formula

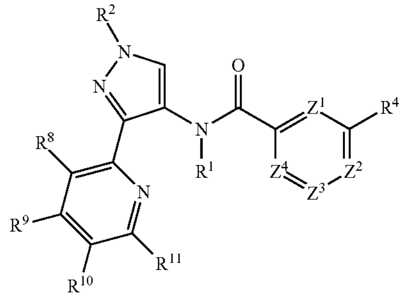

and each of $R^8$, $R^9$, $R^{10}$ and $R^{11}$ independently is H, aliphatic, halogen, heterocycloaliphatic, alkoxy, or O-heterocycloaliphatic.

6. The compound of claim 5, wherein each of $R^8$, $R^9$, $R^{10}$ and $R^{11}$ independently is H, halogen, 3- to 6-membered heterocycloaliphatic, alkoxy, or —O-(3- to 6-membered heterocycloaliphatic).

7. The compound of claim 6, wherein $R^8$ is H or halogen.

8. The compound of claim 6, wherein $R^9$ and $R^{11}$ are H.

9. The compound of claim 6, wherein $R^{10}$ is H, F, morpholino, N-methylpiperidin-1-yl, methoxy, 2-hydroxy-2-methylpropoxy, or —O-oxetanyl.

10. The compound of claim 5, wherein the compound has a formula

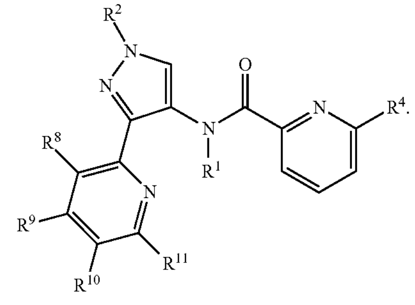

11. The compound of claim 1, wherein $R^1$ is H or $C_{1-6}$ alkyl.

12. The compound of claim 1, wherein $R^2$ is H, 3- to 10-membered heteroaliphatic, tetrahydropyranyl, oxetanyl, cyclobutyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$ alkyl substituted with —OH, amino, alkoxy, or heterocycloaliphatic.

13. The compound of claim 1, wherein $R^2$ is H, $CH_3$,

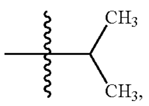
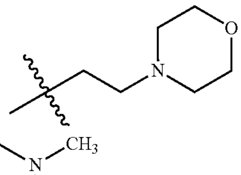
,
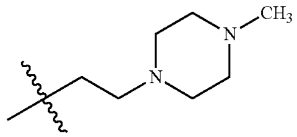
,
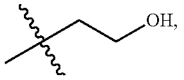

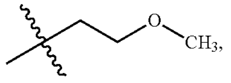
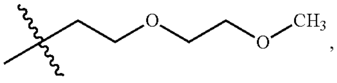
,

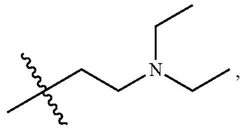
,
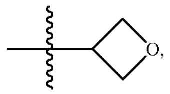

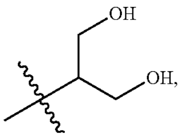
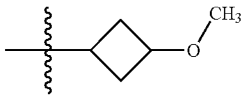
,

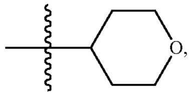
or
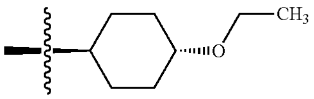
.

14. The compound of claim 1, wherein:

ring A is pyridinyl, pyrazinyl, pyrrolidinyl, piperidinyl, or morpholino;

$R^1$ is H; and $R^2$ is H, 3- to 10-membered heteroaliphatic, tetrahydropyranyl, oxetanyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$ alkyl substituted with —OH, amino, alkoxy, or heterocycloaliphatic.

15. The compound of claim 1, wherein each $R^3$ independently is H, or $C_{1-6}$ alkyl.

16. The compound of claim 15, wherein the

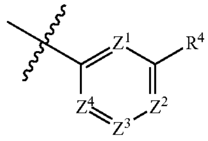

moiety is pyridinyl, pyrimidinyl, or pyrazinyl.

17. The compound of claim 15, wherein $Z^1$ is N.

18. The compound of claim 15, wherein:

$Z^1$ is N, and $Z^2$, $Z^3$, and $Z^4$ are $CR^3$;

$Z^1$ and $Z^2$ are N, and $Z^3$ and $Z^4$ are $CR^3$;

$Z^1$ and $Z^3$ are N, and $Z^2$ and $Z^4$ are $CR^3$;

$Z^1$ and $Z^4$ are N, and $Z^2$ and $Z^3$ are $CR^3$; or $Z^3$ is N, and $Z^1$, $Z^2$, and $Z^4$ are $CR^3$.

19. The compound of claim 1, wherein $R^4$ is halogen, heterocycloaliphatic, aryl, heteroaryl, —NH-heteroaryl, or —O-heteroaryl.

20. The compound of claim 19, wherein $R^4$ is Br, 5- to 10-membered heteroaryl, 3- to 6-membered heterocycloaliphatic, 6- to 10-membered aryl, —NH-(5- to 10-membered heteroaryl), or —O-(5- to 10-membered heteroaryl).

21. The compound of claim 19, wherein $R^4$ is pyridinyl, pyrimidinyl, pyrazolyl, —NH-pyrazolyl, pyrrolyl, —O-pyridinyl, —NH-pyridinyl, indolyl, furanyl, —NH-benzopyrazolyl, pyrrolopyridinyl, phenyl, tetrahydropyridinyl, piperidinyl, or 2-oxo-1,2-dihydropyridinyl.

22. The compound of claim 19, wherein $R^4$ is Br,

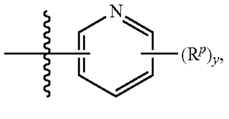 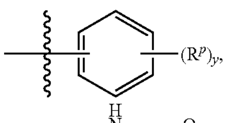

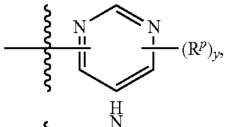 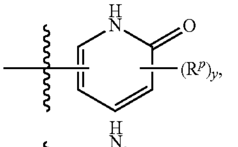

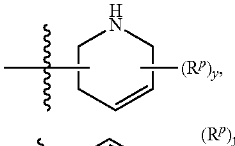 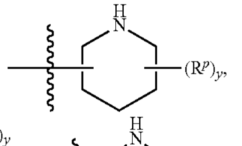

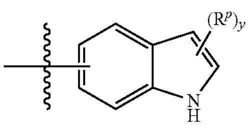 , 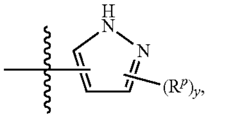

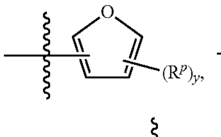 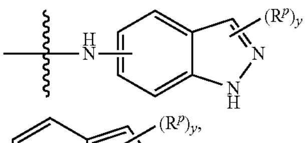 ,

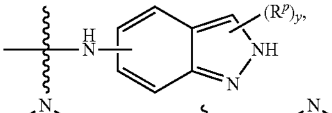

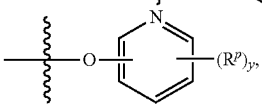 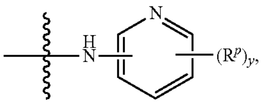

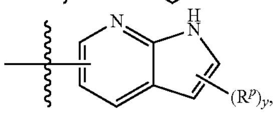 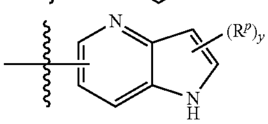 ,

-continued

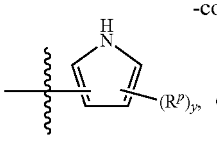 or 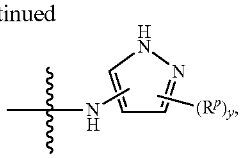

where y is 0, 1 or 2, and each $R^p$ independently is $R^a$, $R^b$, $R^a$ substituted with $R^b$, or $R^a$ substituted with $R^c$;

$R^a$ is independently for each occurrence H, D, $C_{1-6}$alkyl, $C_{3-6}$cycloalkyl, $C_{5-10}$aromatic, or $C_{3-6}$heterocycloaliphatic;

$R^b$ is independently for each occurrence —OH, —$CF_3$, —CN, —$OR^c$, —$SO_2R^c$, —$NR^dR^d$, —$N(H)SO_2R^c$, —C(O)OH, —N(H)C(O)$R^c$, —C(O)O$R^c$, —C(O)$NR^dR^d$, =O, or halogen;

$R^c$ is independently for each occurrence $C_{1-6}$alkyl, $C_{3-6}$cycloalkyl, $C_{3-6}$heteroalicyclyl, aralkyl, $C_{1-6}$alkyl substituted with 1, 2 or 3 $R^e$, $C_{5-10}$aromatic, $C_{5-10}$aromatic substituted with 1, 2 or 3 $R^e$;

$R^d$ is independently for each occurrence H, $C_{1-6}$alkyl optionally substituted with 1, 2 or 3 $R^e$, $C_{3-6}$cycloalkyl optionally substituted with 1, 2 or 3 $R^e$, $C_{3-6}$heteroalicyclyl optionally substituted with 1, 2 or 3 $R^e$, $C_{5-10}$aromatic optionally substituted with 1, 2 or 3 $R^a$ or $R^b$, or two $R^d$ groups together with the nitrogen bound thereto form a $C_{3-6}$heteroalicyclyl moiety optionally substituted with $C_{1-6}$alkyl and optionally interrupted with one or two —O— or —N($R^g$) wherein $R^g$ is H, $C_{1-10}$aliphatic, heteroaliphatic, or cycloaliphatic; and $R^e$ is independently for each occurrence halogen, $C_{1-6}$alkyl, $C_{3-6}$cycloalkyl, or —$OR^a$.

23. The compound of claim 22, wherein each $R^P$ independently is —$CH_3$, —$OCH_3$, —$NH_2$, —$CF_3$, F, —CN,

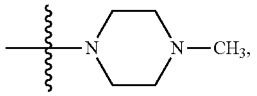 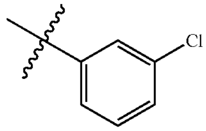 ,

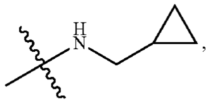 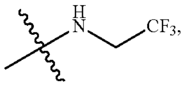

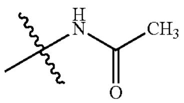 , 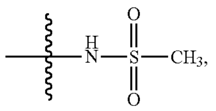 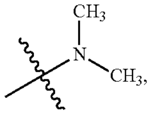

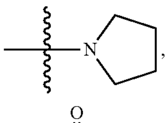 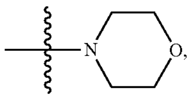 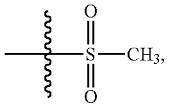

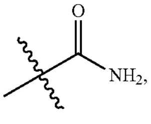 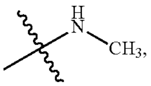 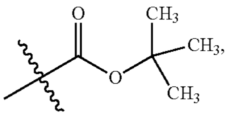

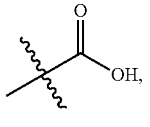 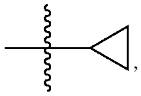 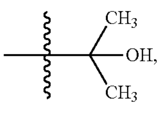

-continued

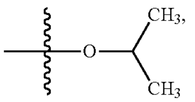 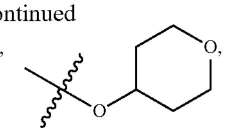

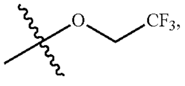 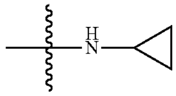, 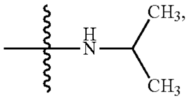

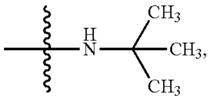 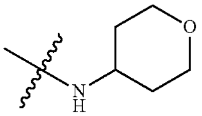,

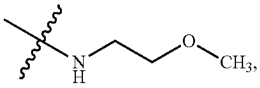 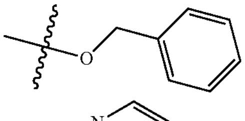,

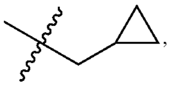, or 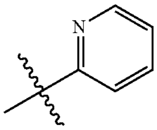.

24. The compound of claim 10, wherein:

$R^1$ is H;

$R^2$ is H, 3- to 10-membered heteroaliphatic, tetrahydropyranyl, oxetanyl, cyclobutyl, cyclobutyl substituted with alkoxy and/or hydroxy, cyclohexyl, cyclohexyl substituted with alkoxy and/or hydroxy, unsubstituted $C_{1-6}$ alkyl, or $C_{1-6}$alkyl substituted with —OH, amino, alkoxy, or heterocycloaliphatic;

$R^4$ is Br; unsubstituted pyridinyl; pyridinyl substituted with $C_{1-6}$alkyl, haloalkyl, amino, heterocycloaliphatic, cycloalkyl, —CN, alkoxy, —O-heterocycloaliphatic, —NH-heterocycloaliphatic, halogen, sulfonamide, —O-benzyl, carboxyl, sulfonyl, —NH-cycloalkyl, or amide; unsubstituted pyrimidinyl; unsubstituted pyrazolyl; pyrazolyl substituted with $C_{1-6}$alkyl; unsubstituted —NH-pyrazolyl; —NH-pyrazolyl substituted with $C_{1-6}$alkyl, or heteroaryl; pyrrolyl; unsubstituted —O-pyridinyl; —O-pyridinyl substituted with amino; —NH-pyridinyl substituted with $C_{1-6}$alkyl, haloalkyl, or heterocycloaliphatic; unsubstituted indolyl; indolyl substituted with alkoxy; furanyl; —NH-benzopyrazolyl; pyrrolopyridinyl; unsubstituted phenyl; phenyl substituted with halogen, $C_{1-6}$alkyl, alkoxy, —CN, amino, or sulfonamide; unsubstituted tetrahydropyridinyl; tetrahydropyridinyl substituted with tert-butoxycarbonyl; piperidinyl; or 2-oxo-1,2-dihydropyridinyl;

$R^8$ is H or F;

$R^9$ and $R^{11}$ are H; and $R^{10}$ is H, F, morpholino, N-methylpiperidinyl, methoxy, 2-hydroxy-2-methylpropoxy, or —O-oxetanyl.

25. The compound of claim 24, wherein each of $R^8$, $R^9$, $R^{10}$ and $R^{11}$ is H;

$R^8$, $R^9$, and $R^{11}$ are H and $R^{10}$ is 3- to 6-membered morpholino or N-methylpiperidinyl, methoxy, 2-hydroxy-2-methylpropoxy, or —O-oxetanyl; or $R^8$ and $R^{10}$ are F, and $R^9$ and $R^{11}$ are H.

26. A compound or salt thereof, selected from:

I-1: 6-bromo-N-(1-methyl-3-(pyridin-2-yl)-1H-pyrazol-4-yl)picolinamide;

I-2: N-(1-methyl-3-(pyridin-2-yl)-1H-pyrazol-4-yl)-[2,3'-bipyridine]-6-carboxamide;

I-3: 5'-fluoro-N-(1-methyl-3-(pyridin-2-yl)-1H-pyrazol-4-yl)-[2,3'-bipyridine]-6-carboxamide;

I-4: 5'-cyano-N-(1-methyl-3-(pyridin-2-yl)-1H-pyrazol-4-yl)-[2,3'-bipyridine]-6-carboxamide;

I-5: N-(1-methyl-3-(pyridin-2-yl)-1H-pyrazol-4-yl)-6-(pyrimidin-5-yl)picolinamide;

I-6: N-(1-methyl-3-(pyridin-2-yl)-1H-pyrazol-4-yl)-6-(1H-pyrazol-5-yl)picolinamide;

I-7: 6-(3-methyl-1H-pyrazol-5-yl)-N-(1-methyl-3-(pyridin-2-yl)-1H-pyrazol-4-yl)picolinamide;

I-8: 6-(1-methyl-1H-pyrazol-4-yl)-N-(1-methyl-3-(pyridin-2-yl)-1H-pyrazol-4-yl)picolinamide;

I-9: N-(1-methyl-3-(pyridin-2-yl)-1H-pyrazol-4-yl)-6-(1H-pyrazol-4-yl)picolinamide;

I-10: N-(1-methyl-3-(pyridin-2-yl)-1H-pyrazol-4-yl)-6-(1H-pyrrol-2-yl)picolinamide;

I-11: N-(1-methyl-3-(pyridin-2-yl)-1H-pyrazol-4-yl)-6-(1H-pyrrol-3-yl)picolinamide;

I-12: 5'-methyl-N-(1-methyl-3-(pyridin-2-yl)-1H-pyrazol-4-yl)-[2,3'-bipyridine]-6-carboxamide;

I-13: 5'-cyclopropyl-N-(1-methyl-3-(pyridin-2-yl)-1H-pyrazol-4-yl)-[2,3'-bipyridine]-6-carboxamide;

I-14: 5'-(2-hydroxypropan-2-yl)-N-(1-methyl-3-(pyridin-2-yl)-1H-pyrazol-4-yl)-[2,3'-bipyridine]-6-carboxamide;

I-15: 2'-methyl-N-(1-methyl-3-(pyridin-2-yl)-1H-pyrazol-4-yl)-[2,4'-bipyridine]-6-carboxamide;

I-16: 6'-methyl-N-(1-methyl-3-(pyridin-2-yl)-1H-pyrazol-4-yl)-[2,3'-bipyridine]-6-carboxamide;

I-17: N-(1-methyl-3-(pyridin-2-yl)-1H-pyrazol-4-yl)-5'-(trifluoromethyl)-[2,3'-bipyridine]-6-carboxamide;

I-18: N-(1-methyl-3-(pyridin-2-yl)-1H-pyrazol-4-yl)-2'-(trifluoromethyl)-[2,4'-bipyridine]-6-carboxamide;

I-19: 5'-methoxy-N-(1-methyl-3-(pyridin-2-yl)-1H-pyrazol-4-yl)-[2,3'-bipyridine]-6-carboxamide;

I-20: 6'-methoxy-N-(1-methyl-3-(pyridin-2-yl)-1H-pyrazol-4-yl)-[2,3'-bipyridine]-6-carboxamide;

I-21: 2'-methoxy-N-(1-methyl-3-(pyridin-2-yl)-1H-pyrazol-4-yl)-[2,4'-bipyridine]-6-carboxamide;

I-22: 5'-isopropoxy-N-(1-methyl-3-(pyridin-2-yl)-1H-pyrazol-4-yl)-[2,3'-bipyridine]-6-carboxamide;

I-23: N-(1-methyl-3-(pyridin-2-yl)-1H-pyrazol-4-yl)-5'-((tetrahydro-2H-pyran-4-yl)oxy)-[2,3'-bipyridine]-6-carboxamide;

I-24: N-(1-methyl-3-(pyridin-2-yl)-1H-pyrazol-4-yl)-5'-(2,2,2-trifluoroethoxy)-[2,3'-bipyridine]-6-carboxamide;

I-25: 5'-amino-N-(1-methyl-3-(pyridin-2-yl)-1H-pyrazol-4-yl)-[2,3'-bipyridine]-6-carboxamide;

I-26: N-(1-methyl-3-(pyridin-2-yl)-1H-pyrazol-4-yl)-5'-(methylamino)-[2,3'-bipyridine]-6-carboxamide;

I-27: 5'-(cyclopropylamino)-N-(1-methyl-3-(pyridin-2-yl)-1H-pyrazol-4-yl)-[2,3'-bipyridine]-6-carboxamide;

I-28: 5'-(isopropylamino)-N-(1-methyl-3-(pyridin-2-yl)-1H-pyrazol-4-yl)-[2,3'-bipyridine]-6-carboxamide;

I-29: 5'-(tert-butylamino)-N-(1-methyl-3-(pyridin-2-yl)-1H-pyrazol-4-yl)-[2,3'-bipyridine]-6-carboxamide;

I-30: N-(1-methyl-3-(pyridin-2-yl)-1H-pyrazol-4-yl)-5'-((tetrahydro-2H-pyran-4-yl)amino)-[2,3'-bipyridine]-6-carboxamide;

I-31: 5'-((2-methoxyethyl)amino)-N-(1-methyl-3-(pyridin-2-yl)-1H-pyrazol-4-yl)-[2,3'-bipyridine]-6-carboxamide;

I-32: 5'-((cyclopropylmethyl)amino)-N-(1-methyl-3-(pyridin-2-yl)-1H-pyrazol-4-yl)-[2,3'-bipyridine]-6-carboxamide;

I-33: N-(1-methyl-3-(pyridin-2-yl)-1H-pyrazol-4-yl)-5'-((2,2,2-trifluoroethyl)amino)-[2,3'-bipyridine]-6-carboxamide;

I-34: N-(1-methyl-3-(pyridin-2-yl)-1H-pyrazol-4-yl)-5'-(methylsulfonamido)-[2,3'-bipyridine]-6-carboxamide;

I-35: 5'-(dimethylamino)-N-(1-methyl-3-(pyridin-2-yl)-1H-pyrazol-4-yl)-[2,3'-bipyridine]-6-carboxamide;

I-36: N-(1-methyl-3-(pyridin-2-yl)-1H-pyrazol-4-yl)-5'-(pyrrolidin-1-yl)-[2,3'-bipyridine]-6-carboxamide;

I-37: N-(1-methyl-3-(pyridin-2-yl)-1H-pyrazol-4-yl)-5'-morpholino-[2,3'-bipyridine]-6-carboxamide;

I-38: N-(1-methyl-3-(pyridin-2-yl)-1H-pyrazol-4-yl)-5'-(4-methylpiperazin-1-yl)-[2,3'-bipyridine]-6-carboxamide;

I-39: N-(1-methyl-3-(pyridin-2-yl)-1H-pyrazol-4-yl)-5'-(methylsulfonyl)-[2,3'-bipyridine]-6-carboxamide;

I-40: N6-(1-methyl-3-(pyridin-2-yl)-1H-pyrazol-4-yl)-[2,3'-bipyridine]-5',6-dicarboxamide;

I-41: N6-(1-methyl-3-(pyridin-2-yl)-1H-pyrazol-4-yl)-[2,4'-bipyridine]-2',6-dicarboxamide;

I-42: 2'-cyano-N-(1-methyl-3-(pyridin-2-yl)-1H-pyrazol-4-yl)-[2,4'-bipyridine]-6-carboxamide;

I-43: 6'-amino-N-(1-methyl-3-(pyridin-2-yl)-1H-pyrazol-4-yl)-[2,3'-bipyridine]-6-carboxamide;

I-44: N-(1-methyl-3-(pyridin-2-yl)-1H-pyrazol-4-yl)-6-(1H-pyrrolo[2,3-b]pyridin-5-yl)picolinamide;

I-45: N-(1-methyl-3-(pyridin-2-yl)-1H-pyrazol-4-yl)-6-(1H-pyrrolo[3,2-b]pyridin-6-yl)picolinamide;

I-46: 6-(1H-indol-5-yl)-N-(1-methyl-3-(pyridin-2-yl)-1H-pyrazol-4-yl)picolinamide;

I-47: 6-(1H-indol-6-yl)-N-(1-methyl-3-(pyridin-2-yl)-1H-pyrazol-4-yl)picolinamide;

I-48: N-(1-methyl-3-(pyridin-2-yl)-1H-pyrazol-4-yl)-6-phenylpicolinamide;

I-49: N-(1-methyl-3-(pyridin-2-yl)-1H-pyrazol-4-yl)-6-(m-tolyl)picolinamide;

I-50: N-(1-methyl-3-(pyridin-2-yl)-1H-pyrazol-4-yl)-6-(p-tolyl)picolinamide;

I-51: 6-(3-methoxyphenyl)-N-(1-methyl-3-(pyridin-2-yl)-1H-pyrazol-4-yl)picolinamide;

I-52: 6-(4-methoxyphenyl)-N-(1-methyl-3-(pyridin-2-yl)-1H-pyrazol-4-yl)picolinamide;

I-53: 6-(3-cyanophenyl)-N-(1-methyl-3-(pyridin-2-yl)-1H-pyrazol-4-yl)picolinamide;

I-54: 6-(4-cyanophenyl)-N-(1-methyl-3-(pyridin-2-yl)-1H-pyrazol-4-yl)picolinamide;

I-55: 6-(3-fluorophenyl)-N-(1-methyl-3-(pyridin-2-yl)-1H-pyrazol-4-yl)picolinamide;

I-56: 6-(4-fluorophenyl)-N-(1-methyl-3-(pyridin-2-yl)-1H-pyrazol-4-yl)picolinamide;

I-57: 6-(3-aminophenyl)-N-(1-methyl-3-(pyridin-2-yl)-1H-pyrazol-4-yl)picolinamide;

I-58: N-(1-methyl-3-(pyridin-2-yl)-1H-pyrazol-4-yl)-6-(3-(methylamino)phenyl)picolinamide;

I-59: 6-(3-(dimethylamino)phenyl)-N-(1-methyl-3-(pyridin-2-yl)-1H-pyrazol-4-yl)picolinamide;

I-60: N-(1-methyl-3-(pyridin-2-yl)-1H-pyrazol-4-yl)-6-(3-(methylsulfonamido)phenyl)picolinamide;

I-61: tert-butyl 6-((1-methyl-3-(pyridin-2-yl)-1H-pyrazol-4-yl)carbamoyl)-3',6'-dihydro-[2,4'-bipyridine]-1'(2'H)-carboxylate;

I-62: N-(1-methyl-3-(pyridin-2-yl)-1H-pyrazol-4-yl)-1',2',3',6'-tetrahydro-[2,4'-bipyridine]-6-carboxamide;

I-63: N-(1-methyl-3-(pyridin-2-yl)-1H-pyrazol-4-yl)-6-(piperidin-4-yl)picolinamide;

I-64: tert-butyl 6-((1-methyl-3-(pyridin-2-yl)-1H-pyrazol-4-yl)carbamoyl)-5',6'-dihydro-[2,3'-bipyridine]-1'(2'H)-carboxylate;

I-65: N-(1-methyl-3-(pyridin-2-yl)-1H-pyrazol-4-yl)-1',2',5',6'-tetrahydro-[2,3'-bipyridine]-6-carboxamide;

I-66: 6-bromo-N-(3-(5-methoxypyridin-2-yl)-1-methyl-1H-pyrazol-4-yl)picolinamide;

I-67: N-(3-(5-methoxypyridin-2-yl)-1-methyl-1H-pyrazol-4-yl)-6-(1H-pyrazol-5-yl)picolinamide;

I-68: N-(3-(5-methoxypyridin-2-yl)-1-methyl-1H-pyrazol-4-yl)-6-(1H-pyrazol-4-yl)picolinamide;

I-69: N-(3-(5-methoxypyridin-2-yl)-1-methyl-1H-pyrazol-4-yl)-5'-methyl-[2,3'-bipyridine]-6-carboxamide;

I-70: 5'-isopropoxy-N-(3-(5-methoxypyridin-2-yl)-1-methyl-1H-pyrazol-4-yl)-[2,3'-bipyridine]-6-carboxamide;

I-71: 5'-(isopropylamino)-N-(3-(5-methoxypyridin-2-yl)-1-methyl-1H-pyrazol-4-yl)-[2,3'-bipyridine]-6-carboxamide;

I-72: N-(1-methyl-3-(pyrrolidin-1-yl)-1H-pyrazol-4-yl)-6-(1H-pyrazol-4-yl)picolinamide;

I-73: N-(1-methyl-3-(piperidin-1-yl)-1H-pyrazol-4-yl)-6-(1H-pyrazol-4-yl)picolinamide;

I-74: N-(1-methyl-3-morpholino-1H-pyrazol-4-yl)-6-(1H-pyrazol-4-yl)picolinamide;

I-75: 5'-methyl-N-(1-methyl-3-(pyrrolidin-1-yl)-1H-pyrazol-4-yl)-[2,3'-bipyridine]-6-carboxamide;

I-76: 5'-methyl-N-(1-methyl-3-(piperidin-1-yl)-1H-pyrazol-4-yl)-[2,3'-bipyridine]-6-carboxamide;

I-77: 5'-methyl-N-(1-methyl-3-morpholino-1H-pyrazol-4-yl)-[2,3'-bipyridine]-6-carboxamide;

I-78: 6-(3-methyl-1H-pyrazol-4-yl)-N-(1-methyl-3-(pyridin-2-yl)-1H-pyrazol-4-yl)picolinamide;

I-79: 6-bromo-N-(1-isopropyl-3-(pyridin-2-yl)-1H-pyrazol-4-yl)picolinamide;

I-80: N-(1-isopropyl-3-(pyridin-2-yl)-1H-pyrazol-4-yl)-6-(1H-pyrazol-4-yl)picolinamide;

I-81: N-(1-isopropyl-3-(pyridin-2-yl)-1H-pyrazol-4-yl)-5'-methyl-[2,3'-bipyridine]-6-carboxamide;

I-82: 6-bromo-N-(1-(2-morpholinoethyl)-3-(pyridin-2-yl)-1H-pyrazol-4-yl)picolinamide;

I-83: N-(1-(2-morpholinoethyl)-3-(pyridin-2-yl)-1H-pyrazol-4-yl)-6-(1H-pyrazol-4-yl)picolinamide;

I-84: 5'-methyl-N-(1-(2-morpholinoethyl)-3-(pyridin-2-yl)-1H-pyrazol-4-yl)-[2,3'-bipyridine]-6-carboxamide;

I-85: 6-bromo-N-(1-(2-(4-methylpiperazin-1-yl)ethyl)-3-(pyridin-2-yl)-1H-pyrazol-4-yl)picolinamide;

I-86: N-(1-(2-(4-methylpiperazin-1-yl)ethyl)-3-(pyridin-2-yl)-1H-pyrazol-4-yl)-6-(1H-pyrazol-4-yl)picolinamide;

I-87: 5'-methyl-N-(1-(2-(4-methylpiperazin-1-yl)ethyl)-3-(pyridin-2-yl)-1H-pyrazol-4-yl)-[2,3'-bipyridine]-6-carboxamide;

I-88: N-(1-(2-hydroxyethyl)-3-(pyridin-2-yl)-1H-pyrazol-4-yl)-[2,4'-bipyridine]-6-carboxamide;

I-89: N-(1-(2-(2-methoxyethoxy)ethyl)-3-(pyridin-2-yl)-1H-pyrazol-4-yl)-6-(pyridin-4-yloxy)picolinamide;

I-90: N-(1-(2-(2-methoxyethoxy)ethyl)-3-(pyridin-2-yl)-1H-pyrazol-4-yl)-[2,4'-bipyridine]-6-carboxamide;

I-91: N-(1-methyl-3-(pyridin-2-yl)-1H-pyrazol-4-yl)-2'-oxo-1',2'-dihydro-[2,4'-bipyridine]-6-carboxamide;

I-92: N-(1-methyl-3-(pyridin-2-yl)-1H-pyrazol-4-yl)-6'-oxo-1',6'-dihydro-[2,3'-bipyridine]-6-carboxamide;

I-93: N-(1-methyl-3-(pyrazin-2-yl)-1H-pyrazol-4-yl)-5'-(2,2,2-trifluoroethoxy)-[2,3'-bipyridine]-6-carboxamide;

I-94: N-(3-(pyridin-2-yl)-1H-pyrazol-4-yl)-[2,4'-bipyridine]-6-carboxamide;

I-95: N-(1-(2-methoxyethyl)-3-(pyridin-2-yl)-1H-pyrazol-4-yl)-[2,4'-bipyridine]-6-carboxamide;

I-96: 2'-methoxy-N-(1-(2-(2-methoxyethoxy)ethyl)-3-(pyridin-2-yl)-1H-pyrazol-4-yl)-[2,4'-bipyridine]-6-carboxamide;

I-97: 6'-amino-N-(1-(2-(2-methoxyethoxy)ethyl)-3-(pyridin-2-yl)-1H-pyrazol-4-yl)-[2,3'-bipyridine]-6-carboxamide;

I-98: 6'-acetamido-N-(1-(2-(2-methoxyethoxy)ethyl)-3-(pyridin-2-yl)-1H-pyrazol-4-yl)-[2,3'-bipyridine]-6-carboxamide;

I-99: 2'-methoxy-N-(1-methyl-3-(pyrazin-2-yl)-1H-pyrazol-4-yl)-[2,4'-bipyridine]-6-carboxamide;

I-100: N-(1-methyl-3-(pyrazin-2-yl)-1H-pyrazol-4-yl)-[2,4'-bipyridine]-6-carboxamide;

I-101: N-(1-methyl-3-(pyrazin-2-yl)-1H-pyrazol-4-yl)-[2,3'-bipyridine]-6-carboxamide;

I-102: 6'-acetamido-N-(1-methyl-3-(pyrazin-2-yl)-1H-pyrazol-4-yl)-[2,3'-bipyridine]-6-carboxamide;

I-103: 2'-(benzyloxy)-N-(1-methyl-3-(pyrazin-2-yl)-1H-pyrazol-4-yl)-[2,4'-bipyridine]-6-carboxamide;

I-104: N-(1-(2-(diethylamino)ethyl)-3-(pyridin-2-yl)-1H-pyrazol-4-yl)-[2,4'-bipyridine]-6-carboxamide;

I-105: N-(1-methyl-3-(pyrazin-2-yl)-1H-pyrazol-4-yl)-5'-(2,2,2-trifluoroethoxy)-[2,3'-bipyridine]-6-carboxamide formate;

I-106: N-(3-(pyridin-2-yl)-1H-pyrazol-4-yl)-[2,4'-bipyridine]-6-carboxamide formate;

I-107: N-(1-(2-methoxyethyl)-3-(pyridin-2-yl)-1H-pyrazol-4-yl)-[2,4'-bipyridine]-6-carboxamide formate;

I-108: N-(1-(2-hydroxyethyl)-3-(pyridin-2-yl)-1H-pyrazol-4-yl)-[2,4'-bipyridine]-6-carboxamide formate;

I-109: 5-(1-(cyclopropylmethyl)-1H-pyrazol-4-yl)-N-(1-methyl-3-(pyridin-2-yl)-1H-pyrazol-4-yl)nicotinamide;

I-110: N-(1-methyl-3-(pyridin-2-yl)-1H-pyrazol-4-yl)-[3,4'-bipyridine]-5-carboxamide;

I-111: N-(1-methyl-3-(pyridin-2-yl)-1H-pyrazol-4-yl)-[3,3'-bipyridine]-5-carboxamide;

I-112: N-(1-(oxetan-3-yl)-3-(pyridin-2-yl)-1H-pyrazol-4-yl)-[2,3'-bipyridine]-6-carboxamide;

I-113: 6-bromo-N-(1-(oxetan-3-yl)-3-(pyridin-2-yl)-1H-pyrazol-4-yl)picolinamide;

I-114: 5'-methyl-N-(1-(oxetan-3-yl)-3-(pyridin-2-yl)-1H-pyrazol-4-yl)-[2,3'-bipyridine]-6-carboxamide;

I-115: 5'-(methylsulfonamido)-N-(1-(oxetan-3-yl)-3-(pyridin-2-yl)-1H-pyrazol-4-yl)-[2,3'-bipyridine]-6-carboxamide;

I-116: N-(1-(oxetan-3-yl)-3-(pyridin-2-yl)-1H-pyrazol-4-yl)-6-(1H-pyrazol-4-yl)picolinamide;

I-117: N-(1-(oxetan-3-yl)-3-(pyridin-2-yl)-1H-pyrazol-4-yl)-6-(1H-pyrazol-3-yl)picolinamide;

I-118: N-(1-methyl-3-(pyridin-2-yl)-1H-pyrazol-4-yl)-4-((1-methyl-3-(pyridin-2-yl)-1H-pyrazol-4-yl)amino)pyrimidine-2-carboxamide;

I-119: sodium (methylsulfonyl)(6-((1-(oxetan-3-yl)-3-(pyridin-2-yl)-1H-pyrazol-4-yl)carbamoyl)-[2,3'-bipyridin]-5'-yl)amide;

I-120: N-(1-methyl-3-(pyridin-2-yl)-1H-pyrazol-4-yl)-4-(5-methylpyridin-3-yl)pyrimidine-2-carboxamide;

I-121: N-(1-methyl-3-(pyridin-2-yl)-1H-pyrazol-4-yl)-6-(5-methylpyridin-3-yl)pyrazine-2-carboxamide;

I-122: N-(1-methyl-3-(pyridin-2-yl)-1H-pyrazol-4-yl)-6-(1H-pyrazol-4-yl)pyrazine-2-carboxamide;

I-123: N-(1-methyl-3-(pyridin-2-yl)-1H-pyrazol-4-yl)-6-(1H-pyrazol-3-yl)pyrazine-2-carboxamide;

I-124: N-(1-methyl-3-(pyridin-2-yl)-1H-pyrazol-4-yl)-4-(1H-pyrazol-4-yl)pyrimidine-2-carboxamide;

I-125: N-(1-(1,3-dihydroxypropan-2-yl)-3-(pyridin-2-yl)-1H-pyrazol-4-yl)-[2,3'-bipyridine]-6-carboxamide;

I-126: N-(1-(1,3-dihydroxypropan-2-yl)-3-(pyridin-2-yl)-1H-pyrazol-4-yl)-5'-methyl-[2,3'-bipyridine]-6-carboxamide;

I-127: N-(1-(1,3-dihydroxypropan-2-yl)-3-(pyridin-2-yl)-1H-pyrazol-4-yl)-6-(1H-pyrazol-4-yl)picolinamide;

I-128: 4-((1H-pyrazol-3-yl)amino)-N-(1-methyl-3-(pyridin-2-yl)-1H-pyrazol-4-yl)pyrimidine-2-carboxamide;

I-129: 4-((3-methyl-1H-pyrazol-4-yl)amino)-N-(1-methyl-3-(pyridin-2-yl)-1H-pyrazol-4-yl)pyrimidine-2-carboxamide;

I-130: 5'-isopropoxy-N-(1-(oxetan-3-yl)-3-(pyridin-2-yl)-1H-pyrazol-4-yl)-[2,3'-bipyridine]-6-carboxamide;

I-131: 5'-fluoro-N-(1-(oxetan-3-yl)-3-(pyridin-2-yl)-1H-pyrazol-4-yl)-[2,3'-bipyridine]-6-carboxamide;

I-132: N-(1-(oxetan-3-yl)-3-(pyridin-2-yl)-1H-pyrazol-4-yl)-5'-(trifluoromethyl)-[2,3'-bipyridine]-6-carboxamide;

I-133: N6-(1-(oxetan-3-yl)-3-(pyridin-2-yl)-1H-pyrazol-4-yl)-[2,3'-bipyridine]-5',6-dicarboxamide;

I-134: 6-(1-methyl-1H-pyrazol-4-yl)-N-(1-(oxetan-3-yl)-3-(pyridin-2-yl)-1H-pyrazol-4-yl)picolinamide;

I-135: 6-((1-(oxetan-3-yl)-3-(pyridin-2-yl)-1H-pyrazol-4-yl)carbamoyl)-[2,3'-bipyridine]-5'-carboxylic acid;

I-136: 6-(3-methyl-1H-pyrazol-5-yl)-N-(1-(oxetan-3-yl)-3-(pyridin-2-yl)-1H-pyrazol-4-yl)picolinamide;

I-137: N-(1-methyl-3-(pyridin-2-yl)-1H-pyrazol-4-yl)-2-(1H-pyrazol-4-yl)pyrimidine-4-carboxamide;

I-138: N-(1-methyl-3-(pyridin-2-yl)-1H-pyrazol-4-yl)-2-(1H-pyrazol-3-yl)pyrimidine-4-carboxamide;

I-139: N-(1-(2-(2-methoxyethoxy)ethyl)-3-(pyridin-2-yl)-1H-pyrazol-4-yl)-6-(pyridin-4-yloxy)picolinamide formate;

I-140: N-(1-(2-(2-methoxyethoxy)ethyl)-3-(pyridin-2-yl)-1H-pyrazol-4-yl)-[2,4'-bipyridine]-6-carboxamide formate;

I-141: 2'-methoxy-N-(1-(2-(2-methoxyethoxy)ethyl)-3-(pyridin-2-yl)-1H-pyrazol-4-yl)-[2,4'-bipyridine]-6-carboxamide formate;

I-142: 6'-amino-N-(1-(2-(2-methoxyethoxy)ethyl)-3-(pyridin-2-yl)-1H-pyrazol-4-yl)-[2,3'-bipyridine]-6-carboxamide formate;

I-143: 6'-acetamido-N-(1-(2-(2-methoxyethoxy)ethyl)-3-(pyridin-2-yl)-1H-pyrazol-4-yl)-[2,3'-bipyridine]-6-carboxamide formate;

I-144: 3'-fluoro-N-(1-(2-(2-methoxyethoxy)ethyl)-3-(pyridin-2-yl)-1H-pyrazol-4-yl)-[2,4'-bipyridine]-6-carboxamide formate;

I-145: N-(1-(2-(2-methoxyethoxy)ethyl)-3-(pyridin-2-yl)-1H-pyrazol-4-yl)-3'-methyl-[2,4'-bipyridine]-6-carboxamide formate;

I-146: N-(1-(2-(2-methoxyethoxy)ethyl)-3-(pyridin-2-yl)-1H-pyrazol-4-yl)-2'-methyl-[2,4'-bipyridine]-6-carboxamide formate;

I-147: 6-(6-methoxy-1H-indol-2-yl)-N-(1-(2-(2-methoxyethoxy)ethyl)-3-(pyridin-2-yl)-1H-pyrazol-4-yl)picolinamide formate;

I-148: 6-(1-(3-chlorophenyl)-1H-pyrazol-4-yl)-N-(1-(2-(2-methoxyethoxy)ethyl)-3-(pyridin-2-yl)-1H-pyrazol-4-yl)picolinamide formate;

I-149: N-(1-(2-(2-methoxyethoxy)ethyl)-3-(pyridin-2-yl)-1H-pyrazol-4-yl)-5'-methyl-[2,3'-bipyridine]-6-carboxamide formate;

I-150: N-(1-(2-(2-methoxyethoxy)ethyl)-3-(pyridin-2-yl)-1H-pyrazol-4-yl)-6-(1H-pyrazol-3-yl)picolinamide formate;

I-151: 6-(furan-3-yl)-N-(1-(2-(2-methoxyethoxy)ethyl)-3-(pyridin-2-yl)-1H-pyrazol-4-yl)picolinamide 2,2,2-trifluoroacetate;

I-152: 6-(furan-2-yl)-N-(1-(2-(2-methoxyethoxy)ethyl)-3-(pyridin-2-yl)-1H-pyrazol-4-yl)picolinamide 2,2,2-trifluoroacetate;

I-153: N-(1-(2-(2-methoxyethoxy)ethyl)-3-(pyridin-2-yl)-1H-pyrazol-4-yl)-6-(1H-pyrazol-4-yl)picolinamide formate;

I-154: 6-((1H-indazol-5-yl)amino)-N-(1-(2-(2-methoxyethoxy)ethyl)-3-(pyridin-2-yl)-1H-pyrazol-4-yl)picolinamide formate;

I-155: 6-((2H-indazol-5-yl)amino)-N-(1-(2-(2-methoxyethoxy)ethyl)-3-(pyridin-2-yl)-1H-pyrazol-4-yl)picolinamide formate;

I-156: 6-((2-aminopyridin-4-yl)oxy)-N-(1-(2-(2-methoxyethoxy)ethyl)-3-(pyridin-2-yl)-1H-pyrazol-4-yl)picolinamide formate;

I-157: 6-((2,5-dimethylpyridin-4-yl)amino)-N-(1-(2-(2-methoxyethoxy)ethyl)-3-(pyridin-2-yl)-1H-pyrazol-4-yl)picolinamide formate;

I-158: N-(1-(2-(2-methoxyethoxy)ethyl)-3-(pyridin-2-yl)-1H-pyrazol-4-yl)-6-((6-(4-methylpiperazin-1-yl)-5-(trifluoromethyl)pyridin-3-yl)amino)picolinamide formate;

I-159: 2'-((cyclopropylmethyl)amino)-N-(1-methyl-3-(pyridin-2-yl)-1H-pyrazol-4-yl)-[2,4'-bipyridine]-6-carboxamide formate;

I-160: N-(1-methyl-3-(pyridin-2-yl)-1H-pyrazol-4-yl)-[2,4'-bipyridine]-6-carboxamide 2,2,2-trifluoroacetate;

I-161: N-(1-methyl-3-(pyridin-2-yl)-1H-pyrazol-4-yl)-2'-((2,2,2-trifluoroethyl)amino)-[2,4'-bipyridine]-6-carboxamide formate;

I-162: N-(1-(3-methoxycyclobutyl)-3-(pyridin-2-yl)-1H-pyrazol-4-yl)-5'-methyl-[2,3'-bipyridine]-6-carboxamide formate;

I-163: N-(1-(3-methoxycyclobutyl)-3-(pyridin-2-yl)-1H-pyrazol-4-yl)-6-(1H-pyrazol-4-yl)picolinamide formate;

I-164: 5'-methyl-N-(3-(pyridin-2-yl)-1-(tetrahydro-2H-pyran-4-yl)-1H-pyrazol-4-yl)-[2,3'-bipyridine]-6-carboxamide;

I-165: 6-(1H-pyrazol-4-yl)-N-(3-(pyridin-2-yl)-1-(tetrahydro-2H-pyran-4-yl)-1H-pyrazol-4-yl)picolinamide;

I-166: 6-(1H-pyrazol-3-yl)-N-(3-(pyridin-2-yl)-1-(tetrahydro-2H-pyran-4-yl)-1H-pyrazol-4-yl)picolinamide;

I-167: N-(3-(pyridin-2-yl)-1-(tetrahydro-2H-pyran-4-yl)-1H-pyrazol-4-yl)-[2,4'-bipyridine]-6-carboxamide;

I-168: N-(1-(2-methoxyethyl)-3-(pyridin-2-yl)-1H-pyrazol-4-yl)-5'-methyl-[2,3'-bipyridine]-6-carboxamide;

I-169: N-(1-(3-methoxypropyl)-3-(pyridin-2-yl)-1H-pyrazol-4-yl)-5'-methyl-[2,3'-bipyridine]-6-carboxamide;

I-170: 5'-methyl-N-(1-methyl-3-(5-morpholinopyridin-2-yl)-1H-pyrazol-4-yl)-[2,3'-bipyridine]-6-carboxamide;

I-171: N-(1-methyl-3-(5-morpholinopyridin-2-yl)-1H-pyrazol-4-yl)-6-(1H-pyrazol-4-yl)picolinamide;

I-172: N-(1-methyl-3-(5-morpholinopyridin-2-yl)-1H-pyrazol-4-yl)-6-(1H-pyrazol-3-yl)picolinamide;

I-173: 5'-methyl-N-(1-methyl-3-(5-(4-methylpiperazin-1-yl)pyridin-2-yl)-1H-pyrazol-4-yl)-[2,3'-bipyridine]-6-carboxamide;

I-174: N-(1-methyl-3-(5-(4-methylpiperazin-1-yl)pyridin-2-yl)-1H-pyrazol-4-yl)-6-(1H-pyrazol-4-yl)picolinamide;

I-175: N-(1-methyl-3-(5-(4-methylpiperazin-1-yl)pyridin-2-yl)-1H-pyrazol-4-yl)-6-(1H-pyrazol-3-yl)picolinamide;

I-176: 5'-methyl-N-(1-methyl-3-(5-morpholinopyridin-2-yl)-1H-pyrazol-4-yl)-[2,3'-bipyridine]-6-carboxamide dihydrochloride;

I-177: 5'-methyl-N-(1-methyl-3-(5-(4-methylpiperazin-1-yl)pyridin-2-yl)-1H-pyrazol-4-yl)-[2,3'-bipyridine]-6-carboxamide dihydrochloride;

I-178: N-(3-(5-(2-hydroxy-2-methylpropoxy)pyridin-2-yl)-1-methyl-1H-pyrazol-4-yl)-5'-methyl-[2,3'-bipyridine]-6-carboxamide;

I-179: N-(3-(5-(2-hydroxy-2-methylpropoxy)pyridin-2-yl)-1-methyl-1H-pyrazol-4-yl)-6-(1H-pyrazol-4-yl)picolinamide;

I-180: N-(3-(5-(2-hydroxy-2-methylpropoxy)pyridin-2-yl)-1-methyl-1H-pyrazol-4-yl)-6-(1H-pyrazol-3-yl)picolinamide;

I-181: 5'-methyl-N-(1-methyl-3-(5-(oxetan-3-yloxy)pyridin-2-yl)-1H-pyrazol-4-yl)-[2,3'-bipyridine]-6-carboxamide;

I-182: N-(1-methyl-3-(5-(oxetan-3-yloxy)pyridin-2-yl)-1H-pyrazol-4-yl)-6-(1H-pyrazol-4-yl)picolinamide;

I-183: N-(1-methyl-3-(5-(oxetan-3-yloxy)pyridin-2-yl)-1H-pyrazol-4-yl)-6-(1H-pyrazol-3-yl)picolinamide;

I-184: N-(3-(3,5-difluoropyridin-2-yl)-1-((1r,4r)-4-ethoxycyclohexyl)-1H-pyrazol-4-yl)-6-(1H-pyrazol-4-yl)picolinamide;

I-185: 3'-fluoro-N-(1-(2-(2-methoxyethoxy)ethyl)-3-(pyridin-2-yl)-1H-pyrazol-4-yl)-[2,4'-bipyridine]-6-carboxamide;

I-186: N-(1-(2-(2-methoxyethoxy)ethyl)-3-(pyridin-2-yl)-1H-pyrazol-4-yl)-3'-methyl-[2,4'-bipyridine]-6-carboxamide;

I-187: N-(1-(2-(2-methoxyethoxy)ethyl)-3-(pyridin-2-yl)-1H-pyrazol-4-yl)-2'-methyl-[2,4'-bipyridine]-6-carboxamide;

I-188: 6-(6-methoxy-1H-indol-2-yl)-N-(1-(2-(2-methoxyethoxy)ethyl)-3-(pyridin-2-yl)-1H-pyrazol-4-yl)picolinamide;

I-189: 6-(1-(3-chlorophenyl)-1H-pyrazol-4-yl)-N-(1-(2-(2-methoxyethoxy)ethyl)-3-(pyridin-2-yl)-1H-pyrazol-4-yl)picolinamide;

I-190: N-(1-(2-(2-methoxyethoxy)ethyl)-3-(pyridin-2-yl)-1H-pyrazol-4-yl)-5'-methyl-[2,3'-bipyridine]-6-carboxamide;

I-191: N-(1-(2-(2-methoxyethoxy)ethyl)-3-(pyridin-2-yl)-1H-pyrazol-4-yl)-6-(1H-pyrazol-3-yl)picolinamide;

I-192: 6-(furan-3-yl)-N-(1-(2-(2-methoxyethoxy)ethyl)-3-(pyridin-2-yl)-1H-pyrazol-4-yl)picolinamide;

I-193: 6-(furan-2-yl)-N-(1-(2-(2-methoxyethoxy)ethyl)-3-(pyridin-2-yl)-1H-pyrazol-4-yl)picolinamide;

I-193: 6-(furan-2-yl)-N-(1-(2-(2-methoxyethoxy)ethyl)-3-(pyridin-2-yl)-1H-pyrazol-4-yl)picolinamide;

I-194: N-(1-(2-(2-methoxyethoxy)ethyl)-3-(pyridin-2-yl)-1H-pyrazol-4-yl)-6-(1H-pyrazol-4-yl)picolinamide;

I-195: 6-((1H-indazol-5-yl)amino)-N-(1-(2-(2-methoxyethoxy)ethyl)-3-(pyridin-2-yl)-1H-pyrazol-4-yl)picolinamide;

I-196: 6-((2H-indazol-5-yl)amino)-N-(1-(2-(2-methoxyethoxy)ethyl)-3-(pyridin-2-yl)-1H-pyrazol-4-yl)picolinamide;

I-197: 6-((2-aminopyridin-4-yl)oxy)-N-(1-(2-(2-methoxyethoxy)ethyl)-3-(pyridin-2-yl)-1H-pyrazol-4-yl)picolinamide;

I-198: 6-((2,5-dimethylpyridin-4-yl)amino)-N-(1-(2-(2-methoxyethoxy)ethyl)-3-(pyridin-2-yl)-1H-pyrazol-4-yl)picolinamide;

I-199: N-(1-(2-(2-methoxyethoxy)ethyl)-3-(pyridin-2-yl)-1H-pyrazol-4-yl)-6-((6-(4-methylpiperazin-1-yl)-5-(trifluoromethyl)pyridin-3-yl)amino)picolinamide;

I-200: 2'-((cyclopropylmethyl)amino)-N-(1-methyl-3-(pyridin-2-yl)-1H-pyrazol-4-yl)-[2,4'-bipyridine]-6-carboxamide;

I-201: N-(1-methyl-3-(pyridin-2-yl)-1H-pyrazol-4-yl)-[2,4'-bipyridine]-6-carboxamide;

I-202: N-(1-methyl-3-(pyridin-2-yl)-1H-pyrazol-4-yl)-2'-((2,2,2-trifluoroethyl)amino)-[2,4'-bipyridine]-6-carboxamide;

I-203: N-(1-(3-methoxycyclobutyl)-3-(pyridin-2-yl)-1H-pyrazol-4-yl)-5'-methyl-[2,3'-bipyridine]-6-carboxamide;

I-204: N-(1-(3-methoxycyclobutyl)-3-(pyridin-2-yl)-1H-pyrazol-4-yl)-6-(1H-pyrazol-4-yl)picolinamide;

I-205: N-(1-((1r,4r)-4-ethoxycyclohexyl)-3-(pyrazin-2-yl)-1H-pyrazol-4-yl)-6-(1H-pyrazol-4-yl)picolinamide;

I-206: N-(1-((1r,4r)-4-ethoxycyclohexyl)-3-(pyrazin-2-yl)-1H-pyrazol-4-yl)-5'-methyl-[2,3'-bipyridine]-6-carboxamide;

I-207: N-(1-methyl-3-(pyrazin-2-yl)-1H-pyrazol-4-yl)-6-(1H-pyrazol-4-yl)picolinamide; or I-208: 5'-methyl-N-(1-methyl-3-(pyrazin-2-yl)-1H-pyrazol-4-yl)-[2,3'-bipyridine]-6-carboxamide.

27. A composition, comprising a compound of claim 1, and/or a salt thereof, and a pharmaceutically acceptable excipient.

28. The compound of claim 1, having a formula

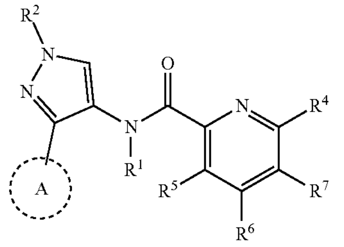

or a salt thereof, wherein:

ring A is heterocyclic;

$R^1$ is H;

$R^2$ is H, alkyl or heterocyclic;

each of $Z^1$, $Z^2$, $Z^3$, and $Z^4$, independently is N or $CR^3$, wherein at least one of $Z^1$, $Z^2$, $Z^3$, and $Z^4$ is N;

$R^4$ is halogen, heterocycloaliphatic, aromatic, —O-aromatic, or —NH-aromatic; and each of $R^5$, $R^6$, and $R^7$ independently is H or alkyl.

29. A compound, having a formula 1

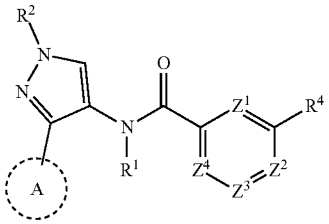

1 or a salt thereof, wherein:

ring A is heterocyclic;

$R^1$ is H;

$R^2$ is heterocyclic;

each of $Z^1$, $Z^2$, $Z^3$, and $Z^4$ independently is N or $CR^3$, wherein at least one of $Z^1$, $Z^2$, $Z^3$, and $Z^4$ is N;

each $R^3$ independently is H or alkyl; and $R^4$ is heterocyclic.

* * * * *